United States Patent
Inoue et al.

(10) Patent No.: US 9,522,140 B2
(45) Date of Patent: *Dec. 20, 2016

(54) ARYL SUBSTITUTED CARBOXAMIDE DERIVATIVES AS CALCIUM OR SODIUM CHANNEL BLOCKERS

(71) Applicant: RaQualia Pharma Inc., Aichi (JP)

(72) Inventors: Tadashi Inoue, Aichi (JP); Shuzo Watanabe, Aichi (JP); Tatsuya Yamagishi, Aichi (JP); Yoshimasa Arano, Aichi (JP); Mikio Morita, Aichi (JP); Kaoru Shimada, Aichi (JP)

(73) Assignee: RAQUALIA PHARMA INC., Aichi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/790,596

(22) Filed: Jul. 2, 2015

(65) Prior Publication Data
US 2015/0322052 A1    Nov. 12, 2015

Related U.S. Application Data

(62) Division of application No. 13/375,117, filed as application No. PCT/JP2010/003649 on May 31, 2010, now Pat. No. 9,101,616.

(Continued)

(51) Int. Cl.
| | |
|---|---|
| *C07D 405/12* | (2006.01) |
| *C07D 213/65* | (2006.01) |
| *C07D 401/12* | (2006.01) |
| *A61K 31/44* | (2006.01) |
| *A61K 31/444* | (2006.01) |
| *A61K 31/443* | (2006.01) |
| *A61K 31/4433* | (2006.01) |
| *A61K 31/4436* | (2006.01) |
| *A61K 31/4439* | (2006.01) |
| *A61K 31/4706* | (2006.01) |
| *A61K 31/4709* | (2006.01) |
| *A61K 31/4725* | (2006.01) |
| *A61K 31/497* | (2006.01) |
| *A61K 31/506* | (2006.01) |

(Continued)

(52) U.S. Cl.
CPC ............. *A61K 31/44* (2013.01); *A61K 31/443* (2013.01); *A61K 31/444* (2013.01); *A61K 31/4433* (2013.01); *A61K 31/4436* (2013.01); *A61K 31/4439* (2013.01); *A61K 31/4706* (2013.01); *A61K 31/4709* (2013.01); *A61K 31/4725* (2013.01); *A61K 31/497* (2013.01); *A61K 31/506* (2013.01); *C07D 213/65* (2013.01); *C07D 215/40* (2013.01); *C07D 241/18* (2013.01); *C07D 401/12* (2013.01); *C07D 401/14* (2013.01); *C07D 405/12* (2013.01); *C07D 409/12* (2013.01); *C07D 413/12* (2013.01); *C07D 417/12* (2013.01)

(58) Field of Classification Search
CPC .... A61K 31/498; A61K 31/497; A61K 31/44; A61K 31/444; C07D 401/12; C07D 213/65
USPC .......................................... 514/249; 546/261
See application file for complete search history.

(56) References Cited

U.S. PATENT DOCUMENTS

| | | | |
|---|---|---|---|
| 9,101,616 B2 * | 8/2015 | Inoue .................... | A61K 31/44 |
| 2004/0010015 A1 | 1/2004 | Haque | |

(Continued)

FOREIGN PATENT DOCUMENTS

| | | |
|---|---|---|
| EP | 0 686 625 | 12/1995 |
| EP | 1 942 104 | 7/2008 |

(Continued)

OTHER PUBLICATIONS

Russian Office Action issued May 5, 2014 in corresponding Russian Application No. 2011154139/04(081421), (with English translation).

(Continued)

*Primary Examiner* — Jennifer M Kim
(74) *Attorney, Agent, or Firm* — Wenderoth, Lind & Ponack, L.L.P.

(57) ABSTRACT

The present invention relates to aryl substituted carboxamide derivatives of formula (I) or a pharmaceutically acceptable salt thereof, which have blocking activities of T-type calcium channels or voltage gated sodium channels as the tetrodotoxin-sensitive (TTX-S) blocker such as $Na_{V1.3}$ and $Na_{V1.7}$, and which are useful in the treatment or prevention of disorders and diseases in which T-type calcium channels or voltage gated sodium channels are involved. The invention also relates to pharmaceutical compositions comprising these compounds and the use of these compounds and compositions in the prevention or treatment of such diseases in which T-type calcium channels or voltage gated sodium channels are involved.

(I)

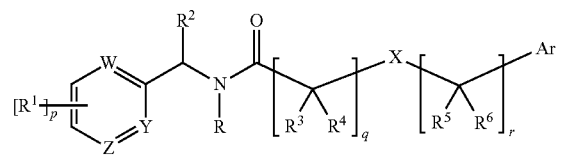

4 Claims, No Drawings

Related U.S. Application Data

(60) Provisional application No. 61/282,534, filed on Feb. 26, 2010, provisional application No. 61/272,581, filed on Oct. 7, 2009, provisional application No. 61/213,324, filed on May 29, 2009.

(51) Int. Cl.

| | | |
|---|---|---|
| C07D 215/40 | (2006.01) | |
| C07D 241/18 | (2006.01) | |
| C07D 401/14 | (2006.01) | |
| C07D 409/12 | (2006.01) | |
| C07D 413/12 | (2006.01) | |
| C07D 417/12 | (2006.01) | |

(56) References Cited

U.S. PATENT DOCUMENTS

| | | |
|---|---|---|
| 2004/0192738 A1 | 9/2004 | Brendel et al. |
| 2005/0038083 A1 | 2/2005 | Brendel et al. |
| 2005/0054673 A1 | 3/2005 | Wirth et al. |
| 2005/0113576 A1 | 5/2005 | Lee et al. |
| 2006/0211741 A1 | 9/2006 | Hanazawa et al. |
| 2007/0043091 A1 | 2/2007 | Wirth |

FOREIGN PATENT DOCUMENTS

| | | |
|---|---|---|
| JP | 8-188563 | 7/1996 |
| JP | 2004-502757 | 1/2004 |
| JP | 2005-519876 | 7/2005 |
| JP | 2005-526100 | 9/2005 |
| JP | 2005-526789 | 9/2005 |
| JP | 2006-520342 | 9/2006 |
| JP | 2006-520343 | 9/2006 |
| JP | 2007-505036 | 3/2007 |
| JP | 2007-509846 | 4/2007 |
| JP | 2007-523926 | 8/2007 |
| JP | 2007-527919 | 10/2007 |
| JP | 2007-523621 | 11/2007 |
| JP | 2008-535801 | 9/2008 |
| JP | 2011-514894 | 5/2011 |
| WO | 95/18087 | 7/1995 |
| WO | 03/045313 | 6/2003 |
| WO | 03/070247 | 8/2003 |
| WO | 03/080578 | 10/2003 |
| WO | 03/080596 | 10/2003 |
| WO | 2004/007459 | 1/2004 |
| WO | 2005/016890 | 2/2005 |
| WO | 2005/040100 | 5/2005 |
| WO | 2005/087750 | 9/2005 |
| WO | 2005/100305 | 10/2005 |
| WO | 2007/120729 | 10/2007 |
| WO | 2007/124849 | 11/2007 |
| WO | 2008/000645 | 1/2008 |
| WO | 2008/080511 | 7/2008 |
| WO | 2008/118758 | 10/2008 |
| WO | 2009/054982 | 4/2009 |
| WO | 2009/054983 | 4/2009 |
| WO | 2009/054984 | 4/2009 |
| WO | 2009/058299 | 5/2009 |
| WO | 2009/110985 | 9/2009 |
| WO | 2009/133387 | 11/2009 |

OTHER PUBLICATIONS

V. N. Uebele et al., "Positive Allosteric Interaction of Structurally Diverse T-Type Calcium Channel Antagonists", Cell Biochemistry and Biophysics, vol. 55, No. 2, pp. 81-93, Jul. 7, 2009.
Database Registry, Chemical Abstract, Mar. 20, 2007, XP002688804, Database Accession No. 927579-62-2.
Database Registry, Chemical Abstract, Oct. 14, 2008, XP002688805, Database Accession No. 1061289-26-6.
Database Registry, Chemical Abstract, Mar. 31, 2008, XP002688806, Database Accession No. 1011091-47-6.
Database Registry, Chemical Abstract, May 20, 2009, XP002688807, Database Accession No. 1147703-08-9.
Database Registry, Chemical Abstract, May 19, 2009, XP002688808, Database Accession No. 1147517-46-1.
Database Registry, Chemical Abstract, Dec. 26, 2008, XP002688809, Database Accession No. 1090435-84-9.
Database Registry, Chemical Abstract, Mar. 30, 2008, XP002688810, Database Accession No. 1010968-44-1.
Database Registry, Chemical Abstract, Oct. 10, 2007, XP002688811, Database Accession No. 950103-58-9.
English translation of International Preliminary Report on Patentability and Written Opinion dated Nov. 29, 2011.
International Search Report issued Jul. 13, 2010 in International (PCT) Application No. PCT/JP2010/003649 along with the Written Opinion.
Supplementary European Search Report dated Jan. 11, 2013 in EP Application No. 10780311.6.

* cited by examiner

ARYL SUBSTITUTED CARBOXAMIDE DERIVATIVES AS CALCIUM OR SODIUM CHANNEL BLOCKERS

TECHNICAL FIELD

The present invention relates to aryl substituted carboxamide derivatives which have blocking activities of T-type calcium channels or voltage gated sodium channels as the tetrodotoxin-sensitive (TTX-S) blockers such as $Na_{V1.3}$ and $Na_{V1.7}$, and which are useful in the treatment or prevention of disorders and diseases in which T-type calcium channels or voltage gated sodium channels are involved. The invention also relates to pharmaceutical compositions comprising these compounds and the use of these compounds and compositions in the prevention or treatment of such diseases in which T-type calcium channels or voltage gated sodium channels are involved.

BACKGROUND ART

Plasma membrane calcium channels are members of a diverse superfamily of voltage gated channel proteins. Calcium channels are membrane-spanning, multi-subunit proteins that allow controlled entry of $Ca^{2+}$ ions into cells from the extracellular fluid. Excitable cells throughout the animal kingdom, and at least some bacterial, fungal and plant cells, possess one or more types of calcium channel. Nearly all "excitable" cells in animals, such as neurons of the central nervous system (CNS), peripheral nerve cells and muscle cells, including those of skeletal muscles, cardiac muscles, and venous and arterial smooth muscles, have voltage dependent calcium channels.

Multiple types of calcium channels have been identified in mammalian cells from various tissues, including skeletal muscle, cardiac muscle, lung, smooth muscle and brain. A major type of this family is the L-type calcium channels, whose function is inhibited by the familiar classes of calcium channel blockers (dihydropyridines such as nifedipine, phenylalkylamines such as verapamil, and benzothiazepines such as diltiazem). Additional classes of plasma membrane calcium channels are referred to as T-type, N-type, P-type, Q-type and R-type.

The "T-type" (or "low voltage-activated") calcium channels are so named because their openings are of briefer duration (T=transient) than the longer (L=long-lasting) openings of the L-type calcium channels. The L, N, P and Q-type channels activate at more positive potentials (high voltage activated) and display diverse kinetics and voltage-dependent properties.

T-type calcium channels have been implicated in pathologies related to various diseases and disorders, including epilepsy, essential tremor, pain, neuropathic pain, schizophrenia, Parkinson's disease, depression, anxiety, sleep disorders, sleep disturbances, insomnia, psychosis, cardiac arrhythmia, hypertension, cancer, diabetes, infertility and sexual dysfunction (J Neuroscience, 14, 5485 (1994); Drugs Future 30 (6), 573-580 (2005); EMBO J, 24, 315-324 (2005); Drug Discovery Today, 11, 5/6, 245-253 (2006); Neuropharmacology 53, 308-317 (2007) and J. Biol. Chem., 283 (15), 10162-10173 (2008)).

On the other hand, blockers of voltage gated sodium channels as the TTX-S channels also relates to a number of therapeutic applications.

The rat $Na_{V1.3}$ channel and the human $Na_{V1.3}$ channel have been cloned in 1988 and 1998/2000 respectively (FEBS Lett. 228 (1), 187-194, 1988; J. Mol Neurosci, 10 (1), 67-70, 1998; Eur. J. Neurosci. 12 (12), 4281-4289, 2000). The $Na_{V1.3}$ channel was formerly known as brain type III sodium channel. $Na_{V1.3}$ is present at relatively high levels in the nervous system of rat embryos but is barely detectable in adult rats. $Na_{V1.3}$ is up-regulated following axotomy in the Spinal Nerve Ligation (SNL), Chronic Constriction Injury (CCI), and diabetic neuropathy models (J Neurophysiol 82, 2776-2785, 1999. J. A. Black et al; Ann Neurol 52, 786-792, 2002. M J. Cranner et. al.; Pain 83, 591-600, 1999. S. Dib-Hajj et al.; J Biol Chem. 279, 29341-29350, 2004. S. Hong et al.; Mol Brain Res 95, 153-161, 2001, C. H. Kim et al.) The up-regulation of $Na_{V1.3}$ channel contributes to rapidly reprinting sodium current in small dorsal root ganglion (DRG) neurons (J Neurophysiol 82, 2776-2785, 1999, J. A. Black et al.). These observations suggest that $Na_{V1.3}$ may make a key contribution to neuronal hyperexcitability.

In order to validate the contribution of $Na_{V1.3}$ sodium channel in the pain states, specific antisense oligonucleotides (ASO) were used in animal pain models. $Na_{V1.3}$ sodium channel ASO treatment significantly attenuated pain-related behaviors after CCI operation (J. Neurosci. 24, 4832-4839, 2004, Hains, B. C. et al.). These finding suggest that $Na_{V1.3}$ sodium channel antagonist is useful to treat neuropathic pain conditions.

The $Na_{V1.7}$ channel appears to be the best 'validated' pain target. The most exciting findings with respect to $Na_{V1.7}$ have come from human genetic studies. Cox et al. (Nature 444, 894-898, 2006) discovered SCN9A mutations that cause a loss of $Na_{V1.7}$ function in three families from Pakistan. Their observations link loss of $Na_{V1.7}$ function with a congenital inability to experience pain, adding to the evidence indicating $Na_{V1.7}$ channel as an essential participant in human nociception.

By contrast, Gain-of-function mutations have also been described that lead to enhanced pain, for example. Primary Erythermalgia in one case and Paroxysmal Extreme Pain Disorder in another. These gain-of-function mutations in patients led to different types of gating changes in $Na_{V1.7}$ sodium currents and, interestingly, different degrees of effectiveness of specific sodium channel blocking drugs. The implication from these findings is that a selective $Na_{V1.7}$ blocker may be an effective treatment for pain in man.

A local anaesthetic lidocalne and a volatile anaesthetic halothane are known to act on both TTX-R and TTX-S sodium channels with poor selectivity and low potency ($IC_{50}$ values range from 50 mM to 10 mM). These anaesthetics at high systemic concentrations could cause devastating side effects, e.g., paralysis and cardiac arrest. However, systemic administration of lidocaine at low concentrations is effective to treat chronic pain (Trends in Pharm. Sci 22, 27-31, 2001, Baker, M. D. et al.). In rats, application of a very low dose of TTX to the DRG of the injured segment of the L5 spinal nerve significantly reduces mechanical allodynic behavior (Brain Res 871, 98-103, 2000, Lyu, Y. S. et al.). This suggests that TTX-S subtypes of sodium channels play an important role in maintaining allodynic behaviors in an animal model of neuropathic pain.

The $Na_{V1.5}$ channel is also a member of TTX-resistant sodium channels. The $Na_{V1.5}$ channel is almost exclusively expressed in cardiac tissue and has been shown to underlie a variety of cardiac arrhythmias and conduction disorders.

In particular, the aryl substituted carboxamide derivatives of the present invention are selective for the TTX-S channels over the $Na_{V1.5}$ channel, leading to improvements in the side-effect profile.

The aryl substituted carboxamide derivatives are therefore useful for the treatment of a wide range of disorders, particularly pain, acute pain, chronic pain, neuropathic pain, inflammatory pain, visceral pain, nociceptive pain including post-surgical pain, and mixed pain types involving the viscera, gastrointestinal tract, cranial structures, musculoskeletal system, spine, urogenital system, cardiovascular system and CNS, including cancer pain, back and orofacial pain.

Other conditions that may be treated with the picolinamide derivatives of the present invention include multiple sclerosis, neurodegenerative disorders, irritable bowel syndrome, osteoarthritis, rheumatoid arthritis, neuropathological disorders, functional bowel disorders, inflammatory bowel diseases, pain associated with dysmenorrhea, pelvic pain, cystitis, pancreatitis, migraine, cluster and tension headaches, diabetic neuropathy, peripheral neuropathic pain, sciatica, fibromyalgia Crohn's disease, epilepsy or epileptic conditions, bipolar depression, tachyarrhythmias, mood disorder, bipolar disorder, psychiatric disorders such as anxiety and depression, myotonia, arrhythmia, movement disorders, neuroendocrine disorders, ataxia, incontinence, visceral pain, trigeminal neuralgia, herpetic neuralgia, general neuralgia, postherpetic neuralgia, radicular pain, sciatica, back pain, head or neck pain, severe or intractable pain, breakthrough pain, postsurgical pain, stroke, cancer pain, seizure disorder and causalgia.

WO2007120729, WO2009054982, WO2009054983, and WO2009054984 disclose a series of heterocycle amide compounds which are blockers of T-type calcium channels.

The compounds of the present invention, however, differ structurally from known compounds in the above cited arts by the presence of unique spacer between carbony group and terminal aryl group. Namely, disclosed compounds of the prior arts are introducing only one carbon atom as a spacer between carbonyl group and heteroaryl, whereas the compounds of the present invention are characterized by introducing different unique spacers between carbony group and terminal aryl group.

WO 2003037274 discloses pyrazole derivatives as sodium channel blockers. Then WO2002091830 disclosed pyridinyl fused bicyclic amides as fungicides.

The novel compounds with trifluoroethoxy or methoxy on the pyridine ring or pyrazine ring; and alkyl side chain; are useful for the treatment of a condition or disorder in which voltage gated sodium channels are involved.

On the contrary, cyclopropane carboxamide besides trifluoroethoxy or methoxy on the pyridine ring or pyrazine ring is important for the treatment of a condition or disorder in which T-type calcium channels are involved. The compounds have advantage over the compounds disclosed in WO2007120729, WO2009054982, WO2009054983, and WO2009054984 in terms of metabolism.

The above cited arts, however, have never disclosed the voltage gated sodium channels. Therefore aryl substituted carboxamide derivatives of this invention provide the first knowledge of blocking not only the T-type calcium channels but also voltage gated sodium channels.

It is an objective of the invention to provide new T-type calcium channel blockers or TTX-S blockers that are good drug candidates. Preferred compounds should bind potently to the TTX-S ($Na_{V1.3}$ and $Na_{V1.7}$) channels whilst showing little affinity for other sodium channels, particularly the $Na_{V1.5}$ channel. They should be well absorbed from the gastrointestinal tract, be metabolically stable and possess favorable pharmacokinetic properties. For example, the compounds of this invention have excellent metabolic properties comparing with the compounds disclosed in WO 2007120729, WO 2009054982, WO 2009054983, and WO 2009054984. They should be non-toxic and demonstrate few side-effects. Furthermore, the ideal drug candidate will exist in a physical form that is stable, non-hygroscopic and easily formulated.

SUMMARY OF INVENTION

The present invention is directed to aryl substituted carboxamide derivatives which are blockers of T-type calcium channels or voltage gated sodium channels, and which are useful in the treatment or prevention of neurological and psychiatric disorders and diseases in which T-type calcium channels or voltage gated sodium channels are involved. The invention is also directed to pharmaceutical compositions comprising these compounds and the use of these compounds and compositions in the prevention or treatment of such diseases in which T-type calcium channels or voltage gated sodium channels are involved. It is needless to say that T-type calcium channels or voltage gated sodium channels does cover T-type calcium channels and voltage gated sodium channels.

DESCRIPTION OF EMBODIMENTS

The present invention provides a use of a compound of the following formula (I) for the manufacture of a medicament for the treatment of a condition or disorder in which T-type calcium channels or voltage gated sodium channels are involved:

[Chem. 1]

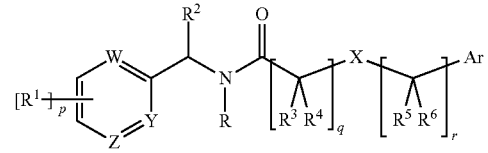

wherein:

R is hydrogen $C_{1-6}$ alkyl which may be substituted with one or more substituents independently selected from $R^7$;

$R^1$ is independently selected from the group consisting of:
(1) hydrogen, (2) halogen, (3) hydroxyl, (4) —$O_n$—$C_{1-6}$ alkyl, where the alkyl is unsubstituted or substituted with one or more substituents independently selected from $R^7$, (5) —$O_n$—$C_{3-6}$cycloalkyl, where the cycloalkyl is unsubstituted or substituted with one or more substituents independently selected from $R^7$, (6) $C_{2-4}$ alkenyl, where the alkenyl is unsubstituted or substituted with one or more substituents independently selected from $R^7$, (7) —$O_n$-phenyl or —$O_n$-naphthyl, where the phenyl or napthyl is unsubstituted or substituted with one or more substituents independently selected from $R^7$, (8) —$O_n$-heterocyclic group, where the heterocyclic group is unsubstituted or substituted with one or more substituents independently selected from $R^7$, (9) —(C=O)—$NR^9R^{10}$, (10) —$NR^9R^{10}$, (11) —$S(O)_2$—$NR^9R^{10}$, (12) —$NR^9$—$S(O)^2R^{10}$, (13) —$S(O)_tR^{10}$, where t is 0, 1 or 2, (14) —$NR^9(C=O)R^{10}$, (15) —CN, and (16) —$NO_2$;

wherein n is 0 or 1, when n is 0, a chemical bond is present in the place of $O_n$;

p is 1, 2, 3, or 4; when p is two or more than two, $R^1$ may be same or different;

$R^2$ is selected from the group consisting of:
(1) hydrogen, (2) $C_{1-6}$alkyl, which is unsubstituted or substituted with one or more substituents independently selected from $R^7$, (3) $C_{3-6}$cycloalkyl, which is unsubstituted or substituted with one or more substituents independently selected from $R^7$, (4) $C_{2-6}$ alkenyl, which is unsubstituted or substituted with one or more substituents independently selected from $R^7$, (5) $C_{2-6}$alkynyl, which is unsubstituted or substituted with one or more substituents independently selected from $R^7$, (6) phenyl, which is unsubstituted or substituted with one or more substituents independently selected from $R^7$, (7) —(C=O)—$NR^9R^{10}$, and (8) —(C=O)—O—$C_{1-6}$; alkyl, which is unsubstituted or substituted with one or more substituents independently selected from $R^7$;

or $R^2$ form a 5 to 7 membered ring with $R^1$ which may contain nitrogen atom, oxygen atom, sulfur atom or double bond, wherein the 5 to 7 membered ring is optionally substituted with 1 to 6 substituents independently selected from the group consisting of: (1) hydrogen, (2) hydroxyl, (3) halogen, (4) $C_{1-6}$ alkyl, which is unsubstituted or substituted with one or more substituents independently selected from $R^7$, (5) $C_{3-6}$cycloalkyl, which is unsubstituted or substituted with one or more substituents independently selected from $R^7$, (6) —O—$C_{1-6}$ alkyl, which is unsubstituted or substituted with one or more substituents independently selected from $R^7$ and (7) —O—$C_{3-6}$ cycloalkyl, which is unsubstituted or substituted with one or more substituents independently selected from $R^7$;

X is a chemical bond, —C≡C—, -cycloalkylene-, -cycloalkylene-$C_{1-4}$-alkylene-O—, oxygen atom, sulfur atom, or nitrogen atom; when X is —C≡C—, -cycloalkylene-, -cycloalkylene-$C_{1-4}$-alkylene-O—, or nitrogen atom, said substituent X may have a substituent independently selected from the definitions of $R^9$ and $R^{10}$;

W, Y and Z are independently selected from nitrogen atom and carbon atom, which are independently optionally substituted with $R^1$;

at least one of W, Y and Z is nitrogen and W, Y and Z are not carbon at the same time;

$R^3$, $R^4$, $R^5$ and $R^6$ are independently selected from the group consisting of:
(1) hydrogen, (2) hydroxyl, (3) halogen, (4) $C_{1-6}$alkyl, which is unsubstituted or substituted with one or more substituents independently selected from $R^7$, (5) $C_{3-6}$cycloalkyl, which is unsubstituted or substituted with one or more substituents independently selected from $R^7$, (6) —O—$C_{1-6}$ alkyl, which is unsubstituted or substituted with one or more substituents independently selected from $R^7$, (7) —O—$C_{3-6}$ cycloalkyl, which is unsubstituted or substituted with one or more substituents independently selected from $R^7$, and (8) —$NR^7R^8$;

or $R^3$ and $R^4$ and the carbon atom to which they are attached form an oxo group;

or $R^3$ and $R^4$ and the carbon atom to which they are attached form a $C_{3-6}$ cycloalkyl ring, which is unsubstituted or substituted with $R^7$;

or $R^5$ and $R^6$ and the carbon atom to which they are attached form an oxo group;

or $R^5$ and $R^6$ and the carbon atom to which they are attached form a $C_{3-6}$cycloalkyl ring, which is unsubstituted or substituted with $R^7$;

q is 0, 1, 2, 3, or 4; when q is one or more than one, $R^3$ and $R^4$ may be same or different;

r is 0, 1, 2, 3, or 4; when r is one or more than one, $R^5$ and $R^6$ may be same or different;

when (i) q is 1 and r is 0 or (ii) q is 0 and r is 1, X is not a chemical bond;

$R^7$ is selected from the group consisting of:
(1) hydrogen, (2) halogen, (3) hydroxyl, (4) —(C=O)$_m$—O$_l$—$C_{1-6}$ alkyl, where the alkyl is unsubstituted or substituted with one or more substituents independently selected from $R^8$, (5) —O$_l$—($C_{1-3}$)perfluoroalkyl, (6) —(C=O)$_m$—O$_l$—$C_{3-6}$cycloalkyl, where the cycloalkyl is unsubstituted or substituted with one or more substituents independently selected from $R^8$, (7) —(C=O)$_m$—$C_{2-4}$alkenyl, where the alkenyl is unsubstituted or substituted with one or more substituents independently selected from $R^8$, (8) —(C=O)$_m$—O$_l$-phenyl or —(C=O)$_m$—O$_l$-napthyl, where the phenyl or napthyl is unsubstituted or substituted with one or more substituents independently selected from $R^8$, (9) —(C=O)$_m$—O$_l$-heterocyclic group, where the heterocyclic group is unsubstituted or substituted with one or more substituents independently selected from $R^8$, (10) —(C=O)$_m$—$NR^9R^{10}$, (11) —$NR^9R^{10}$, (12) —$S(O)_2$—$NR^9R^{10}$, (13) —$S(O)_t$—$R^9$, where t is 0, 1 or 2, (14) —$CO_2H$, (15) —CN, and (16) —$NO_2$;

wherein l is 0 or 1 and m is 0 or 1; when l is 0 or m is 0, a chemical bond is present in the place of (C=O)$_m$ or O$_l$, and when l is 0 and m is 0, a chemical bond is present in the place of (C=O)$_m$—O$_l$;

$R^8$ is independently selected from the group consisting of:
(1) hydrogen, (2) hydroxyl, (3) halogen, (4) $C_{1-6}$ alkyl, (5) —$C_{3-6}$cycloalkyl, (6) —O—$C_{1-6}$ alkyl, (7) —O(C=O)—$C_{1-6}$ alkyl (8) —NH—$C_{1-6}$ alkyl, (9) phenyl, (10) heterocyclic group, and (11) —CN;

$R^9$ and $R^{10}$ are independently hydrogen or $C_{1-6}$ alkyl, which is unsubstituted or substituted with one or more substituents independently selected from halogen, hydroxyl, and —O—$C_{1-6}$ alkyl; or $R^9$ form a 4 to 7 membered ring with $R^{10}$ which may contain nitrogen atom, oxygen atom, sulfur atom or double bond, wherein the 4 to 7 membered ring is optionally substituted with 1 to 6 substituents independently selected from the group consisting of: (1) hydrogen, (2) hydroxyl, (3) halogen, (4) $C_{1-6}$ alkyl, which is unsubstituted or substituted with one or more substituents independently selected from $R^8$, (5) $C_{3-6}$ cycloalkyl, which is unsubstituted or substituted with one or more substituents independently selected from $R^8$, (6) —O—$C_{1-6}$ alkyl, which is unsubstituted or substituted with one or more substituents independently selected from $R^8$, and (7) —O—$C_{3-6}$ cycloalkyl, which is unsubstituted or substituted with one or more substituents independently selected from $R^8$;

Ar is aryl which is optionally substituted with 1 to 5 substituents independently selected from the group consisting of:
(1) halogen, (2) hydroxyl, (3) —O$_n$-phenyl or —O$_n$-napthyl, where the phenyl or napthyl is unsubstituted or substituted with one or more substituents independently selected from $R^7$, (4) —O$_n$-heterocyclic group, where the heterocyclic group is unsubstituted or substituted with one or more substituents independently selected, from $R^7$, (5) —O$_n$—$C_{1-6}$ alkyl, where the alkyl is unsubstituted or substituted with one or more substituents independently selected from $R^7$, (6) —O$_p$—$C_{3-6}$ cycloalkyl where the cycloalkyl is unsubstituted or substituted with one or more substituents independently selected from $R^7$, (7) —$C_{2-4}$ alkenyl, where the alkenyl is unsubstituted or substituted with one or more substituents independently selected from $R^7$, (8) —(C=O)—$NR^9R^{10}$, (9) —$NR^9R^{10}$, (10) —$S(O)_2NR^9R^{10}$, (11) —$NR^9$—$S(O)_2R^{10}$, (12) —$S(O)_t$—$R^9$, where t is 0, 1 or 2, (13) —$NR^9$(C=O)$R^{10}$, (14) —CN, and (15) —$NO_2$;

wherein n is 0 or 1, when n is 0, a chemical bond is present in the place of $O_n$;

or a pharmaceutically acceptable salt thereof.

The present invention provides the compounds of the formula (II)

[Chem. 2]

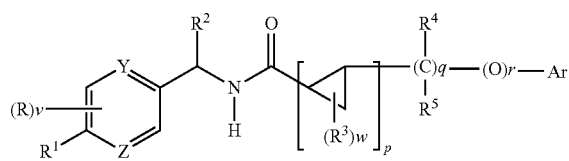

(II)

wherein

R is halogen, or $C_{1-6}$ alkyl, which is unsubstituted or substituted with one or more substituents independently selected from halogen, hydroxyl, and —O—$C_{1-6}$ alkyl;

v is 0, 1, 2, or 3; when v is two or more than two, R may be same or different;

$R^1$ is —OCH$_2$CF$_3$ or —OCH$_3$;

$R^2$ is $C_{1-6}$ alkyl, which is unsubstituted or substituted with one or more substituents independently selected from halogen, hydroxyl, and —O—$C_{1-6}$ alkyl;

$R^3$ is independently selected from the group consisting of:

(1) halogen, (2) $C_{1-6}$ alkyl, which is unsubstituted or substituted with one or more substituents independently selected from $R^6$, (3) $C_{3-6}$cycloalkyl, which is unsubstituted or substituted with one or more substituents independently selected from $R^6$, (4) —O—$C_{1-6}$ alkyl, which is unsubstituted or substituted with one or more substituents independently selected from $R^6$, (5) —O—$C_{3-6}$ cycloalkyl, which is unsubstituted or substituted with one or more substituents independently selected from $R^6$, and (6) —NR$^7$R$^8$;

Preferable $R^3$ is independently selected from the group consisting of:

(1) halogen, (2) $C_{1-6}$ alkyl, which is unsubstituted or substituted with one or more substituents independently selected from halogen;

w is 0, 1, 2, 3 or 4; when w is two or more than two, $R^3$ may be same or different;

$R^4$ and $R^5$ are independently hydrogen, halogen, or $C_{1-6}$ alkyl which is unsubstituted or substituted with one or more substituents independently selected from halogen, hydroxyl, and —O—$C_{1-6}$ alkyl;

Preferable $R^4$ and $R^5$ are independently hydrogen, halogen, or $C_{1-6}$ alkyl which is unsubstituted or substituted with one or more substituents independently selected from halogen;

$R^6$ is independently selected from the group consisting of:
(1) hydrogen, (2) hydroxyl, (3) halogen, (4) —O$_l$R$^7$, (5) —CN, (6) —(C=O)—NR$^7$R$^8$, (7) —NR$^7$R$^8$, (8) —S(O)$_2$NR$^7$R$^8$, (9) —S(O)$_t$—R$^7$, where t is 0, 1 or 2, (10) —CN, and (11) —NO$_2$; wherein l is 0 or 1; when l is 0, a chemical bond is present in the place of $O_l$;

$R^7$ and $R^8$ are independently hydrogen, $C_{1-6}$ alkyl, or $C_{3-8}$ cycloalkyl, which are unsubstituted or substituted with one or more substituents independently selected from halogen, hydroxyl, and —O—$C_{1-6}$ alkyl; or $R^7$ form a 4 to 7 membered ring with $R^8$ which may contain nitrogen atom, or oxygen atom, wherein the 4 to 7 membered ring is optionally substituted with 1 to 6 substituents independently selected from the group consisting of: (1) hydrogen, (2) hydroxyl, (3) halogen, (4) $C_{1-6}$ alkyl, and (5) —O—$C_{1-6}$ alkyl;

p, q, and r are independently 0 or 1; when p is 0, both q and r are 1 or both q and r are 0.

Y and Z are independently selected from nitrogen atom and carbon atom; Y and Z are not carbon atom at the same time;

when p is 0, Ar is selected from the group consisting of phenyl, indolyl and quinolinyl; wherein Ar is optionally substituted with 1 to 5 substituents independently selected from the group consisting of:

(1) halogen, (2) hydroxyl, (3) —O-phenyl or —O-napthyl, where the phenyl or napthyl is unsubstituted or substituted with one or more substituents independently selected from $R^6$, (4) —O$_n$-heterocyclic group, where the heterocyclic group is unsubstituted or substituted with one or more substituents independently selected from $R^6$, (5) —O$_n$—$C_{1-6}$ alkyl, where the alkyl is unsubstituted or substituted with one or more substituents independently selected from $R^6$, (6) —O$_n$—$C_{3-6}$ cycloalkyl, where the cycloalkyl is unsubstituted or substituted with one or more substituents independently selected from $R^6$, (7) —NR$^7$R$^8$, (8) —S(O)$_2$—NR$^7$R$^8$, (9) —S(O)$_t$R$^7$, where t is 0, 1 or 2, (10) —NR$^7$SO$_2$R$^8$, (11) —(C=O)—NR$^7$R$^8$, (12) —NR$^7$(C=O)R$^8$, (13) —CN, and (14) —NO$_2$;

wherein preferable Ar is optionally substituted with 1 to 5 substituents independently selected from the group consisting of:

(1) halogen, (2) hydroxyl, (3) —O-phenyl, where the phenyl is unsubstituted or substituted with one or more substituents independently selected from halogen, methyl, trifluoromethyl, and trifluoromethoxy, (4) —O$_n$-heterocyclic group, where the heterocyclic group is unsubstituted or substituted with one or more substituents independently selected from halogen, methyl, trifluoromethyl, and trifluoromethoxy, (5) —O$_n$—$C_{1-6}$ alkyl, where the alkyl is unsubstituted or substituted with one or more substituents independently selected from halogen, (6) —O$_n$—$C_{3-6}$ cycloalkyl, where the cycloalkyl is unsubstituted or substituted with one or more substituents independently selected from halogen, and (7) —CN;

wherein n is 0 or 1, when n is 0, a chemical bond is present in the place of $O_n$;

when p is 1, Ar is aryl which is optionally substituted with 1 to 5 substituents independently selected from the group consisting of:

(1) halogen, (2) hydroxyl, (3) —O$_n$-heterocyclic group, where the heterocyclic group is unsubstituted or substituted with one or more substituents independently selected from $R^6$, (4) —O$_n$—$C_{1-6}$ alkyl, where the alkyl is unsubstituted or substituted with one or more substituents independently selected from $R^6$, (5) —O$_n$—$C_{3-6}$ cycloalkyl, where the cycloalkyl is unsubstituted or substituted with one or more substituents independently selected from $R^6$, (6) —NR$^7$R$^8$, (7) —S(O)$_2$—R$^7$R$^8$, (8) —S(O)$_t$—R$^7$, where t is 0, 1 or 2, (9) —NR$^7$SO$_2$R$^8$, (10) —(C=O)—NR$^7$R$^8$, (11) —NR$^7$(C=O)R$^8$, (12) —CN, and (13) —NO$_2$;

when p is 1, preferable Ar is aryl which is optionally substituted with 1 to 5 substituents independently selected from the group consisting of:

(1) halogen, (2) hydroxyl, (3) —O$_n$—$C_{1-6}$ alkyl, where the alkyl is unsubstituted or substituted with one or more substituents independently selected from halogen, (4) —O$_n$—$C_{3-6}$ cycloalkyl, where the cycloalkyl is unsubstituted or substituted with one or more substituents independently selected from halogen, and (5) —CN;

wherein n is 0 or 1, when n is 0, a chemical bond is present in the place of O$_n$; or a pharmaceutically acceptable salt thereof.

Suitable compounds of the invention are:
(R)—N-(1-(5-(2,2,2-trifluoroethoxy)pyridin-2-yl)ethyl)-2-(4-(trifluoromethyl)phenoxy)acetamide;
(R)-3,5-dichloro-N-(1-(5-(2,2,2-trifluoroethoxy)pyridin-2-yl)ethyl)benzamide;
(R)—N-(1-(5-(2,2,2-trifluoroethoxy)pyridin-2-yl)ethyl)quinoline-2-carboxamide;
(1R,2R)-2-methyl-N-((R)-1-(5-(2,2,2-trifluoroethoxy)pyridin-2-yl)ethyl)-2-(4-(trifluoromethyl)phenyl)cyclopropanecarboxamide;
(R)-4-tert-butyl-N-(1-(5-(2,2,2-trifluoroethoxy)pyridin-2-yl)ethyl)benzamide;
(R)—N-(1-(6-(2,2,2-trifluoroethoxy)pyridin-3-yl)ethyl)-2-(4-(trifluoromethyl)phenoxy)acetamide;
(R)-2-(p-tolyloxy)-N-(1-(5-(2,2,2-trifluoroethoxy)pyridin-2-yl)ethyl)acetamide;
(R)-4-(2,2,2-trifluoroethoxy)-N-(1-(5-(2,2,2-trifluoroethoxy)pyridin-2-yl)ethyl)benzamide;
(R)—N-(1-(5-(2,2,2-trifluoroethoxy)pyridin-2-yl)ethyl)-1H-indole-2-carboxamide;
(R)-1-methyl-N-(1-(5-(2,2,2-trifluoroethoxy)pyridin-2-yl)ethyl)-1H-indole-2-carboxamide;
(R)-2-(2,4-dichlorophenoxy)-N-(1-(5-(2,2,2-trifluoroethoxy)pyridin-2-yl)ehtyl)acetamide;
(R)-2-(4-bromophenoxy)-N-(1-(5-(2,2,2-trifluoroethoxy)pyridin-2-yl)ethyl)acetamide;
(R)-3-(3-fluorophenyl)-N-(1-(5-(2,2,2-trifluoroethoxy)pyridin-2-yl)ethyl)propanamide;
(R)-3-methyl-N-(1-(5-(2,2,2-trifluoroethoxy)pyridin-2-yl)ethyl)benzofuran-2-carboxamide:
(R)-5-tert-butyl-2-methyl-N-(1-(5-(2,2,2-trifluoroethoxy)pyridin-2-yl)ethyl)furan-3-carboxamide;
(R)—N-(1-(5-(2,2,2-trifluoroethoxy)pyridin-2-yl)ethyl)-3-(trifluoromethyl)benzamide;
(R)—N-(1-(5-(2,2,2-trifluoroethoxy)pyridin-2-yl)ethyl)-4-(trifluoromethyl)benzamide;
(R)-5-phenyl-N-(1-(5-(2,2,2-trifluoroethoxy)pyridin-2-yl)ethyl)-2-(trifluoromethyl)furan-3-carboxamide;
(R)-3-fluoro-N-(1-(5-(2,2,2-trifluoroethoxy)pyridin-2-yl)ethyl)-5-trifluoromethyl)benzamide;
(R)-3-fluoro-N-(1-(5-(2,2,2-trifluoroethoxy)pyridin-2-yl)ethyl)-4-(trifluoromethyl)benzamide;
(R)-4-fluoro-N-(1-(5-(2,2,2-trifluoroethoxy)pyridin-2-yl)ethyl)-3-(trifluoromethyl)benzamide;
(R)-2-methyl-N-(1-(5-(2,2,2-trifluoroethoxy)pyridin-2-yl)ethyl)-6-(trifluoromethyl)-2H-indazole-3-carboxamide;
(R)—N-(1-(5-(2,2,2-trifluoroethoxy)pyridin-2-yl)ethyl)-5-(trifluoromethyl)picolinamide;
(R)—N-(1-(5-(2,2,2-trifluoroethoxy)pyridin-2-yl)ethyl)-1H-indole-3-carboxamide;
(R)-1-methyl-N-(1-(5-(2,2,2-trifluoroethoxy)pyridin-2-yl)ethyl)-1H-indole-3-carboxamide;
(R)-3-(1H-indol-1-yl)-N-(1-(5-(2,2,2-trifluoroethoxy)pyridin-2-yl)ethyl)propanamide;
(R)-1-methyl-N-(1-(5-(2,2,2-trifluoroethoxy)pyridin-2-yl)ethyl)-5-(trifluoromethyl)-1H-indole-2-carboxamide;
(R)—N-(1-(5-(cyclopropylmethoxy)pyridin-2-yl)ethyl)-5-fluoro-1H-indole-2-carboxamide;
(R,E)-N-(1-(5-cyclopropylmethoxy)pyridin-2-yl)ethyl)-3-(4-trifluoromethyl)phenyl)acrylamide
(R,E)-N-(1-(5-benzyloxy)pyridin-2-yl)ethyl)-3-(4-(trifluoromethyl)phenyl)acrylamide
(R)—N-(1-(5-(2,2,2-trifluoroethoxy)pyridin-2-yl)ethyl)-2-(4-trifluoromethyl)phenyl)thiazole-4-carboxamide;

(R)-3-(6-fluoro-1H-indol-1-yl)-N-(1-(5-(2,2,2-trifluoroethoxy)pyridin-2-yl)ethyl)propanamide;
(R)—N-(1-(5-(cyclopropylmethoxy)pyridin-2-yl)ethyl)-3-(6-fluoro-1H-indol-1-yl)propanamide;
(R)—N-(1-(5-(2-fluorobenzyloxy)pyridin-2-yl)-2-(4-(trifluoromethyl)phenoxy)acetamide;
(R)-(5)-(2,2,2-trifluoroethoxy)-N-(1-(5-(2,2,2-trifluoroethoxy)pyridin-2-yl)ethyl)picolinamide;
(R)—N-(1-(5-(pryidin-2-ylmethoxy)pyridin-2-yl)ethyl)-2-(4-(trifluoromethyl)phenoxy)acetamide;
N—((R)-1-(5-(2,2,2-trifluoroethoxy)pyridin-2-yl)ethyl)-1,2,3,4-tetrahydronaphthalene-2-carboxamide;
(R,E)-3-(1-indol-3-yl)-N-(1-(5-(2,2,2-trifluoroethoxy)pyridin-2-yl)ethyl)acrylamide
(1R,2R)—N—((R)-1-(6-(2,2,2-trifluoroethoxy)pyridin-3-yl)ethyl)-2-(4-(trifluoromethyl)phenyl)cyclopropanecarboxamide;
(R)—N-(1-(5-((1-methylcyclopropyl)methoxy)pyridin-2-yl)ethyl)-2-(4-trifluoromethyl)phenoxy)acetamide;
trans-2-(7-fluoro-1H-indol-3-yl)-N—((R)—N-(1-(5-(2,2,2-trifluoroethoxy)pyridin-2-yl)ethyl)cyclopropanecarboxamide;
(R)-3-chloro-4-methyl-N-(1-(5-(2,2,2-trifluoroethoxy)pyridin-2-yl)ethyl)benzamide;
(R)-4-tert-butyl-N-(1-(6-(2,2,2-trifluoroethoxy)pyridin-3-yl)ethyl)benzamide;
(R)-3-chloro-N-(1-(5-(2,2,2-trifluoroethoxy)pyridin-2-yl)ethyl)benzamide;
(R)—N-(1-(5-(2,2,2-trifluoroethoxy)pyridin-2-yl)ethyl)quinoxaline-2-carboxamide;
(R)-4-methoxy-N-(1-(5-(2,2,2-trifluoroethoxy)pyridin-2-yl)ethyl)quinoline-2-carboxamide;
(R)-5-isobutyl-N-(1-(5-(2,2,2-trifluoroethoxy)pyridin-2-yl)ethyl)isoxazole-3-carboxamide;
(R)-3-(2-methylthiazol-4-yl)-N-(1-(5-(2,2,2-trifluoroethoxy)pyridin-2-yl)ethyl)benzamide;
(R)—N-(1-(5-(2,2,2-trifluoroethoxy)pyridin-2-yl)ethyl)benzo[b]thiophene-2-carboxamide;
(R)-3-(benzyloxy)-4-methoxy-N-(1-(5-(2,2,2-trifluoroethoxy)pyridin-2-yl)ethyl)benzamide;
(R)-3-phenoxy-N-(1-(5-(2,2,2-trifluoroethoxy)pyridin-2-yl)ethyl)benzamide;
(1S*,2S*)-2-(1H-indol-3-yl)-N—((R)-1-(5-(2,2,2-trifluoroethoxy)pyridin-2-yl)ethyl)cyclopropanecarboxamide;
(1R*,2R*)-2-(1H-indol-3-yl)-N—((R)-1-(5-(2,2,2-trifluoroethoxy)pyridin-2-yl)ethyl)cyclopropanecarboxamide;
(R)-5-chloro-1-methyl-N-(1-(5-(2,2,2-trifluoroethoxy)pyridin-2-yl)ethyl)-1H-indole-3-carboxamide;
(R)-5-methoxy-1-methyl-N-(1-(5-(2,2,2-trifluoroethoxy)pyridin-2-yl)ethyl)-1H-indole-3-carboxamide;
(R)-1,6-dimethyl-N-(1-(5-(2,2,2-trifluoroethoxy)pyridin-2-yl)ethyl)-1H-indole-3-carboxamide;
(R)-6-fluoro-1-methyl-N-(1-(5-(2,2,2-trifluoroethoxy)pyridin-2-yl)ethyl)-1H-indole-3-carboxamide;
(R)-5-methyl-N-(1-(5-(2,2,2-trifluoroethoxy)pyridin-2-yl)ethyl)-1H-indole-3-carboxamide;
(R)-5-fluoro-N-(1-(5-(2,2,2-trifluoroethoxy)pyridin-2-yl)ethyl)-1H-indole-3-carboxamide;
(R)-5-chloro-N-(1-(5-(2,2,2-trifluoroethoxy)pyridin-2-yl)ethyl)-1H-indole-3-carboxamide;
(R)-6-chloro-N-(1-(5-(2,2,2-trifluoroethoxy)pyridin-2-yl)ethyl)-1H-indole-3-carboxamide;
trans-2-(1H-indol-6-yl)-N—((R)-(1-(6-(2,2,2-trifluoroethoxy)pyridin-3-yl)ethyl)-cyclopropanecarboxamide;
(R)-1,5-dimethyl-N-(1-(5-(2,2,2-trifluoroethoxy)pyridin-2-yl)ethyl)-1H-indole-2-carboxamide;

(R)-5-fluoro-1-methyl-N-(1-(5-(2,2,2-trifluoroethoxy)pyridin-2-yl)ethyl)-1H-indole-2-carboxamide;
(R)-5-chloro-1-methyl-N-(1-(5-(2,2,2-trifluoroethoxy)pyridin-2-yl)ethyl)-1H-indole-2-carboxamide;
(R)-6-fluoro-1-methyl-N-(1-(5-(2,2,2-trifluoroethoxy)pyridin-2-yl)ethyl)-1H-indole-2-carboxamide;
(R)—N-(1-(5-(2,2,2-trifluoroethoxy)pyridin-2-yl)ethyl)-4-trifluoromethoxy)benzamide;
(R)-5-phenyl-N-(1-(5-(2,2,2-trifluoroethoxy)pyridin-2-yl)ethyl)-isoxazole-3-carboxamide;
(R)-5-bromo-N-(1-(5-(2,2,2-trifluoroethoxy)pyridin-2-yl)ethyl)-1H-indole-2-carboxamide;
(R)-6-chloro-1-methyl-N-(1-(5-(2,2,2-trifluoroethoxy)pyridin-2-yl)ethyl)-1H-indole-2-carboxamide;
(R)-1-methyl-N-(1-(5-(2,2,2-trifluoroethoxy)pyridin-2-yl)ethyl)-5-(trifluoromethoxy)-1H-indole-2-carboxamide;
(R)—N-(1-(5-(2,2,2-trifluoroethoxy)pyridin-2-yl)ethyl)-3-(trifluoromethoxy)benzamide;
trans-2-(quinolin-7-yl)-N—((R)-1-(5-(2,2,2-trifluoroethoxy)pyridin-2-yl)ethyl)cyclopropanecarboxamide;
trans-2-(quinolin-7-yl)-N—((R)-1-(5-(2,2,2-trifluoroethoxy)pyrazin-2-yl)ethyl)cyclopropanecarboxamide;
trans-2-(isoquinolin-3-yl)-N—((R)-1-(5-(2,2,2-trifluoroethoxy)pyridin-2-yl)ethyl)cyclopropanecarboxamide;
trans-2-(quinolin-3-yl)-N—((R)-1-(5-(2,2,2-trifluoroethoxy)pyrazin-2-yl)ethyl)cyclopropanecarboxamide;
trans-2-((4-chlorophenoxy)methyl)-N—((R)-1-(5-(2,2,2-trifluoroethoxy)pyrazin-2-yl)ethyl)cyclopropanecarboxamide;
trans-2-(2-fluoro-5-methoxyphenyl)-N—((R)-1-(5-(2,2,2-trifluoroethoxy)pyridin-2-yl)ethyl)cyclopropanecarboxamide;
trans-2-((1H-indol-1-yl)methyl)-N—((R)-1-(5-(2,2,2-trifluoroethoxy)pyridin-2-yl)ethyl)cyclopropanecarboxamide;
(R)-6-fluoro-1-methyl-N-(1-(5-(2,2,2-trifluoroethoxy)pyrazin-2-yl)ethyl)-1H-indole-2-carboxamide;
trans-2-(2,5-difluorophenyl)-N—((R)-1-(5-(2,2,2-trifluoroethoxy)pyridin-2-yl)ethyl)cyclopropanecarboxamide;
trans-N—((R)-1-(5-cyclopropylmethoxy)pyridin-2-yl)ethyl)-2-(2,5-difluorophenyl)cyclopropanecarboxamide;
trans-2-(2,5-difluorophenyl)-N—((R)-1-(5-(2,2,2-trifluoroethoxy)pyrazin-2-yl)ethyl)cyclopropanecarboxamide;
trans-N—((R)-1-(5-(cyclopropylmethoxy)pyridin-2-yl)ethyl)-2-(1H-indol-4-yl)cyclopropanecarboxamide;
trans-2-(4-methoxy-3-methylphenyl)-N—((R)-1-(5-(2,2,2-trifluoroethoxy)pyridin-2-yl)ethyl)cyclopropanecarboxamide;
(1R*,2R*)-2-(1H-indol-6-yl)-N—((R)—N-(1-(5-(2,2,2-trifluoroethoxy)pyridin-2-yl)ethyl)cyclopropanecarboxamide;
trans-2-(quinolin-6-yl)-N—((R)-1-(6-(2,2,2-trifluoroethoxy)pyridin-3-yl)ethyl)cyclopropanecarboxamide;
trans-2-(5-fluoro-1H-indol-2-yl)-N—((R)-1-(6-(2,2,2-trifluoroethoxy)pyridin-3-yl)ethyl)cyclopropanecarboxamide;
trans-2-(quinolin-3-yl)-N—((R)-1-(6-(2,2,2-trifluoroethoxy)pyridin-3-yl)ethyl)cyclopropanecarboxamide;
trans-2-(1H-indol-4-yl)-N—((R)-1-(6-(2,2,2-trifluoroethoxy)pyridin-3-yl)ethyl)cyclopropanecarboxamide;
(1S*,2S*)-2-(8-chloroquinolin-2-yl)-N—((R)-1-(5-(2,2,2-trifluoroethoxy)pyrazin-2-yl)ethyl)cyclopropanecarboxamide;
(R)-5-methoxy-N-(1-(6-(2,2,2-trifluoroethoxy)pyridin-3-yl)ethyl)-1H-indole-2-carboxamide;
(R)—N-(1-(6-(2,2,2-trifluoroethoxy)pyridin-3-yl)ethyl)-4-(trifluoromethoxy)benzamide;
(R)-3-phenoxy-N-(1-(6-(2,2,2-trifluoroethoxy)pyridin-3-yl)ethyl)benzamide;
(R)-6-methoxy-N-(1-(5-(2,2,2-trifluoroethoxy)pyridin-2-yl)ethyl)quinoline-2-carboxamide;
(1S*,2S*)-2-(1H-indol-2-yl)-N—((R)-1-(6-(2,2,2-trifluoroethoxy)pyridin-3-yl)ethyl)cyclopropanecarboxamide;
(1R*,2R*)-2-(1H-indol-2-yl)-N—((R)-1-(6-(2,2,2-trifluoroethoxy)pyridin-3-yl)ethyl)cyclopropanecarboxamide;
(1S*,2S*)-2-(1H-indol-2-yl)-N—((R)-1-(5-(2,2,2-trifluoroethoxy)pyrazin-2-yl)ethyl)cyclopropanecarboxamide;
trans-2-(1-methyl-1H-indazol-6-yl)-N—((R)-1-(6-(2,2,2-trifluoroethoxy)pyridin-3-yl)ethyl)cyclopropanecarboxamide;
(1R*,2R*)-2-(4-(benzyloxy)-N—((R)-1-(5-(2,2,2-trifluoroethoxy)pyridin-2-yl)ethyl)cyclopropanecarboxamide;
(R,E)-3-(quinolin-2-yl)-N-(1-(5-(2,2,2-trifluoroethoxy)pyridin-2-yl)ethyl)-acrylamide;
(1S*,2S*)—N—((R)-1-(5-(2,2,2-trifluoroethoxy)pyridin-2-yl)ethyl)-2-(2,4,6-trifluorophenyl)cyclopropanecarboxamide;
(1S*,2S*)-2-(3,5-difluorophenyl)-N—((R)-1-(5-(2,2,2-trifluoroethoxy)pyridin-2-yl)ethyl)cyclopropanecarboxamide;
(1S*,2S*)-2-(3-methoxyphenyl)-N—((R)-1-(5-(2,2,2-trifluoroethoxy)pyridin-2-yl)ethyl)cyclopropanecarboxamide;
(1S*,2S*)-2-(4-methoxyphenyl)-N—((R)-1-(5-(2,2,2-trifluoroethoxy)pyridin-2-yl)ethyl)cyclopropanecarboxamide;
(1R*,2R*)-2-(2-chloro-4-fluorophenyl)-N—((R)-1-(5-cyclopropylmethoxy)pyridin-2-yl)ethyl)cyclopropanecarboxamide;
(1R*,2R*)—N—((R)-1-(5-(cyclopropylmethoxy)pyridin-2-yl)ethyl)-2-(2-fluoro-4-methoxyphenyl)cyclopropanecarboxamide;
(1S*,2S*)—N—((R)-1-(5-(cyclopropylmethoxy)pyridin-2-yl)ethyl)-2-(2,4,6-trifluorophenyl)cyclopropanecarboxamide;
(1S*,2S*)—N—((R)-1-(5-(2,2,2-trifluoroethoxy)pyrazin-2-yl)ethyl)-2-(2,4,6-trifluorophenyl)cyclopropanecarboxamide;
(1R*,2R*)—N—((R)-1-(5-(2,2,2-trifluoroethoxy)pyrazin-2-yl)ethyl)-2-(2,4,6-trifluorophenyl)cyclopropanecarboxamide;
(1S*,2S*)-2-(1H-indol-4-yl)-N—((R)-1-(5-(2,2,2-trifluoroethoxy)pyrazin-2-yl)ethyl)cyclopropanecarboxamide;
(1R*,2R*)-2-phenyl-N—((R)-1-(5-(2,2,2-trifluoroethoxy)pyridin-2-yl)ethyl)cyclopropanecarboxamide;
(1S*,2S*)-2-phenyl-N—((R)-1-(5-(2,2,2-trifluoroethoxy)pyrazin-2-yl)ethyl)cyclopropanecarboxamide;
(1R*,2R*)-2-phenyl-N—((R)-1-(5-(2,2,2-trifluoroethoxy)pyrazin-2-yl)ethyl)cyclopropanecarboxamide;
(1S*,2S*)-2-phenyl-N—((R)-1-(6-(2,2,2-trifluoroethoxy)pyridin-3-yl)ethyl)cyclopropanecarboxamide;
(1R*,2R*)-2-phenyl-N—((R)-1-(6-(2,2,2-trifluoroethoxy)pyridin-3-yl)ethyl)cyclopropanecarboxamide;
(1S*,2S*)-2-(1H-benzo[d]imidazol-2-yl)-N—((R)-1-(5-(2,2,2-trifluoroethoxy)pyrazin-2-yl)ethyl)cyclopropanecarboxamide;
(1S*,2S*)-2-(1H-benzo[d]imidazol-2-yl)-N—((R)-1-(6-(2,2,2-trifluoroethoxy)pyridin-3-yl)ethyl)cyclopropanecarboxamide;
(1R*,2R*)-2-(1H-benzo[d]imidazol-2-yl)-N—((R)-1-(6-(2,2,2-trifluoroethoxy)pyridin-3-yl)ethyl)cyclopropanecarboxamide;
(1S*,2S*)-2-(phenoxymethyl)-N—((R)-1-(5-(2,2,2-trifluoroethoxy)pyridin-2-yl)ethyl)cyclopropanecarboxamide;

(1S*,2S*)-2-((3-fluorophenxoy)methyl)-N—((R)-1-(5-(2,2,2-trifluoroethoxy)pyridin-2-yl)ethyl)cyclopropanecarboxamide;
(1S*,2S*)-2-((3-cyanophenoxy)methyl)-N—((R)-1-(5-(2,2,2-trifluoroethoxy)pyridin-2-yl)ethyl)cyclopropanecarboxamide;
(1S*,2S*)-2-((4-fluorophenoxyl)methyl)-N—((R)-1-(5-(2,2,2-trifluoroethoxy)pyridin-2-yl)ethyl)cyclopropanecarboxamide;
(1S*,2S*)-2-((4-cyanophenoxy)methyl)-N—((R)-1-(5-(2,2,2-trifluoroethoxy)pyridin-2-yl)ethyl)cyclopropanecarboxamide;
(1R*,2R*)-2-(phenoxymethyl)-N—((R)-1-(5-(2,2,2-trifluoroethoxy)pyridin-2-yl)ethyl)cyclopropanecarboxamide;
(1R*,2R*)-2-((3-fluorophenoxy)methyl)-N—((R)-1-(5-(2,2,2-trifluoroethoxy)pyridin-2-yl)ethyl)cyclopropanecarboxamide;
(1R*,2R*)-2-((3-cyanophenoxy)methyl)-N—((R)-1-(5-(2,2,2-trifluoroethoxy)pyridin-2-yl)ethyl)cyclopropanecarboxamide;
(1R*,2R*)-2-((4-fluorophenoxy)methyl)-N—((R)-1-(5-(2,2,2-trifluoroethoxy)pyridin-2-yl)ethyl)cyclopropanecarboxamide;
(1R*,2R*)-2-((4-cyanophenoxy)methyl)-N—((R)-1-(5-(2,2,2-trifluoroethoxy)pyridin-2-yl)ethyl)cyclopropanecarboxamide;
(1S*,2S*)-2-(4-((3-methyloxetan-3-yl)methoxy)phenyl)-N—((R)-1-(5-(2,2,2-trifluoroethoxy)pyridin-2-yl)ethyl)cyclopropanecarboxamide;
(1S*,2S*)—N—((R)-1-(5-(cyclopropylmethoxy)pyridin-2-yl)ethyl)-2-(1H-indol-7-yl)cyclopropanecarboxamide;
(1S*,2S*)-2-(phenoxymethyl)-N—((R)-1-(6-(2,2,2-trifluoroethoxy)pyridin-3-yl)ethyl)cyclopropanecarboxamide;
(1R*,2R*)-2-(quinolin-2-yl)-N—((R)-1-(5-(2,2,2-trifluoroethoxy)pyridin-2-yl)ethyl)cyclopropanecarboxamide;
4-(benzyloxy)-3-methoxy-N-((6-(trifluoromethyl)-pyridin-3-yl)methyl)benzamide;
2-(4-trifluoromethyl)phenoxy)-N-((6-trifluoromethyl)pyridin-3-yl)methyl)acetamide;
(R)—N-(1-(6-methyl-3-(2,2,2-trifluoroethoxy)pyridin-2-yl)ethyl)-2-(4-trifluoromethyl)phenoxy)acetamide;
(R)-5-fluoro-N-(1-(6-methyl-3-(2,2,2-trifluoroethoxy)pyridin-2-yl)ethyl)-1H-indole-2-carboxamide;
(S)-4-isopropyl-N-(1-(5-(2,2,2-trifluoroethoxy)pyridin-2-yl)ethyl)benzamide;
(S)-2-(4-chlorophenoxy)-N-(1-(5-(2,2,2-trifluoroethoxy)pyridin-2-yl)ethyl)acetamide;
(S)—N-(2,2,2-trifluoroethoxy)-N-(1-(5-(2,2,2-trifluoroethoxy)pyridin-2-yl)ethyl)benzamide;
(1S*,2S*)-2-(4-(benzyloxy)phenyl)-N—((S)-1-(5-(2,2,2-trifluoroethoxy)pyridin-2-yl)ethyl)cyclopropanecarboxamide;
(1R*,2R*)-2-(4-benzyloxy)phenyl)-N—((S)-1-(5-(2,2,2-trifluoroethoxy)pyridin-2-yl)ethyl)cyclopropanecarboxamide;
(1S*,2S*)-2-(2-fluoro-4-methoxyphenyl)-N—((S)-1-(5-(2,2,2-trifluoroethoxy)pyridin-2-yl)ethyl)cyclopropanecarboxamide;
(1R*,2R*)-2-(2-fluoro-4-methoxyphenyl)-N—((S)-1-(5-(2,2,2-trifluoroethoxy)pyridin-2-yl)ethyl)cyclopropanecarboxamide;
(1S*,2S*)-2-(2-chloro-4-fluorophenyl)-N—((S)-1-(5-(2,2,2-trifluoroethoxy)pyridin-2-yl)ethyl)cyclopropanecarboxamide;
(1R*,2R*)-2-(2-chloro-4-fluorophenyl)-N—((S)-1-(5-(2,2,2-trifluoroethoxy)pyridin-2-yl)ethyl)cyclopropanecarboxamide;
(1S*,2S*)-2-phenyl-N—((S)-1-(5-(2,2,2-trifluoroethoxy)pyridin-2-yl)ethyl)cyclopropanecarboxamide;
(1R*,2R*)-2-phenyl-N—((S)-1-(5-(2,2,2-trifluoroethoxy)pyridin-2-yl)ethyl)cyclopropanecarboxamide;
tert-butyl ((R)-1-oxo-1-(((R)-(1-(5-(2,2,2-trifluoroethoxy)pyridin-2-yl)ethyl)amino)-3-(2-trifluoromethoxy)phenyl)propan-2-yl)carbamate;
tert-butyl ((R)-1-oxo-(((R)-1-(5-(2,2,2-trifluoroethoxy)pyridin-2-yl)ethyl)amino)-3-(2-(trifluoromethyl)phenyl)propan-2-yl)carbamate;
(R)—N-(1-(5-(5-methoxypyridin-2-yl)ethyl)-3-phenoxybenzamide;
(R)-2-hydroxy-4-phenyl-N—((R)-1-(5-(2,2,2-trifluoroethoxy)pyridin-2-yl)ethyl)-butanamide;
tert-butyl ((S)-1-(4-chlorophenyl)-3-oxo-3-(((R)-1-(5-(2,2,2-trifluoroethoxy)pyridin-2-yl)ethyl)amino)propyl)carbamate;
tert-butyl ((R)-1-(4-chlorophenyl)-3-oxo-3-(((R)-1-(5-(2,2,2-trifluoroethoxy)pyridin-2-yl)ethyl)amino)propyl)carbamate;
tert-butyl ((R)-3-(4-chlorophenyl)-1-oxo-1-(((R)-1-(5-(2,2,2-trifluoroethoxy)pyridin-2-yl)ethyl)amino)propan-2-yl)carbamate;
tert-butyl ((S)-3-(2-chlorophenyl)-1-oxo-1-(((R)-1-(5-(2,2,2-trifluoroethoxy)pyridin-2-yl)ethyl)amino)propan-2-yl)carbamate;
tert-butyl ((S)-3-(2-fluorophenyl)-1-oxo-1-(((R)-1-(5-(2,2,2-trifluoroethoxy)pyridin-2-yl)ethyl)amino)propan-2-yl)carbamate;
(R)-2-(2-chlorophenoxy)-N-(1-(5-(2,2,2-trifluoroethoxy)pyridin-2-yl)ethyl)acetamide;
(R)-2-(3-chlorophenoxy)-N-(1-(5-(2,2,2-trifluoroethoxy)pyridin-2-yl)ethyl)acetamide;
(R)-2-(2-chlorophenoxy)-2-methyl-N-(1-(5-(2,2,2-trifluoroethoxy)pyridin-2-yl)propanamide;
(R)-2-(2,3-dichlorophenoxy)-N-(1-(5-(2,2,2-trifluoroethoxy)pyridin-2-yl)ethyl)acetamide;
(R)-2-(o-tolyloxy)-N-(1-(5-(2,2,2-trifluoroethoxy)pyridin-2-yl)ethyl)acetamide;
(R)-2-(m-tolyloxy)-N-(1-(5-(2,2,2-trifluoroethoxy)pyridin-2-yl)ethyl)acetamide;
(R)-2-(2,4-dimethylphenoxy)-N-(1-(5-(2,2,2-trifluoroethoxy)pyridin-2-yl)ethyl)acetamide;
(R)-2-(2-chloro-6-methylphenoxy)-N-(1-(5-(2,2,2-trifluoroethoxy)pyridin-2-yl)ethyl)acetamide;
(R)-2-(4-tert-butyl)phenoxy)-N-(1-(5-methoxypyridin-2-yl)ethyl)acetamide;
(R)-2-amino-N—((R)-1-(5-(2,2,2-trifluoroethoxy)pyridin-2-yl)ethyl)-3-(2-(trifluoromethyl)phenyl)propanamide;
isobutyl ((R)-1-oxo-1-(((R)-1-(5-(2,2,2-trifluoroethoxy)pyridin-2-yl)ethyl)amino)-3-(2-(trifluoromethyl)phenyl)propan-2-yl)carbamate;
ethyl ((R)-1-oxo-1-(((R)-1-(5-(2,2,2-trifluoroethoxy)pyridin-2-yl)ethyl)amino)-3-(2-(trifluoromethyl)phenyl)propan-2-yl)carbamate;
N-((5-(2,2,2-trifluoroethoxy)pyridin-2-yl)methyl)-3-(trifluoromethoxy)benzamide;
4-(2,2,2-trifluoroethoxy)-N-((5-(2,2,2-trifluoroethoxy)pyridin-2-yl)methyl)benzamide 6-fluoro-1-methyl-N-((5-(2,2,2-trifluoroethoxy)pyridin-2-yl)methyl)-1H-indole-2-carboxamide;
3-(2,2,2-trifluoroethoxy)-N-((5-(2,2,2-trifluoroethoxy)pyridin-2-yl)methyl)benzamide;
(R)—N-(1-(5-(2,2,2-trifluoroethoxy)pyridin-2-yl)ethyl)-2-(3-(trifluoromethyl)phenoxy)acetamide;
(R)—N-(1-(5-(2,2,2-trifluoroethoxy)pyridin-2-yl)ethyl)-2-(2-(trifluoromethyl)phenoxy)acetamide;
(R)—N-(1-(5-methoxypyridin-2-yl)ethyl)-2-(3-(trifluoromethyl)phenoxy)acetamide;
(R)-3-(2,2,2-trifluoroethoxy)-N-(1-(5-(2,2,2-trifluoroethoxy)pyridin-2-yl)ethyl)benzamide;
(R)—N-(1-(5-methoxypyridin-2-yl)ethyl-2-(4-(trifluoromethyl)phenyl)thiazole-4-carboxamide;
(R)—N-(1-(5-methoxypyridin-2-yl)ethyl-1-methyl-5-(trifluoromethoxy)-1H-indole-2-carboxamide;
(R)-2-(4-chlorophenoxy)-N-(1-(5-(2,2,2-trifluoroethoxy)pyrazin-2-yl)ethyl)acetamide;
(R)-5-(2,2,2-trifluoroethoxy)-N-(1-(5-(2,2,2-trifluoroethoxy)pyridin-2-yl)ethyl)picolinamide;
(R)—N-(1-(5-(2,2,2-trifluoroethoxy)pyridin-2-yl)ethyl)-3-(trifluoromethoxy)benzamide;
(R)-4-fluoro-3-phenoxy-N-(1-(5-(2,2,2-trifluoroethoxy)pyridin-2-yl)ethyl)benzamide;
4-(tert-butyl)-N-((6-methoxypyridin-3-yl)methyl)benzamide;
N-((6-methoxypyridin-3-yl)methyl)-2-(4-(trifluoromethyl)phenoxy)acetamide;
4-(tert-butyl)-N-((5-methoxypyridin-2-yl)methyl)benzamide;
(S)-4-(tert-butyl)-N-(1-(5-(2,2,2-trifluoroethoxy)pyridin-2-yl)ethyl)benzamide;
(S)—N-(1-(5-(2,2,2-trifluoroethoxy)pyridin-2-yl)ethyl)-3-(trifluoromethoxy)benzamide;
(S)—N-(1-(5-(2,2,2-trifluoroethoxy)pyridin-2-yl)ethyl)-4-(trifluoromethoxy)benzamide;
(S)-3-(2,2,2-trifluoroethoxy)-N-(1-(5-(2,2,2-trifluoroethoxy)pyridin-2-yl)ethyl)benzamide;
(R)—N-(1-(5-(2,2,2-trifluoroethoxy)pyrazin-2-yl)ethyl)-4-(trifluoromethoxy)benzamide;
(R)-4-(2,2,2-trifluoroethoxy)-N-(1-(5-(2,2,2-trifluoroethoxy)pyrazin-2-yl)ethyl)benzamide;
(R)-3-(2,2,2-trifluoroethoxy)-N-(1-(5-(2,2,2-trifluoroethoxy)pyrazin-2-yl)ethyl)benzamide;
4-(tert-butyl)-N-((5-trifluoromethyl)pyridin-2-yl)methyl)benzamide;
3-trifluoromethoxy)-N-((5-(trifluoromethyl)pyridin-2-yl)methyl)benzamide;
4-(trifluoromethoxy)-N-((5-(trifluoromethyl)pyridin-2-yl)methyl)benzamide;
4-(2,2,2-trifluoroethoxy)-N-((5-(trifluoromethyl)pyridin-2-yl)methyl)benzamide;
3-(2,2,2-trifluoroethoxy))-N-((5-(trifluoromethyl)pyridin-2-yl)methyl)benzamide;
4-(tert-butyl)-N-((6-(piperidin-1-yl)pyridin-3-yl)methyl)benzamide;
N-((6-(piperidin-1-yl)pyridin-3-yl)methyl)-3-(trifluoromethoxy)benzamide;
N-((6-(piperidin-1-yl)pyridin-3-yl)methyl)-4-(2,2,2-trifluoroethoxy)benzamide;
4-(tert-butyl)-N-((6-(pyrrolidin-1-yl)pyridin-3-yl)methyl)benzamide;
N-((6-(pyrrolidin-1-yl)pyridin-3-yl)methyl)-3-(trifluoromethoxy)benzamide;
N-((6-(pyrrolidin-1-yl)pyridin-3-yl)methyl)-4-(2,2,2-trifluoroethoxy)benzamide;
4-(tert-butyl)-N-((6-(trifluoromethyl)pyridin-3-yl)methyl)benzamide;
3-trifluoromethoxy)-N-((6-(trifluoromethyl)pyridin-3-yl)methyl)benzamide;
4-(tert-butyl)-N-((6-(pyrrolidin-1-yl)pyridin-2-yl)methyl)benzamide;
N-((6-(pyrrolidin-1-yl)pyridin-2-yl)methyl)-3-(trifluoromethoxy)benzamide;
N-((6-(pyrrolidin-1-yl)pyridin-2-yl)methyl)-4-(2,2,2-trifluoroethoxy)benzamide;
(R)-4-chloro-2-methoxy-N-(1-(5-(2,2,2-(trifluoroethoxy)pyridin-2-yl)ethyl)benzamide;
(R)-4-(2-cyanopropan-2-yl)-N-(1-(5-(2,2,2-trifluoroethoxy)pyridin-2-yl)ethyl)benzamide;
(R)-3-chloro-4-methoxy-N-(1-(5-(2,2,2-trifluoroethoxy)pyridin-2-yl)ethyl)benzamide;
(R)-6-methoxy-1-methyl-N-(1-(5-(2,2,2-trifluoroethoxy)pyridin-2-yl)ethyl)-1H-indole-2-carboxamide;
(R)—N-(1-(6-methyl-3-(2,2,2-trifluoroethoxy)pyridin-2-yl)ethyl)-3-(trifluoromethoxy)benzamide;
(R)—N-(1-(6-methyl-3-(2,2,2-(trifluoroethoxy)pyridin-2-yl)ethyl)-4-(2,2,2-trifluoroethoxy)benzamide;
(S)-2-(3-chlorophenoxy)-N-(1-(5-(2,2,2-trifluoroethoxy)pyridin-2-yl)ethyl)acetamide;
2-(3-chlorophenoxy)-N-((5-(2,2,2-trifluoroethoxy)pyridin-2-yl)methyl)acetamide;
(R)-2-(3-chlorophenoxy)-N-(1-(5-(2,2,2-trifluoroethoxy)pyrazin-2-yl)ethyl)acetamide;
(R)-4-ethyl-N-(1-(5-(2,2,2-trifluoroethoxy)pyridin-2-yl)ethyl)benzamide;
(R)-3-fluoro-4-methyl-N-(1-(5-(2,2,2-trifluoroethoxy)pyridin-2-yl)ethyl)benzamide;
(R)-5-chloro-2-methoxy-N-(1-(5-(2,2,2-trifluoroethoxy)pyridin-2-yl)ethyl)benzamide;
(R)—N-(1-(5-(2,2,2-trifluoroethoxy)pyrazin-2-yl)ethyl)quinoxaline-2-carboxamide;
(R)—N-(1-(5-(2,2,2-trifluoroethoxy)pyridin-2-yl)ethyl)-5-(trifluoromethyl)picolinamide;
and salts thereof.

Also, the present invention provides the use of a compound of formula (I) or a pharmaceutically acceptable salt thereof, each as described herein, for the manufacture of a medicament for the treatment of a condition or disorder mediated by T-type calcium channels or voltage gated sodium channels; in particular, T-type calcium channels blocking activity or voltage gated sodium channels blocking activity. In order to use the compounds of formula (I) and pharmaceutically acceptable salts thereof in therapy, they will normally be formulated into a pharmaceutical composition in accordance with standard pharmaceutical practice. The present invention also provides a pharmaceutical composition, which comprises a compound of formula (I) or a pharmaceutically acceptable salt thereof, and a pharmaceutically acceptable carrier or excipient.

Preferably, the present invention also provides the use of a compound of formula (I) or a pharmaceutically acceptable salt thereof, each as described herein, for the manufacture of a medicament for the treatment of diseases selected from T-type calcium channels related diseases or voltage gated sodium channels related diseases.

Also, the present invention provides the use of a compound of the formula (I) or the pharmaceutically acceptable salt thereof, each as described herein, for the manufacture of a medicament for the treatment of a condition or disorder in which voltage gated sodium channels are involved, as described in formula (I) herein wherein when Y is nitrogen atom, and at the same time (i) q is 1 and r is 0 or (ii) q is 0 and r is 1, then X may be a chemical bond;

or as described in formula (I) herein wherein when Y is carbon atom, Z is nitrogen atom, W is nitrogen atom, and at the same time (i) q is 1 and r is 0 or (ii) q is 0 and r is 1, then X may be a chemical bond;

the definition of the other descriptors is the same as described herein.

Also, the present invention provides a pharmaceutical composition comprising a compound of formula (I) or a pharmaceutically acceptable salt thereof, each as described herein, together with a pharmaceutically acceptable carrier for said compound.

Also, the present invention provides a pharmaceutical composition comprising a compound of formula (I) or a pharmaceutically acceptable salt thereof, each as described herein, together with a pharmaceutically acceptable carrier for said compound and another pharmacologically active agent.

Also, the present invention provides a process for preparing a pharmaceutical composition, the process comprising mixing a compound of formula (I) or a pharmaceutically acceptable salt thereof and a pharmaceutically acceptable carrier or excipient.

Also, the present invention provides an intermediate in a process for preparing a compound of formula (I) or a pharmaceutically acceptable salt thereof.

Further, the present invention provides a method of treatment of a condition or disorder mediated by T-type calcium channels blocking activity or voltage gated sodium channels blocking activity, in a mammalian subject, which comprises administering to a mammal in need of such treatment a therapeutically effective amount of a compound of formula (I) or a pharmaceutically acceptable salt thereof, each as described herein.

In a further aspect, the present invention provides a process for preparing a pharmaceutical composition, the process comprising mixing a compound of formula (I) or a pharmaceutically acceptable salt thereof and a pharmaceutically acceptable carrier or excipient.

Examples of conditions or disorders mediated by T-type calcium channels blocking activity or voltage gated sodium channels blocking activity include, but are not limited to, T-type calcium channels related diseases or voltage gated sodium channels related diseases. The compounds of the present invention show the T-type calcium channels blocking activity or voltage gated sodium channels blocking activity. The compounds of the present invention may show less toxicity, good absorption, distribution, good solubility, less protein binding affinity other than T-type calcium, channels or voltage gated sodium channels, less drug-drug interaction, good metabolic stability, reduced inhibitory activity at HERG channel and reduced QT prolongation.

As appreciated by those of skill in the art, "halogen" or "halo" as used herein are intended to include fluoro, chloro, bromo and iodo. Similarly, $C_{1-6}$, as in $C_{1-6}$ alkyl is defined to identify the group as having 1, 2, 3, 4, 5 or 6 carbons in a linear or branched arrangement, such that $C_{1-8}$ alkyl specifically includes methyl, ethyl, n-propyl, iso-propyl, n-butyl, iso-butyl, tert-butyl, pentyl, and hexyl. Similarly, $C_{2-6}$alkenyl is defined to identify the group as having 2, 3, 4, 5 or 6 carbons which incorporates at least one double bond, which may be in a E- or a Z-arrangement. A group which is designated as being independently substituted with substituents may be independently substituted with multiple numbers of such substituents.

The term "alkenyl", as used herein, means a hydrocarbon, radical having at least one double bond including, but not limited to, ethenyl, propenyl, 1-butenyl, 2-butenyl and the like.

The term "cycloalkyl", as used herein, means a mono- or bicyclic ring, but not limited to, cyclopropyl, cyclobutyl, cyclopentyl cyclohexyl, cycloheptyl norboranyl, and adamantyl groups and the like.

The term "aryl", as used herein, means mono- or bi-carbocyclic or mono- or bi-heterocyclic ring which may contain 0-4 heteroatoms selected from O, N and S, but not limited to, phenyl, furyl, thienyl, oxazolyl, tetrazolyl, thiadiazolyl, pyridyl, pyrimidinyl, pyrrolyl, thiophenyl, pyrazinyl, pyridazinyl, isooxazolyl, isothiazolyl, triazolyl, furazanyl, naphthyl, tetrahydronaphthyl, indanyl benzofuranyl, isobenzofuranyl, benzothiophenyl, indolyl, isoindolyl, benzoxazolyl, benzothiazolyl, indazolyl, benzoimidazolyl, benzotriazolyl, imidazopyridinyl, pyrazolopyrimidinyl, quinolyl, isoquinolyl, cinnolinyl, naphthyridinyl, phthalazinyl, quinazolinyl, quinoxalinyl, triazolopyrimidinyl, and the said rings which are fully or partially saturated, such as pyridin-2-onyl, piperidinyl, pyrrolidinyl, tetrehydronaphthalenyl, and the like.

The term "heterocyclic group" as used herein includes both unsaturated and saturated heterocyclic moieties, wherein the unsaturated, heterocyclic moieties (i.e. "heteroaryl") include benzoimidazolyl, benzimidazolonyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyrazinyl, pyrazolyl, pyridazinyl, pyridopyridinyl, pyridazinyl, pyridyl, pyrimidinyl, pyrrolyl, quinazolinyl, quinolyl, quinoxalinyl, tetrazolyl, tetrazolopyridyl, thiadiazolyl, thiazolyl, thienyl, triazolyl, and N-oxides thereof, and wherein the saturated heterocyclic moieties include azetidinyl, 1,4-dioxanyl, hexahydroazepinyl, piperazinyl, piperidinyl, pyridin-2-onyl, pyrrolidinyl, morpholinyl, tetrahydrofuranyl, thiomorpholinyl, and tetrahydrothienyl, and N-oxides thereof and S-oxides thereof.

The term "$C_0$", as used herein, means direct bond.

The term "protecting group", as used herein, means a hydroxy or amino protecting group which is selected from typical hydroxy or amino protecting groups described in Protective Groups in Organic Synthesis edited by T. W. Greene et al. (John Wiley & Sons, 1991);

The term "treating" and "treatment", as used herein, refers to curative, palliative and prophylactic treatment, including reversing, alleviating, inhibiting the progress of, or preventing the disorder or condition to which such term applies, or one or more symptoms of such disorder or condition.

As used herein, the article "a" or "an" refers to both the singular and plural form of the object to which it refers unless indicated otherwise.

Included within the scope of the "compounds of the invention" are all salts, solvates, hydrates, complexes, polymorphs, prodrugs, radiolabeled derivatives, stereoisomers and optical isomers of the compounds of formula (I).

The compounds of formula (I) can form acid addition salts thereof. It will be appreciated that for use in medicine the salts of the compounds of formula (I) should be pharmaceutically acceptable. Suitable pharmaceutically acceptable salts will be apparent to those skilled in the art and include those described in J. Pharm. Sci., 1977, 66, 1-19, such as acid addition salts formed with inorganic acids e.g.

hydrochloric, hydrobromic, sulfuric, nitric or phosphoric acid; and organic acids e.g. succinic, maleic, formic, acetic, trifluoroacetic, propionic, fumaric, citric, tartaric, benzoic, p-toluenesulfonic, methanesulfonic or naphthalenesulfonic acid. Certain of the compounds of formula (I) may form acid addition sails with one or more equivalents of the acid. The present invention includes within its scope all possible stoichiometric and non-stoichiometric forms. In addition, certain compounds containing an acidic function such as a carboxy can be isolated in the form of their inorganic salt in which the counter ion can be selected from sodium, potassium, lithium, calcium, magnesium and the like, as well as from organic bases.

The compounds of formula (I) and salts thereof may be prepared in crystalline or non-crystalline form, and, if crystalline, may optionally be hydrated or solvated. This invention includes within its scope stoichiometric hydrates or solvates as well as compounds containing variable amounts of water and/or solvent.

Salts and solvates having non-pharmaceutically acceptable counter-ions or associated solvents are within the scope of the present invention, for example, for use as intermediates in the preparation of other compounds of formula (I) and their pharmaceutically acceptable salts.

The compounds of formula (I) may have polymorphs in crystalline form, which are within the scope of the present invention.

Additionally, the compounds of formula (I) may be administered as prodrugs. As used herein, a "prodrug" of a compound of formula (I) is a functional derivative of the compound which, upon administration to a patient, eventually liberates the compound of formula (I) in vivo. Administration of a compound of formula (I) as a prodrug may enable the skilled artisan to do one or more of the following: (a) modify the onset of action of the compound in vivo; (b) modify the duration of action of the compound in vivo; (c) modify the transportation or distribution of the compound in vivo; (d) modify the solubility of the compound in vivo; and (e) overcome a side effect or other difficulty encountered with the compound. Typical functional derivatives used to prepare prodrugs include modifications of the compound that are chemically or enzymatically cleaved in vivo. Such modifications, which include the preparation of phosphates, amides, esters, thioesters, carbonates, and carbamates, are well known to those skilled in the art.

In certain of the compounds of formula (I), there may be some chiral carbon atoms. In such cases, compounds of formula (I) exist as stereoisomers. The invention extends to all optical isomers such as steieoisomeric forms of the compounds of formula (I) including enantiomers, diastereoisomers and mixtures thereof, such as racemates. The different stereoisomeric forms may be separated or resolved one from the other by conventional methods or any given isomer may be obtained by conventional stereoselective or asymmetric syntheses.

Certain of the compounds herein can exist in various tautomeric forms and it is to be understood that the invention encompasses ail such tautomeric forms.

The invention also includes isotopically-labeled compounds, which are identical to those described herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine, iodine, and chlorine, such as $^3H$, $^{11}C$, $^{14}C$ $^{18}F$, $^{123}I$ and $^{125}I$. Compounds of the invention that contain the aforementioned isotopes and/or other isotopes of other atoms are within the scope of the present invention. Isotopically-labeled compounds of the present invention, for example those into which radioactive isotopes such as $^3H$, $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. $^{11}C$ and $^{18}F$ isotopes are particularly useful in PET (positron emission tomography), and $^{125}I$ isotopes are particularly useful in SPECT (single photon emission computerized tomography), all useful in brain imaging. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labeled compounds of the invention can generally be prepared by carrying out the procedures disclosed in the Schemes and/or in the Examples below, then substituting a readily available isotopically labeled reagent for a non-isotopically labeled reagent.

The potencies and efficacies of the compounds of this invention for T-type calcium channels or voltage gated sodium channels can be determined by methodology well known in the art, including the "$Ca^{2+}$ influx Assay", "Electrophysiology assay for T-type $Ca^{2+}$", "FRET Assay for Navs" and "Electrophysiology assay for Navs" as described herein. Compounds of formula (I) have demonstrated blocking activity at the T-type calcium channels, using the assays described herein.

The intrinsic T-type calcium channels blocking activity or voltage gated sodium channels blocking activity of a compound which may be used in the present invention may be determined by these assays. In particular, the compounds of the following examples had activity in blocking the T-type calcium channel or voltage gated sodium channels in the aforementioned assays, generally with an $IC_{50}$ of less than about 10 microM, preferably less than about 1 microM, more preferably less than about 0.3 microM. Some of the compounds within the present invention had activity in blocking the T-type calcium channels or voltage gated sodium channels in the aforementioned assays with an $IC_{50}$ of less than about 1 microM. Such a result is indicative of the intrinsic activity of the compounds in use as blockers of T-type calcium channels activity or voltage gated sodium channels activity.

With respect to other compounds disclosed in the art, the present compounds exhibit unexpected properties, such as with respect to duration of action and/or metabolism, such as increased metabolic stability, enhanced oral bioavailability or absorption, and/or decreased drug-drug interactions.

T-type calcium channels have been implicated in a wide range of biological functions. This has suggested a potential role for these receptors in a variety of disease processes in humans or other species. The compounds of the present invention have utility in treating, preventing, ameliorating, controlling or reducing the risk of a variety of neurological and psychiatric disorders associated with calcium channels, including one or more of the following conditions or diseases: movement disorders, including akinesias and akinetic-rigid syndromes (including Parkinson's disease, drug-induced parkinsonism, postencephalitic parkinsonism, progressive supranuclear palsy, multiple system atrophy, corticobasal degeneration, parkinsonism-ALS dementia complex and basal ganglia calcification), chronic fatigue syndrome, fatigue, including Parkinson's fatigue, multiple sclerosis fatigue, fatigue caused by a sleep disorder or a circadian rhythm disorder, medication-induced parkinsonism (such as neurolepticinduced parkinsonism, neuroleptic malignant syndrome, neuroleptic-induced acute dystonia, neuroleptic-induced acute akathisia, neuroleptic-induced tardive dyskinesia and medication induced postural tremor), Gilles de la Tourette's syndrome, seizure disorders, epilepsy, and dyskinesias [including tremor (such as rest tremor, essential tremor, postural tremor and intention tremor), chorea (such as Sydenham's chorea, Huntington's disease, benign hereditary chorea, neuroacanthocytosis, symptomatic chorea, drug-induced chorea and hemiballism), myoclonus (including generalised myoclonus and focal myoclonus), tics (including simple tics, complex tics and symptomatic tics), restless leg syndrome and dystonia (including generalised dystonia such as iodiopathic dystonia, drug-induced dystonia, symptomatic dystonia and paroxymal dystonia, and focal dystonia such as blepharospasm, oromandibular dystonia, spasmodic dysphonia, spasmodic torticollis, axial dystonia, dystonic writer's cramp and hemiplegic dystonia); heart disease, abnormal heart rhythms and arrythmias, myocardial infarction, congestive heart failure, coronary heart disease, sudden death, stroke, sexual and reproductive dysfunction, such as impaired fertility, infertility, diseases or disorders where abnormal oscillatory activity occurs in the brain, including depression, migraine, neuropathic pain, Parkinson's disease, psychosis and schizophrenia, as well as diseases or disorders where there is abnormal coupling of activity, particularly through the thalamus; enhancing cognitive function; enhancing memory; increasing memory retention; increasing trained performance; increasing immune response; increasing immune function; hot flashes; night sweats; extending life span; schizophrenia; muscle-related disorders that are controlled by the excitation/relaxation rhythms imposed by the neural system such as cardiac rhythm and other disorders of the cardiovascular system; conditions related to proliferation of cells such as vasodilation or vasorestriction and blood pressure; cancer; cardiac arrhythmia; hypertension; congestive heart failure; conditions of the genital/urinary system; disorders of sexual function and fertility; adequacy of renal function; responsivity to anesthetics; sleep disorders, sleep disturbances, including enhancing sleep quality, improving sleep quality, increasing sleep efficiency, augmenting sleep maintenance; increasing the value which is calculated from the time that a subject sleeps divided by the time that a subject is attempting to sleep; improving sleep initiation; decreasing sleep latency or onset (the time it takes to fall asleep); decreasing difficulties in falling asleep; increasing sleep continuity; decreasing the number of awakenings during sleep; decreasing intermittent wakings during sleep; decreasing nocturnal arousals; decreasing the time spent awake following the initial onset of sleep; increasing the total amount of sleep; reducing the fragmentation of sleep; altering the timing, frequency or duration of REM sleep bouts; altering the timing, frequency or duration of slow wave (i.e. stages 3 or 4) sleep bouts; increasing the amount and percentage of stage 2 sleep; promoting slow wave sleep; enhancing EEG-delta activity during sleep; increasing the amount of Delta sleep early in the sleep cycle, increasing REM sleep late in the sleep cycle; decreasing nocturnal arousals, especially early morning awakenings; increasing daytime alertness; reducing daytime drowsiness; treating or reducing excessive daytime sleepiness; increasing satisfaction with the intensity of sleep; increasing sleep maintenance; idiopathic insomnia; sleep problems; insomnia, hypersomnia, idiopathic hypersomnia, repeatability hypersomnia, intrinsic hypersomnia, narcolepsy, interrupted sleep, sleep apnea, obstructive sleep apnea, wakefulness, nocturnal myoclonus, REM sleep interruptions, jet-lag, shift workers' sleep disturbances, dyssomnias, night terror, insomnias associated with depression, emotional/mood disorders, Alzheimer's disease or cognitive impairment, as well as sleep walking and enuresis, and sleep disorders which accompany aging; Alzheimer's sundowning; conditions associated with circadian rhythmicity as well as mental and physical disorders associated with travel across time zones and with rotating shift-work schedules, conditions due to drugs which cause reductions in REM sleep as a side effect; fibromyalgia; syndromes which are manifested by non-restorative sleep and muscle pain or sleep apnea which is associated with respiratory disturbances during sleep; conditions which result from a diminished quality of sleep; mood disorders, such as depression or more particularly depressive disorders, for example, single episodic or recurrent major depressive disorders and dysthymic disorders, or bipolar disorders, for example, bipolar I disorder, bipolar II disorder and cyclothymic disorder, mood disorders due to a general medical condition, and substance-induced mood disorders; anxiety disorders including acute stress disorder, agoraphobia, generalized anxiety disorder, obsessive-compulsive disorder, panic attack, panic disorder, post-traumatic stress disorder, separation anxiety disorder, social phobia, specific phobia, substance-induced anxiety disorder and anxiety due to a general medical condition; acute neurological and psychiatric disorders such as cerebral deficits subsequent to cardiac bypass surgery and grafting, stroke, ischemic stroke, cerebral ischemia, spinal cord trauma, head trauma, perinatal hypoxia, cardiac arrest, hypoglycemic neuronal damage; Huntington's Chorea; amyotrophic lateral sclerosis; multiple sclerosis; ocular damage; retinopathy; cognitive disorders; idiopathic and drug-induced Parkinson's disease; muscular spasms and disorders associated with muscular spasticity including tremors, epilepsy, convulsions; cognitive disorders including dementia (associated with Alzheimer's disease, ischemia, trauma, vascular problems or stroke, HIV disease, Parkinson's disease, Huntington's disease, Pick's disease, Creutzfeldt-Jacob disease, perinatal hypoxia, other general medical conditions or substance abuse); delirium, amnestic disorders or age related cognitive decline; schizophrenia or psychosis including schizophrenia (paranoid, disorganized, catatonic or undifferentiated), schizophreniform disorder, schizoaffective disorder, delusional disorder, brief psychotic disorder, shared psychotic disorder, psychotic disorder due to a general medical condition and substance-induced psychotic disorder; substance-related disorders and addictive behaviors (including substance-induced delirium, persisting dementia, persisting amnestic disorder, psychotic disorder or anxiety disorder; tolerance, dependence or withdrawal from substances including alcohol, amphetamines, cannabis, cocaine, hallucinogens, inhalants, nicotine, opioids, phencyclidine, sedatives, hypnotics or anxiolytics); attention deficit/hyperactivity disorder (ADHD); conduct disorder; migraine (including migraine headache); urinary incontinence; overactive bladder (DAB); urge urinary incontinence (UUI); lower urinary tract symptoms (LUTS); substance tolerance, substance withdrawal (including, substances such as opiates, nicotine, tobacco products, alcohol, benzodiazepines, cocaine, sedatives, hypnotics, etc.); psychosis; schizophrenia; anxiety (including generalized anxiety disorder, panic disorder, and obsessive compulsive disorder); mood disorders (including depression, mania, bipolar disorders); trigeminal neuralgia; hearing loss; tinnitus; neuronal damage including ocular damage; retinopathy; macular degeneration of the eye; emesis; brain edema; pain, including acute pain, chronic pain, severe pain, intractable pain, inflammatory pain, chronic inflammatory pain, diabetic neuropathy, chronic neuropathic pain, post-traumatic pain, bone and joint pain (osteoarthritis), repetitive motion pain, dental pain, cancer pain, myofascial pain (muscular injury, fibromyalgia), perioperative pain (general surgery, gynecological), chronic pain, neuropathic pain, post-traumatic pain, trigeminal neuralgia, migraine and migraine headache.

Thus, in an embodiment the present invention provides methods for: treating, controlling, ameliorating or reducing the risk of epilepsy, including absence epilepsy; treating or controlling Parkinson's disease; treating essential tremor; treating or controlling pain, including neuropathic pain; enhancing the quality of sleep; augmenting sleep maintenance; increasing REM sleep; increasing slow wave sleep; decreasing fragmentation of sleep patterns; treating insomnia; enhancing cognition; increasing memory retention; treating or controlling depression; treating or controlling psychosis; or treating, controlling, ameliorating or reducing the risk of schizophrenia, in a mammalian patient in need thereof which comprises administering to the patient a therapeutically effective amount of the compound of the present invention. The subject compounds are further useful in a method for the prevention, treatment, control, amelioration, or reduction of risk of the diseases, disorders and conditions noted herein.

In a similar fashion to T-type calcium channels, tetrodotoxin-sensitive (TTX-S) voltage gated sodium channels such as $Na_{V1.3}$ and $Na_{V1.7}$ have been also implicated in a wide range of biological functions. This has suggested a potential role for these receptors in a variety of disease processes in humans or other species. The compounds of the present invention have utility in treating, preventing, ameliorating, controlling or reducing the risk of a variety of neurological and psychiatric disorders associated with TTX-S sodium channels, including one or more of the following conditions or diseases: pain, acute pain, chronic pain, neuropathic pain, inflammatory pain, visceral pain, nociceptive pain, multiple sclerosis, neurodegenerative disorder, irritable bowel syndrome, osteoarthritis, rheumatoid arthritis, neuropathological disorders, functional bowel disorders, inflammatory bowel diseases, pain associated with dysmenorrhea, pelvic pain, cystitis, pancreatitis, migraine, cluster and tension headaches, diabetic neuropathy, peripheral neuropathic pain, sciatica, fibromyalgia Crohn's disease, epilepsy or epileptic conditions, bipolar depression, tachyarrhythmias, mood disorder, bipolar disorder, psychiatric disorders such as anxiety and depression, myotonia, arrhythmia, movement disorders, neuroendocrine disorders, ataxia, incontinence, visceral pain, trigeminal neuralgia, herpetic neuralgia, general neuralgia, postherpetic neuralgia, radicular pain, sciatica, back pain, head or neck pain, severe or intractable pain, breakthrough pain, postsurgical pain, stroke, cancer pain, seizure disorder and causalgia.

The dosage of active ingredient in the compositions of this invention may be varied, however, it is necessary that the amount of the active ingredient be such that a suitable dosage form is obtained. The active ingredient may be administered to patients (animals and human) in need of such treatment in dosages that will provide optimal pharmaceutical efficacy.

The selected dosage depends upon the desired therapeutic effect, on the route of administration, and on the duration of the treatment. The dose will vary from patient to patient depending upon the nature and severity of disease, the patient's weight, special diets then being followed by a patient, concurrent medication, and other factors which those skilled in the art will recognize.

Generally, dosage levels of between 0.0001 to 20 mg/kg of body weight daily are administered to the patient, e.g., humans and elderly humans, to obtain effective blockage of T-type calcium channel. The dosage range will generally be about 0.5 mg to 1.0 g per patient per day which may be administered in single or multiple doses.

In one embodiment, the dosage range will be about 0.5 mg to 500 mg per patient per day; in another embodiment about 0.5 mg to 200 mg per patient per day; in another embodiment about 1 mg to 100 mg per patient per day; and in another embodiment about 5 mg to 50 mg per patient per day; in yet another embodiment about 1 mg to 30 mg per patient per day. Pharmaceutical compositions of the present invention may be provided in a solid dosage formulation such as comprising about 0.5 mg to 500 mg active ingredient, or comprising about 1 mg to 250 mg active ingredient. The pharmaceutical composition may be provided in a solid dosage formulation comprising about 1 mg, 5 mg, 10 mg, 25 mg, 50 mg, 100 mg, 200 mg or 250 mg active ingredient. For oral administration, the compositions may be provided in the form of tablets containing 1.0 to 1000 milligrams of the active ingredient, such as 1, 5, 10, 15, 20, 25, 50, 75, 100, 150, 200, 250, 300, 400, 500, 600, 750, 800, 900, and 1000 milligrams of the active ingredient for the symptomatic adjustment of the dosage to the patient to be treated. The compounds may be administered on a regimen of 1 to 4 times per day, such as once or twice per day.

The compounds of the present invention may be used in combination with one or more other drugs in the treatment, prevention, control, amelioration, or reduction of risk of diseases or conditions for which compounds of the present invention or the other drugs may have utility, where the combination of the drugs together are safer or more effective than either drug alone. Such other drug(s) may be administered, by a route and in an amount commonly used therefore, contemporaneously or sequentially with a compound of the present invention. When a compound of the present invention is used contemporaneously with one or more other drugs, a pharmaceutical composition in unit dosage form containing such other drugs and the compound of the present invention is envisioned. However, the combination therapy may also include therapies in which the compound of the present invention and one or more other drugs are administered on different overlapping schedules. It is also contemplated that when used in combination with one or more other active ingredients, the compounds of the present invention and the other active ingredients may be used in lower doses than when each is used singly.

Accordingly, the pharmaceutical compositions of the present invention include those that contain one or more other active ingredients, in addition to a compound of the present invention. The above combinations include combinations of a compound of the present invention not only with one other active compound, but also with two or more other active compounds.

Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefore, contemporaneously or sequentially with a compound of the present invention. When a compound of the present invention is used contemporaneously with one or more other drugs, a pharmaceutical composition containing such other drugs in addition to the compound of the present invention is envisioned. Accordingly, the pharmaceutical compositions of the present invention include those that also contain one or more other active ingredients, in addition to a compound of the present invention.

The weight ratio of the compound of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1.000, including about 200:1 to about 1:200. Combinations of a compound of the present invention, and other active ingredients will generally also be within the aforementioned range, but in each case, an effective dose of each active ingredient should be used. In such combinations the compound of the present invention and other active agents may be administered separately or in conjunction. In addition, the administration of one element may be prior to, concurrent to, or subsequent to the administration of other agent(s).

A T-type calcium channels blocker or voltage gated sodium channels blocker may be usefully combined with same or another pharmacologically active compound, or with two or more same or other pharmacologically active compounds, particularly in the treatment of inflammatory, pain and urological diseases or disorders. For example, a T-type calcium channels blocker or a voltage gated sodium channels blocker, particularly a compound of formula (I), or a pharmaceutically acceptable salt or solvate thereof, as defined above, may be administered simultaneously, sequentially or separately in combination with one or more agents selected from:

an opioid analgesic, e.g. morphine, heroin, hydromorphone, oxymorphone, levorphanol, levallorphan, methadone, meperidine, fentanyl, cocaine, codeine, dihydrocodeine, oxycodone, hydrocodone, propoxyphene, nalmefene, nalorphine, naloxone, naltrexone, buprenorphine, butorphanol, nalbuphine or pentazocine;

a nonsteroidal antiinflammatory drug (NSAID), e.g. aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin or zomepirac;

a barbiturate sedative, e.g. amobarbital, aprobarbital, butabarbital, butabital, mephobarbital, metharbital, methohexital, pentobarbital, phenobartital, secobarbital, talbutal, theamylal or thiopental;

a benzodiazepine having a sedative action, e.g. chlordiazepoxide, clorazepate, diazepam, flurazepam, lorazepam, oxazepam, temazepam or triazolam;

an H1 antagonist having a sedative action, e.g. diphenhydramine, pyrilamine, promethazine, chlorpheniramine or chlorcyclizine;

a sedative such as glutethimide, meprobamate, methaqualone or dichloralphenazone;

a skeletal muscle relaxant, e.g. baclofen, carisoprodol, chlorzoxazone, cyclobenzaprine, methocarbamol or orphrenadine;

an NMDA receptor antagonist, e.g. dextromethorphan ((+)-3-hydroxy-N-methylmorphinan) or its metabolite dextrorphan ((+)-3-hydroxy-N-methylmorphinan), ketamine, memantine, pyrroloquinoline quinine, cis-4-(phosphonomethyl)-2-piperidinecarboxylic acid, budipine, EN-3231 (MorphiDex (registered trademark), a combination formulation of morphine and dextromethorphan), topiramate, neramexane or perzinfotel including an NR2B antagonist, e.g. ifenprodil, traxoprodil or (−)-(R)-6-{2-[4-(3-fluorophenyl)-4-hydroxy-1-piperidinyl]-1-hydroxyethyl-3,4-dihydro-2(1H)-quinolinone;

an alpha-adrenergic, e.g. doxazosin, tamsulosin, clonidine, guanfacine, dexmetatomidine, modafinil, or 4-amino-6,7-dimethoxy-2-(5-methane-sulfonamido-1,2,3,4-tetrahydroisoquinol-2-yl)-5-(2-pyridyl)quinazoline;

a tricyclic antidepressant, e.g. despiramine, imipramine, amitriptyline or nortriptyline;

an anticonvulsant, e.g. carbamazepine, lamotrigine, topiratmate or valproate;

a tachykinin (NK) antagonist, particularly an NK-3, NK-2 or NK-1 antagonist, e.g. alphaR,9R)-7-(3,5-bis(trifluoromethyl)benzyl)-8,9,10,11-tetrahydro-9-methyl-5-(4-methylphenyl)-7H-[1,4]diazocino[2,1-g][1,7]-naphthyridine-6-13-dione (TAK-637), 5-[[(2R,3S)-2-[(1R)-1-[3,5-bis(trifluoromethyl)phenyl]ethoxy-3-(4-fluorophenyl)-4-morpholinyl]-methyl]-1,2-dihydro-3H-1,2,4-triazol-3-one (MK-869), aprepitant, lanepitant, dapitant or 3-[[2-methoxy-5-(trifluoromethoxy)phenyl]-methylamino]-2-phenylpiperidine (2S,3S);

a muscarinic antagonist, e.g oxybutynin, tolterodine, propiverine, tropsium chloride, darifenacin, solifenacin, temiverine and ipratropium;

a COX-2 selective inhibitor, e.g. celecoxib, rofecoxib, parecoxib, valdecoxib, deracoxib, etoricoxib, or lumiracoxib;

a coal-tar analgesic, in particular paracetamol;

a neuroleptic such as droperidol, chlorpromazine, haloperidol, perphenazine, thioridazine, mesoridazine, trifluoperazine, fluphenazine, clozapine, olanzapine, risperidone, ziprasidone, quetiapine, sertindole, aripiprazole, sonepiprazole, blonanserin, iloperidone, perospirone, raclopride, zotepine, bifeprunox, asenapine, lurasidone, amisulpride, balaperidone, palindore, eplivanserin, osanetant, rimonabant, meclinertant, Miraxion (registered trademark) or sarizotan;

a vanilloid receptor agonist (e.g. resinferatoxin) or antagonist (e.g. capsazepine);

a beta-adrenergic such as propranolol;

a local anaesthetic such as mexiletine;

a corticosteroid such as dexamethasone;

a 5-HT receptor agonist or antagonist, particularly a 5-HT1B/1D agonist such as eletriptan, sumatriptan, naratriptan, zolmitriptan or rizatriptan;

a 5-HT2A receptor antagonist such as

R(+)-alpha-(2,3-dimethoxy-phenyl)-1-[2-(4-fluorophenylethyl)]-4-piperidinemethanol (MDL-100907);

a cholinergic (nicotinic) analgesic, such as ispronicline (TC-1734), (E)-N-methyl-4-(3-pyridinyl)-3-buten-1-amine (RJR-2403), (R)-5-(2-azetidinylmethoxy)-2-chloropyridine (ABT-594) or nicotine;

Tramadol (registered trademark);

a PDEV inhibitor, such as

5-[2-ethoxy-5-(4-methyl-1-piperazinyl-sulphonyl)phenyl]-1-methyl-3-n-propyl-1,6-dihydro-7H-pyrazolo[4,3-d]pyrimidin-7-one (sildenafil), (6R,12aR)-2,3,6,7,12,12a-hexahydro-2-methyl-6-(3,4-methylenedioxyphenyl)-pyrazin[2',1':6,1]-pyrido[3,4-b]indole-1,4-dione (IC-351 or tadalafil), 2-[2-ethoxy-5-(4-ethyl-piperazin-1-yl-1-sulphonyl)-phenyl]-5-methyl-7-propyl-3H-imidazo[5,1-f][1,2,4]triazin-4-one (vardenafil), 5-(5-acetyl-2-butyoxy-3-pyridinyl)-3-ethyl-2-(1-ethyl-3-azetidinyl)-2,6-dihydro-7H-pyrazolol[4,3-d]pyrimidin-7-one, 5-(5-acetyl-2-propoxy-3-pyridinyl)-3-ethyl-2-(1-isopropyl-3-azetidinyl)-2,6-dihydro-7H-pyrazolo[4,3-d]pyrimidin-7-one, 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one, 4-[(3-chloro-4-methoxybenzyl)amino]-2-[(2S)-2-(hydroxymethyl)pyrrolidin-1-yl]-N-(pyrimidin-2-ylmethyl)pyrimidine-5-carboxamide, 3-(1-methyl-7-oxo-3-propyl-6,7-dihydro-1H-pyrazolo[4,3-d]pyrimidin-5-yl)-N-[2-(1-methylpyrrolidin-2-yl)ethyl]-4-propoxybenzenesulfonamide;

an alpha-2-delta ligand such as gabapentin, pregabalin, 3-methylgabapentin, (1alpha,3 alpha, 5 alpha)(3-amino-methyl-bicyclo[3.2.0]hept-3-yl)-acetic acid, (3S,5R)-3 aminomethyl-5 methyl-heptanoic acid, (3S, 5R)-3 amino-5 methyl-heptanoic acid, (3S,5R)-3-amino-5 methyl-octanoic acid, (2S,4S)-4-(3-chlorophenoxy)proline, (2S,4S)-4-(3-fluorobenzyl)-proline,

[(1R,5R,6S)-6-(aminomethyl)bicyclo[3.2.0]hept-6-yl]acetic acid, 3-(1-aminomethyl-cyclohexylmethyl)-4H-[1,2,4]oxadiazol-5-one, C-[1-(1H-tetrazol-5-ylmethyl)-cycloheptyl]-methylamine, (3S,4S)-(1-aminomethyl-3,4-dimethyl-cyclopentyl)-acetic acid, (3S,5R)-3 aminomethyl-5 methyl-octanoic acid (3S, 5R)-3 amino-5 methyl-nonanoic acid, (3S,5R)-3 amino-5 methyl-octanoic acid, (3R,4R,5R)-3-amino-4,5-dimethyl-heptanoic acid and (3R,4R,5R)-3-amino-4,5-dimethyl-octanoic acid;

a cannabinoid;

metabotropic glutamate subtype 1 receptor (mGluR1) antagonist;

a serotonin reuptake inhibitor such as sertraline, sertraline metabolite demethylsertraline, fluoxetine, norfluoxetine (fluoxetine desmethyl metabolite), fluvoxamine, paroxetine, citalopram, citalopram metabolite desmethylcitalopram, escitalopram, d,l-fenfluramine, femoxetine, ifoxetine, cyanodothiepin, litoxetine, dapoxetine, nefazodone, cericlamine and trazodone;

a noradrenaline (norepinephrine) reuptake inhibitor, such as maprotiline, lofepramine, mirtazepine, oxaprotiline, fezolamine, tomoxetine, mianserin, buprorion, buprorion metabolite hydroxybuprorion, nomifensine and viloxazine (VivalanR), especially a selective noradrenaline reuptake inhibitor such as reboxetine, in particular (S,S)-reboxetine;

a dual serotonin-noradrenaline reuptake inhibitor, such as venlafaxine, venlafaxine metabolite O-desmethylvenlafaxine, clomipramine, clomipramine metabolite desmethylclomipramine, duloxetine, milnacipran and imipramine;

an inducible nitric oxide synthase (iNOS) inhibitor such as S-[2-[(1-iminoethyl)amino]ethyl]-L-homocysteine, S-[2-[(1-iminoethyl)-amino]ethyl]-4,4-dioxo-L-cysteine, S-[2-[(1-iminoethyl)amino]ethyl]-2-methyl-L-cysteine, (2S,5Z)-2-amino-2-methyl-7-[(1-iminoethyl)amino]-5-heptenoic acid, 2-[[(1R,3S)-3-amino-4-hydroxy-1-(5-thiazolyl)-butyl]thiol]-5-chloro-3-pyridinecarbonitrile;

2-[[(1R,3S)-3-amino-4-hydroxy-1-(5-thiazolyl)butyl]thiol]-4-chlorobenzonitrile, (2S,4R)-2-amino-4-[[2-chloro-5-(trifluoromethyl)phenyl]thio]-5-thiazolebutanol, 2-[[(1R, 3S)-3-amino-4-hydroxyl-1-(5-thiazolyl)butyl]thio]-6-(trifluoromethyl)-3 pyridinecarbonitrile, 2-[[(1R,3S)-3-amino-4-hydroxy-1-(5-thiazolyl)butyl]thiol]-5-chlorobenzonitrile, N-[4-[2-(3-chlorobenzylamino)ethyl]phenyl]thiophene-2-carboxamidine, or guanidinoethyldisulfide;

an acetylcholinesterase inhibitor such as donepezil;

a prostaglandin E2 subtype 4 (EP4) antagonist such as N-[({2-[4-(2-ethyl-4,6-dimethyl-1H-imidazo[4,5-c] pyridin-1-yl)phenyl]ethyl}amino)-carbonyl]-4-methylbenzesulfonamide or 4-[(1S)-1-({[5-chloro-2-(3-fluorophenoxy)pyridin-3-yl]carbonyl}amino)ethyl] benzoic acid;

a leukotriene B4 antagonist; such as 1-(3-biphenyl-4-ylmethyl-4-hydroxy-chroman-7-yl)-cyclopentanecarboxylic acid (CP-105696), 5-[2-(2-Carboxyethyl)-3-[6-(4-methoxyphenyl)-5E-hexenyl]oxyphenoxy]-valeric acid (ONO-4057) or DPC-11870, a 5-lipoxygenase inhibitor, such as zileuton, 6-[(3-fluoro-5-[4-methoxy-3,4,5,6-tetrahydro-2H-pyran-4-])phenoxy-methyl]-1-methyl-2-quinolone (ZD-2138), or 2,3,5-trimethyl-6-(3-pyridylmethyl), 1,4-benzoquinone (CV-6504);

a sodium channel blocker, such as lidocaine;

a calcium channel blocker, such as ziconotide, zonisamide, mibefrazil;

a 5-HT3 antagonist, such as ondansetron;

and the pharmaceutically acceptable salts and solvates thereof.

Such combinations offer significant advantages, including synergistic activity, in therapy.

A pharmaceutical composition of the invention, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusible solutions or suspensions or suppositories. Orally administrate compositions are generally preferred. Tablets and capsules for oral administration may be in unit dose form, and may contain conventional exclpients, such as binding agents (e.g. pregelatinised maize starch, polyvinylpyrrolidone or hydroxypropyl methylcellulose); fillers (e.g. lactose, microcrystalline cellulose or calcium hydrogen phosphate); tabletting lubricants (e.g. magnesium stearate, talc or silica); disintegrants (e.g. potato starch or sodium starch glycollate); and acceptable wetting agents (e.g. sodium lauryl sulphate). The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents (e.g. sorbitol syrup, cellulose derivatives or hydrogenated edible fats), emulsifying agents (e.g. lecithin or acacia), non-aqueous vehicles (which may include edible oils e.g. almond oil, oily esters, ethyl alcohol or fractionated vegetable oils), preservatives (e.g. methyl or propyl-p-hydroxybenzoates or sorbic acid), and, if desired, conventional, flavourings or colorants, buffer salts and sweetening agents as appropriate. Preparations for oral administration may be suitably formulated to give controlled release of the active compound or pharmaceutically acceptable salt thereof.

For parenteral administration, fluid unit dosage forms are prepared utilising a compound of formula (I) or pharmaceutically acceptable salt thereof and a sterile vehicle. Formulations for injection may be presented in unit dosage form e.g. in ampoules or in multi-dose, utilising a compound, of formula (I) or pharmaceutically acceptable salt thereof and a sterile vehicle, optionally with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilisation cannot be accomplished by filtration. The compound can be sterilised by exposure to ethylene oxide before suspension in a sterile vehicle. Advantageously, a surfactant or wetting agent is included in the composition to facilitate uniform distribution of the compound.

Lotions may be formulated with an aqueous or oily base and will in general also contain one or more emulsifying agents, stabilising agents, dispersing agents, suspending agents, thickening agents, or colouring agents. Drops may be formulated with an aqueous or non-aqueous base also comprising one or more dispersing agents, stabilising agents, solubilising agents or suspending agents. They may also contain a preservative.

The compounds of formula (I) or pharmaceutically acceptable salts thereof may also be formulated in rectal compositions such as suppositories or retention enemas, e.g. containing conventional suppository bases such as cocoa butter or other glycerides.

The compounds of formula (I) or pharmaceutically acceptable salts may also be formulated as depot preparations. Such long acting formulations may be administered by implantation (for example subcutaneously or intramuscularly) or by intramuscular injection. Thus, for example, the compounds of formula (I) or pharmaceutically acceptable salts may be formulated with suitable polymeric or hydrophobic materials (for example as an emulsion in an acceptable oil) or ion exchange resins, or as sparingly soluble derivatives, for example, as a sparingly soluble salt.

For intranasal administration, the compounds formula (I) or pharmaceutically acceptable salts thereof may be formulated as solutions for administration via a suitable metered or unitary dose device or alternatively as a powder mix with a suitable carrier for administration using a suitable delivery device. Thus compounds of formula (I) or pharmaceutically acceptable salts thereof may be formulated for oral, buccal, parenteral, topical (including ophthalmic and nasal), depot or rectal administration or in a form suitable for administration by inhalation or insufflation (either through the mouth or nose). The compounds of formula (I) and pharmaceutically acceptable salts thereof may be formulated for topical administration in the form of ointments, creams, gels, lotions, pessaries, aerosols or drops (e.g. eye, ear or nose drops). Ointments and creams may, for example, be formulated with an aqueous or oily base with the addition of suitable thickening and/or gelling agents. Ointments for administration to the eye may be manufactured in a sterile manner using sterilized components.

General Synthesis

Throughout the instant application, the following abbreviations are used with the following meanings:
DIBAL-H Diisoburylaluminium hydride
DMF N,N-dimethylformamide
DMSO Dimethyl sulfoxide
EDC 1-Ethyl-3-(3-dimethylaminopropyl)carbodiimide Hydrochloride
HOBT 1-Hydroxybenztriazole
HBTU O-(Benzotriazol-1-yl)-N,N,N',N'-tetramethyluronium Hexafluorophosphate
HPLC High pressure liquid chromatography
TEMPO 2,2,6,6-Tetramethyl-1-piperidinyloxy
tR Retention time
MHz Megahertz
NMR Nuclear Magnetic Resonance
TEA Trifluoroacetic acid
THF Tetrahydrofuran
TLC Thin layer chromatography The term of "base" is likewise no particular restriction on the nature of the bases used, and any base commonly used in reactions of this type may equally be used here. Examples of such bases include: alkali metal hydroxides, such as lithium hydroxide, sodium hydroxide, potassium hydroxide, and barium hydroxide; alkali metal hydrides, such as lithium hydride, sodium hydride, and potassium hydride; alkali metal alkoxides, such as sodium methoxide, sodium ethoxide, and potassium t-butoxide; alkali metal carbonates, such as lithium carbonate, sodium carbonate, potassium carbonate, and cesium carbonate; alkali metal hydrogencarbonates, such as lithium hydrogencarbonate, sodium hydrogenearbonate, and potassium hydrogenearbonate; amines, such as N-methylmorpholine, triethylamine, tripropylamine, tributylamine, diisopropylethylamine, N-methylpiperidine, pyridine, 4-pyrrolidinopyridine, picoline, 2,6-di(t-butyl)-4-methylpyridine, quinoline, N,N-dimethylaniline, N,N-diethylaniline, 1,5-diazabicyclo[4.3.0]non-5-ene (DBN), 1,4-diazabicyclo[2.2.2]octane (DABCO), 1,8-diazabicyclo[5.4.0]undec-7-ene (DBU), lutidine, and colidine; alkali metal amides, such as lithium amide, sodium amide, potassium amide, lithium diisopropyl amide, potassium diisopropyl amide, sodium diisopropyl amide, lithium bis(trimethylsilyl)amide and potassium bis(trimethylsilyl)amide. Of these, triethylamine, diisopropylethylamine, DBU, DBN, DABCO, pyridine, lutidine, colidine, sodium carbonate, sodium hydrogencarbonate, sodium hydroxide, potassium carbonate, potassium hydrogencarbonate, potassium hydroxide, barium hydroxide, and cesium carbonate are preferred.

The reactions are normally and preferably effected in the presence of inert solvent. There is no particular restriction on the nature of the solvent to be employed, provided that it has no adverse effect on the reaction or the reagents involved and that it can dissolve reagents, at least to some extent. Examples of suitable solvents include, but not limited to: halogenated hydrocarbons, such as dichloromethane, chloroform, carbon tetrachloride, and dichloroethane; ethers, such as diethyl ether, diisopropyl ether, THF, and dioxane;

aromatic hydrocarbons, such as benzene, toluene and nitrobenzene; amides, such as, DMF, N,N-dimethylacetamide, and hexamethylphosphoric triamide; amines, such as N-methylmorpholine, triethylamine, tripropylamine, tributylamine, diisopropylethylamine, N-methylpiperidine, pyridine, 4-pyrrolidinopyridine, N,N-dimethylaniline, and N,N-diethylaniline; alcohols, such as methanol, ethanol, propanol, isopropanol, and butanol; nitriles, such as acetonitrile and benzonitrile; sulfoxides, such as dimethyl sulfoxide (DMSO) and sulfolane; ketones, such as acetone and diethylketone. Of these solvents, including but not limited to DMF, DMSO, THF, diethylether, diisopropylether, dimethoxyethane, acetonitrile, dichloromethane, dichloroethane and chloroform are preferred.

EXAMPLES

The invention is illustrated in the following non-limiting examples in which, unless stated otherwise: all reagents are commercially available, all operations were carried out at room, or ambient temperature, that is, in the range of about 18-25° C.; evaporation of solvent was carried out using a rotary evaporator under reduced pressure with a bath temperature of up to about 60° C.; reactions were monitored by thin layer chromatography (tlc) and reaction times are given for illustration only; the structure and purity of all isolated compounds were assured by at least one of the following techniques: tlc (Merck silica gel 60 $F_{254}$ precoated TLC plates or Merck $NH_2$ $F_{254}$ precoated HPTLC plates), mass spectrometry or nuclear magnetic resonance (NMR). Yields are given for illustrative purposes only. Flash column chromatography was carried out using Merck silica gel 60 (230-400 mesh ASTM) or Fuji Silysia Chromatorex (registered trademark) DU3050 (Amino Type, 30-50 micrometer) or Biotage silica (32-63 micrometer, KP-Sil) or Biotage amino bounded silica (35-75 micrometer, KP-NH) or Hi-Flash Column™ (40 micrometer, Silica gel). Low-resolution mass spectral data (ESI) were obtained by the following apparatus and conditions: Apparatus; Waters Alliance HPLC system on ZQ or ZMD mass spectrometer and UV detector. NMR data was determined at 270 MHz (JEOL JNM-LA 270 spectrometer) or 300 MHz (JEOL JNM-LA300) using deuterated chloroform (99.8% D) or dimethylsulfoxide (99.9% D) as solvent unless indicated otherwise, relative to tetramethylsilane (TMS) as internal standard in parts per million (ppm); conventional abbreviations used are: s=singlet, d=doublet, t=triplet, q=quartet, m=multiplet, br=broad, etc. Chemical symbols have their usual meanings:
μm (micrometers)), μL (microliter(s)), μg (microgram(s)), M (mol(s) per liter), L (liter(s)), mL (milliliters)), g (gram(s)), mg (milligram(s)), mol (moles), mmol (millimoles).
Purification Methods:
Achiral Reversed-Phase HPLC:
Apparatus: Waters MS-trigger Autopurification™ System (2525 Binary pump module, 2767 Sample manager, 2996 PDA detector and ZQ2000 mass spectrometer)
Column: XBridge™ Prep C18 5 μm, 19×50 mm
Column temperature: ambient (room temperature)
Flow rate: 20 mL/min
Mobile phase A: Methanol or Acetonitrile/0.05% (v/v) formic acid aqueous solution
Mobile phase B: Methanol or Acetonitrile/0.05% (v/v) ammonia aqueous solution
Elution: Optimized gradient program with selected mobile phases
Run time: 7 min MPLC:
Apparatus: Biotage SP System
Column: Hi-Rash™ Column Silica gel 40 μm, 60 Å
Column Temperature: room temperature
Solvents:
Less polar solvent: hexane
High polar solvent: ethyl acetate
Chiral Noraml Phase HPLC:
Apparatus: Shimadzu Preparative-HPLC system
Column: DAICEL Chiralpak AD-H, 20×250 mm
DAICEL Crtiralpak AS-H, 20×250 mm
DAICEL Chiralcel OJ-H, 20×250 mm
DAICEL Chiralcel OD-H, 20×250 mm
Column temperature: 40° C.
Solvents:
A1: n-Hexane
B1: Ethanol or 2-propanol
Elution: Optimized isocratic condition with the selected column and mobile phases
Purity Evaluation Method:
Method A:
Apparatus: Waters Acquity Ultra Performance LC on TUV Detector and ZQ mass spectrometer
Column: XTerra MS C18 3.5 μm, 2.1×30 mm
Column Temperature: 45° C.
Solvents:
A1: acetonitrile
B1: 5 mM ammonium acetate aqueous solution

TABLE 1

| Time (min) | A1 (%) | B1 (%) |
|---|---|---|
| 0 | 4 | 96 |
| 2 | 96 | 4 |
| 4 | 96 | 4 |
| | run time | 4.0 min |
| | flow | 0.5 mL/min |

Method B:
Achiral Reversed-Phase-UPLC:
Apparatus: Waters ACQUITY Ultra Performance LC (UPLC™) with TUV Detector and ZQ2000 mass spectrometer
Column: Waters ACQUITY UPLC™ BEH C18, 2.1×100 mm, 1.7 μm
Column temperature: 60° C.
Flow rate: 0.7 mL/min
Solvents:
A1: 10 mM ammonium acetate aqueous solution
B1: Acetonitrile

TABLE 2

| Eluting program: | | |
|---|---|---|
| Time (min) | A1 (%) | B1 (%) |
| 0 | 95 | 5 |
| 0.1 | 95 | 5 |
| 1.8 | 5 | 95 |
| 2.3 | 95 | 5 |

Run time: 3 min

All of the aryl substituted carboxamide derivatives of the formula (I) can be prepared by the procedures described in the general methods presented below or by the specific methods described in the Examples section and the Preparations section, or by routine modifications thereof. The present invention also encompasses any one or more of these processes for preparing the aryl substituted carboxamide derivatives of formula (I), in addition to any novel intermediates used therein.

In the following general methods, Ar, W, X, Y, Z, $R^1$, $R^2$, $R^3$, $R^4$, $R^5$, $R^6$, p, q and r are as previously defined for aryl substituted carboxamide derivatives of the formula (I) unless otherwise stated.

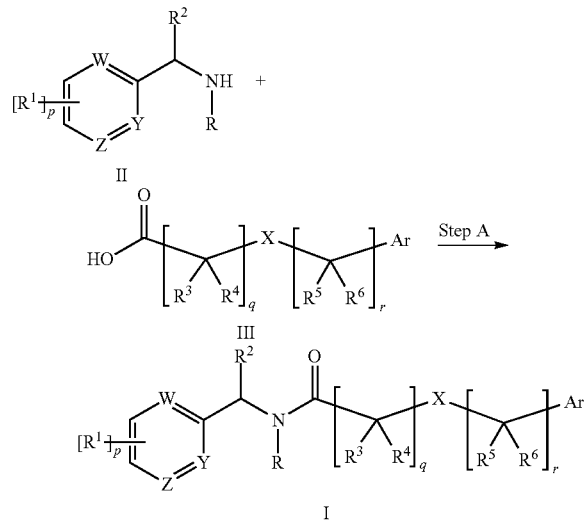

In Step A, a compound of formula (I) can be prepared from a compound of formula (III) by amidation with a compound of formula (II) with using a suitable condensation agent such as EDC, preferably under the presence of a base such as a combination of trimethylamine and HOBT, in a suitable solvent such as dichloromethane at a temperature of from 5 to 40° C. for 5-20 hours.

In order to obtain some other compounds of formula (I), the appropriate conversion reaction of the substituents will be used.

For example, alkyl substituted derivatives can be prepared from a compound of the corresponding halide by coupling reaction with a suitable boronic acid using a suitable catalyst such as tetra kls triphenylphosphine palladium under the presence of a base such as potassium phosphate and a suitable solvent such as dioxane at a temperature of from 5 to 90° C. for 12-24 hours; cyclopropane derivatives can be prepared from a compound of the corresponding alpha, beta-unsaturated, amide by cyclization reaction with a suitable alkyl diiodide using a suitable reagent such as diethylzinc in a suitable solvent such as dichloromethane at a temperature of from 5 to 90° C. for 12-24 hours or by cyclization reaction with a suitable trialkyl sulfoxonium halide such as trimethylsulfoxonium iodide and suitable base such as sodium hydride in a suitable solvent such as DMSO at a temperature of from 5 to 90° C. for 1-24 hours; hydroxyl derivatives can be prepared from a compound of the corresponding benzyloxy derivative by hydrogenation with a suitable palladium catalyst such as hydroxyl palladium in a suitable solvent such as ethanol under hydrogen; ether derivatives can be prepared from a compound of the corresponding hydroxyl derivative by alkylation with alkyl alcohol under the presence of a condensation reagent such as di-ter-butyl azodicarboxylate and triphenyl phosphine and base such as N—N-diisopropylethylamine and a suitable solvent such as tetrahydrofuran or with alkyl halide under the presence of a base such as potassium carbonate and a suitable solvent such as dimethylforamide; N-alkylated derivatives can be prepared from a compound of the corresponding NH-amide derivative by alkylation with a suitable alkyl halide using a base such as sodium, hydride in a suitable solvent such as dimethylformiamide;

All starting materials in the following general syntheses may be commercially available or obtained by conventional methods known to those skilled in the art, otherwise noted in the intermediate synthesis part.

Intermediate Synthesis Part

Amine Intermediate-1

(R)-1-(5-(cyclopropylmethoxy)pyridin-2-yl)ethanamine 2 HCL Salt

Step-1: 5-(cyclopropylmethoxy)-2-methylpyridine

To a solution of 6-methylpyridin-3-ol (5.0 g, 46 mmol) in DMF (45 mL) were added cesium carbonate (16.5 g, 53 mmol) and (bromomethyl)cyclopropane (7.1 g, 53 mmol) at room temperature. After being stirred at room temperature for 18 hours, the mixture was poured into $H_2O$, and the aqueous phase was extracted with ethyl acetate (twice). The combined organic layers were dried over magnesium sulfate and concentrated in vacuo. The residue was purified by column chromatography on silica gel eluting with hexane/ethyl acetate (3:1 (v/v)) to give 3.9 g (52% yield) of the title compound as a yellow oil:

$^1$H-NMR (300 MHz, $CDCl_3$) δ 8.20 (1H, d, J=2.9 Hz), 7.04-7.14 (2H, m), 3.82 (2H, d, J=6.6 Hz), 2.49 (3H, s), 1.21-1.34 (1H, m), 0.67 (2H, q, J=7.3 Hz), 0.37 (2H, q, J=5.9 Hz), LCMS (Method A) m/z: M+1 obs 164.3, tR=2.07 min.

Step-2: (5-(cyclopropylmethoxy)pyridin-2-yl)methanol

To a solution of 5-(cyclopropylmethoxy)-2-methylpyridine (3.9 g, 24 mmol) in dichloromethane (50 mL) was added 3-chlorobenzoperoxoic acid (7.6 g, 32 mmol) at room temperature. After being stirred at room temperature for 1 hour, the mixture was poured into saturated aqueous sodium bicarbonate solution. The organic phase was extracted with dichloromethane (twice). The combined organic layers were dried over magnesium sulfate and concentrated in vacuo. The residue was dissolved in acetic anhydride (50 mL) and the mixture was stirred at 100° C. for 2 hours. Half of the solvent was removed under the reduced pressure. The residue was dissolved into methanol (50 mL). Potassium carbonate (20 g, 143 mmol) was added to the mixture carefully. The mixture was stirred at room temperature for 1 hour. The mixture was poured into $H_2O$, and the aqueous phase was extracted with ethyl acetate (twice). The combined organic layers were dried over magnesium sulfate and concentrated in vacuo. The residue was purified by column chromatography on silica gel eluting with hexane/ethyl acetate (1:1 (v/v)) to give 4.5 g (quantitative yield) of the title compound as a brown oil:

$^1$H-NMR (300 MHz, $CDCl_3$) δ 8.25 (1H, d, J=2.9 Hz), 7.21 (1H, dd, J=8.8, 2.9 Hz), 7.17 (1H, d, J=8.8 Hz), 4.70 (2H, s), 3.85 (2H, d, J=7.4 Hz), 1.28 (1H, m), 0.75-0.63 (2H, m), 0.40-0.28 (2H, m), LCMS (Method A) m/z: M+1 obs 180.3, tR=2.09 min.

Step-3

(R,E)-N-((5-cyclopropylmethoxy)pyridin-2-yl)methylene)-2-methylpropane-2-sulfinamide To a solution of (5-(cyclopropylmethoxy)pyridin-2-yl) methanol (4.5 g, 25 mmol) in dichloromethane (50 ml), was added a 15% potassium bromide aqueous solution (20 mL) followed by a saturated bicarbonate solution (20 ml). The biphasic mixture was cooled in an ice bath and TEMPO (200 mg, 1.3 mmol) was added. After stirring for 10 min, 5% sodium hypochlorite (30 ml) was dropwised. The reaction mixture was stirred for 10 min. The solution was poured into a separator funnel and the organic layer was dried over magnesium sulfate and concentrated in vacuo. The residue was dissolved in dichloromethane (50 mL). Copper(II) sulfate (10.1 g, 63 mmol) followed by (R)-(+)-2-methyl-2-propanesulfinamide (3.1 g, 25 mmol) were added to the mixture respectively and the mixture was stirred for 18 hours at room temperature. The reaction mixture was filtrated off and the filtrate was concentrated in vacuo. The residue was purified by column chromatography on silica gel eluting with hexane/ethyl acetate (1:1 (v/v)) to give 6.2 g (87% yield) of the title compound as a flaky solid:

$^1$H-NMR (300 MHz, CDCl$_3$) δ 8.63 (1H, S), 8.42 (1H, d, J=2.2 Hz), 7.96 (1H, d, J=8.8 Hz), 7.34-7.28 (1H, m), 3.92 (2H, d, J=6.6 Hz), 1.27 (10H, m), 0.67-0.73 (2H, m), 0.39-0.42 (2H, m), LCMS (Method A) m/z: M+1 obs 281.2, tR=2.98 min.

Step-4

(R)—N—((R)-1-(5-(cyclopropylmethoxy)pyridin-2-yl)ethyl)-2-methylpropane-2-sulfinamide A solution of (R,E)-N-((5-(cyclopropylmethoxy)pyridin-2-yl)methylene)-2-methylpropane-2-sulfinamide (6.2 g, 22 mmol) was dissolved into dichloromethane (110 ml). Methyl magnesium bromide (44 ml, 44 mmol, 1.0M in THF) was added to the mixture at −78° C. dropwise. The mixture was stirred for 1 h at −78° C. The mixture was poured into saturated ammonium chloride aqueous solution, and the aqueous phase was extracted with ethyl acetate (twice). The combined organic layers were dried over magnesium sulfate, and concentrated in vacuo. The residue was purified by column chromatography on silica gel editing with hexane/ethyl acetate (1:1 (v/v)) to give 3.2 g (49% yield) of the title compound as a white solid:

$^1$H-NMR (300 MHz, CDCl$_3$) δ 8.24 (1H, d, J=2.2 Hz), 7.15-7.23 (2H, m), 4.51-4.57 (2H, m), 3.83 (2H; d, J=6.6 Hz), 1.49 (3H, d, J=6.6 Hz), 1.25 (10H, m), 0.59-0.75 (2H, m) 0.34-0.44 (2H, m), LCMS (Method A) m/z: M+1 obs 297.3, tR=2.81 min.

Step-5: (R)-1-(5-(cyclopropylmethoxy)pyridin-2-yl)ethanamine 2 HCl salt (R)—N—((R)-1-(5-(cyclopropylmethoxy)pyridin-2-yl) ethyl)-2-methylpropane-2-sulfinamide (3.2 g, 10.9 mmol) was dissolved in 10N HCl/MeOH (50 mL). The mixture was stirred at room temperature for 3 hours. The mixture was concentrated by N$_2$-flow to give the white precipitate. The solid was collected by filtration and washed with diisopropyl ether to give 3.2 g (49% yield) of the title compound as a white solid:

$^1$H-NMR (300 MHz, DMSO-d$_6$) δ 8.67 (3H, brs), 8.41 (1H, d, J=2.2 Hz), 7.70-7.55 (2H, m), 4.56 (1H, m), 4.01 (2H, d, J=7.3 Hz), 1.57 (3H, d, J=6.6 Hz), 1.33 (1H, m), 0.70-0.60 (2H, m), 0.45-0.35 (2H, m), LCMS (Method A) m/z: M+1 obs 193.3, tR=1.90 min.

Amine Intermediate-2

(R)-1-(5-(benzyloxy)pyridin-2-yl)ethanamine 2HCl Salt

Step-1

(R,E)-N-((5-(benzyloxy)pyridin-2-yl)methylene)-2-methylpropane-2-sulfinamide

Prepared as in Step 3 of Amine intermediate-1 from (5-(benzyloxy)pyridin-2-yl)methanol.

$^1$H-NMR (300 MHz, CDCl$_3$) δ 8.64 (1H, s), 8.49 (1H, d, J=2.94 Hz), 7.97 (1H, d, J=8.1 Hz), 7.31-7.45 (6H, m), 5.19 (2H, s), 1.27 (9H, s), LCMS (Method A) m/z: M+1 obs 317.2, tR=3.15 min.

Step-2

(R)—N—((R)-1-(5-(benzyloxy)pyridin-2-yl)ethyl)-2-methylpropane-2-sulfinamide

Prepared as in Step-4 of Amine intermediate-1 from (R,E)-N-((5-(benzyloxy)pyridin-2-yl)methylene)-2-methylpropane-2-sulfinamide.

$^1$H-NMR (300 MHz, CDCl$_3$) δ 8.31 (1H, d, J=2.2 Hz), 7.50-7.30 (5H, m), 7.23 (2H, d, J=2.2 Hz), 5.09 (2H, s), 4.57 (2H, m), 1.49 (3H, d, J=6.6 Hz), 1.25 (9H, s), LCMS (Method A) m/z: M+1 obs 333.2, tR=2.97 min.

Step-3: (R)-1-(5-(benzyloxy)pyridin-2-yl)ethanamine 2HCl Salt

Prepared as in Step-5 of Amine intermediate-1 from (R)—N—((R)-1-(5-(benzyloxy)pyridin-2-yl)ethyl)-2-methylpropane-2-sulfinamide.

$^1$H-NMR (300 MHz, DMSO-d$_6$) δ 7.50 (2H, brs), 8.38 (1H, d, J=2.9 Hz), 7.65-6.25 (7H, m), 6.01 (2H, brs), 5.22 (2H, s), 4.45 (1H, m), 1.46 (3H, d, J=6.8 Hz), LCMS (Method A) m/z: M+1 obs 229.3, tR=2.24 min.

Amine Intermediate-3

(R)-1-(5-(2-fluorobenzyloxy)pyridin-2-yl)ethanamine 2HCl Salt

Step-1: 5-(2-fluorobenzyloxy)picolinonitrile

To a mixture of 2-bromo-5-(2-fluorobenzyloxy)pyridine (1.5 g, 5.3 mmol) and zinc cyanide (0.81 g, 6.9 mmol) in DMF (20 mL) was added Tetrakis(triphenylphosphine)palladium(0) (0.61 g, 0.53 mmol) at room temperature. After being stirred at 60° C. for 4 hours, sat. sodium bicarbonate aqueous solution was added to the mixture. The mixture was filtered off through a pad of Celite. The filtrate was extracted with ethyl acetate, dried over sodium sulfate and concentrated in vacuo. The residue was purified by column chromatography on silica gel eluting with hexane/ethyl acetate (2:1 (v/v)) to give 0.69 g (57% yield) of the title compound as a light yellow solid:

¹H-NMR (300 MHz, CDCl₃) δ 8.45 (1H, d, J=2.9 Hz), 7.65 (1H, d, J=8.7 Hz), 7.50-7.28 (3H, m), 7.24-7.05 (2H, m), 5.24 (2H, s), LCMS (Method A) m/z: M+1 obs 229.3, tR=2.94 min.

Step-2

(R,E)-N-((5-(2-fluorobenzyloxy)pyridin-2-yl)methylene)-2-methylpropane-2-sulfinamide To a solution of Reactant 5-(2-fluorobenzyloxy)picolinonitrile (690 mg, 3.0 mmol) in dichloromethane (20 mL) was added DIBAL-H (3.7 mL, 3.6 mmol, 0.99 M) at −78° C. After being stirred at −78° C. for 4 hours, methanol (2 mL) was added to the mixture. 1N hydrochloric acid (0.5 mL) was added to the mixture at room temperature. The mixture was stirred at room temperature for 1 hour. Sat. sodium bicarbonate aqueous solution was added to the mixture until the pH was neutrized. The organic layer was extracted with dichloromethane, dried over sodium sulfate and concentrated in vacuo. The residue was dissolved in dichloromethane (20 mL). Copper(II) sulfate (1.2 g, 7.6 mmol) followed by (R)-(+)-2-methyl-2-propanesulfinamide (370 mg, 3.0 mmol) were added to the mixture respectively and the mixture was stirred for overnight at room temperature. The reaction mixture was filtrated off through a pad of Celite and the filtrate was concentrated in vacuo. The residue was purified by column chromatography on silica gel eluting with hexane/ethyl acetate (2:1 (v/v)) to give 360 mg (36% yield) of the title compound as a colorless oil:
¹H-NMR (300 MHz, CDCl₃) δ 8.64 (1H, s), 8.49 (1H, d, J=2.9 Hz), 7.98 (1H, d, J=8.8 Hz), 7.49 (1H, td, J=7.3, 1.5 Hz), 7.40-7.30 (2H, m), 7.23-7.05 (2H, m), 5.26 (2H, s), 1.27 (9H, s), LCMS (Method A) m/z: M+1 obs 335.3, tR=3.14 min.

Step-3

(R)—N—((R)-1-(5-(2-fluorobenzyloxy)pyridin-2-yl)ethyl-2-methylpropane-2-sulfinamide Prepared as in Step-4 of Amine intermediate-1 from (R,E)-N-((5-(2-fluorobenzyloxy)pyridin-2-yl)methylene)-2-methylpropane-2-sulfinamide
¹H-NMR (300 MHz, CDCl₃) δ 8.32 (1H, d, J=1.4 Hz), 7.48 (1H, t, J=7.3 Hz), 7.40-7.05 (5H, m), 5.16 (2H, s), 4.60-4.50 (2H, m), 1.49 (3H, d, J=5.9 Hz), 1.25 (9H, s), LCMS (Method A) m/z: M+1 obs 351.3, tR=2.97 min.

Step-4: (R)-1-(5-(2-fluorobenzyloxy)pyridin-2-yl)ethanamine 2HCl Salt

Prepared as in Step-5 of Amine intermediate-1 from (R)—N—((R)-1-(5-(2-fluorobenzyloxy)pyridin-2-yl)ethyl)-2-methylpropane-2-sulfinamide
¹H-NMR (300 MHz, DMSO-d₆) δ 8.97 (2H, brs), 8.40 (1H, m), 7.87 (1H, d, J=8.8 Hz), 7.64 (1H, d, J=8.8 Hz), 7.55-7.35 (2H, m), 7.30-7.08 (2H, m), 5.24 (2H, s), 4.78 (1H, m), 1.76 (3H, d, J=6.6 Hz), LCMS (Method A) m/z: M+1 obs 247.3, tR=2.34 min.

Amine Intermediate-4

(R)-1-(6-methyl-5-(2,2,2-trifluoroethoxy)pyridin-2-yl)ethanamine

Step-1: 2,6-dimethyl-3-(2,2,2-trifluoroethoxy)pyridine

Prepared as in Step-1 of Amine intermediate-1 from 2,6-dimethylpyridin-3-ol and 2,2,2-trifluoroethyl trifluoromethanesulfonate.

To a suspension of 2,6-dimethylpyridin-3-ol (5.0 g, 41 mmol) and cesium carbonate (15 g, 47 mmol) in DMF (50 mL) was added 2,2,2-trifluoroethyl trifluoromethanesulfonate (11 mL, 47 mmol) dropwise. The reaction mixture was stirred at room temperature for 1 hour. After being stirred at room temperature for 18 hours, the mixture was poured into H₂O, and the aqueous phase was extracted with ethyl acetate (twice). The combined organic layers were dried over magnesium sulfate and concentrated in vacuo to give 8.3 g (quantitative yield) of the title compound as a brown oil:
¹H-NMR (300 MHz, CDCl₃) δ 7.01 (1H, d, J=8.0 Hz), 6.95 (1H, d, J=8.0 Hz), 4.33 (2H, q, J=8.0 Hz), 2.48 (8H, s), LCMS (Method A) m/z: M+1 obs 206.2, tR=2.58 min.

Step-2: (6-methyl-5-(2,2,2-trifluoroethoxy)pyridin-2-yl)methanol

Prepared as in Step-2 of Amine intermediate-1 from 2,6-dimethyl-3-(2,2,2-trifluoroethoxy)pyridine as a minor product.
¹H-NMR (300 MHz, CDCl₃) δ 7.12 (1H, d, J=8.0 Hz), 7.08 (1H, d, J=8.0 Hz), 4.68 (2H, s), 4.37 (2H, q, J=8.0 Hz), 2.52 (3H, s), 2.05 (1H, brs) (minor product).

Step-3

(R,E)-2-methyl-N-((6-methyl-5-(2,2,2-trifluoroethoxy)pyridin-2-yl)methylene)propane-2-sulfinamide Prepared as in Step-3 of Amine intermediate-1 from (6-methyl-5-(2,2,2-trifluoroethoxy)pyridin-2-yl)methanol.
¹H-NMR (300 MHz, CDCl₃) δ 8.63 (1H, s), 7.89 (1H, d, J=8.1 Hz), 7.16 (1H, d, J=8.1 Hz), 4.44 (2H, q, J=8.1 Hz), 2.58 (3H, s), 1.27 (9H, s), LCMS (Method A) m/z: M+1 obs 323.2, tR=3.00 min.

Step-4

(R)-2-methyl-N—((R)-1-(6-methyl-5-(2,2,2-trifluoroethoxy)pyridin-2-yl)ethyl)propane-2-sulfinamide Prepared as in Step-4 of Amine intermediate-1 from (R,E)-2-methyl-N-((6-methyl-5-(2,2,2-trifluoroethoxy)pyridin-2-yl)methylene)propane-2-sulfinamide.
¹H-NMR (300 MHz, CDCl₃) δ 7.11 (1H, d, J=8.0 Hz), 7.05 (1H, d, J=8.0 Hz), 4.79 (1H, d, J=5.1 Hz), 4.55 (1H, m), 4.33 (2H, q, J=8.1 Hz), 2.42 (3H, s), 1.48 (3H, d, J=6.6 Hz), 1.25 9H, s).

Step-5: (R)-1-(6-methyl-5-(2,2,2-trifluoroethoxy)pyridin-2-yl)ethanamine 2 HCl salt Prepared as in Step-5 of Amine intermediate-1 from (R)-2-methyl-N—((R)-1-(6-methyl-5-(2,2,2-trifluoroethoxy)pyridin-2-yl)ethyl)propane-2-sulfinamide.
LCMS (Method A) m/z: M+1 obs 235.3, tR=2.24 min.

Amine Intermediate-5

(R)-1-(6-methyl-3-(2,2,2-trifluoroethoxy)pyridin-2-yl)ethanamine

Step-1: (6-methyl-3-(2,2,2-trifluoroethoxy)pyridin-2-yl)methanol

Prepared as in Step-2 of Amine intermediate-1 from 2,6-dimethyl-3-(2,2,2-trifluoroethoxy)pyridine as a major product.

¹H-NMR (300 MHz, CDCl₃) δ 7.03-7.09 (2H, m), 4.74 (2H, d, J=4.4 Hz), 4.36 (2H, q, J=8.1 Hz), 2.52 (3H, s), 1.64 (1H, brs), LCMS (Method A) m/z: M+1 obs 222.3, tR=2.17 min.

Step-2

(R,E)-2-methyl-N-((6-methyl-3-(2,2,2-trifluoroethoxy)pyridin-2-yl)methylene)propane-2-sulfinamide Prepared as in Step-3 of Amine intermediate-1 from (6-methyl-3-(2,2,2-trifluoroethoxy)pyridin-2-yl)methanol.
¹H-NMR (300 MHz, CDCl₃) δ 8.95 (1H, s), 7.28 (2H, s), 4.44 (2H, m), 2.60 (3H, s), 1.27 (9H, s), LCMS (Method A) m/z: M+1 obs 323.2, tR=2.84 min.

Step-3

(R)-2-methyl-N—((R)-1-(6-methyl-3-(2,2,2-trifluoroethoxy)pyridin-2-yl)ethyl)propane-2-sulfinamide Prepared as in Step-4 of Amine intermediate-1 from (R,E)-2-methyl-N-((6-methyl-3-(2,2,2-trifluoroethoxy)pyridin-2-yl)methylene)propane-2-sulfinamide.
¹H-NMR (300 MHz, CDCl₃) δ 7.04 (1H, d, J=8.1 Hz), 6.99 (1H, d, J=8.1 Hz), 5.21 (1H, d, J=7.3 Hz), 4.86 (1H, m), 4.38 (2H, q, J=8.0 Hz), 2.48 (3H, S), 1.41 (3H, d, J=6.6 Hz), 1.26 (9H, s)

Step-4: (R)-1-(6-methyl-3-(2,2,2-trifluoroethoxy)pyridin-2-yl)ethanamine 2HCl salt Prepared as in Step-5 of Amine intermediate-1 from (R)-2-methyl-N—((R)-1-(6-methyl-3-(2,2,2-trifluoroethoxy)pyridin-2-yl)ethyl)propane-2-sulfinamide.
¹H-NMR (300 MHz, CDCl₃-DMSO-d₆) δ 8.43 (3H, brs), 7.60 (1H, d, J=8.8 Hz), 7.32 (1H, d, J=8.1 Hz), 4.91 (2H, q, J=8.8 Hz), 4.54 (1H, m), 2.48 (3H, s), 1.41 (3H, d, J=6.6 Hz).

Amine Intermediate-6

(R)-1-(6-(2-fluorobenzyloxy)pyridin-3-yl)ethanamine

Step-1

(R,E)-N-((6-(2-fluorobenzyloxy)pyridin-3-yl)methylene)-2-methylpropane-2-sulfinamide To a suspension of sodium hydride (640 mg, 16 mmol, 60%) in DMF (20 mL) was added (2-fluorophenyl)methanol (1.9 g, 15 mmol) at 0° C. After being stirred at room temperature for 30 min, 6-chloronicotinonitrile (2.6 g, 19 mmol) was added to the mixture. The mixture was stirred at room temperature for 14 hours. The mixture was poured into saturated ammonium chloride aqueous solution, and the aqueous phase was extracted with ethyl acetate (twice). The combined organic layers were dried over magnesium sulfate and concentrated in vacuo. The residue was purified by column chromatography on silica gel eluting with hexane/ethyl acetate (19:1 (v/v)) to give the intermediate. The intermediate was dissolved into dichloromethane (30 mL). DIBAL-H (6.3 mL, 6.4 mmol. 0.99 M) was added to the mixture at −78° C. After being stirred at −78° C. for 4 hours, methanol (2 mL) was added to the mixture. 1N hydrochloric acid (0.5 mL) was added to the mixture at room temperature. The mixture was stirred at room temperature for 1 hour. Sat. sodium bicarbonate aqueous solution was added to the mixture until the pH was neutralized. The organic layer was extracted with dichloromethane, dried over sodium sulfate and concentrated in vacuo. The residue was dissolved in dichloromethane (20 mL). Copper(II) sulfate (2.3 g, 14 mmol) followed by (R)-(+)-2-methyl-2-propanesulfinamide (700 mg, 5.8 mmol) were added to the mixture respectively and the mixture was stirred for 18 hours at room temperature. The reaction mixture was filtrated off through a pad of Celite and the filtrate was concentrated in vacuo. The residue was purified by column chromatography on silica gel eluting with hexane/ethyl acetate (4:1 (v/v)) to give 155 mg (3% yield) of the title compound as a white solid:
¹H-NMR (300 MHz, CDCl₃) δ 8.55-8.62 (2H, m), 8.14 (1H, dd, J=8.0 Hz), 7.30-7.53 (2H, m), 7.07-7.18 (1H, m), 6.89 (1H, d, J=8.8 Hz), 5.53 (2H, s), 1.26 (9H, s).

Step-2

(R)—N—((R)-1-(6-(2-fluorobenzyloxy)pyridin-3-yl)ethyl)-2-methylpropane-2-sulfinamide Prepared as in Step-4 of Amine intermediate-1 from (R,E)-N-((6-(2-fluorobenzyloxy)pyridin-3-yl)methylene)-2-methylpropane-2-sulfinamide.
¹H-NMR (300 MHz, CDCl₃) δ 7.51-7.58 (2H, m), 7.29-7.33 (1H, m), 7.06-7.18 (2H, m), 6.80 (1H, d, 8.0 Hz), 5.44 (2H, S), 4.55-4.59 (2H, m), 1.54 (3H, d, J=6.6 Hz), 1.20 (9H, s).

Step-3: (R)-1-(6-(2-(fluorobenzyloxy)pyridin-3-yl)ethanamine 2HCl Salt

Prepared as in Step-5 of Amine intermediate-1 from (R)—N—((R)-1-(6-(2-fluorobenzyloxy)pyridin-3-yl)ethyl)-2-methylpropane-2-sulfinamide.
1H-NMR (300 MHz, CDCl₃-DMSO-d₆) δ 8.60 (2H, brs), 8.31 (1H, d, J=3.0 Hz), 7.96 (1H, dd, J=2.2 Hz), 7.51-7.61 (1H, m), 7.38-7.45 (1H, m), 7.20-7.27 (2H, m), 6.76 (1H, d, J=8.0 Hz), 6.49 (2H, m), 5.41 (2H, s), 4.40-4.44 (1H, m), 1.53 (3H, d, J=7.3 Hz), LCMS (Method A) m/z: M+1 obs 247.3, tR=2.44 min.

Amine Intermediate-7

(R)-1-(5-((1-methylcyclopropyl)methoxy)pyridin-2-yl)ethanamine 2 HCl salt

Step-1:
2-methyl-5-((1-methylcyclopropyl)methoxy)pyridine

To a solution of 6-methylpyridin-3-ol (0.5 g, 4.6 mmol) in toluene (6 mL) was added (1-methylcyclopropyl)methanol (0.59 g, 6.9 mmol) and stirred under nitrogen atmosphere. The solution was added cyanomethylenetri-n-butylphosphorane (CMBP, 2.5 ml, 9.53 mmol) and stirred at 100° C. for 3 hours. The reaction mixture was evaporated. The residue was purified by column chromatography on silica gel eluting with hexane/ethyl acetate (2:1 (v/v)) to give 820 mg (quantitative yield) of the title compound as a brown oil:
¹H-NMR (300 MHz, CDCl₃) δ 8.18 (1H, d, J=2.9 Hz), 7.03-7.13 (2H, m), 3.74 (2H, s), 2.48 (3H, S) 1.24 (3H, s), 0.31-0.56 (4H, m), LCMS (Method A) m/z: M+1 obs 178.3, tR=2.54 min.

Step-2: (5-((1-methylcyclopropyl)methoxy)pyridin-2-yl)methanol

Prepared as in Step-2 of Amine intermediate-1 from 2-methyl-5-((1-methylcyclopropyl)methoxy)pyridine.

1H-NMR (300 MHz, CDCl$_3$) δ 8.24 (1H, d, J=1.4 Hz), 7.16-7.27 (2H, m), 4.70 (2H, s), 3.78 (2H, s), 2.83 (1H, brs), 1.25 (3H, s), 0.45-0.58 (4H, m), LCMS (Method A) m/z: M+1 obs 194.32, tR=2.37 min.

Step-3

(R,E)-2-methyl-N-((5-((1-methylcyclopropyl)methoxy)pyridin-2-yl)methylene)propane-2-sulfinamide Prepared as in Step-3 of Amine intermediate-1 from (5-((1-methylcyclopropyl)methoxy)pyridin-2-yl)methanol.

1H-NMR (300 MHz, CDCl$_3$) δ 8.64 (1H, s), 8.42 (1H, d, J=2.9 Hz), 7.96 (1H, d, J=8.8 Hz), 7.24 (1H, d, J=2.9 Hz), 3.85 (2H, s), 1.28 (9H, s), 1.24 (3H, s), 0.51-0.59 (4H, m), LCMS (Method A) m/z: M+1 obs 295.3, tR=3.14 min.

Step-4

(R)-2-methyl-N—((R)-1-(5-((1-methylcyclopropyl)methoxy)pyridin-2-yl)ethyl)propane-2-sulfinamide Prepared as in Step-4 of Amine intermediate-1 from (R,E)-2-methyl-N-((5-((1-methylcyclopropyl)methoxy)pyridin-2-yl)methylene)propane-2-sulfinamide.

$^1$H-NMR (300 MHz, CDCl$_3$) δ 8.23 (1H, d, J=2.2 Hz), 7.13-7.22 (2H, m), 4.52-4.56 (2H, m), 3.75 (2H, s), 1.49 (3H, d, J=6.6 Hz), 1.25 (9H, s), 1.23 (3H, s) 0.44-0.56 (4H, m), LCMS (Method A) m/z: M+1 obs 311.3, tR=2.95 min.

Step-5: (R)-1-(5-((1-methylcyclopropyl)methoxy)pyridin-2-yl)ethanamine 2 HCl salt Prepared as in Step-5 of Amine intermediate-1 from (R)-2-methyl-N—((R)-1-(5-((1-methylcyclopropyl)methoxy)pyridin-2-yl)ethyl)propane-2-sulfinamide.

$^1$H-NMR (300 MHz, CDCl$_3$-DMSO-d$_6$) δ 8.52 (2H, brs), 8.34 (1H, s), 7.52 (2H, s), 5.80 (2H, brs), 4.48 (1H, m), 3.88 (2H, s), 1.49 (3H, d, J=6.6 Hz), 1.19 (3H, s), 0.41-0.56 (4H, m), LCMS (Method A) m/z: M+1 obs 207.3, tR=2.07 min.

Amine Intermediate-8

3-(2,2,2-trifluoroethoxy)-5,6,7,8-tetrahydroquinolin-8-amine

Step-1: 3-(2,2,2-trifluoroethoxy)quinoline

Prepared as in Step-1 of Amine intermediate-4 from qunoilin-3-ol.

$^1$H-NMR (300 MHz, CDCl$_3$) δ 8.77 (1H, d, J=2.9 Hz), 8.08 (1H, d, J=8.0 Hz), 7.75 (1H, d, J=8.1 Hz), 7.67-7.50 (2H, m), 7.45 (1H, d, J=2.9 Hz), 4.50 (2H, q, J=8.0 Hz), LCMS (Method A) m/z: M+1 obs 228.3, tR=2.90 min.

Step-2: 3-(2,2,2-trifluoroethoxy)-5,6,7,8-tetrahydroquinoline

A mixture of 3-(2,2,2-trifluoroethoxy)quinoline (1.13 g, 5.0 mmol) and platinum (IV) oxide (50 mg) in TFA (8 mL) was stirred at room temperature for 12 hours under hydrogen atmosphere (1 atm). Then the mixture was filtered off through a pad of Celite, and the filtrate was concentrated in vacuo. The residue was purified by column chromatography on silica gel eluting with hexane/ethyl acetate (1.0:1-7:1) to give 495 mg (43% yield) of the title compound as a colorless oil:

$^1$H-NMR (300 MHz, CDCl$_3$) δ 8.12 (1H, d, J=2.9 Hz), 6.96 (1H, d, J=2.9 Hz), 4.36 (2H, q, J=8.1 Hz), 2.87 (2H, t, J=6.6 Hz), 2.77 (2H, t, J=6.6 Hz), 1.93-1.75 (4H, m), LCMS (Method A) m/z: M+1 obs 232.3, tR=2.84 min.

Step-3: 3-(2,2,2-trifluoroethoxy)-5,6,7,8-tetrahydroquinoline 1-oxide

A mixture of 3-(2,2,2-trifluoroethoxy)-5,6,7,8-tetrahydroquinoline (495 mg, 2.1 mmol) and 3-chloroperbenzoic acid (ca 75%, 739 mg, 3.2 mmol) in dichloromethane (10 mL) was stirred at room temperature for 1.5 hour. Then, the mixture was poured into saturated sodium bicarbonate aqueous solution (50 mL), and the aqueous phase was extracted with dichloromethane. The organic layer was dried over magnesium sulfate and concentrated in vacuo to give 740 mg of the crude title compound. This was used for the next step without further purification:

LCMS (Method A) m/z: M+1 obs 248.3, tR=2.52 min.

Step-4: 3-(2,2,2-trifluoroethoxy)-5,6,7,8-tetrahydroquinolin-8-ol

A mixture of 3-(2,2,2-trifluoroethoxy)-5,6,7,8-tetrahydroquinoline 1-oxide (530 mg, 2.1 mmol) and acetic anhydride (3 mL) was stirred at 100° C. for 2 hours. After cooling to room temperature, acetic anhydride was removed in vacuo. To the residue, methanol (5 mL) and potassium carbonate (1.77 g, 13 mmol) were added, and the mixture was stirred at room temperature for 20 hours. Then, methanol was evaporated in vacuo. To the residue was added ethyl acetate, and the mixture was filtered through a pad of Celite. The filtrate was concentrated in vacuo. The residue was purified by column chromatography on silica gel eluting with hexane/ethyl acetate. (1:1-1:2) to give 193 mg (36% yield) of the title compound as a white solid:

$^1$H-NMR (300 MHz, CDCl$_3$) δ 8.17 (1H, d, J=2.9 Hz), 7.00 (1H, d, J=2.9 Hz), 4.69 (1H, brt, J=5.9 Hz), 4.38 (2H, q, J=8.1 Hz), 3.64 (1H, s), 2.85-2.75 (2H, m), 2.31-2.20 (1H, m), 2.05-1.94 (1H, m), 1.88-1.75 (2H, m), LCMS (Method A) m/z: M+1 obs 248.2, tR=2.52 min.

Step-5: 3-(2,2,2-trifluoroethoxy)-6,7-dihydroquinolin-8(5H)-one

A mixture of 3-(2,2,2-trifluoroethoxy)-5,6,7,8-tetrahydroquinolin-8-ol (193 mg, 0.78 mmol) and manganese (IV) oxide (543 mg, 6.3 mmol) in dichloromethane (10 mL) was stirred at room temperature for 3 hours. Then, the mixture was filtered through a pad of Celite, and the filtrate was concentrated in vacuo. The residual solid was washed with diethyl ether to give 155 mg (81% yield) of the title compound as a pale yellow solid:

$^1$H-NMR (300 MHz, CDCl$_3$) δ 8.44 (1H, d, J=2.9 Hz), 7.11 (1H, d, J=2.9 Hz), 4.48 (2H, q, J=8.1 Hz), 3.03 (2H, t, J=5.9 Hz), 2.79 (2H, t, J=5.9 Hz), 2.20 (2H, quintet, J=5.9 Hz), LCMS (Method A) m/z: M+1 obs 246.3, tR=2.48 min.

Step-6: 3-(2,2,2-trifluoroethoxy)-6,7-dihydroquinolin-8(5H)-one oxime

A mixture of 3-(2,2,2-trifluoroethoxy)-6,7-dihydroquinolin-8(5H)-one (155 mg, 0.63 mmol), hydroxylamine hydrochloride (88 mg, 1.3 mmol), and sodium acetate (104 mg, 1.3 mmol) in ethanol-water (3:1, 4 mL) was refluxed with stirring for 2 hours. After cooling to room temperature, the mixture was poured into water, and the aqueous layer was extracted with dichloromethane (twice). The combined organic layers were dried over Magnesium sulfate and concentrated in vacuo to give 167 mg of the crude title compound as a brown solid. This was used for the next step without purification:

$^1$H-NMR (300 MHz, DMSO-$d_6$): δ 8.25 (1H, d, J=2.9 Hz), 7.37 (1H, d, J=2.9 Hz), 4.88 (2H, q, J=8.8 Hz), 2.79-2.68 (2H, m), 1.95-1.75 (4H, m) (a signal due to OH was not observed), LCMS (Method A) m/z: M+1 obs 261.3, tR=2.62 min.

Step-7: 3-(2,2,2-trifluoroethoxy)-5,6,7,8-tetrahydroquinolin-8-amine

A mixture of 3-(2,2,2-trifluoroethoxy)-6,7-dihydroquinolin-8(5H)-one oxime (167 mg) and 10% palladium on carbon (100 mg) in methanol (7 ml) was stirred at room temperature for 24 h under hydrogen atmosphere (4 atm). Then, the mixture was filtered through a pad of Celite, and the filtrate was concentrated in vacuo. The residue was purified by column chromatography on NH-gel eluting with hexane/ethyl acetate (1:1-0:1) to give 68 mg (43% yield) of the title compound as a pale brown oil:

$^1$H-NMR (300 MHz, CDCl$_3$): δ 8.18 (1H, s), 7.96 (1H, s), 4.37 (2H, q, J=8.1 Hz), 4.03-3.95 (1H, m), 2.90-2.68 (2H, m), 2.24-2.13 (1H, m), 2.03-1.90 (1H, m), 1.85-1.66 (2H, m) (a signals due to NH2 were not observed), LCMS (Method A) m/z: M+1 obs 247.3, tR=2.14 min.

Amine Intermediate-9

(R)-1-(3-fluoro-5-(2,2,2-trifluoroethoxy)pyridin-2-yl)ethanamine 2 HCl salt

Step-1:
3-fluoro-5-(2,2,2-trifluoroethoxy)picolinonitrile

60% sodium hydride (0.219 g, 5.71 mmol) was added to a solution of 2,2,2-trifluoroethanol (0.257 ml, 3.57 mmol) in N,N,N',N',N",N"-hexamethylphosphoric triamide (6 ml) at 0° C. and stirred for 1 hour. Then 3,5-difluoropicolinonitrile (1.0 g, 7.1 mmol) in N,N,N',N',N",N"-hexamethylphosphoric triamide (4 mL) was added to the reaction mixture and stirred at room temperature for 20 hours. Then 2,2,2-trifluoroethanol (0.257 ml, 3.57 mmol) and 60% sodium hydride (0.22 g, 5.7 mmol) were added to the reaction mixture and stirred at room temperature for 3 hours. After reaction, the mixture was poured into water, and the aqueous phase was extracted with ethyl acetate. The organic layer was dried over magnesium sulfate and concentrated in vacuo. The residue was purified by column chromatography on silica gel eluting with hexane/ethyl acetate (6:1-4:1) to give 398 mg (25% yield) of the title compound as a oily solution:

$^1$H-NMR (300 MHz, CDCl$_3$) δ 8.31 (1H, d, J=2.6 Hz), 7.15 (1H, dd, J=9.5, 2.6 Hz), 4.50 (2H, q, J=7.7 Hz).

Step-2

(R,E)-N-((3-fluoro-5-(2,2,2-trifluoroethoxy)pyridin-2-yl)methylene)-2-methylpropane-2-sulfinamide Prepared as in Step-2 of Amine intermediate-3 from 3-fluoro-5-(2,2,2-trifluoroethoxy)picolinonitrile.

$^1$H-NMR (300 MHz, CDCl$_3$) δ 8.83 (1H, S) 8.39 (1H, d, J=2.2 Hz), 7.11 (1H, dd, J=2.2 Hz), 4.89 (2H, q, J=7.4 Hz), 1.30 (9H, s), LCMS (Method A) m/z: M+1 obs 327.2, tR=2.94 min.

Step-3

(R)—N—((R)-1-(3-fluoro-5-(2,2,2-trifluoroethoxy)pyridin-2-yl)ethyl)-2-methylpropane-2-sulfinamide Prepared as in Step-4 of Amine intermediate-1 from (R,E)-N-((3-fluoro-5-(2,2,2-trifluoroethoxy)pyridin-2-yl)methylene)-2-methylpropane-2-sulfinamide.

$^1$H-NMR (300 MHz, CDCl$_3$) δ 8.14 (1H, s), 7.02 (1H, dd, J=1.5, 2.2 Hz), 4.70-4.88 (2H, m), 4.38 (2H, q, J=6.6 Hz), 1.45 (3H, d, J=6.6 Hz), 1.25 (9H, s), LCMS (Method A) m/z: M+1 obs 343.2, tR=2.92 min.

Step-4: (R)-1-(3-fluoro)-5-(2,2,2-trifluoroethoxy)pyridin-2-yl)ethanamine 2HCl salt Prepared as in Step-5 of Amine intermediate-1 from (R)—N—((R)-1-(3-fluoro-5-(2,2,2-trifluoroethoxy)pyridin-2-yl)ethyl)-2-methylpropane-2-sulfinamide.

LCMS (Method A) m/z: M+1 obs 222.3, tR=2.00 min.

Amine Intermediate-10

(R)-1-(3-methyl-5-(2,2,2-trifluoroethoxy)pyridin-2-yl)ethanamine dihydrochloride Step-1:
3-methyl-5-(2,2,2-trifluoroethoxy)picolinonitrile Prepared as in Step-1 of Amine intermediate-4 from commercially available 5-hydroxy-3-methylpicolinonitrile:

$^1$H-NMR (300 MHz, CDCl$_3$) δ 8.28 (1H, d, J=2.9 Hz), 7.18 (1H, d, J=2.9 Hz), 4.46 (2H, q, J=7.4 Hz), 2.58 (3H, s), LCMS (Method A) m/z: M+1 obs 217.3, tR=2.79 min.

Step-2

(R,E)-2-methyl-N-((3-methyl-5-(2,2,2-trifluoroethoxy)ethoxy)pyridin-2-yl)methylene)propane-2-sulfinamide Prepared as in Step-2 of Amine intermediate-3 from 3-methyl-5-(2,2,2-trifluoroethoxy)picolinonitrile.

LCMS (Method A) m/z: M+1 obs 323.3, tR=3.02 min.

Step-3

(R)-2-methyl-N—((R)-1-(3-methyl-5-(2,2,2-trifluoroethoxy)pyridin-2-yl)ethyl)propane-2-sulfinamide Prepared as in Step-4 of Amine intermediate-1 from (R,E)-2-methyl-N-((3-methyl-5-(2,2,2-trifluoroethoxy)-2-yl)methylene)propane-2-sulfinamide:

$^1$H-NMR (270 MHz, CDCl$_3$) δ 8.13 (1H, d, J==3.3 Hz), 7.05 (1H, d, J=3.3 Hz), 4.88 (1H, d, J=7.2 Hz), 4.89 (1H, quintet, J=6.5 Hz), 4.38 (2H, q, J=7.9 Hz), 2.38 (3H, s), 1.39 (3H, d, J=6.6 Hz), 1.25 (9H, s), LCMS (Method A) m/z: M+1 obs 339.3, tR=2.95 min.

Step-4: (R)-1-(3-methyl-5-(2,2,2-trifluoroethoxy) pyridin-2-yl)ethanamine dihydrochloride Prepared as in Step-5 of Amine intermediate-1 from (R)-2-methyl-N—((R)-1-(3-methyl-5-(2,2,2-trifluoroethoxy)pyridin-2-yl)ethyl)propane-2-sulfinamide:

LCMS (Method A) m/z: M+1 obs 235.3, tR=2.20 min.

Amine Intermediate-11

(S)-1-(5-(2,2,2-trifluoroethoxy)pyridin-2-yl)ethanamine dihydrochloride

The title compound was prepared according to the similar procedure for (R)-isomer using (S)-(−)-2-methyl-2-propanesulfinamide:

$[\alpha]_D^{22}$ −16.7° (c=1.61, MeOH).

Carboxylic Acid Intermediate-1

1-methyl-6-(trifluoromethyl)-1H-indazole-3-carboxylic acid

Step-1: methyl 1-methyl-6-(trifluoromethyl)-1H-indazole-3-carboxylate

To an acetonitrile (5 ml) solution of methyl 6-(trifluoromethyl)-1H-indazole-3-carboxylate (300 mg, 1.2 mmol) were added potassium carbonate (1.0 g, 7.4 mmol) and iodomethane (350 mg, 2.5 mmol) at room temperature respectively. The mixture was stirred at room temperature for 4 hours. The solid was removed by filtration and washed with acetonitrile. The filtrate was concentrated in vacuo. After being filtered off, the filtrate was concentrated under reduced pressure, the residue was applied to a silica gel chromatography column and eluted with a hexane/ethyl acetate=4/1 to furnish 239 mg (75% yield, major product) of the title as a white solid:

$^1$H-NMR (300 MHz, CDCl$_3$) δ 8.36 (1H, d, J=8.0 Hz), 7.79 (1H, s), 7.55 (1H, d, J=8.0 Hz), 4.24 (3H, s), 4.06 (3H, s), LCMS (Method A) m/z: M+1 obs 259.1; tR=3.15 min.

Step-2: 1-methyl-6-(trifluoromethyl)-1H-indazole-3-carboxylic acid

To a tetrahydrofuran (2 mL) of methyl 1-methyl-6-(trifluoromethyl)-1H-indazole-3-carboxylate (50 mg, 0.19 mmol) was added 2N sodium hydroxide (0.2 ml, 4.0 mmol) at room temperature. The mixture was refluxed at 90° C. with stirring for 3 hours. After being cooled to room temperature, 2N hydrochloric acid was added to the mixture until pH became 4.0. The organic layer was extracted with ethyl acetate, washed with brine, and dried over magnesium sulfate. After the filtration to separate solvent and magnesium sulfate, the solvent was removed under reduced pressure to give 47 mg (quantitative yield) of the title as a white solid that was used in the next step without further purification.

LCMS (Method A) m/z: M+1 obs 245.0; tR=2.57 min.

Carboxylic Acid Intermediate-2

2-methyl-6-(trifluoromethyl-2H-indazole-3-carboxylic acid

Step-1: methyl 2-methyl-6-(trifluoromethyl)-2H-indazole-3-carboxylate

Prepared as in Step 1 of Carboxylic acid intermediate-1 as a minor product.

$^1$H-NMR (300 MHz, CDCl$_3$) δ 8.13 (1H, d, J=8.8 Hz), 8.10 (1H, S), 7.45 (1H, d, J=8.8 Hz), 4.56 (3H, s), 4.06 (3H, s), LCMS (Method A) m/z. M+1 obs 259.1, tR=2.99 min.

Step-2: 2-methyl-6-(trifluoromethyl)-2H-indazole-3-carboxylic acid

Prepared as in Step 2 of Carboxylic acid intermediate-1 from methyl 2-methyl-6-(trifluoromethyl)-2H-indazole-3-carboxylate.

LCMS (Method A) m/z: M+1 obs 245.0, tR=2.52 min.

Carboxylic Acid Intermediate-3

1-methyl-6-(trifluoromethyl)-1H-indole-2-carboxylic acid

Step-1: ethyl 1-methyl-6-(trifluoromethyl)-1H-indole-2-carboxylate

A mixture of ethyl 6-(trifluoromethyl)-1H-indole-2-carboxylate (100 mg, 0.39 mmol), iodomethane (36 microL, 0.58 mmol), and potassium carbonate (1.34 mg, 0.97 mmol) in DMF was stirred at room temperature for 7 hours. Then, the mixture was poured into water, and the aqueous layer was extracted with dichloromethane (three times). The combined organic layers were dried over magnesium sulfate and concentrated in vacuo. The residue was purified by column chromatography on silica gel eluting with hexane/ethyl acetate (20:1-10:1) to give 95.3 mg (90% yield) of the title compound as a white solid:

$^1$H-NMR (300 MHz, CDCl$_3$) δ 7.98 (1H, s), 7.56 (1H, d, J=8.8 Hz), 7.47 (1H, d, J=8.8 Hz), 7.37 (1H, s), 4.40 (2H, q, J=7.4 Hz), 4.11 (3H, s), 1.43 (3H, t, J=7.4 Hz), LCMS (Method A) m/z: M+1 obs 272.1, tR=3.45 min.

Step-2: 1-methyl-6-(trifluoromethyl)-1H-indole-2-carboxylic acid

A mixture of ethyl 1-methyl-6-(trifluoromethyl)-1H-indole-2-carboxylate (90 mg, 0.33 mmol) and 2 mol/L aqueous sodium hydroxide solution (0.42 mL, 0.83 mmol) in methanol (2 mL) was stirred at room temperature for 2 hours. Then, 2 mol/L hydrochloric acid was added, and the formed precipitate was collected by filtration to give 75.6 mg (94% yield) of the title compound as a white solid:

$^1$H-NMR (300 MHz, DMSO-d$_6$) δ 13.23 (1H, br), 8.12 (1H, s), 7.80 (1H, d, J=8.8 Hz), 7.60 (1H, d, J=8.8 Hz), 7.39 (1H, S), 4.08 (3H, s), LCMS (Method A) m/z: M−1 obs 242.1, tR=2.88 min.

Carboxylic Acid Intermediate-4

1-methyl-6-(trifluoromethyl)-1H-indole-3-carboxylic acid

Step-1: 2,2,2-trifluoro-1-[6-(trifluoromethyl)-1H-indol-3-yl]ethanone

To a solution of 6-(trifluoromethyl)-1H-indole (460 mg, 2.5 mmol) in tetrahydrofuran (5 mL) was added trifluoroacetic anhydride (0.52 mL, 3.7 mmol) at 0° C., and the resulting mixture was stirred at the same temperature for 1 hour and at room temperature for 1 hour. Then, the mixture was poured into water, and the formed precipitate was collected by filtration to give 583 mg (83% yield) of the title compound as a pale brown solid:
$^1$H-NMR (300 MHz, DMSO-$d_6$) δ 13.04 (1H, br), 8.72 (1H, s), 8.37 (1H, d, J=8.8 Hz), 7.93 (1H, s), 7.66 (1H, d, J=8.1 Hz), LCMS (Method A) m/z: M−1 obs 280.0, tR=3.20 min.

Step-2: 2,2,2-trifluoro-1-(1-methyl-6-(trifluoromethyl)-1H-indol-3-yl)ethanone

To a mixture of 2,2,2-trifluoro-1-[6-trifluoromethyl)-1H-indol-3-yl]ethanone (200 mg, 0.71 mmol) and potassium carbonate (246 mg, 1.8 mmol) in DMF (2 mL) was added iodomethane (0.067 mL, 1.1 mmol) at room temperature. After stirring at the same temperature for 2 hours, the mixture was poured into water, and the aqueous phase was extracted with EtOAc (ethyl acetate)-hexane (2:1, twice). The combined organic layers were dried over magnesium sulfate and concentrated in vacuo. The residue was purified by column chromatography on silica gel eluting with hexane/ethyl acetate (4:1 (v/v)) to give 195 mg (93% yield) of the title compound as a pale brown solid:
$^1$H-NMR (300 MHz, CDCl$_3$) δ 8.51 (1H, d, J=8.0 Hz), 8.04 (1H, s), 7.70 (1H, s), 7.64 (1H, d, J=8.1 Hz), 3.99 (3H, s), LCMS (Method A) m/z: M+1 obs 296.0, tR=3.32 min.

Step-3: 1-methyl-6-(trifluoromethyl)-1H-indole-3-carboxylic acid

A mixture of 2,2,2-trifluoro-1-(1-methyl-6-(trifluoromethyl)-1H-indol-3-yl)ethanone (195 mg, 0.66 mmol) and 20% aqueous sodium hydroxide solution (5 mL) was refluxed with stirring for 10 hours. After cooling to room temperature, the mixture was poured into 1 M hydrochloric acid, and the aqueous phase was extracted with ethyl acetate (twice). The combined organic layers were dried over magnesium sulfate and concentrated in vacuo. The residual solid was washed with 2-propanol to give 107 mg (67% yield) of the title compound as a pale orange solid:
$^1$H-NMR (300 MHz, DMSO-$d_6$) δ 12.25 (1H, S), 8.26 (1H, S), 8.18 (1H, d, J=8.8 Hz), 7.98 (1H, s), 7.50 (1H, d, J=8.6 Hz), 3.94 (3H, s), LCMS (Method A) m/z: M−1 obs 242.1, tR=2.84 min.

Carboxylic Acid Intermediate-5

5-(2,2,2-trifluoroethoxy)picolinic acid

Step-1: ethyl 5-(2,2,2-trifluoroethoxy)picolinate

Prepared as in Step-1 of Amine intermediate-4 from ethyl 5-hydroxypicolinate (EP1748048):
$^1$H-NMR (300 MHz, CDCl$_3$) δ 8.47 (1H, d, J=2.9 Hz), 8.15 (1H, d, J=8.8 Hz), 7.32 (1H, dd, J=2.9 & 8.8 Hz), 4.52-5.52 (4H, m), 1.44 (3H, t, J=7.2 Hz), LCMS (Method A) m/z: M+1 obs 250.3, tR=2.72 min.

Step-2: 5-(2,2,2-trifluoroethoxy)picolinic acid

A mixture of ethyl 5-(2,2,2-trifluoroethoxy)picolinate (253 mg, 1.0 mmol) and 2 mol/L aqueous sodium hydroxide solution (1.0 mL, 2.0 mmol) in methanol (5 mL) was stirred at room temperature for 4 h. Then, methanol was removed in vacuo. To the residue were added water (2 mL) and 2 mol/L hydrochloric acid (pH~4). The formed precipitate was collected by filtration to give 118 mg (52% yield) of the title compound as a gray solid:
$^1$H-NMR (300 MHz, CDCl$_3$) δ 8.49 (1H, d, J=2.9 Hz), 8.06 (1H, d, J=8.8 Hz), 7.66 (1H, dd, J=2.9 & 8.8 Hz), 4.99 (2H, q, J=8.8 Hz) (a signal due to COOH was not observed), LCMS (Method A) m/z: M+1 obs 222.3, tR=1.59 min.

Carboxylic Acid Intermediate-6 trans-2-(1-methyl-1H-indol-3-yl)cyclopropanecarboxylic acid

Step-1: ethyl trans-2-(1-methyl-1H-indol-3-yl)cyclopropanecarboxylate

To a suspension of sodium hydride (ca 60%, 21 mg, 0.52 mmol) in DMSO (1 mL) was added trimethylsulfoxonium iodide (115 mg, 0.52 mmol), and the mixture was stirred at room temperature for 20 minutes. Then, ethyl (E)-3-(1-methyl-1H-indol-3-yl)acrylate (Synlett, (9), 1319-1322 (2006)) (100 mg, 0.44 mmol) was added to the mixture, and the mixture was stirred at room temperature for 1 hour and at 60° C. for 20 hours. After cooling to room temperature, the mixture was poured into water (30 mL), and the aqueous phase was extracted with ethyl acetate (twice). The combined organic layers were dried over Magnesium sulfate and concentrated in vacuo. The residue was purified by column chromatography on silica gel eluting with hexane/ethyl acetate (7:1) to give 23 mg (21% yield) of the title compound as a pale yellow oil:
$^1$H-NMR (300 MHz, CDCl$_3$) δ 7.65 (1H, d, J=8.0 Hz), 7.30-7.19 (2H, m), 7.16-7.07 (1H, m), 6.79 (1H, s), 4.20 (2H, q, J=8.0 Hz), 3.71 (3H, S), 2.65-2.55 (1H, m), 1.91-1.82 (1H, m), 1.61-1.51 (1H, m), 1.30 (3H, t, J=8.0 Hz), 1.35-1.25 (1H, m), LCMS (Method A) m/z: M+1 obs 244.4, tR=3.22 min.

Step-2: trans-2-(1-methyl-1H-indol-3-yl)cyclopropanecarboxylic acid

A mixture of ethyl trans-2-(1-methyl-1H-indol-3-yl)cyclopropanecarboxylate (20 mg, 0.082 mmol) and 2 mol/L aqueous sodium hydroxide solution (0.20 mL, 0.40 mmol) in methanol (3 mL) was stirred at 60° C. for 3 hours. After cooling to room temperature, 2 mol/L hydrochloric acid (0.20 mL, 0.40 mmol) was added, and the solvent was removed in vacuo. To the residue was added THF (2 mL) and filtered off. The filtrate was concentrated in vacuo to give 25 mg of the title compound as a pale yellow oil. This was used for the next step without purification:
$^1$H-NMR (300 MHz, CDCl$_3$) δ 7.68 (1H, d, J=8.8 Hz), 7.31-7.20 (2H, m), 7.18-7.09 (1H, m), 6.82 (1H, s), 3.73

(3H, s), 2.75-2.64 (1H, m), 1.90-1.80 (1H, m), 1.69-1.60 (1H, m), 1.45-1.35 (1H, m), LCMS (Method A) m/z: M+1 obs 216.4, tR=2.72 min.

Carboxylic Acid Intermediate-7 trans-2-(7-fluoro-1H-indol-3-yl)cyclopropanecarboxylic acid

Step-1: ethyl (E)-3-(7-fluoro-1-tosyl-1H-indol-3-yl)acrylate

To a suspension of sodium hydride (ca 60%, 240 mg, 6.3 mmol) in THF (10 mL) was added dropwise a solution of triethyl phosphonoacetate (1.33 g, 5.9 mmol) in THF (5 mL) at 0° C. After stirring at room temperature for 0.5 hour, a solution of 7-fluoro-1-tosyl-1H-indole-3-carbaldehyde (J. Med. Chem., 48 (19), 6023-6034 (2005)) (1.10 g, 3.48 mmol) in THF (5 mL) was added to the mixture at 0° C. The resulting mixture was stirred at 0° C. for 0.5 hour and at room temperature for 19 hours. The mixture was poured into water, extracted with dichloromethane, dried over sodium sulfate, filtered and concentrated in vacuo. The residual solid was washed with ethyl acetate to give 864 mg (65% yield) of the title compound as a white solid:
$^1$H-NMR (270 MHz, CDCl$_3$) δ 8.03 (1H, s), 7.85-7.75 (3H, m), 7.57 (1H, d, J=7.6 Hz), 7.31-7.15 (3H, m), 6.99 (1H, dd, J=8.2 & 12.2 Hz), 6.50 (1H, d, J=16.1 Hz), 4.27 (2H, q, J=7.2 Hz), 2.37 (3H, s), 1.33 (3H, t, J=7.2 Hz).

Step-2: ethyl trans-2-(7-fluoro-1-tosyl-1H-indol-3-yl)cyclopropanecarboxylate

Prepared as in Step-1 of Carboxylic acid intermediate-6 from ethyl (E)-3-(7-fluoro-1-tosyl-1H-indol-3-yl)acrylate:
$^1$H-NMR (720 MHz, CDCl$_3$) δ 7.78 (2H, d, J=7.6 Hz), 7.45 (1H, s), 7.34 (1H, d, J=6.9 Hz), 7.28-7.22 (2H, m), 7.13 (1H, dt, J=4.3 & 7.9 Hz), 6.94 (1H, dd, J=7.9 & 12.2 Hz), 4.19 (2H, q, J=7.3 Hz), 2.51-2.42 (1H, m), 2.36 (3H, s), 1.92-1.84 (1H, m), 1.61-1.52 (1H, m), 1.30 (3H, t, J=7.3 Hz), 1.33-1.20 (1H, m).

Step-3: trans-2-(7-fluoro-1H-indol-3-yl)cyclopropanecarboxylic acid

Prepared as in Step-2 of Carboxylic acid intermediate-6 from ethyl trans-2-(7-fluoro-1-tosyl-1H-indol-3-yl)cyclopropanecarboxylate:
$^1$H-NMR (300 MHz, CDCl$_3$) δ 8.16 (1H, brs), 7.44 (1H, d, J=8.0 Hz), 7.1-6.8 (3H, m), 2.71-2.59 (1H, m), 1.95-1.85 (1H, m), 1.70-1.60 (1H, m), 1.48-1.35 (1H, m) (a signal due to COOH was not observed), LCMS (Method A) m/z: M+1 obs 220.3, tR=2.57 min.

Carboxylic Acid Intermediate-8 trans-2-(5-fluoro-1H-indol-3-yl)cyclopropanecarboxylic acid

Step-1: ethyl(E)-3-(5-fluoro-1-tosyl-1H-indol-3-yl)acrylate

Prepared as in Step-1 of Carboxylic acid intermediate-7 from 5-fluoro-1-tosyl-1H-indole-3-carbaldehyde (J. Med. Chem., 41 (25), 4995-5001 (1998)):
$^1$H-NMR (270 MHz, CDCl$_3$): δ 7.95 (1H, dd, J=4.6 & 9.2 Hz), 7.88 (1H, s), 7.79-7.68 (3H, m), 7.44 (1H, dd, J=2.6 & 8.6 Hz), 7.29-7.24 (2H, m), 7.11 (1H, dt, J=2.6 & 8.6 Hz), 6.43 (1H, d, J=16.5 Hz), 4.27 (2H, q, J=7.2 Hz), 2.37 (3H, s), 1.35 (3H, t, J=7.2 Hz), LCMS (Method A) m/z: M+1 obs 388.2, tR=3.52 min.

Step-2: ethyl trans-2-(5-fluoro-1-tosyl-1H-indol-3-yl)cyclopropanecarboxylate

Prepared as in Step-1 of Carboxylic acid intermediate-6 from ethyl(E)-3-(5-fluoro-1-tosyl-1H-indol-3-yl)acrylate:
$^1$H-NMR (300 MHz, CDCl$_3$): δ 7.93-7.86 (1H, m), 7.71 (2H, d, J=9.5 Hz), 7.30-7.17 (4H, m), 7.09-7.00 (1H, m), 4.20 (2H, q, J=7.3 Hz), 2.46-2.35 (1H, m), 2.35 (3H, s), 1.88-1.80 (1H, m), 1.63-1.55 (1H, m), 1.31 (3H, t, J=7.3 Hz), 1.30-1.20 (1H, m), LCMS (Method A) m/z: M+1 obs 402.3, tR=3.54 min.

Step-3: trans-2-(5-fluoro-1H-indol-3-yl)cyclopropanecarboxylic acid

Prepared as in Step-2 of Carboxylic acid intermediate-6 from ethyl trans-2-(5-fluoro-1-tosyl-1H-indol-3-yl)cyclopropanecarboxylate:
$^1$H-NMR (300 MHz, DMSO-d$_6$): δ 11.00 (1H, brs), 7.36-7.22 (3H, m), 6.98-6.88 (1H, m), 2.43-2.33 (1H, m), 1.75-1.67 (1H, m), 1.42-1.28 (2H, m) (a signal due to COOH was not observed), LCMS (Method A) m/z: M+1 obs 220.3, tR=2.59 min.

Carboxylic Acid Intermediate-9 trans-2-(1H-indol-6-yl)cyclopropanecarboxylic acid

Step-1: ethyl(E)-3-(1-tosyl-1H-indol-6-yl)acrylate

Prepared as in Step-1 of Carboxylic acid intermediate 7 from 1-tosyl-1H-indole-6-carbaldehyde.
$^1$H-NMR (300 MHz, CDCl$_3$): δ 8.13 (1H, S), 7.90-7.75 (3H, m), 7.62 (1H, d, J=3.7 Hz), 7.52 (1H, d, J=8.8 Hz), 7.43 (1H, d, J=8.8 Hz), 7.24 (2H, d, J=8.1 Hz), 6.66 (1H, d, J=3.7 Hz), 6.49 (1H d, J=16.1 Hz), 4.29 (2H, q, J=7.3 Hz), 2.35 (3H, s), 1.37 (3H, t, J=7.3 Hz), LCMS (Method A) m/z: M+1 obs 370.2, tR=3.44 min.

Step-2: ethyl trans-2-(1-tosyl-1H-indol-6-yl)cyclopropanecarboxylate

Prepared as in Step-1 of Carboxylic acid intermediate-6 from ethyl(E)-3-(1-tosyl-1H-indol-6-yl)acrylate.
$^1$H-NMR (300 MHz, CDCl$_3$): δ 7.76 (2H, d, J=8.1 Hz), 7.76 (1H, s), 7.53 (1H, d, J=3.7 Hz), 7.43 (1H, d, J=8.1 Hz), 7.25 (2H, d, J=8.1 Hz), 6.97 (1H, dd, J=8.1, 1.5 Hz), 6.62 (1H, d, J=3.7 Hz), 4.21 (2H, q, 7.3 Hz), 2.67 (1H, m), 2.37 (3H, s), 1.95 (1H, m), 1.67 (1H, m), 1.39 (1H, m), 1.32 (3H, t, J=7.3 Hz), LCMS (Method A) m/z: M+1 obs 384, tR=3.44 min.

Step-3: trans-2-(1H-indol-6-yl)cyclopropanecarboxylic acid

Prepared as in Step-2 of Carboxylic acid intermediate-6 from ethyl trans-2-(1-tosyl-1H-indol-6-yl) cyclopropanecarboxylate.
$^1$H-NMR (300 MHz, DMSO-d$_6$): δ 11.00 (1H, s), 7.44 (1H, d, J=8.0 Hz), 7.29 (1H, t, J=2.2 Hz), 7.18 (1H, s), 6.79

(1H, d, J=8.1 Hz), 6.37 (1H, m), 2.50 (1H, m), 1.78 (1H, m), 1.48-1.30 (2H, m), LCMS (Method A) m/z: M−1 obs 200.3, tR=2.52 min.

Carboxylic Acid Intermediate-10 trans-2-(5-cyano-1H-indol-3-yl)cyclopropanecarboxylic acid

Step-1: ethyl(E)-3-(5-cyano-1-tosyl-1H-indol-3-yl)acrylate

Prepared as in Step-1 of Carboxylic acid intermediate 7 from 3-formyl-1-tosyl-1H-indole-5-carbonitrile.
$^1$H-NMR (300 MHz, CDCl$_3$): δ 8.14 (1H, s), 8.11 (1H, d, J=8.8 Hz), 7.94 (1H, s), 7.81 (2H, d, J=8.1 Hz), 7.74 (1H, d, J=16.1 Hz), 7.63 (1H, dd, J=8.8, 1.5 Hz), 7.30 (2H, d, J=8.0 Hz), 6.49 (1H, d, J=16.1 Hz), 4.29 (2H, q, J=6.6 Hz), 2.39 (3H, s), 1.36 (3H, t, J=6.6 Hz), LCMS (Method A) m/z: M+1 obs 395.2, tR=3.40 min.

Step-2: trans-2-(5-cyano-1H-indol-3-yl)cyclopropanecarboxylic acid

Prepared as in Step-1 of Carboxylic acid intermediate 6 and in Step-2 of Carboxylic acid intermediate 6 from ethyl(E)-3-(5-cyano-1-tosyl-1H-indol-3-yl)acrylate. LCMS (Method A) m/z: M+1 obs 227.3, tR=2.39 min.

Carboxylic Acid Intermediate-11 trans-2-(1H-indol-7-yl)cyclopropanecarboxylic acid

Step-1: 1-tosyl-1H-indole-7-carbaldehyde

To a suspension of sodium hydride (240 mg, 5.9 mmol) in THF (10 mL) was added 1H-indole-7-carbaldehyde (570 mg, 3.9 mmol) at room temperature. After being stirred at room temperature for 20 min, 4-methylbenzene-1-sulfonyl chloride (1.1 g, 5.9 mmol) was added to the mixture. The mixture was stirred at room temperature for 1 hour. The mixture was poured into saturated ammonium chloride aqueous solution, and the aqueous phase was extracted with ethyl acetate (twice). The combined organic layers were dried over magnesium sulfate and concentrated in vacuo. The residue was purified by column chromatography on silica gel eluting with hexane/ethyl acetate (4:1 (v/v)) to give 1.0 g (89% yield) of the title compound as a white solid:
$^1$H-NMR (300 MHz, CDCl$_3$): δ 10.73 (1H, s), 7.82 (1H, d, J=8.8 Hz), 7.75-7.65 (2H, m), 7.47 (2H, d, J=8.8 Hz), 7.38 (1H, t, J=8.3 Hz), 7.17 (2H, d, J=8.8 Hz), 6.79 (1H, d, J=3.7 Hz), 2.34 (3H, s), LCMS (Method A) m/z: M+1 obs 300.2, tR=3.15 min.

Step-2: ethyl(E)-3-(1-tosyl-1H-indol-7-yl)acrylate

Prepared as in Step-1 of Carboxylic acid intermediate 7 from 1-tosyl-1H-indole-7-carbaldehyde.
$^1$H-NMR (300 MHz, CDCl$_3$): δ 8.64 (1H, d, J=15.4 Hz), 7.84 (1H, d, J=3.7 Hz), 7.65-7.55 (3H, m), 7.34 (1H, d, J=7.3 Hz), 7.26-7.10 (3H, m), 6.72 (1H, d, J=4.4 Hz), 6.10 (1H, d, J=15.4 Hz), 4.32 (2H, q, J=7.3 Hz), 2.34 (3H, s), 1.41 (3H, t, J=7.3 Hz), LCMS (Method A) m/z: M+1 obs 370.3, tR=3.40 min.

Step-3: ethyl trans-2-(1-tosyl-1H-indol-7-yl)cyclopropanecarboxylate

Prepared as in Step-1 of Carboxylic acid intermediate-6 from (E)-ethyl 3-(1-tosyl-1H-indol-7-yl)acrylate.

$^1$H-NMR (300 MHz, CDCl$_3$): δ 7.75 (1H, d, J=3.7 Hz), 7.54 (2H, d, J=8.1 Hz), 7.38 (1H, d, J=8.9 Hz), 7.21-7.10 (3H, m), 6.91 (1H, d, J=8.0 Hz), 6.67 (1H, d, J=3.7 Hz), 4.29-4.19 (2H, m), 3.17 (1H, m), 2.34 (3H, s), 1.92 (1H, m), 1.48 (1H, m), 1.33 (3H, t, J=6.6 Hz), 1.24 (1H, m), LCMS (Method A) m/z: M+1 obs 384.2, tR=3.42 min.

Step-4: trans-2-(1H-indol-7-yl)cyclopropanecarboxylic acid

Prepared as in Step-2 of Carboxylic acid intermediate 6 from ethyl trans-2-(1-tosyl-1H-indol-7-yl)cyclopropanecarboxylate.
$^1$H-NMR (300 MHz, DMSO-d$_6$): δ 11.31 (1H, s), 7.39 (1H, d, J=8.1 Hz), 7.33 (1H, t, J=1.5 Hz), 6.91 (1H, t, J=7.3 Hz), 6.68 (1H, d, J=7.3 Hz), 6.44 (1H, t, J=1.5 Hz), 2.79 (1H, m), 1.88 (1H, m), 1.51 (1H, m), 1.34 (1H, m), LCMS (Method A) m/z: M−1 obs 200.3, tR=2.62 min.

Carboxylic Acid Intermediate-12 trans-2-(1H-indol-2-yl)cyclopropanecarboxylic acid

Step-1: ethyl(E)-3-(1-tosyl-1H-indol-2-yl)acrylate

Prepared as in Step-1 of Carboxylic acid intermediate-7 from 1-tosyl-1H-indole-2-carbaldehyde (Heterocycles, 76 (2), 1155-1170; 2008).
$^1$H-NMR (300 MHz, CDCl$_3$): δ 8.37 (1H, d, J=16.1 Hz), 8.22 (1H, d, J=8.4 Hz), 7.62 (2H, d, J=8.4 Hz), 7.48 (1H, d, J=8.1 Hz), 7.36 (1H, dt, J=7.3, 1.1 Hz), 7.26 (1H, m), 7.16 (2H, d, J=8.1 Hz), 6.96 (1H, s), 6.36 (1H, d, J=16.1 Hz), 4.30 (2H, q, J=7.3 Hz), 2.32 (3H, s), 1.37 (3H, t, J=7.3 Hz).

Step-2: ethyl trans-2-(1-tosyl-1H-indol-2-yl)cyclopropanecarboxylate

Prepared as in Step-1 of Carboxylic acid intermediate-6 from ethyl(E)-3-(1-tosyl-1H-indol-2-yl)acrylate:
$^1$H-NMR (300 MHz, CDCl$_3$): δ 8.20 (1H, d, J=8.1 Hz), 7.73 (2H, d, J=8.1 Hz), 7.42-7.19 (5H, m), 6.28 (1H, s), 4.28-4.11 (2H, m), 2.93 (1H, m), 2.34 (3H, s), 1.82 (1H, m), 1.62 (1H, m), 1.35-1.22 (4H, m).

Step-3: trans-2-(1H-indol-2-yl)cyclopropanecarboxylic acid

Prepared as in Step-2 of Carboxylic acid intermediate-6 from ethyl trans-2-(1-tosyl-1H-indol-2-yl)cyclopropanecarboxylate:
$^1$H-NMR (300 MHz, CDCl$_3$): δ 8.04 (1H, s), 7.49 (1H, d, J=7.3 Hz), 7.23 (1H, d, J=8.8 Hz), 7.10 (2H, m); 6.14 (1H, S), 2.60 (1H, m), 1.92 (1H, m), 1.62 (1H, m), 1.41 (1H, m), LCMS (Method A) m/z: M+1 obs 202.3, tR=2.59 min.

Carboxylic Acid Intermediate-13 trans-2-(5-fluoro-1H-indol-2-yl)cyclopropanecarboxylic acid

Step-1: 5-fluoro-N-methoxy-N-methyl-1H-indole-2-carboxamide

N,O-dimethylhydroxylamine hydrochloride (1.089 g, 11.16 mmol) and triethylamine (3.92 ml, 27.9 mmol) were added to a solution of 5-fluoro-1H-indole-2-carboxylic acid (2.0 g, 11.16 mmol) in dichloromethane (30 mL) and stirred at room temperature for 5 min. Then 1-ethyl-3-(3-dimethylaminopropyl)carbodiimide hydrochloride (2.140 g, 11.16 mmol) was added and stirred for 20 hours. After reaction, solvent was removed. The residue was suspended in minimum volume of acetone and the insoluble white solid was removed by filtration. After vacuo, the mixture was poured into saturated sodium bicarbonate aqueous solution, and the aqueous phase was extracted with ethyl acetate. The organic layer was dried over magnesium sulfate and concentrated in vacuo. The residue was purified by column chromatography on silica gel eluting with hexane/ethyl acetate (2:1) to give 690 mg (28% yield) of the title compound as a white crystal:

$^1$H-NMR (300 MHz, DMSO-d$_6$): δ 11.6 (1H, s), 7.44 (1H, m), 7.38 (1H, d, J=2.6 Hz), 7.12 (1H, d, J=1.5 Hz), 7.06 (1H, dt, J=9.5, 2.6 Hz), 3.78 (3H, s), 3.32 (3H, s).

Step-2: 5-fluoro-1H-indole-2-carbaldehyde

Lithium aluminium hydride (0.094 g, 2.488 mmol) was added to a solution of 5-fluoro-N-methoxy-N-methyl-1H-indole-2-carboxamide (0.691 g, 3.11 mmol) in tetrahydrofuran (10 ml) at 0° C. and stirred for 1 hour. The reaction mixture was cooled to 0° C. and 25% ammonia solution was added dropwise to the reaction mixture until lithium aluminium hydride color turn gray to white. Then dichloromethane and cerite was added to the reaction mixture and stirred for 30 min. The mixture was filtered through a pad of Celite and concentrated in vacuo to give 523 mg of the crude title compound. This was used for the next step without further purification:

$^1$H-NMR (300 MHz, CDCl$_3$): δ 9.85 (1H, s), 9.13 (1H, brs), 7.42-7.36 (2H, m), 7.24 (1H, d, J=1.1 Hz), 7.16 (1H, dt, J=9.2, 2.6 Hz).

Step-3: 5-fluoro-1-tosyl-1H-indole-2-carbaldehyde p-Toluenesulfonyl chloride (2.445 g, 12.82 mmol), N,N-dimethyl-4-aminopyridine (0.1% g, 1.603 mmol) and triethylamine (2.253 ml, 16.03 mmol) were added to a solution of 5-fluoro-1H-indole-2-carbaldehyde (0.523 g, 3.21 mmol) in dichloromethane (10 ml) and stirred at room temperature for 20 hours. After reaction, the mixture was poured into saturated sodium bicarbonate aqueous solution, and the aqueous phase was extracted with ethyl acetate. The organic layer was dried over magnesium sulfate and concentrated in vacuo. The residue was purified by column chromatography on silica gel eluting with hexane/ethyl acetate (10:1) to give 823 mg (81% yield) of the title compound as a white crystal:

$^1$H-NMR (300 MHz, CDCl$_3$): δ 10.5 (1H, s), 8.20 (1H, dd, J=10.0, 4.2 Hz), 7.62 (2H, d, J=8.4 Hz), 7.40 (1H, s), 7.29-7.19 (4H, m), 2.34 (3H, s).

Step-4: ethyl(E)-3-(5-fluoro-1-tosyl-1H-indol-2-yl)acrylate

Prepared as in Step-1 of Carboxylic acid intermediate-7 from 5-fluoro-1-tosyl-1H-indole-2-carbaldehyde.

$^1$H-NMR (300 MHz, CDCl$_3$): δ 8.33 (1H, d, J=16.1 Hz), 8.17 (1H, dd, J=9.2, 4.4 Hz), 7.59 (2H, d, J=8.4 Hz), 7.19-7.05 (4H, m), 6.90 (1H, S), 6.35 (1H, d, J=16.1 Hz), 4.30 (2H, q, J=7.3 Hz), 2.33 (3H, s), 1.37 (3H, t, J=7.3 Hz).

Step-5: ethyl trans-2-(5-fluoro-1-tosyl-1H-indol-2-yl)cyclopropanecarboxylate

Prepared as in Step-1 of Carboxylic acid intermediate-6 from ethyl (E)-3-(5-fluoro-1-tosyl-1H-indol-2-yl)acrylate.

$^1$H-NMR (300 MHz, CDCl$_3$): δ 8.14 (1H, dd, J=8.8, 4.4 Hz), 7.69 (2H, d, J=8.1 Hz), 7.21 (2H, d, J=8.1 Hz), 7.07-6.98 (2H, m), 6.23 (1H, s), 4.23 (2H, m), 2.91 (1H, m), 2.35 (3H, s), 1.82 (1H, m), 1.62 (1H, m), 1.32 (3H, t, J=7.3 Hz), 1.28 (1H, m).

Step-6: trans-2-(5-fluoro-1H-indol-2-yl)cyclopropanecarboxylic acid

Prepared as in Step-2 of Carboxylic acid intermediate-6 from ethyl trans-2-(5-fluoro-1-tosyl-1H-indol-2-yl)cyclopropanecarboxylate.

$^1$H-NMR (300 MHz, DMSO-d$_6$): 11.1 (1H, s), 7.21 (1H, dd, J=8.8, 4.8 Hz), 7.10 (1H, dd, J=10.3, 2.6 Hz), 6.81 (1H, dt, J=8.8, 2.6 Hz), 6.18 (1H, d, J=1.8 Hz), 2.48 (1H, m), 1.87 (1H, m), 1.42 (2H, m), LCMS (Method A) m/z: M+1 obs 220.3, tR=2.64 min.

Carboxylic Acid Intermediate-14 trans-2-(4-fluoro-1H-indol-3-yl)cyclopropanecarboxylic acid

Step-1: ethyl(E)-3-(4-fluoro-1-tosyl-1H-indol-3-yl)acrylate

Prepared as in Step-1 of Carboxylic acid intermediate-7 from 4-fluoro-1-tosyl-1H-indole-3-carbaldehyde.

$^1$H-NMR (270 MHz, CDCl$_3$): δ 7.88-7.72 (5H, m), 7.32-7.20 (3H, m), 6.95 (1H, dd, J=8.2 & 10.9 Hz), 6.48 (1H, d, J=16.1 Hz), 4.24 (2H, q, J=7.2 Hz), 2.35 (3H, s), 1.32 (3H, t, J=7.2 Hz).

Step-2: ethyl trans-2-(4-fluoro-1-tosyl-1H-indol-3-yl)cyclopropanecarboxylate

Prepared as in Step-1 of Carboxylic acid intermediate-6 from ethyl (E)-3-(4-fluoro-1-tosyl-1H-indol-3-yl)acrylate.

$^1$H-NMR (300 MHz, CDCl$_3$): δ 7.77-7.70 (3H, m), 7.6-7.3 (4H, m), 6.95-6.86 (1H, m), 4.18 (2H, q, J=7.3 Hz), 2.72-2.62 (1H, m), 2.36 (3H, s), 1.87-1.79 (1H, m), 1.65-1.55 (1H, m), 1.35-1.25 (1H, m), 1.29 (3H, t, J=7.3 Hz).

Step-3: trans-2-(4-fluoro-1H-indol-3-yl)cyclopropanecarboxylic acid

Prepared as in Step-2 of Carboxylic acid intermediate-6 from ethyl trans-2-(4-fluoro-1-tosyl-1H-indol-3-yl)cyclopropanecarboxylate LCMS (Method A) m/z: M−1 obs 218.3, tR=2.52 min.

Carboxylic Acid Intermediate-15 trans-2-(quinolin-2-yl)cyclopropanecarboxylic acid

Step-1: ethyl trans-2-(quinolin-2-yl)cyclopropanecarboxylate

Prepared as in Step-1 of Carboxylic acid intermediate-6 from (E)-ethyl 3-(quinolin-2-yl)acrylate.

$^1$H-NMR (300 MHz, CDCl$_3$): δ 8.04 (1H, d, J=8.8 Hz), 7.93 (1H, d, J=8.1 Hz), 7.75 (1H, d, J=8.1 Hz), 7.65 (1H, t, J=8.1 Hz), 7.46 (1H, t, J=8.1 Hz), 7.33 (1H, d, J=8.8 Hz), 4.18 (2H, q, J=7.3 Hz), 2.80-2.73 (1H, m), 2.47-2.40 (1H, m), 1.82-1.75 (1H, m), 1.71-1.64 (1H, m), 1.29 (3H, t, J=7.3 Hz), LCMS (Method A) m/z: M+1 obs 242.2, tR=3.09 min.

Step-2: trans-2-(quinolin-2-yl)cyclopropanecarboxylic acid

Prepared as in Step-2 of Carboxylic acid intermediate-6 from ethyl trans-2-(quinolin-2-yl)cyclopropanecarboxylate.
$^1$H-NMR (300 MHz, DMSO-d$_6$): δ 8.27 (1H, d, J=8.8 Hz), 7.94 (1H, d, J=8.0 Hz), 7.87 (1H, d, J=8.0 Hz), 7.70 (1H, t, J=8.0 Hz), 7.58 (1H, d, J=8.8 Hz), 7.52 (1H, t, J=8.0 Hz), 2.75 (1H, br), 2.20 (1H, br), 1.68-1.48 (2H, m) (a signal due to COOH was not observed), LCMS (Method A) m/z: M−1 obs 212.2, tR=2.27 min.

Carboxylic Acid Intermediate-16 trans-2-(1H-indazol-3-yl)cyclopropanecarboxylic acid

Step-1: methyl(E)-3-(1-tosyl-1H-indazol-3-yl)acrylate

Prepared as in Step-1 of Carboxylic acid intermediate-11 from methyl (E)-3-(1H-indazol-3-yl)acrylate.
$^1$H-NMR (300 MHz, CDCl$_3$): δ 8.25 (1H, d, J=8.8 Hz), 7.93-7.84 (4H, m), 7.60 (1H, t, J=7.7 Hz), 7.41 (1H, t, J=7.7 Hz), 7.30-7.24 (2H, m), 6.87 (1H, d, J=16.8 Hz), 3.84 (3H, s), 2.37 (3H, s), LCMS (Method A) m/z: M+1 obs 357.2, tR=3.32 min.

Step-2: methyl trans-2-(1-tosyl-1H-indazol-3-yl)cyclopropanecarboxylate

Prepared as in Step 1 of Carboxylic acid intermediate-6 from methyl (E)-3-(1-tosyl-1H-indazol-3-yl)acrylate.
$^1$H-NMR (300 MHz, CDCl$_3$): δ 8.16 (1H, d, J=8.0 Hz), 7.79 (2H, d, J=8.0 Hz), 7.69 (1H, d, J=8.0 Hz), 7.55 (1H, t, d=8.0 Hz), 7.33 (1H, t, J=8.0 Hz), 7.22 (2H, d, J=8.0 Hz), 3.73 (3H, s), 2.80-2.70 (1H, m), 2.35 (3H, s), 2.33-2.27 (1H, m), 1.72-1.62 (2H, m), LCMS (Method A) m/z: M+1 obs 371.2, tR=3.25 min.

Step-3: trans-2-(1H-indazol-3-yl)cyclopropanecarboxylic acid

Prepared as in Step-2 of Carboxylic acid intermediate-6 from methyl trans-2-(1-tosyl-1H-indazol-3-yl)cyclopropanecarboxylate.
$^1$H-NMR (300 MHz, DMSO-d$_6$): δ 12.75 (1H, br), 7.78 (1H, d, J=8.0 Hz), 7.46 (1H, d, J=8.0 Hz), 7.33 (1H, t, J=8.0 Hz), 7.09 (1H, t, J=8.0 Hz), 2.77-2.65 (1H, m), 2.08-2.00 (1H, m), 1.58-1.47 (2H, m), LCMS (Method A) m/z: M−1 obs 201.3, tR=2.29 min.

Carboxylic Acid Intermediate-17 trans-2-(quinolin-7-yl)cyclopropanecarboxylic acid

Step-1: ethyl (E)-3-(quinolin-7-yl)acrylate

Prepared as in Step-1 of Carboxylic acid intermediate-7 from quinoline-7-carbaldehyde.
$^1$H-NMR (300 MHz, CDCl$_3$): δ 8.95 (1H, d, J=4.4 Hz), 8.20 (1H, s), 8.15 (1H, d, J=8.8 Hz), 7.87 (1H, d, J=16.1 Hz), 7.83 (1H, d, d=8.8 Hz), 7.73 (1H, d, J=8.8 Hz), 7.42 (1H, dd, J=4.4 & 8.0 Hz), 6.62 (1 h, d, J=16.1 Hz), 4.31 (2H, q, J=7.3 Hz), 1.37 (3H, t, J=7.3 Hz), LCMS (Method A) m/z: M+1 obs 228.3, tR=2.82 min.

Step-2: ethyl trans-2-(quinolin-7-yl)cyclopropanecarboxylate

Prepared as in Step-1 of Carboxylic acid intermediate-6 from ethyl (E)-3-(quinolin-7-yl)acrylate.
$^1$H-NMR (300 MHz, CDCl$_3$): δ *8.91-8.85 (1H, m), 8.11 (1H, d, J=8.8 Hz), 7.80 (1H, s), 7.74 (1H, d, J=8.8 Hz), 7.40-7.30 (2H, m), 4.19 (2H, q, J=8.0 Hz), 2.76-2.67 (1H, m), 2.10-2.02 (1H, m), 1.76-1.68 (1H, m), 1.54-1.45 (1H, m), 1.30 (3H, t, J=8.0 Hz), LCMS (Method A) m/z: M+1 obs 242.3, tR=2.79 min.

Step-3: trans-2-(quinolin-7-yl)cyclopropanecarboxylic acid

Prepared as in Step-2 of Carboxylic acid intermediate-6 from ethyl trans-2-(quinolin-7-yl)cyclopropanecarboxylate.
$^1$H-NMR (300 MHz, DMSO-d$_6$): δ 8.86 (1H, d, J=4.4 Hz), 8.31 (1H, d, J=8.8 Hz), 7.90 (1H, d, J=9.5 Hz), 7.81 (1H, s), 7.46 (1H, dd, J=4.4 & 8.8 Hz), 7.40 (1H, d, J=9.5 Hz), 2.66-2.58 (1H, m), 2.03-1.95 (1H, m), 1.57-1.50 (2H, m) (a signal due to COOH was not observed), LCMS (Method A) m/z: M−1 obs 212.3, tR=2.13 min.

Carboxylic Acid Intermediate-18 trans-2-(1-methyl-1H-indol-6-yl)cyclopropanecarboxylic acid

Step-1: ethyl(E)-3-(1-methyl-1H-indol-6-yl)acrylate

Prepared as in Step-1 of Carboxylic acid intermediate-7 from 1-methyl-1H-indole-6-carbaldehyde.
$^1$H-NMR (300 MHz, CDCl$_3$): δ 7.85 (1H, d, J=15.4 Hz), 7.60 (1H, d, J=8.0 Hz), 7.47 (1H, s), 7.34 (1H, d, J=8.0 Hz), 7.13 (1H, d, J=2.9 Hz), 6.49 (1H, d, J=2.9 Hz), 6.47 (1H, d, J=15.4 Hz), 4.27 (2H, q, J=7.3 Hz), 3.82 (3H, s), 1.35 (3H, t, J=7.3 Hz), LCMS (Method A) m/z: M+1 obs 230.3, tR=3.15 min.

Step-2: ethyl trans-2-(1-methyl-1H-indol-6-yl)cyclopropanecarboxylate

Prepared as in Step-1 of Carboxylic acid intermediate-6 from ethyl (E)-3-(1-methyl-1H-indol-6-yl)acrylate.
$^1$H-NMR (300 MHz, CDCl$_3$): δ 7.52 (1H, d, J=8.1 Hz), 7.08 (1H, s), 7.00 (1H, d, J=2.9 Hz), 6.86 (1H, d, J=8.1 Hz), 6.43 (1H, d, J=2.9 Hz), 4.18 (2H, q, J=7.4 Hz), 3.76 (3H, s), 2.72-2.63 (1H, m), 1.99-1.90 (1H, m), 1.66-1.59 (1H, m), 1.44-1.35 (1H, m), 1.29 (3H, t, J=7.4 Hz), LCMS (Method A) m/z: M+1 obs 244.3, tR=3.17 min.

Step-3: trans-2-(1-methyl-1H-indol-6-yl)cyclopropanecarboxylic acid

Prepared as in Step-2 of Carboxylic acid intermediate-6 from ethyl trans-2-(1-methyl-1H-indol-6-yl)cyclopropanecarboxylate.
$^1$H-NMR (300 MHz, DMSO-d$_6$): δ 12.2 (1H, br), 7.42 (1H, d, J=8.1 Hz), 7.26-7.20 (2H, m), 6.82 (1H, d, J=8.0 Hz), 6.35 (1H, d, J=2.9 Hz), 3.75 (3H, s), 2.50-2.44 (1H, m), 1.85-1.77 (1H, m), 1.47-1.38 (2H, m), LCMS (Method A) m/z: M−1 obs 214.2, tR=2.67 min.

Carboxylic Acid Intermediate-19 trans-2-(6-fluoro-1H-indol-3-yl)cyclopropanecarboxylic acid

Step-1: ethyl(E)-3-(6-fluoro-1-tosyl-1H-indol-3-yl)acrylate

Prepared as in Step-1 of Carboxylic acid intermediate-7 from 6-fluoro-1-tosyl-1H-indole-3-carbaldehyde.
$^1$H-NMR (300 MHz, CDCl$_3$): δ 7.82-7.70 (6H, m), 7.34-7.25 (2H, m), 7.08 (1H, t J=8.8 Hz), 6.48 (1H, d, J=16.1 Hz), 4.27 (2H, q, J=7.3 Hz), 2.38 (3H, S), 1.34 (3H, t, J=7.3 Hz), LCMS (Method A) m/z: M+1 obs 388.2, tR=3.57 min.

Step-2: ethyl trans-2-(6-fluoro-1-tosyl-1H-indol-3-yl)cyclopropanecarboxylate

Prepared as in Step-1 of Carboxylic acid intermediate-6 from ethyl (E)-3-(6-fluoro-1-tosyl-1H-indol-3-yl)acrylate.
$^1$H-NMR (300 MHz, CDCl$_3$): δ 7.73 (2H, d, J=8.0 Hz), 7.68 (1H, dd, J=2.2 & 9.5 Hz), 7.47 (1H, dd, J=5.1 & 8.8 Hz), 7.28-7.22 (2H, m), 7.00 (1H, dt, J=2.2 & 8.8 Hz), 4.19 (2H, q, J=7.3 Hz), 2.50-2.40 (1H, m), 2.36 (3H, s), 1.87-1.80 (1H, m), 1.61-1.53 (1H, m), 1.31 (3H, t, J=7.3 Hz), 1.28-1.21 (1H, m), LCMS (Method A) m/z: M+1 obs 402.2, tR=3.48 min.

Step-3: trans-2-(6-fluoro-1H-indol-3-yl)cyclopropanecarboxylic acid

Prepared as in Step-2 of Carboxylic acid intermediate-6 from ethyl trans-2-(6-fluoro-1-tosyl-1H-indol-3-yl)cyclopropanecarboxylate. LCMS (Method A) m/z: M−1 obs 218.3, tR=2.54 min.

Carboxylic Acid Intermediate-20 trans-2-((4-chlorophenoxy)methyl)cyclopropanecarboxylic acid

Step-1: ethyl trans-2-((4-chlorophenoxy)methyl)cyclopropanecarboxylate

To a suspension of sodium hydride (60%, 650 mg, 16.3 mmol) in toluene (25 mL) was added dropwise a solution of triethyl phosphonoacetate (3.64 g, 16.3 mmol) in toluene (5 mL) at 0° C. After stirring at room temperature for 10 min, 2-((4-chlorophenoxy)methyl)oxirane (1.50 g, 8.1 mmol) was added, and the mixture was refluxed with stirring for 1 day. After cooling to room temperature, the mixture was poured into brine, and the aqueous layer was extracted with EtOAc twice. The combined organic layer was dried over sodium sulfate and concentrated in vacuo. The residue was purified by column chromatography on silica gel eluting with hexane/ethyl acetate (10:1-5:1) to give 1.25 g (60%) of the title compound as a colorless oil.
$^1$H-NMR (300 MHz, CDCl$_3$): δ 7.22 (2H, d, J=8.8 Hz), 6.80 (2H, d, J=8.8 Hz), 4.15 (2H, q, J=7.3 Hz), 3.92 (1H, dd, J=6.6 & 10.2 Hz), 3.83 (1H, dd, J=6.6 & 10.2 Hz), 1.93-1.82 (1H, m), 1.71-1.65 (1H, m), 1.27 (3H, t, J=7.3 Hz). 1.01-0.93 (1H, m), 0.90-0.76 (1H, m), LCMS (Method A) m/z: M+1 obs 255.2, tR=3.25 min.

Step-2: trans-2-((4-chlorophenoxy)methyl)cyclopropanecarboxylic acid

Prepared as in Step-2 of Carboxylic acid intermediate-6 from trans-2-((4-chlorophenoxy)methyl)cyclopropanecarboxylic acid.
$^1$H-NMR (300 MHz, CDCl$_3$): δ 7.22 (2H, d, J=8.8 Hz), 6.80 (2H, d, J=8.8 Hz), 3.96 (1H, dd, J=5.9 & 10.3 Hz), 8.81 (1H, dd, J=6.6 & 10.3 Hz), 2.00-1.90 (1H, m), 1.75-1.68 (1H, m), 1.41-1.32 (1H, m), 1.12-1.05 (1H, m) (a signal due to COOH was not observed), LCMS (Method A) m/z: M−1 obs 225.2, tR=2.80 min.

Carboxylic Acid Intermediate-21 trans-2-(isoquinolin-3-yl)cyclopropanecarboxylic acid

Step-1: ethyl (E)-3-(isoquinolin-3-yl)acrylate

Prepared as in Step-1 of Carboxylic acid intermediate-7 from isoquinoline-3-carbaldehyde.
$^1$H-NMR (300 MHz, CDCl$_3$) δ (300 MHz, CDCl3) 9.25 (1H, s), 7.99 (1H, d, J=8.0 Hz), 7.85 (1H, d, J=7.3 Hz), 7.83 (1H, d, J=15.4 Hz), 7.75-7.62 (3H, m), 7.19 (1H, d, d=15.4 Hz), 4.29 (2H, q, J=6.6 Hz), 1.35 (3H, t, J=6.6 Hz), LCMS (Method A) m/z: M+1 obs 228.2, tR=2.99 min.

Step-2: ethyl trans-2-(isoquinolin-3-yl)cyclopropanecarboxylate

Prepared as in Step-1 of Carboxylic acid intermediate-6 from ethyl (E)-3-(isoquinolin-3-yl)acrylate.
$^1$H-NMR (300 MHz, CDCl$_3$): δ 9.11 (1H, s), 7.92 (1H, d, J=8.0 Hz), 7.75 (1H, d, J=7.4 Hz), 7.66 (1H, m), 7.58 (1H, s), 7.53 (1H, m), 4.19 (2H, q, J=6.6 Hz), 2.76 (1H, m), 2.33 (1H, m), 1.77-1.63 (2H, m), 1.29 (3H, t, J=6.6 Hz).

Step-3: trans-2-(isoquinolin-3-yl)cyclopropanecarboxylic acid

Prepared as in Step-2 of Carboxylic acid intermediate-6 from ethyl trans-2-(isoquinolin-3-yl)cyclopropanecarboxylate.
LCMS (Method A) m/z: M+1 obs 214.3, tR=2.40 min.

Carboxylic Acid Intermediate-22 trans-2-(quinolin-3-yl)cyclopropanecarboxylic acid

Step-1: ethyl trans-2-(quinolin-3-yl)cyclopropanecarboxylate

Prepared as in Step-1 of Carboxylic acid intermediate-6 from ethyl (E)-3-(quinolin-3-yl)acrylate.
$^1$H-NMR (300 MHz, CDCl$_3$): δ 8.77 (1H, d, J=2.2 Hz), 8.08 (1H, d, J=8.8 Hz), 7.80 (1H, d, J=2.2 Hz), 7.75 (1H, dd, J=8.0, 1.5 Hz), 7.68 (1H, td, J=6.6, 1.5 Hz), 7.54 (1H, m), 4.22 (2H, q, J=7.3 Hz), 2.73 (1H, m), 2.07 (1H, m), 1.75 (1H, m), 1.46 (1H, m), 1.31 (3H, t, J=7.3 Hz), LCMS (Method A) m/z: M+1 obs 242.3, tR=2.85 min.

Step-2: trans-2-(quinolin-3-yl)cyclopropanecarboxylic acid

Prepared as in Step-2 of Carboxylic acid intermediate-6 from ethyl trans-2-(quinolin-3-yl)cyclopropanecarboxylate.

¹H-NMR (300 MHz, DMSO-d₆): δ 8.83 (1H, d, J=2.2 Hz), 8.10 (1H, d, J=2.2 Hz), 7.99 (1H, d, J=8.0 Hz), 7.89 (1H, d, J=7.3 Hz), 7.71 (1H, m), 7.59 (1H, t, J=8.1 Hz), 2.63 (1H, m), 2.05 (1H, m), 1.55 (2H, t, J=6.6 Hz), LCMS (Method A) m/z: M+1 obs 214.3, tR=2.30 min.

Carboxylic Acid Intermediate-23

2-(3-(difluoromethoxy)phenyl)cyclopropanecarboxylic acid

Step-1: ethyl(E)-3-(3-(difluoromethoxy)phenyl)acrylate

Prepared as in Step-1 of Carboxylic acid intermediate-7 from 3-(difluoromethoxy)benzaldehyde.
¹H-NMR (300 MHz, CDCl₃): δ 7.95 (1H, d, J=16.1 Hz), 7.62 (1H, dd, J=7.7, 1.8 Hz), 7.38 (1H, dt, J=7.7, 1.5 Hz), 7.26-7.16 (2H, m), 6.56 (1H, t, J=73 Hz), 6.48 (1H, d, J=16.1 Hz), 4.27 (2H, q, J=7.0 Hz), 1.34 (3H, t, J=7.0 Hz).

Step-2: ethyl trans-2-(3-(difluoromethoxy)phenyl)cyclopropanecarboxylate

Prepared as in Step-1 of Carboxylic acid intermediate-6 from ethyl (E)-3-(3-(difluoromethoxy)phenyl)acrylate.
¹H-NMR (300 MHz, CDCl₃): δ 7.25-7.09 (3H, m), 6.97 (1H, dd, J=7.7, 1.8 Hz), 6.52 (1H, t, J=74 Hz), 4.19 (2H, m), 2.71 (1H, m), 1.83 (1H, m), 1.61 (1H, m), 1.31 (1H, m), 1.28 (3H, t, J=7.0 Hz).

Step-3: trans-2-(3-(difluoromethoxy)phenyl)cyclopropanecarboxylic acid

Prepared as in Step-2 of Carboxylic acid intermediate-6 from ethyl trans-2-(3-(difluoromethoxy)phenyl)cyclopropanecarboxylate.
LCMS (Method A) m/z: M−1 obs 228.2, tR=2.66 min.

Carboxylic Acid Intermediate-24 trans-2-(2-fluoro-5-methoxyphenyl)cyclopropanecarboxylic acid

Step-1: ethyl trans-2-(2-fluoro-5-methoxyphenyl)cyclopropanecarboxylic acid

Prepared as in Step-1 of Carboxylic acid intermediate-6 from ethyl (E)-3-(2-fluoro-5-methoxyphenyl)acrylate.
¹H-NMR (300 MHz, CDCl₃): δ 6.93 (1H, t, J=9.2 Hz), 6.66 (1H, dt, J=8.9, 3.3 Hz), 6.45 (1H, dd, J=5.9, 3.0 Hz), 4.17 (2H, q, J=7.3 Hz), 3.75 (3H, s), 2.62 (1H, m), 1.93 (1H, m), 1.58 (1H, m), 1.33 (1H, m), 1.28 (3H, t, J=7.3 Hz).

Step-2: trans-2-(2-fluoro-5-methoxyphenyl)cyclopropanecarboxylic acid

Prepared as in Step-2 of Carboxylic acid intermediate-6 from ethyl trans-2-(2-fluoro-5-methoxyphenyl)cyclopropanecarboxylate.
LCMS (Method A) m/z: M−1 obs 209.2, tR=2.59 min.

Carboxylic Acid Intermediate-25 trans-2-((1H-indol-1-yl)methyl)cyclopropanecarboxylic acid

Step-1: ethyl trans-2-((1H-indol-1-yl)methyl)cyclopropanecarboxylate

To a suspension of sodium hydride (60%, 55 mg, 1.4 mmol) in DMF (5 mL) was added indole (135 mg, 1.2 mmol). After stirring at room temperature for 10 min, ethyl 2-(((methylsulfonyl)oxy)methyl)cyclopropanecarboxylate (307 mg, 1.4 mmol) was added. After stirring at room temperature for 6 h, the mixture was poured into water, and the aqueous layer was extracted with EtOAc twice. The combined organic layer was dried over sodium sulfate and concentrated in vacuo. The residue was purified by column chromatography on silica gel eluting with hexane/ethyl acetate (10:1-5:1) to give 153 mg (54%) of the title compound as a pale brown oil;
¹H-NMR (300 MHz, CDCl₃): δ 7.67-7.60 (1H, m), 7.42-7.09 (4H, m), 6.57-6.50 (1H, m), 4.22-4.02 (4H, m), 1.96-1.86 (1H, m), 1.69-1.62 (1H, m), 1.31-1.25 (1H, m), 1.24 (3H, t, J=7.3 Hz), 0.95-0.87 (1H, m), LCMS (Method A) m/z: M+1 obs 244.3, tR=3.17 min.

Step-2: trans-2-((1H-indol-1-yl)methyl)cyclopropanecarboxylic acid

Prepared as in Step-2 of Carboxylic acid intermediate-6 from ethyl trans-2-((1H-indol-1-yl)methyl)cyclopropanecarboxylate.
¹H-NMR (300 MHz, CDCl₃): δ 7.66-7.61 (1H, m), 7.43-7.08 (4H, m), 6.58-6.50 (1H, m), 4.20-4.06 (2H, m), 2.00-1.91 (1H, m), 1.70-1.62 (1H, m), 1.36-1.27 (1H, m), 1.01-0.94 (1H, m) (a signal due to COOH was not observed), LCMS (Method A) m/z: M−1 obs 214.3, tR=2.72 min.

Carboxylic Acid Intermediate-26 trans-2-(1-((3-methyloxetan-3-yl)methyl)-1H-indol-6-yl)cyclopropanecarboxylic acid Step-1: 1-((3-methyloxetan-3-yl)methyl)-1H-indole-6-carbaldehyde Prepared as in Step-1 of Carboxylic acid intermediate-11 from 1H-indole-6-carbaldehyde.
¹H-NMR (300 MHz, CDCl₃): δ 10.06 (1H, s), 7.93 (1H, s), 7.73 (1H, d, J=8.0 Hz), 7.64 (1H, d, J=8.0 Hz), 7.30 (1H, d, J=3.7 Hz), 6.63 (1H, d, J=3.7 Hz), 4.67 (2H, d, J=6.6 Hz), 4.45 (2H, s), 4.42 (2H, d, J=6.6 Hz), 1.31 (3H, s), LCMS (Method A) m/z: M+1 obs 230.2, tR=2.62 min.

Step-2: ethyl(E)-3-(1-((3-methyloxetan-3-yl)methyl)-1H-indol-6-yl)acrylate

Prepared as in Step-1 of Carboxylic acid intermediate-7 from 1-((3-methyloxetan-3-yl)methyl)-1H-indole-6-carbaldehyde.
¹H-NMR (300 MHz, CDCl₃): δ 7.83 (1H, d, J=16.1 Hz), 7.62 (1H, d, J=8.1 Hz), 7.50 (1H, s), 7.36 (1H, d, J=8.1 Hz), 7.15 (1H, d, J=3.0 Hz), 6.55 (1H, d, J=3.0 Hz), 6.47 (1H, d, J=16.1 Hz), 4.68 (2H, d, J=5.9 Hz), 4.43 (2H, d, J=5.9 Hz), 4.40 (2H, s), 4.29 (2H, q, J=7.4 Hz), 1.36 (3H, t, J=7.4 Hz), 1.32 (3H, s), LCMS (Method A) m/z: M+1 obs 300.2, tR=3.09 min.

Step-3: ethyl trans-2-(1-((3-methyloxetan-3-yl)methyl)-1H-indol-6-yl)cyclopropanecarboxylate Prepared as in Step-1 of Carboxylic acid intermediate-6 from ethyl (E)-3-(1-((3-methyloxetan-3-yl)methyl)-1H-indol-6-yl)acrylate.

$^1$H-NMR (300 MHz, CDCl$_3$): δ 7.52 (1H, d, J=8.1 Hz), 7.13 (1H, s), 7.01 (1H, d, J=2.9 Hz), 6.83 (1H, d, J=8.1 Hz), 6.48 (1H, d, J=3.0 Hz), 4.67 (2H, d, J=6.6 Hz), 4.41 (2H, d, J=6.6 Hz), 4.34 (2H, s), 4.18 (2H, q, J=7.3 Hz), 2.67 (1H, m), 1.93 (1H, m), 1.63 (1H, m), 1.40-1.25 (7H, m), LCMS (Method A) m/z: M+1 obs 314.2, tR=3.10 min.

Step-4: trans-2-(1-((3-methyloxetan-3-yl)methyl)-1H-indol-6-yl)cyclopropanecarboxylic acid Prepared as in Step-2 of Carboxylic acid intermediate-6 from ethyl trans-2-(1-((3-methyloxetan-3-yl)methyl)-1H-indol-6-yl)cyclopropanecarboxylate.

$^1$H-NMR (300 MHz, CDCl$_3$): δ 7.54 (1H, d, J=8.1 Hz), 7.17 (1H, S), 7.03 (1H, d, J=3.7 Hz), 6.85 (1H, d, J=8.1 Hz), 6.50 (1H, d, d=3.6 Hz), 4.69 (2H, d, J=6.6 Hz), 4.43 (2H, d, J=5.9 Hz), 4.35 (2H, s), 2.76 (1H, m), 1.96 (1H, m), 1.72 (1H, m), 1.49 (1H, m), 1.32 (3H, s).

Carboxylic Acid Intermediate-27 trans-2-(2-(isopropylamino)pyridin-4-yl)cyclopropanecarboxylic acid

Step-1: ethyl trans-2-(2-chloropyridin-4-yl)cyclopropanecarboxylate

Prepared as in Step-1 of Carboxylic acid intermediate-6 from (E)-ethyl 3-(2-chloropyridin-4-yl)acrylate.

$^1$H-NMR (300 MHz, CDCl$_3$): δ 8.25 (1H, d, J=5.1 Hz), 7.04 (1H, s), 6.91 (1H, dd, J=5.1, 1.4 Hz), 4.18 (2H, q, J=8.6 Hz), 2.46 (1H, m), 2.00 (1H, m), 1.71 (1H, m), 1.36 (1H, m), 1.29 (3H, t, 6.6 Hz), LCMS (Method A) m/z: M+1 obs 226.2, tR=2.82 min.

Step-2: ethyl trans-2-(2-(isopropylamino)pyridin-4-yl)cyclopropanecarboxylate

To a dioxane (5 mL) solution of ethyl trans-2-(2-chloropyridin-4-yl)cyclopropanecarboxylate (250 mg, 1.1 mmol) and iropropylamine (393 mg, 6.7 mmol) were added cesium carbonate (1.1 g, 3.3 mmol), Xantophos (224 mg, 0.4 mmol) and palladium acetate (50 mg, 0.2 mmol) at room temperature respectively. The mixture was sealed and stirred at 100° C. for 14 hours. After being filtered off, the filtrate was concentrated under reduced pressure, the residue was applied to a silica gel chromatography column and eluted with a hexane/ethyl acetate=6/1 to furnish 100 mg (36% yield) of the title as a colorless oil.

$^1$H-NMR (300 MHz, CDCl$_3$): δ 7.93 (1H, d, J=5.9 Hz), 6.18 (1H, d, J=5.9 Hz), 6.11 (1H, s), 4.32 (1H, brd, J=7.3 Hz), 4.16 (2H, q, J=7.3 Hz), 3.87 (1H, m), 2.36 (1H, m), 1.93 (1H, m), 1.60 (1H, m), 1.33-1.18 (10H, m), LCMS (Method A) m/z: M+1 obs 249.3, tR=2.04 min.

Step-3: trans-(2-(2-isopropylamino)pyridin-4-yl)cyclopropanecarboxylic acid

Prepared as in Step-2 of Carboxylic acid intermediate-6 from ethyl trans-2-(2-(isopropylamino)pyridin-4-yl)cyclopropanecarboxylate.

LCMS (Method A) m/z: M+1 obs 221.3, tR=0.82 min.

Carboxylic Acid Intermediate-28

2-(1H-indol-4-yl)cyclopropanecarboxylic acid

Step-1: ethyl 2-(1-tosyl-1H-indol-4-yl)cyclopropanecarboxylate

Prepared as in Step-1 of Carboxylic acid intermediate-6 from (E)-ethyl 3-(1-tosyl-1H-indol-4-yl)acrylate.

$^1$H-NMR (300 MHz, CDCl$_3$): δ 7.86 (1H, d, J=8.8 Hz), 7.76 (2H, d, J=8.1 Hz), 7.59 (1H, d, J=4.4 Hz), 7.26-7.19 (3H, m), 6.85-6.80 (2H, m), 4.19 (2H, q, J=6.6 Hz), 2.73 (1H, m), 2.34 (3H, s), 1.94 (1H, m), 1.64 (1H, m), 1.36 (1H, m), 1.29 (3H, t, J=7.3 Hz), LCMS (Method A) m/z: M+1 obs 384.2, tR=3.47 min.

Step-2: 2-(1H-indol-4-yl)cyclopropanecarboxylic acid

Prepared as in Step-2 of Carboxylic acid intermediate-6 from ethyl 2-(1-tosyl-1H-indol-4-yl)cyclopropanecarboxylate.

$^1$H-NMR (300 MHz, CDCl$_3$): δ 8.25 (1H, brs), 7.33-7.24 (2H, m), 7.14 (1H, t, J=7.3 Hz), 6.80 (1H, d, J=7.3 Hz), 6.72 (1H, m), 2.98 (1H, m), 2.05 (1H, m), 1.75 (1H, m), 1.58 (1H, m), LCMS (Method A) m/z: M+1 obs 202.2, tR=2.38 min.

Carboxylic Acid Intermediate-29

2-(8-chloroquinolin-2-yl)cyclopropanecarboxylic acid

Step-1: (E)-ethyl 3-(8-chloroquinolin-2-yl)acrylate

Prepared as in Step-1 of Carboxylic acid intermediate-7 from 8-chloroquinoline-2-carbaldehyde.

$^1$H-NMR (300 MHz, CDCl$_3$): δ 8.23 (1H, d, J=8.8 Hz), 7.96 (1H, d, J=15.4 Hz), 7.88 (1H, dd, J=7.3, 1.4 Hz), 7.77 (1H, d, J=7.3 Hz), 7.69 (1H, d, J=8.8 Hz), 7.50 (1H, t, J=8.1 Hz), 7.13 (1H, d, J=15.4 Hz), 4.34 (2H, q, J=6.6 Hz), 1.40 (3H, t, J=6.6 Hz), LCMS (Method A) m/z: M+1 obs 262.1, tR=3.24 min.

Step-2: ethyl 2-(8-chloroquinolin-2-yl)cyclopropanecarboxylate

Prepared as in Step-1 of Carboxylic acid intermediate-6 from (E)-ethyl 3-(8-chloroquinolin-2-yl)acrylate.

LCMS (Method A) m/z: M+1 obs 276.1, tR=3.40 min.

Step-3: 2-(8-chloroquinolin-2-yl)cyclopropanecarboxylic acid

Prepared as in Step-2 of Carboxylic acid intermediate-6 from ethyl 2-(8-chloroquinolin-2-yl)cyclopropanecarboxylate.

LCMS (Method A) m/z: M+1 obs 248.2, tR=2.82 min.

Carboxylic Acid Intermediate-30

2-(1-methyl-1H-indazol-6-yl)cyclopropanecarboxylic acid

Step-1: (E)-ethyl 3-(1-methyl-1H-indazol-6-yl)acrylate

Prepared as in Step-1 of Carboxylic acid intermediate-7 from 1-methyl-1H-indazole-6-carbaldehyde.

$^1$H-NMR (270 MHz, CDCl$_3$): δ 7.97 (1H, s), 7.82 (1H, d, J=16.1 Hz), 7.71 (1H, d, J=8.2 Hz), 7.50 (1H, s), 7.35 (1H, dd, J=8.6, 1.0 Hz), 6.53 (1H, d, J=16.1 Hz), 4.28 (2H, q, J=6.9 Hz), 4.09 (3H, s), 1.35 (3H, t, J=6.9 Hz), LCMS (Method A) m/z: M+1 obs 231.2, tR=2.88 min.

Step-2: ethyl 2-(1-methyl-1H-indazol-6-yl)cyclopropanecarboxylate

Prepared as in Step-1 of Carboxylic acid intermediate-6 from (E)-ethyl 3-(1-methyl-1H-indazol-6-yl)acrylate.

$^1$H-NMR (270 MHz, CDCl$_3$): δ 7.91 (1H, s), 7.61 (1H, d, J=8.6 Hz), 7.13 (1H, s), 6.87 (1H, dd, J=8.6, 1.3 Hz), 4.18 (2H, q, J=7.3 Hz), 4.04 (3H, s), 2.67 (1H, m), 1.98 (1H, m), 1.66 (1H, m), 1.41 (1H, m), 1.29 (3H, t, J=7.3 Hz), LCMS (Method A) m/z: M+1 obs 245.3, tR=2.95 min.

Step-3: 2-(1-methyl-1H-indazol-6-yl)cyclopropanecarboxylic acid

Prepared as in Step-2 of Carboxylic acid intermediate-6 from ethyl 2-(1-methyl-1H-indazol-6-yl)cyclopropanecarboxylate.

$^1$H-NMR (300 MHz, DMSO-d$_6$): δ 7.94 (1H, s), 7.62 (1H, d, 8.1 Hz), 7.42 (1H, s), 6.92 (1H, d, J=8.4 Hz), 3.98 (3H, s), 2.49 (1H, m), 1.90 (1H, m), 1.48-1.43 (2H, m), LCMS (Method A) m/z: M+1 obs 217.2, tR=2.37 min.

Carboxylic Acid Intermediate-31

2-(1H-indol-5-yl)cyclopropanecarboxylic acid

Step-1: (E)-ethyl-3-(1-tosyl-1H-indol-5-yl)acrylate

Prepared as in Step-1 of Carboxylic acid intermediate-7 from 1-tosyl-1H-indole-5-carbaldehyde.

$^1$H-NMR (270 MHz, CDCl$_3$): δ 7.98 (1H, d, J=8.6 Hz), 7.76 (2H, d, J=8.6 Hz), 7.74 (1H, d, J=15.8 Hz), 7.66 (1H, s), 7.58 (1H, d, J=3.9 Hz), 7.50 (1H, d, J=8.6 Hz), 7.23 (2H, d, J=8.6 Hz), 6.66 (1H, d, J=3.3 Hz), 6.41 (1H, d, J=15.8 Hz), 4.26 (2H, q, J=7.2 Hz), 2.34 (3H, s), 1.33 (3H, t, J=7.2 Hz), LCMS (Method A) m/z: M+1 obs 370.2, tR=3.45 min.

Step-2: ethyl 2-(1-tosyl-1H-indol-5-yl)cyclopropanecarboxylate

Prepared as in Step-1 of Carboxylic acid intermediate-6 from (E)-ethyl 3-(1-tosyl-1H-indol-5-yl)acrylate.

$^1$H-NMR (300 MHz, CDCl$_3$): δ 7.88 (1H, d, J=8.8 Hz), 7.74 (2H, d, J=8.1 Hz), 7.53 (1H, d, J=3.7 Hz), 7.25 (1H, d, J=2.2 Hz), 7.21 (2H, d, J=8.1 Hz), 7.05 (1H, dd, J=8.8, 2.2 Hz), 6.58 (1H, d, J=3.7 Hz), 4.18 (2H, q, J=7.3 Hz), 2.57 (1H, m), 2.34 (3H, s), 1.88 (1H, m), 1.61 (1H, m), 1.32 (1H, m), 1.27 (3H, t, J=7.3 Hz), LCMS (Method A) m/z: M+1 obs 384.3, tR=3.45 min.

Step-3: 2-(1H-indol-5-yl)cyclopropanecarboxylic acid

Prepared as in Step-2 of Carboxylic acid intermediate-6 from ethyl 2-(1-tosyl-1H-indol-5-yl)cyclopropanecarboxylate.

$^1$H-NMR (300 MHz, DMSO-d$_6$): δ 12.2 (1H, brs), 11.1 (1H, s), 7.36-7.30 (3H, m), 6.92 (1H, d, J=8.1 Hz), 6.39 (1H, s), 2.49 (1H, m), 1.77 (1H, m), 1.49-1.37 (2H, m).

Carboxylic Acid Intermediate-32

2-(3-(benzyloxy)phenyl)cyclopropanecarboxylic acid

Step-1: ethyl 2-(3-(benzyloxy)phenyl)cyclopropanecarboxylate

Prepared as in Step-1 of Carboxylic acid intermediate-6 from (E)-ethyl 3-(3-(benzyloxy)phenyl)acrylate.

$^1$H-NMR (300 MHz, CDCl$_3$): δ 7.44-7.32 (5H, m), 7.19 (1H, m), 6.81 (1H, m), 6.72-6.69 (2H, m), 5.04 (2H, s), 4.16 (2H, q, J=7.3 Hz), 2.48 (1H, m), 1.89 (1H, m), 1.58 (1H, m), 1.30 (1H, m), 1.27 (3H, t, J=7.3 Hz).

Step-2: 2-(3-(benzyloxy)phenyl)cyclopropanecarboxylic acid

Prepared as in Step-2 of Carboxylic acid intermediate-6 from ethyl 2-(3-(benzyloxy)phenyl)cyclopropanecarboxylate.

LCMS (Method A) m/z: M−1 obs 267.2, tR=3.03 min.

Carboxylic Acid Intermediate-33

2-(2-chloro-4-fluorophenyl)cyclopropanecarboxylic acid

Step-1: (E)-ethyl 3-(2-chloro-4-fluorophenyl)acrylate

Prepared as in Step-1 of Carboxylic acid intermediate-7 from 2-chloro-4-fluorobenzaldehyde.

$^1$H-NMR (300 MHz, CDCl$_3$): δ 8.02 (1H, d, J=16.1 Hz), 7.62 (1H, dd, J=8.8, 6.6 Hz), 7.18 (1H, dd, J=7.3, 1.5 Hz), 7.02 (1H, m), 6.38 (1H, d, J=16.1 Hz), 4.28 (2H, q, J=7.3 Hz), 1.35 (3H, t, J=7.3 Hz), LCMS (Method A) m/z: M−1 obs 229.2, tR=3.22 min Step-2: ethyl 2-(2-chloro-4-fluorophenyl)cyclopropanecarboxylate Prepared as in Step-1 of Carboxylic acid intermediate-6 from (E)-ethyl 3-(2-chloro-4-fluorophenyl)acrylate.

$^1$H-NMR (300 MHz, CDCl$_3$): δ 7.12 (1H, dd, J=8.8, 2.9 Hz), 6.99 (1H, m), 6.89 (1H, m), 4.20 (2H, q, J=7.3 Hz), 2.66

(1H, m), 1.77 (1H, m), 1.61 (1H, m), 1.29 (3H, t, J=7.3 Hz), 1.29 (1H, m), LCMS (Method A) m/z: M−1 obs 243.2, tR=3.27 min.

Step-3:
2-(2-chloro-4-fluorophenyl)cyclopropanecarboxylic acid

Prepared as in Step-2 of Carboxylic acid intermediate-6 from ethyl 2-(2-chloro-4-fluorophenyl)cyclopropanecarboxylate.
$^1$H-NMR (300 MHz, CDCl$_3$): δ 7.44 (1H, d, J=8.8 Hz), 7.25-7.10 (2H, m), 2.48 (1H, m), 1.70 (1H, m), 1.45-1.35 (2H, m), LCMS (Method A) m/z: M−1 obs 213.2, tR=2.72 min.

Carboxylic Acid Intermediate-34

2-(2-fluoro-4-methoxyphenyl)cyclopropanecarboxylic acid

Step-1: ethyl 2-(2-fluoro-4-methoxyphenyl)cyclopropanecarboxylate

Prepared as in Step-1 of Carboxylic acid intermediate-6 from (E)-ethyl 3-(2-fluoro-4-methoxyphenyl)acrylate.
$^1$H-NMR (300 MHz, CDCl$_3$): δ 6.90 (1H, t, J=6.6 Hz), 6.65-6.55 (2H, m), 4.17 (2H, q, J=7.3 Hz), 3.77 (3H, s), 2.57 (1H, m), 1.86 (1H, m), 1.54 (1H, m), 1.28 (3H, t, J=7.3 Hz), 1.28 (1H, m), LCMS (Method A) m/z: M+1 obs 239.3, tR=3.13 min.

Step-2:
2-(2-fluoro-4-methoxyphenyl)cyclopropanecarboxylic acid

Prepared as in Step-2 of Carboxylic acid intermediate-6 from ethyl 2-(2-fluoro-4-methoxyphenyl)cyclopropanecarboxylate.
$^1$H-NMR (300 MHz, DMSO-d$_6$): δ 7.01 (1H, t, J=8.8 Hz), 6.79 1H, m), 6.69 (1H, m), 3.72 (3H, s), 2.34 (1H, m), 1.71 (1H, m), 1.40-1.30 (2H, m), LCMS (Method A) m/z: M−1 obs 209.2 tR=2.60 min.

Carboxylic Acid Intermediate-35

2-(2,4,6-trifluorophenyl)cyclopropanecarboxylic acid

Step-1: (E)-ethyl 3-(2,4,6-trifluorophenyl)acrylate

Prepared as in Step-1 of Carboxylic acid intermediate-7 from 2,4,6-trifluorobenzaldehyde.
$^1$H-NMR (300 MHz, CDCl$_3$): δ 7.69 (1H, d, J=16.8 Hz), 6.77-6.65 (3H, m), 4.28 (2H, q, J=7.3 Hz), 1.35 (3H, t, J=7.3 Hz), LCMS (Method A) m/z: M+1 obs 231.2, tR=3.18 min.

Step-2: ethyl 2-(2,4,6-trifluorophenyl)cyclopropanecarboxylate

Prepared as in Step-1 of Carboxylic acid intermediate-6 from (E)-ethyl 3-(2,4,6-trifluorophenyl)acrylate.
$^1$H-NMR (300 MHz, CDCl$_3$): δ 6.66-6.50 (2H, m), 4.18 (2H, q, J=7.3 Hz), 2.40 (1H, m), 2.07 (1H, m), 1.58-1.44 (2H, m), 1.30 (3H, t, J=7.3 Hz), LCMS (Method A) m/z: M+1 obs 245.2 tR=3.23 min.

Step-3:
2-(2,4,6-trifluorophenyl)cyclopropanecarboxylic acid

Prepared as in Step-2 of Carboxylic acid intermediate-6 from ethyl 2-(2,4,6-trifluorophenyl)cyclopropanecarboxylate.
$^1$H-NMR (300 MHz, DMSO-d$_6$): δ 7.18-7.10 (2H, m), 2.17 (1H, m), 1.88 (1H, m), 1.45-1.30 (2H, m), LCMS (Method A) m/z M−1 obs 215.2 tR=2.65 min.

Carboxylic Acid Intermediate-36

2-(5-cyano-1H-benzo[d]imidazol-2-yl)cyclopropanecarboxylic acid

Step-1: ethyl 2-(5-cyano-1H-benzo[d]imidazol-2-yl)cyclopropanecarboxylate

To a mixture of 3,4-diaminobenzonitrile (326 mg, 2.45 mmol), trans-2-(ethoxycarbonyl)cyclopropanecarboxylic acid (323 mg, 2.04 mmol), and triethylamine (1.44 mL, 10.2 mmol) in DMF (10 mL) was added HBTU (1.01 g, 2.66 mmol). After stirring at room temperature for 3 h, the mixture was poured into water, and the aqueous phase was extracted with EtOAc twice. The combined organic layer was dried over sodium sulfate and concentrated in vacuo. To the residue was added acetic acid (10 mL), and the mixture was stirred at 90° C. for 12 h. After cooling to room temperature, the solvent was removed in vacuo. The residue was poured into saturated sodium bicarbonate aqueous solution, and the aqueous layer was extracted with EtOAc twice. The combined organic layers were dried over sodium sulfate and concentrated in vacuo. The residue was purified by column chromatography on silica gel eluting with hexane/ethyl acetate to give 210 mg (40%) of the title compound as a white amorphous:
$^1$H-NMR (300 MHz, CDCl$_3$): δ 9.65 (1H, m), 7.73-7.68 (1H, m), 7.53-7.43 (2H, m), 4.20 (2H, q, J=7.3 Hz), 2.66-2.57 (1H, m), 2.51-2.41 (1H, m), 1.88-1.80 (1H, m), 1.80-1.70 (1H, m), 1.30 (3H, t, J=7.3 Hz), LCMS (Method A) m/z: M+1 obs 256.2, tR=2.61 min.

Step-2: 2-(5-cyano-1H-benzo[d]imidazol-2-yl)cyclopropanecarboxylic acid

Prepared as in Step-2 of Carboxylic acid intermediate-6 from ethyl 2-(5-cyano-1H-benzo[d]imidazol-2-yl)cyclopropanecarboxylate.
$^1$H-NMR (300 MHz, CDCl$_3$): δ 8.01 (1H, s), 7.63 (1H, d, J=8.1 Hz), 7.53 (1H, d, J=8.1 Hz), 2.63-2.55 (1H, m), 2.20-2.12 (1H, m), 1.65-1.51 (2H, m) (signals due to NH and COOH were not observed), LCMS (Method A) m/z: M+1 obs 228.2, tR=1.88 min.

Carboxylic Acid Intermediate-37

4-((1H-imidazol-1-yl)methyl)-1H-indole-2-carboxylic acid

Step-1: Methyl 3-(2-methyl-6-nitrophenyl)propenoate

2-Bromo-3-nitrotoluene (0.5 g, 23 mmol), methyl acrylate (0.39 g, 46 mmol), palladium acetate (29 mg, 1.3 mmol), triphenylphosphine (0.06 g, 0.23 mmol) and TEA (0.4 mL) were combined in a sealed tube and heated to 95° C. for 24 h. The residue was dissolved in MeOH, the solvent was removed and the crude product was purified by column chromatography (EtOAc:hexane=7.5:92.5) to give 0.024 g (48% yield) of the title compound as a yellow oil:

$^1$H-NMR (300 MHz, CDCl$_3$): δ 7.86 (1H, d, J=16.4 Hz), 7.75 (1H, d, J=8.0 Hz), 7.46 (1H, d, J=7.6 Hz), 7.35 (1H, q, J=8.0 Hz, 7.6 Hz), 3.79 (3H, s), 2.37 (3H, s).

Step-2: Methyl 4-methylindole-2-carboxylate

Methyl 3-(2-methyl-6-nitrophenyl)propenoate (0.24 g, 1.1 mmol) was dissolved in triethylphosphite (1 mL) and heated under reflux for 20 h. The solvent was removed in vacuo and the crude product was purified by silica gel chromatography (EtOAc:hexane=8:92) to give 0.15 g (71% yield) of the title compound as a pale yellow solid:

$^1$H-NMR (300 MHz, CDCl$_3$): δ 8.82 (1H, br s), 7.25-7.18 (3H, m), 6.92 (1H, d, J=6.0 Hz), 3.93 (3H, s), 2.54 (3H, s).

Step-3: Methyl 1-tert-butoxycarbonyl-4-methylindole-2-carboxylate

Di-tert-butyl dicarbonate (0.35 g, 1.6 mmol) and DMAP (0.015 g, 0.12 mmol) were added to a solution of Methyl 4-methylindole-2-carboxylate (0.15 g, 0.8 mmol) in acetonitrile (7.5 mL). The resulting mixture was stirred at room temperature for 16 h and the solvent evaporated in vacuo. The residue was portioned between ethyl acetate (7.5 mL) and water (7.5 mL). The aqueous layer was further extracted with ethyl acetate (2×7.5 mL) and the organic extracts combined, washed with saturated sodium bicarbonate, dried over sodium sulfate, evaporated in vacuo and purified by silica gel column (EtOAc:hexane=5:95) to give 0.13 g (59% yield) of the title compound as a pale yellow oil:

$^1$H-NMR (300 MHz, CDCl$_3$): δ 7.88 (1H, d, J=8.4 Hz), 7.31-7.03 (3H, m), 3.90 (3H, s), 2.50 (3H, s), 1.60 (9H, s).

Step-4: Methyl 4-bromomethyl-1-tert-butoxycarbonylindole-2-carboxylate

A solution of methyl 1-tert-butoxycarbonyl-4-methylindole-2-carboxylate (0.13 g, 0.48 mmol), NBS (0.087 g, 0.48 mmol), and AIBN (4 mg, 0.024 mmol) in carbon tetrachloride (1.9 mL) was heated to reflux for 3 h. The reaction mixture was cooled to room temperature and filtered and washed with carbon tetrachloride. The filtrate was evaporated to give a yellow oil that was purified by silica gel chromatography (EtOAc:hexane=8:92) to give 0.12 g (72% yield) of the title compound as a pale yellow solid:

$^1$H-NMR (300 MHz, CDCl$_3$): δ 8.06 (1H, d, J=8.4 Hz), 7.38-7.27 (3H, m), 4.73 (2H, s), 3.94 (3H, s).

Step-5: 4-Imidazol-1-ylmethyl-indole-1,2-dicarboxylic acid 1-tert-butyl ester 2-methy ester A solution of Methyl 4-bromomethyl-1-tert-butoxycarbonylindole-2-carboxylate (0.92 g, 2.4 mmol) and imodazole (0.82 g, 12 mmol) was stirred at 90° C. in acetonitrile (14 mL) for 5 h. The reaction mixture was cooled to room temperature and evaporated to dryness. The residue was purified by silica gel column chromatography (MeOH:DCM-8:92) to give 0.413 g (46% yield) of the title compound as a white solid:

$^1$H-NMR (300 MHz, CDCl$_3$): δ 8.10 (1H, d, J=8.4 Hz), 7.59 (1H, s), 7.39 (1H, q, d=7.6 Hz, 8.4 Hz), 7.08 (1H, s), 7.04 (1H, d, J=7.6 Hz), 6.94 (1H, s), 6.88 (1H, s), 5.33 (2H, S), 3.91 (3H, s), 1.82 (9H, s).

Step-6: 4-((1H-imidazol-1-yl)methyl)-1H-indole-2-carboxylic acid

The mixture of 4-Imidazol-1-ylmethyl-indole-1,2-dicarboxylic acid 1-tert-butyl ester 2-methy ester (350 mg, 0.99 mmol) and 2N aqueous sodium hydroxide solution (1 mL, 2 mmol) in THF (5 mL) was refluxed at 80° C. with stirring for 2 days. 2N hydrochloric acid was added until pH was 7.0. The mixture was concentrated in vacuo. The resulting precipitate was collected by filtration and washed with dichloromethane, methanol, H$_2$O and ethyl acetate to give 63 mg (27% yield) of the title compound as a white solid:

$^1$H-NMR (300 MHz, DMSO-d$_6$): δ 7.82 (1H, s), 6.72 (1H, d, J=8.8 Hz), 6.65 (1H, s), 6.55 (1H, s), 6.50 (1H, t, J=7.3 Hz), 6.36 (1H, s), 6.29 (1H, d, J=6.6 Hz), 4.86 (2H, s).

Example 1

(R)-5-tert-butyl-N-(1-(5-(2,2,2-trifluoroethoxy)pyridin-2-yl)ethyl)isoxazole-3-carboxamide To a suspension of (R)-1-(5-(2,2,2-trifluoroethoxy)pyridin-2-yl)ethanamine 2 HCl salt (18 mg, 0.06 mmol) and 5-tert-butylisoxazole-3-carboxylic acid (10 mg, 0.06 mmol) in dichloromethane (2 mL) were added triethylamine (19 mg, 0.18 mmol), EDC (19 mg, 0.1 mmol) and HOBT (9.4 mg, 0.06 mmol) respectively. The reaction mixture was stirred at room temperature for 18 hours. The solvent was evaporated by N$_2$-flow. The resulting residue was dissolved into ethyl acetate and water was added to the mixture. The organic layer was then washed with brine, and dried over sodium sulfate. After the filtration to separate solvent and sodium sulfate, the solvent was removed under reduced pressure to give the residue. The residue was diluted with methanol and applied onto a strong cation exchange cartridge (BondElute (registered trademark) SCX, 1 g/6 mL, Varian Inc.), and the solid phase matrix was rinsed with methanol (6 mL). The crude mixture was eluted in a collection tube with 1 mol/L ammonia in methanol (6 mL) and concentrated in vacuo. The residue was purified by preparative LC-MS to give 17 mg, (75% yield) of the title compound.

By a method similar to Example 1 except that the reactant is different, the following compounds of Examples 2-27, 30-80, 82-241, 243-254, 258-291, 307-313, 315-423 and 426-464 were similarly prepared (also see Table 1). The reactants were used commercial available materials, otherwise noted in the intermediate parts.

Example 28

(R)-2-(4-bromophenoxy)-N-(1-(5-(2,2,2-trifluoroethoxy)pyridin-2-yl)ethyl)acetamide To a suspension of (R)-1-(5-(2,2,2-trifluoroethoxy)pyridin-2-yl)ethanamine 2 HCl salt (173 mg, 0.79 mmol) and 2-(4-bromophenoxy)acetic acid (200 mg, 0.87 mmol) in dichloromethane (5 mL) were added triethylamine (400 mg, 3.9 mmol), EDC (180 mg, 0.94 mmol) and HOBT (60 mg, 0.39 mmol) respectively. The reaction mixture was stirred at room temperature for 18 hours. Sat. ammonia hydrochloride aqueous solution was added to the mixture. The organic layer was extracted with ethyl acetate, washed with brine, and dried over sodium sulfate. After the filtration to separate solvent and sodium sulfate, the solvent was removed under reduced pressure to give the residue, which was applied to a silica gel chromatography column and eluted with a hexane/ethylacetate=2/1 (v/v) to furnish 276 mg (81% yield) of the title as a colorless oil.

$^1$H-NMR (300 MHz, CDCl$_3$): δ 8.30 (1H, m), 7.66 (1H, brd, J=8.1 Hz), 7.41 (2H, d, J=8.8 Hz), 7.26-7.24 (2H, m), 6.84 (2H, d, J=8.8 Hz), 5.22 (1H, m), 4.48 (2H, qAB, J=14.6 Hz), 4.40 (2H, qAB, J=8.1 Hz), 1.49 (3H, d, J=7.3 Hz), LCMS (Method A) m/z: M+1 434.8; tR=3.15 min.

Example 29

(R)-2-(4-cyclopropylphenoxy)-N-(1-(5-(2,2,2-trifluoroethoxy)pyridin-2-yl)ethyl)acetamide To a solution of (R)-2-(4-bromophenoxy)-N-(1-(5-(2,2,2-trifluoroethoxy)pyridin-2-yl)ethyl)acetamide (100 mg, 0.23 mmol) and cyclopropylboronic acid (26 mg, 0.30 mmol) in dioxane (2 mL) were added 1.27 M potassium phosphate (0.36 mL) and tetrakistriphenyl phosphine palladium (13 mg, 0.012 mmol) at room temperature. The mixture was stirred at 120° C. using microwave oven for 2 hours. The mixture was dried over magnesium sulfate. After the filtration to separate solvent and magnesium sulfate, the solvent was removed under reduced pressure to give the residue. The residue was diluted with methanol and applied onto a strong cation exchange cartridge (BondElute (registered trademark) SCX, 1 g/6 mL, Varian Inc.), and the solid phase matrix was rinsed with methanol (6 mL). The crude mixture was eluted in a collection tube with 1 mol/L ammonia in methanol (6 mL) and concentrated in vacuo. The residue was purified by preparative LC-MS to give 6.5 mg, (7% yield) of the title compound.

Example 81

(R)—N-(1-(5-(pyridin-2-ylmethoxy)pyridin-2-yl)ethyl)-2-(4-trifluoromethyl)phenoxy)acetamide Step-1

(R)—N-(1-(5-hydroxypyridin-2-yl)ethyl)-2-(4-(trifluoromethyl)phenoxy)acetamide

A mixture of (R)—N-(1-(5-(benzyloxy)pyridin-2-yl)ethyl)-2-(4-(trifluoromethyl)phenoxy)acetamide (Example 63, 550 mg, 1.3 mmol) and palladium hydroxide on carbon (20 wt. %, 50 mg) in methanol (30 mL) was hydrogenated for 6 hours. The mixture was filtered through a pad of celite, washed with methanol, the filtrate was concentrated gave 410 mg (94% yield) of (R)—N-(1-(5-hydroxypyridin-2-yl)ethyl)-2-(4-(trifluoromethyl)phenoxy)acetamide as a white crystalline solid;

$^1$H-NMR (300 MHz, CDCl$_3$): δ 8.19 (1H, d, J=2.9 Hz), 7.77 (1H, d, J=7.3 Hz), 7.58 (2H, d, J=8.1 Hz), 7.14 (1H, dd, J=8.8 Hz, 2.9 Hz), 7.08-7.02 (3H, m), 5.20-5.10 (1H, m), 4.58 (1H, d, J=13.9 Hz), 4.51 (1H, d, J=13.9 Hz), 1.48 (3H, d, J=6.6 Hz), LCMS (Method A) m/z: M+1 obs 341.

Step-2

(R)—N-(1-(5-(pyridin-2-ylmethoxy)pyridin-2-yl)ethyl)-2-(4-(trifluoromethyl)phenoxy)acetamide A mixture of (R)—N-(1-(5-hydroxypyridin-2-yl)ethyl)-2-(4-trifluoromethyl)phenoxy)acetamide (30 mg, 0.088 mmol), 2-(bromomethyl)pyridine hydrobromide (22 mg, 0.088 mmol), and cesium carbonate (115 mg, 0.35 mmol) in DMF (3 mL) was heated at 90° C. overnight. After cooling, the mixture was filtered through a pad of celite, washed with dichloromethane, the filtrate was concentrated, and the residue was purified by SCX cartridge to give 34 mg (89% yield) of (R)—N-(1-(5-(pyridin-2-ylmethoxy)pyridin-2-yl)ethyl)-2-(4-(trifluoromethyl)phenoxy)acetamide as a clear colorless oil;

LCMS (Method A) m/z: M+1 obs 432, M−1 obs 430

Alternated Route for Mixture of Example 133 and 134 trans-2-(1H-indol-3-yl)-N—((R)-1-(5-(2,2,2-trifluoroethoxy)pyridin-2-yl)ethyl)cyclopropanecarboxamide Step-1

(R,E)-3-(1H-indol-3-yl)-N-(1-(5-(2,2,2-trifluoroethoxy)pyridin-2-yl)ethyl)acrylamide To a suspension of (R)-1-(5-(2,2,2-trifluoroethoxy)pyridin-2-yl)ethanamine 2 HCl salt (1.1 g, 3.8 mmol) and (E)-3-(1-(tert-butoxycarbonyl)-1H-indol-3-yl)acrylic acid (1.0 g, 3.5 mmol) in dichloromethane (8 mL) were added triethylamine (1.8 g, 17 mmol), EDC (800 mg, 4.2 mmol) and HOBT (270 mg, 1.7 mmol) respectively. The reaction mixture was stirred at room temperature for 6 hours. Sat. sodium bicarbonate aqueous solution was added to the mixture. The organic layer was extracted with ethyl acetate, washed with brine, and dried over sodium sulfate. After the filtration to separate solvent and sodium sulfate, the solvent was removed under reduced pressure to give the residue, which was applied to a silica gel chromatography column and eluted with a hexane/ethylacetate=2/1 (v/v) to furnish 900 mg (53% yield) of the title as a yellow solid.

$^1$H-NMR (300 MHz, CDCl$_3$): δ 8.31 (1H, d, J=1.5 Hz), 8.18 (1H, d, J=8.0 Hz), 7.90-7.70 (3H, m), 7.40-7.20 (4H, m), 6.93 (1H, d, J=8.0 Hz), 6.59 (1H, d, J=16.1 Hz), 5.30 (1H, m), 4.39 (2H, q, J=8.0 Hz), 1.08 (9H, s), 1.53 (3H, d, J=6.6 Hz). LCMS (Method A) m/z: M+1 490.3; tR=3.44 min.

Step-2: trans-2-(1H-indol-3-yl)-N—((R)-1-(5-(2,2,2-trifluoroethoxy)pyridin-2-yl)ethyl)cyclopropanecarboxamide To a solution of (R,E)-3-(1H-indol-3-yl)-N-(1-(5-(2,2,2-trifluoroethoxy)pyridin-2-yl)ethyl)acrylamide (600 mg, 1.3 mmol) in dichloromethane (10 mL) was added ethylzinc (4.1 mL, 4.1 mmol, 1.0 M) at room temperature. After being stirred at room temperature for 3 min, diiodomethane (1.8 g, 6.7 mmol) was added to the mixture. The mixture was refluxed at 55° C. with stirring for 18. hours. sat. ammonia hydrochloride aqueous solution was added to the mixture. The organic layer was extracted with ethyl acetate, washed with brine, dried over sodium sulfate. After the filtration to separate solvent and sodium sulfate, the solvent was removed under reduced pressure to give the residue, which was applied to a silica gel chromatography column and eluted with a hexane/ethylacetate=1/1 (v/v) and preparative LC-MS to give 14 mg, (3% yield) of the title compound as a white solid (2:1 mixture of the diastereomers).

$^1$H-NMR (600 MHz, CDCl$_3$): δ 8.28 (1H, S), 7.99 (1H, brs), 7.60 (1H, m), 7.34 (1H, m), 7.26-7.22 (2H, m), 7.18

(1H, m), 7.08 (1H, m), 6.95-6.86 (2H, m), 5.21 (1H, m), 4.40 (2H, q, J=7.9 Hz), 2.54 (1H, m), 1.68 (1H, m), 1.60 (1H, m), 1.48 (3H, d, J=6.8 Hz), 1.29 (1H, m), LCMS (Method A) m/z: M+1 404.3; tR=2.98 min.

Example 242

(1S*,2S*)-2-(4-hydroxyphenyl)-N—((R)-1-(5-(2,2, 2-trifluoroethoxy)pyridin-2-yl)ethyl)cyclopropan- ecarboxamide A mixture of palladium hydroxide on carbon 20 wt % loading (63 mg) and (1S*,2S*)-2-(4-(benzyloxy)phenyl)-N—(R-1-(5-(2,2,2-trifluoroethoxy)pyridin-2-yl)ethyl)cyclopropanecarboxamide (631 mg, 1.341 mmol) in methanol (30 ml) was stirring for 4 hours at room temperature under H$_2$ atmosphere. The mixture was filtered through a pad of celite, washed with ethyl acetate, the filtrate was concentrated to give 485 mg (95% yield) of title compound as a white amorphous. 8 mg of the residue was purified by preparative LC-MS to give 4.8 mg of the title compound.

Example 255

(1S*,2S*)-2-(3-hydroxyphenyl)-N—((R)-1-(5-(2,2, 2-trifluoroethoxy)pyridin-2-yl)ethyl)cyclopropan- ecarboxamide Prepared as in Example 242 from (1S*,2S*)-2-(3-(3-(benzyloxy)phenyl)-N—((R)-1-(5-(2,2,2-trifluoroethoxy) pyridin-2-yl)ethyl)cyclopropanecarboxamide. The residue was purified by preparative LC-MS to give 5.4 mg of the title compound.

Example 256

(1S*,2S*)-2-(4-(2-(4,4-difluoropiperidin-1-yl)-2-oxoethoxy)phenyl)-N—((R)-1-(5-(2,2,2-trifluoroethoxy)pyridin-2-yl)ethyl)cyclopropanecarboxamide Step-1: tert-butyl 2-(4-(1S*,2S*)-2-(((R)-1-(5-(2,2, 2-trifluoroethoxy)pyridin-2-yl)ethyl)carbamoyl)cyclopropyl)phenoxy)acetate A mixture of tert-butyl 2-bromoacetate (0.063 ml, 0.434 mmol), potassium carbonate (109 mg, 0.789 mmol) and (1S*,2S*)-2-(4-hydroxyphenyl)-N—((R)-1-(5-(2,2,2-trifluoroethoxy)pyridin-2-yl)ethyl)cyclopropanecarboxamide (150 mg, 0.394 mmol) in dichloromethane (4 ml) was refluxed with stirring for 3 hours. After cooling to room temperature, the mixture was poured into water, and the aqueous layer was extracted with ethyl acetate, dried over magnesium sulfate and concentrated in vacuo. The residue was recrystallized from tetrahydrofuran/hexane. To give 137 mg (70% yield) of title compound as a white crystal:
$^1$H-NMR (300 MHz, DMSO-d$_6$): δ 8.55 (1H, d, 8.1 Hz), 8.31 (1H, d, J=2.6 Hz), 7.49 (1H, dd, J=8.8, 2.9 Hz), 7.28 (1H, d, J=8.4 Hz), 7.03 (2H, d, J=8.4 Hz), 6.78 (2H, d, J=8.4 Hz), 4.95 (1H, t, J=7.3 Hz), 4.84 (2H, q, J=8.8 Hz), 4.59 (2H, s), 2.17 (1H, m), 1.89 (1H, m), 1.41 (9H, s), 1.32 (2H, d, J=6.6 Hz), 1.22 (1H, m), 1.09 (1H, m), LCMS (Method A) m/z: M+1 obs 495.1, tR=3.25 min.

Step-2

2-(4-(1S*,2S*)-2-(((R)-1-(5-(2,2,2-trifluoroethoxy) pyridin-2-yl)ethyl)carbamoyl)cyclopropyl)phenoxy) acetic acid A mixture of trifluoroacetic acid (0.213 ml, 2.77 mmol) and tert-butyl 2-(4-((1S*,2S*)-2-(((R)-1-(5-(2,2,2-trifluoroethoxy)pyridin-2-yl)ethyl)carbamoyl)cyclopropyl)phenoxy)acetate (137 mg, 0.277 mmol) in dichloromethane (5 ml) was refluxed with stirring for 6 hours. Excess trifluoroacetic acid and dichloromethane were removed under reduced pressure. To give 200 mg of title compound as white solid. This was used next step without purification:
LCMS (Method A) m/z: M+1 obs 439.0, tR=2.54 min.

Step-3

(1S*,2S*)-2-(4-(2-(4,4-difluoropiperidin-1-yl)-2-oxoethoxy)phenyl)-N—((R)-1-(5-(2,2,2-trifluoroethoxy)pyridin-2-yl)ethyl)cyclopropanecarboxamide A mixture of HBTU (28 mg, 0.075 mmol), triethylamine (0.03 mL, 0.25 mmol), 4,4-difluoropiperidine hydrochloride (9.5 mg, 0.060 mmol) and 2-(4-((1S*,2S*)-2-(((R)-1-(5-(2, 2,2-trifluoroethoxy)pyridin-2-yl)ethyl)carbamoyl)cyclopropyl)phenoxy)acetic acid (28 mg, 0.050 mmol) was stirring for 4 hours at room temperature. The mixture was poured into 2 mol/l hydrochloric acid, and the aqueous layer was extracted with ethyl acetate, dried over sodium sulfate and concentrated in vacuo. The residue was purified by preparative LC-MS to give 13.7 mg (50% yield) of the title compound.

Example 257

(1S*,2S*)-2-(3-(2-(4,4-difluoropiperidin-1-yl)-2-oxoethoxy)phenyl)-N—((R)-1-(5-(2,2,2-trifluoroethoxy)pyridin-2-yl)ethyl)cyclopropanecarboxamide Step-1: tert-butyl 2-(3-(1S*,2S*)-2-(((R)-1-(5-(2,2, 2-trifluoroethoxy)pyridin-2-yl)ethyl)carbamoyl)cyclopropyl)phenoxy)acetate Prepared as in Step-1 of Example 256 from (1S*,2S*)-2-(3-hydroxyphenyl)-N—((R)-1-(5-(2,2,2-trifluoroethoxy) pyridin-2-yl)ethyl)cyclopropanecarboxamide.
$^1$H-NMR (300 MHz, DMSO-d$_6$): δ 8.56 (1H, d, J=7.7 Hz), 8.31 (1H, d, J=2.9 Hz), 7.49 (1H, dd, J=8.4, 2.9 Hz), 7.29 (1H, d, J=8.8 Hz), 7.16 (1H, t, J=7.7 Hz), 6.72-6.65 (3H, m), 4.95 (1H, t, J=7.3 Hz), 4.84 (2H, q, J=8.8 Hz), 4.61 (2H, s), 2.19 (1H, m), 1.98 (1H, m), 1.41 (9H, s), 1.32 (2H, d, J=7.0 Hz), 1.25 (1H, m), 1.15 (1H, m), LCMS (Method A) m/z: M+1 obs 495.1, tR=3.28 min.

Step-2

2-(3-(1S*,2S*)-2-(((R)-1-(5-(2,2,2-trifluoroethoxy) pyridin-2-yl)ethyl)carbamoyl)cyclopropyl)phenoxy) acetic acid Prepared as in Step-2 of Example 256 from tert-butyl 2-(3-((1S*,2S*)-2-(((R)-1-(5-(2,2,2-trifluoroethoxy)pyridin-2-yl)ethyl)carbamoyl)cyclopropyl)phenoxy)acetate.
LCMS (Method A) m/z: M+1 obs 439.0, tR=2.61 min.

Step-3

(1S*,2S*)-2-(3-(2-(4,4-difluoropiperidin-1-yl)-2-oxoethoxy)phenyl)-N—((R)-1-(5-(2,2,2-trifluoroethoxy)pyridin-2-yl)ethyl)cyclopropanecarboxamide Prepared as in Step-3 of Example 256 from 2-(3-(((1S*,2S*)-2-(((R)-1-(5-(2,2,2-trifluoroethoxy)pyridin-2-yl)ethyl)carbamoyl)cyclopropyl)phenoxy)acetic acid. The residue was purified by preparative LC-MS to give 11.4 mg of the title compound.

Example 292

(R)-4-(tert-butyl)-N-(1-(5-hydroxypyridin-2-yl)ethyl)benzamide

Prepared as in Example 242 from (R)—N-(1-(5-(benzyloxy)pyridin-2-yl)ethyl)-4-(tert-butyl)benzamide (Example 313).
$^1$H-NMR (300 MHz, DMSO-$d_6$): δ 9.74 (1H, s), 8.60 (1H, d, d=8.1 Hz), 8.04 (1H, d, J=2.9 Hz), 7.81 (2H, d, J=8.4 Hz), 7.45 (2H, d, J=8.1 Hz), 7.19 (1H, d, J=8.4 Hz), 7.10 (1H, dd, J=8.4, 2.9 Hz), 5.11 (1H, quintet, J=7.0 Hz), 1.43 (3H, d, J=7.0 Hz), 1.28 (9H, s), LCMS (Method A) m/z: M+1 obs 299.2, tR=3.21 min.

Example 293

(1S*,2S*)-2-(phenoxymethyl)-N—((R)-1-(5-(2,2,2-trifluoroethoxy)pyridin-2-yl)ethyl)cyclopropanecarboxamide Step-1

(1R*,2R*)-2-(hydroxymethyl)-N—((R)-1-(5-(2,2,2-trifluoroethoxy)pyridin-2-yl)ethyl)cyclopropanecarboxamide and (1S*,2S*)-2-(hydroxymethyl)-N—((R)-1-(5-(2,2,2-trifluoroethoxy)pyridin-2-yl)ethyl)cyclopropanecarboxamide To a mixture of (R)-1-(5-(2,2,2-trifluoroethoxy)pyridin-2-yl)ethanamine dihydrochloride (997 mg, 3.40 mmol), trans-2-(hydroxymethyl)cyclopropanecarboxylic acid (329 mg, 2.83 mmol), and triethylamine (1.99 mL, 14.2 mmol) in acetonitrile was added HBTU. After stirring at room temperature for 5 h, the mixture was poured into water, and the aqueous layer was extracted with dichloromethane three times. The combined organic layers were dried over sodium sulfate and concentrated in vacuo. The residue was purified by column chromatography on silica gel eluting with dichloromethane/methanol (20:1) to give 263 mg (29%) of upper spot (tentatively assigned as (1R*,2R*)-2-(hydroxymethyl)-N—((R)-1-(5-(2,2,2-trifluoroethoxy)pyridin-2-yl)ethyl)cyclopropanecarboxamide) as a colorless oil and 292 mg of lower spot (tentatively assigned as (1S*,2S*)-2-(hydroxymethyl)-N—((R)-1-(5-(2,2,2-trifluoroethoxy)pyridin-2-yl)ethyl)cyclopropanecarboxamide) as a crystal.
(1R*,2R*)-2-(Hydroxymethyl)-N—((R)-1-(5-(2,2,2-trifluoroethoxy)pyridin-2-yl)ethyl)cyclopropanecarboxamide:
$^1$H-NMR (300 MHz, CDCl$_3$): δ 8.26 (1H, s), 7.27-7.21 (2H, m), 6.91 (1H, d, J=7.3 Hz), 5.11 (quintet, J=6.6 Hz), 3.66 (1H, dd, J=5.9 & 11.0 Hz), 3.41 (1H, dd, J=7.3 & 11.0 Hz), 1.70-1.60 (2H, m), 1.45 (3H, d, J=6.6 Hz), 1.27-1.19 (1H, m), 0.81-0.73 (1H, m) (a signal due to OH was not observed), LCMS (Method A) m/z: M+1 obs 319.1, tR=2.40 min. (1S*,2S*)-2-(Hydroxymethyl)-N—((R)-1-(5-(2,2,2-trifluoroethoxy)pyridin-2-yl)ethyl)cyclopropanecarboxamide: $^1$H-NMR (300 MHz, CDCl$_3$): δ 8.29 (1H, s), 7.27-7.20 (2H, m), 6.89 (1H, d, J=6.6 Hz), 5.11 (1H, quintet, J=6.6 Hz), 4.40 (2H, q, J=8.0 Hz), 3.66 (1H, dd, J=5.9 & 11.7 Hz), 3.49 (1H, dd, J=6.6 & 11.7 Hz), 1.77-1.65 (2H, m), 1.20-1.12 (1H, m), 0.77-0.70 (1H, m) (a signal due to OH was not observed), LCMS (Method A) m/z: M+1 obs 319.1, tR=2.37 min.

Step-2

(1S*,2S*)-2-(phenoxymethyl)-N—((R)-1-(5-(2,2,2-trifluoroethoxy)pyridin-2-yl)ethyl)cyclopropanecarboxamide To a mixture of (1S*,2S*)-2-(hydroxymethyl)-N—((R)-1-(5-(2,2,2-trifluoroethoxy)pyridin-2-yl)ethyl)cyclopropanecarboxamide (30 mg, 0.094 mmol) and phenol (16.0 mg, 0.17 mmol) in tetrahydrofuran (1 mL), triphenylphosphine (45 mg, 0.17 mmol) and di-tert-butyl azodicarboxylate (28.2 mg, 0.12 mmol) were added successively. After stirring at room temperature for 1 day, the mixture was poured into water, and the aqueous layer was extracted with dichloromethane three times. The combined organic layers were dried over sodium sulfate and concentrated in vacuo. The residue was purified by preparative LC-MS to give 12.1 mg (33% yield) of the title compound.

By a method similar to Example 293 except that the reactant is different, the following compounds of Examples 294-302 were similarly prepared (also see Table 3). The reactants were used commercially available materials, otherwise noted in the intermediate parts.

Example 303

(1S*,2S*)-2-(3-((3-methyloxetan-3-yl)methoxy)phenyl)-N—((R)-1-(5-(2,2,2-trifluoroethoxy)pyridin-2-yl)ethyl)cyclopropanecarboxamide A mixture of (1S*,2S*)-2-(3-hydroxyphenyl)-N—((R)-1-(5-(2,2,2-trifluoroethoxy)pyridin-2-yl)ethyl)cyclopropanecarboxamide (15 mg, 0.039 mmol), 3-(Chloromethyl)-3-methyloxetane (24 mg, 0.197 mmol) and potassium carbonate (27 mg, 0.197 mmol) in DMF (2 mL) was heated at 70° C. with stirring for 15 hours. The mixture was poured into water, and the aqueous layer was extracted with ethyl acetate, dried over magnesium sulfate and concentrated in vacuo. The residue was purified by preparative LC-MS to give 8.9 mg (49% yield) of the title compound.

Example 304

(1S*,2S*)-2-(4-((3-methyloxetan-3-yl)methoxy)phenyl)-N—((R)-1-(5-(2,2,2-trifluoroethoxy)pyridin-2-yl)ethyl)cyclopropanecarboxamide Prepared as in Example 303 from (1S*,2S*)-2-(4-hydroxyphenyl)-N—((R)-1-(5-(2,2,2-trifluoroethoxy)pyridin-2-yl)ethyl)cyclopropanecarboxamide. The residue was purified by preparative LC-MS to give 8 mg of the title compound.

Example 305

(1S*,2S*)-2-(4-(pyridin-2-ylmethoxy)phenyl)-N—((R)-1-(5-(2,2,2-trifluoroethoxy)pyridin-2-yl)ethyl)cyclopropanecarboxamide A mixture of (1S*,2S*)-2-(4-hydroxyphenyl)-N—((R)-1-(5-(2,2,2-trifluoroethoxy)pyridin-2-yl)ethyl)cyclopropanecarboxamide (15 mg, 0.039 mmol), 2-(Bromomethyl)pyridine hydrobromide (100 mg, 0.394 mmol) and potassium carbonate (27 mg, 0.197 mmol) in DMF (2 mL) was heated at 70° C. with stirring for 2 days. The mixture was poured into water, and the aqueous layer was extracted with ethyl acetate, dried over magnesium sulfate and concentrated in vacuo. The residue was purified by preparative LC-MS to give 5 mg (27% yield) of the title compound.

Example 306

(1S*,2S*)-2-(3-(pyridin-2-ylmethoxy)phenyl)-N—((R)-1-(5-(2,2,2-trifluoroethoxy)pyridin-2-yl)ethyl)cyclopropanecarboxamide Prepared as in Example 305 from (1S*,2S*)-2-(3-hydroxyphenyl)-N—((R)-1-(5-(2,2,2-trifluoroethoxy)pyridin-2-yl)ethyl)cyclopropanecarboxamide. The residue was purified by preparative LC-MS to give 12 mg of the title compound.

Example 314

(R)-4-tert-butyl-N-(1-(5-(pyridin-2-ylmethoxy)pyridin-2-yl)ethyl)benzamide

Prepared as in Example 81 and Example 305 from (R)—N-(1-(5-(benzyloxy)pyridin-2-yl)ethyl)-4-tert-butylbenzamide (Example 313).

Example 424

(R)-6-fluoro-N,1-dimethyl-N-(1-(5-(2,2,2-trifluoroethoxy)pyridin-2-yl)ethyl)-1H-indole-2-carboxamide To a stirred solution of (R)-6-fluoro-N-(1-(5-(2,2,2-trifluoroethoxy)pyridin-2-yl)ethyl)-1H-indole-2-carboxamide (Example 48, 18 mg, 0.046 mmol) in DMF (1 mL) was added sodium hydride (60%, 1.6 mg, 0.068 mmol) at room temperature. After 20 min, Iodomethane (0.0034 mL, 0.055 mmol) was added and the mixture was stirred at room temperature for 1 hour. The mixture was poured into water, and extracted with ethyl acetate, dried over sodium sulfate and concentrated under reduced pressure. The residue was diluted with methanol and applied onto a strong cation exchange cartridge (BondElute (registered trademark) SCX, 1 g/6 mL. Varian Inc.), and the solid phase matrix was rinsed with methanol (6 mL). The crude mixture was eluted in a collection tube with 1 mol/L ammonia in methanol (6 mL) and concentrated in vacuo. The residue was purified by preparative LC-MS to give 9.4 mg (50% yield) of the title compound Example 425

(1S*,2S*)—N-methyl-2-(quinolin-2-yl)-N—((R)-1-(5-(2,2,2-trifluoroethoxy)pyrazin-2-yl)ethyl)cyclopropanecarboxamide Step-1

(1S*,2S*)-2-(quinolin-2-yl)-N—((R)-1-(5-(2,2,2-trifluoroethoxy)pyrazin-2-yl)ethyl)cyclopropanecarboxamide Prepared as in Example 1 from 2-(quinolin-2-yl)cyclopropanecarboxylic acid (purified by chiral HPLC).
$^1$H-NMR (300 MHz, CDCl$_3$): δ 8.25 (1H, s), 8.07 (1H, s), 8.00 (1H, d, J=8.0 Hz), 7.90 (1H, d, J=8.0 Hz), 7.74 (1H, d, J=8.0 Hz), 7.65 (1H, t, J=8.0 Hz), 7.45 (1H, t, J=8.0 Hz), 7.31 (1H, d, J=8.0 Hz), 6.58 (1H, d, J=8.0 Hz), 5.27 (1H, quintet, J=7.3 Hz), 4.80-4.67 (2H, m), 2.73-2.66 (1H, m), 2.35-2.27 (1H, m), 1.73-1.66 (2H, m), 1.50 (3H, d, J=7.3 Hz).

Step-2

(1S*,2S*)—N-methyl-2-(quinolin-2-yl)-N—((R)-1-(5-(2,2,2-trifluoroethoxy)pyrazin-2-yl)ethyl)cyclopropanecarboxamide Prepared as in Example 424 from (1S*,2S*)-2-(quinolin-2-yl)-N—((R)-1-(5-(2,2,2-trifluoroethoxy)pyrazin-2-yl)ethyl)cyclopropanecarboxamide. The residue was purified by preparative LC-MS to give 11 mg of the title compound.

Example 426

(1R*,2R*)—N-methyl-2-(quinolin-2-yl)-N—((R)-1-(5-(2,2,2-trifluoroethoxy-2-yl)ethyl)cyclopropanecarboxamide Prepared as in Example 424 from (1R*,2R*)-2-(quinolin-2-yl)-N—((R)-1-(5-(2,2,2-trifluoroethoxy)pyrazin-2-yl)ethyl)cyclopropanecarboxamide (Example 222). The residue was purified by preparative LC-MS to give 2.3 mg of the title compound.

Quality control analytical condition (Method B), the amine/carboxylic acid used, the purification method, and spectra data are described below for Examples 1-464 in Table 3 and Table 4.

TABLE 3

| Example | Name | STRUCTURE | Structure of amine part | Structure of caboxylic acid part | Observed MS | Retention Time | Purification Method |
|---|---|---|---|---|---|---|---|
| Example 1 | (R)-5-tert-butyl-N-(1-(5-(2,2,2-trifluoroethoxy)pyridin-2-yl)ethyl)isoxazole-3-carboxamide | 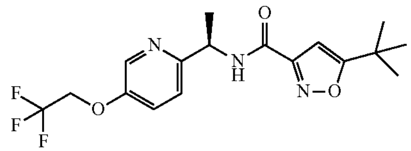 [SMILES: C[C@@H](NC(=O)c1cc(C(C)(C)C)on1)c1ccc(OCC(F)(F)F)cn1] | | | 572.0 | 0.05 min | HPLC |
| Example 2 | (R)-5-tert-butyl-N-(1-(5-(2,2,2-trifluoroethoxy)pyridin-2-yl)ethyl)nicotinamide | 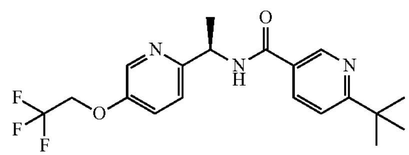 [SMILES: C[C@@H](NC(=O)c1ccc(C(C)(C)C)nc1)c1ccc(OCC(F)(F)F)cn1] | | | 382.0 | 0.79 min | HPLC |
| Example 3 | (R)-N-(1-(6-(2,2,2-trifluoroethoxy)pyridin-2-yl)ethyl)-2-(4-(trifluoromethyl)phenoxy)acetamide | 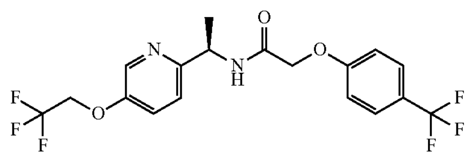 [SMILES: C[C@@H](NC(=O)COc1ccc(C(F)(F)F)cc1)c1ccc(OCC(F)(F)F)cn1] | | | 423.0 | 0.83 min | HPLC |
| Example 4 | (R)-4-(benzyloxy)-N-(1-(6-(2,2,2-trifluoromethoxy)pyridin-2-yl)ethyl)benzamide | 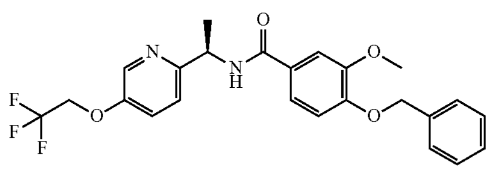 [SMILES: COc1cc(C(=O)N[C@H](C)c2ccc(OCC(F)(F)F)cn2)ccc1OCc1ccccc1] | | | 461.0 | 0.82 min | HPLC |
| Example 5 | (R)-4-tert-butyl-2-methoxy-N-(1-(5-(2,2,2-trifluoroethoxy)pyridin-2-yl)ethyl) | 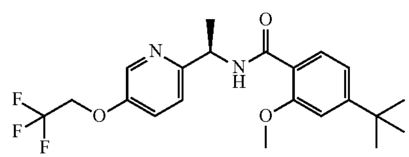 [SMILES: COc1cc(C(C)(C)C)ccc1C(=O)N[C@H](C)c1ccc(OCC(F)(F)F)cn1] | | | 411.0 | 0.9 min | HPLC |

TABLE 3-continued

| Example | Name | STRUCTURE | Structure of amine part | Structure of caboxylic acid part | Observed MS | Retention Time | Purification Method |
|---|---|---|---|---|---|---|---|
| Example 6 | (R)-2-(4-chloro-3-(trifluoromethyl) phenoxy)-N-(1-(5-(2,2,2-trifluoroethoxy) pyridin-2-yl) ethyl)acetamide | 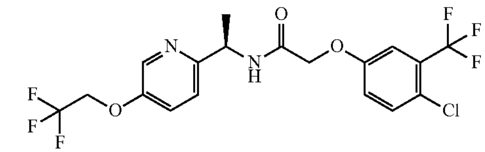 [SMILES: C[C@@H](NC(=O)COc1ccc(Cl)c(C(F)(F)F)c1)c1ccc(OCC(F)(F)F)cn1] | | | 457.8 | 0.86 min | HPLC |
| Example 7 | (R)-3,5-dichloro-N-(1-(5-(2,2,2-trifluoroethoxy) pyridin-2-yl) ethyl)benzamide | 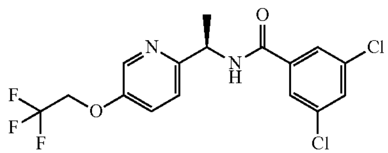 [SMILES: C[C@@H](NC(=O)c1cc(Cl)cc(Cl)c1)c1ccc(OCC(F)(F)F)cn1] | | | 393.0 | 0.86 min | HPLC |
| Example 8 | (R)-N-(1-(5-(2,2,2-trifluoroethoxy) pyridin-2-yl) ethyl)quinoline-2-carboxamide | 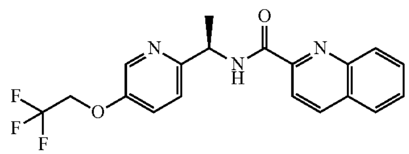 [SMILES: C[C@@H](NC(=O)c1ccc2ccccc2n1)c1ccc(OCC(F)(F)F)cn1] | | | 375.0 | 0.83 min | HPLC |
| Example 9 | (R)-4-(3-(1,1,1-trifluoro-2-methylpropan-2-yl)phenyl)-N-(1-(5-(2,2,2-trifluoromethoxy) pyridin-2-yl) ethyl)thiazole-2-carboxamide | 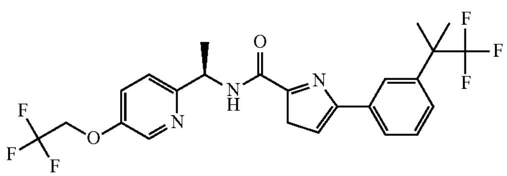 [SMILES: C[C@@H](NC(=O)C1=NC(c2cccc(C(C)(C)C(F)(F)F)c2)=CC1)c1ccc(OCC(F)(F)F)cn1] | | | 518.0 | 2.08 min | HPLC |
| Example 10 | (1R,2R)-2-methyl-N-((R)-1-(5(2,2,2-trifluoroethoxy) pyridin-2-yl)ethyl)-2-(4-(trifluoromethyl) phenyl)cyclopropane-carboxamide | 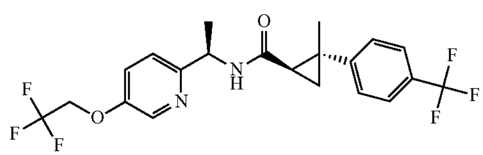 [SMILES: C[C@@H](NC(=O)[C@@H]1C[C@@]1(C)c1ccc(C(F)(F)F)cc1)c1ccc(OCC(F)(F)F)cn1] | | | 447.0 | 1.91 min | HPLC |

TABLE 3-continued

| Example | Name | STRUCTURE | Structure of amine part | Structure of caboxylic acid part | Observed MS | Retention Time | Purification Method |
|---|---|---|---|---|---|---|---|
| Example 11 | (R)-2-(1,1,1-trifluoro-2-methylpropan-2-yl)-N-(1-(5-(2,2,2-trifluoroethoxy)pyridin-2-yl)ethyl)quinoline-6-carboxamide | 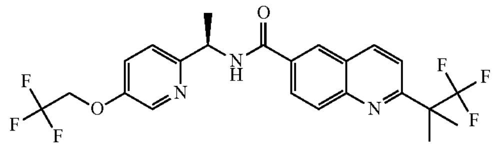 [SMILES: C[C@@H](NC(=O)c1ccc2nc(C(C)(C)C(F)(F)F)ccc2c1)c1ccc(OCC(F)(F)F)cn1] | | | 486.0 | 1.94 min | HPLC |
| Example 12 | trans-2-(4-tert-butylphenyl)-N-((R)-1-(5-(2,2,2-trifluoroethoxy)pyridin-2-yl)ethyl)cyclopropanecarboxamide | 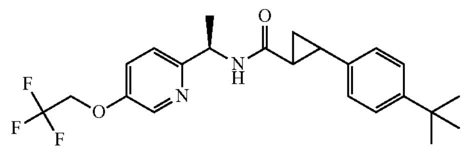 [SMILES: C[C@@H](NC(=O)C1CC1c1ccc(C(C)(C)C)cc1)c1ccc(OCC(F)(F)F)cn1] | | | 421.0 | 1.99 min | HPLC |
| Example 13 | (R)-4-tert-butyl-N-(1-(5-(2,2,2-trifluoroethoxy)pyridin-2-yl)ethyl)benzamide | 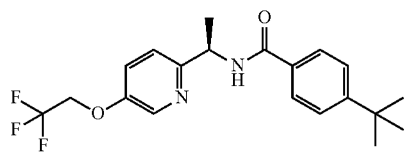 [SMILES: C[C@@H](NC(=O)c1ccc(C(C)(C)C)cc1)c1ccc(OCC(F)(F)F)cn1] | | | 381.2 | 1.89 min | HPLC |
| Example 14 | (R)-4-isopropyl-N-(1-(5-(2,2,2-trifluoroethoxy)pyridin-2-yl)ethyl)benzamide | 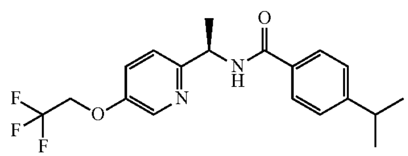 [SMILES: CC(C)c1ccc(C(=O)N[C@H](C)c2ccc(OCC(F)(F)F)cn2)cc1] | | | 367.2 | 1.83 min | HPLC |
| Example 15 | (R)-4-tert-butyl-2-methoxy-N-(1-(6-(2,2,2-trifluoroethoxy)pyridin-3-yl)ethyl)benzamide | 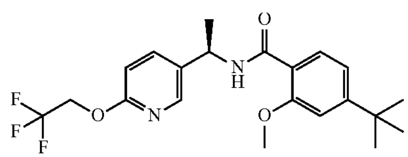 [SMILES: COc1cc(C(C)(C)C)ccc1C(=O)N[C@H](C)c1ccc(OCC(F)(F)F)nc1] | | | 411.2 | 2.06 min | HPLC |
| Example 16 | (R)-N-(1-(6-(2,2,2-trifluoroethoxy)pyridin-3-yl)ethyl)-2-(4-(trifluoromethyl)phenoxy)acetamide | 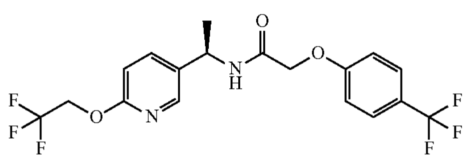 [SMILES: C[C@@H](NC(=O)COc1ccc(C(F)(F)F)cc1)c1ccc(OCC(F)(F)F)nc1] | | | 423.1 | 3.24 min | HPLC |

TABLE 3-continued

| Example | Name | STRUCTURE | Structure of amine part | Structure of caboxylic acid part | Observed MS | Retention Time | Purification Method |
|---|---|---|---|---|---|---|---|
| Example 17 | (R)-2-(p-tolyloxy)-N-(1-(5-(2,2,2-trifluoroethoxy)pyridin-2-yl)ethyl)acetamide | 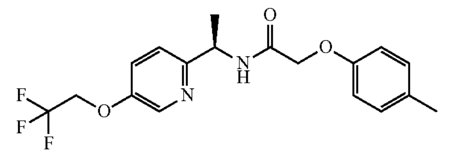 [SMILES: Cc1ccc(OCC(=O)N[C@H](C)c2ccc(OCC(F)(F)F)cn2)cc1] | | | 369.1 | 1.77 min | HPLC |
| Example 18 | (R)-2-(4-chlorophenoxy)-N-(1-(5-(2,2,2-trifluoroethoxy)pyridin-2-yl)ethyl)acetamide | 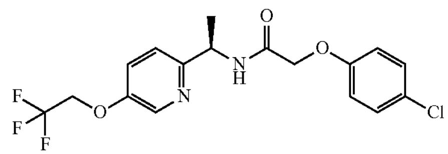 [SMILES: C[C@@H](NC(=O)COc1ccc(Cl)cc1)c1ccc(OCC(F)(F)F)cn1] | | | 389.1 | 1.78 min | HPLC |
| Example 19 | (R)-4-(2,2,2-trifluoroethoxy)-N-(1-(5-(2,2,2-trifluoroethoxy)pyridin-2-yl)ethyl)benzamide | 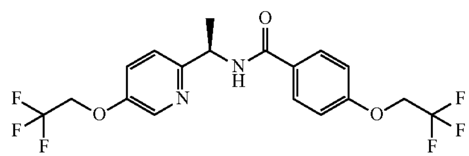 [SMILES: C[C@@H](NC(=O)c1ccc(OCC(F)(F)F)cc1)c1ccc(OCC(F)(F)F)cn1] | | | 423.1 | 1.73 min | HPLC |
| Example 20 | (R)-2-(biphenyl-1-yloxy)-N-(1-(5-(2,2,2-trifluoroethoxy)pyridin-2-yl)ethyl)acetamide | 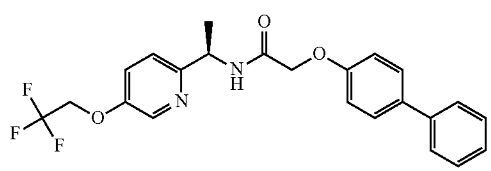 [SMILES: C[C@@H](NC(=O)COc1ccc(-c2ccccc2)cc1)c1ccc(OCC(F)(F)F)cn1] | | | 431.1 | 1.90 min | HPLC |
| Example 21 | (R)-2-(4-phenoxyphenoxy)-N-(1-(5-(2,2,2-trifluoroethoxy)pyridin-2-yl)ethyl)acetamide | 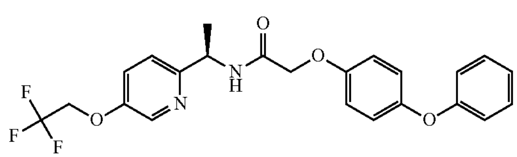 [SMILES: C[C@@H](NC(=O)COc1ccc(Oc2ccccc2)cc1)c1ccc(OCC(F)(F)F)cn1] | | | 447.1 | 1.89 min | HPLC |

TABLE 3-continued

| Example | Name | STRUCTURE | Structure of amine part | Structure of caboxylic acid part | Observed MS | Retention Time | Purification Method |
|---|---|---|---|---|---|---|---|
| Example 22 | (R)-2-(2-tert-butylphenoxy)-N-(1-(5-(2,2,2-trifluoroethoxy)pyridin-2-yl)ethyl)acetamide | 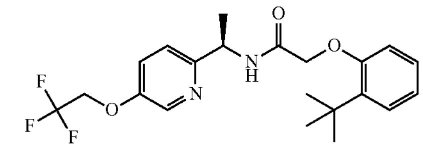 [SMILES: C[C@@H](NC(=O)COc1ccccc1C(C)(C)C)c1ccc(OCC(F)(F)F)cn1] | | | 411.2 | 2.04 min | HPLC |
| Example 23 | (R)-N-(1-(5-(2,2,2-trifluoroethoxy)pyridin-3-yl)ethyl)-2-(2-(trifluoromethyl)phenoxy)acetamide | 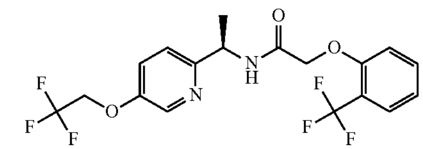 [SMILES: C[C@@H](NC(=O)COc1ccccc1C(F)(F)F)c1ccc(OCC(F)(F)F)cn1] | | | 421.1 | 1.84 min | HPLC |
| Example 24 | (R)-N-(1-(5-(2,2,2-trifluoroethoxy)pyridin-2-yl)ethyl)-1H-indole-2-carboxamide | 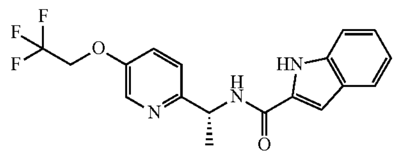 [SMILES: C[C@@H](NC(=O)c1cc2ccccc2[nH]1)c1ccc(OCC(F)(F)F)cn1] | | | 364.2 | 1.67 min | HPLC |
| Example 25 | (R)-5-fluoro-N-(1-(5-(2,2,2-trifluoroethoxy)pyridin-2-yl)ethyl)-1H-indole-2-carboxamide | 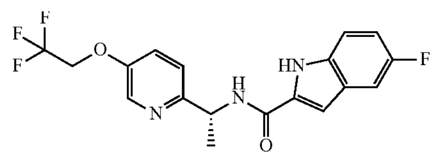 [SMILES: C[C@@H](NC(=O)c1cc2cc(F)ccc2[nH]1)c1ccc(OCC(F)(F)F)cn1] | | | 382.2 | 1.69 min | HPLC |
| Example 26 | (R)-1-methyl-N-(1-(5-(2,2,2-trifluoroethoxy)pyridin-2-yl)ethyl)-1H-indole-2-carboxamide | 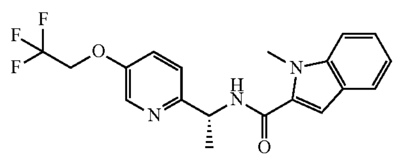 | | | 378.2 | 1.80 min | HPLC |
| Example 27 | (R)-2-(2,4-dichlorophenoxy)-N-(1-(5-(2,2,2-trifluoroethoxy)pyridin-2-yl)ethyl)acetamide | 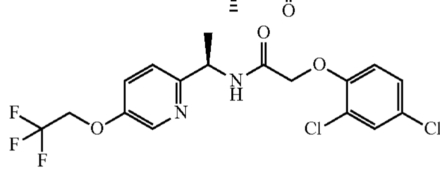 | | | 423.1 | 1.92 min | HPLC |

TABLE 3-continued

| Example | Name | STRUCTURE | Structure of amine part | Structure of caboxylic acid part | Observed MS | Retention Time | Purification Method |
|---|---|---|---|---|---|---|---|
| Example 28 | (R)-2-(4-bromophenoxy)-N-(1-(5-(2,2,2-trifluoroethoxy)pyridin-2-yl)ethyl)acetamide | 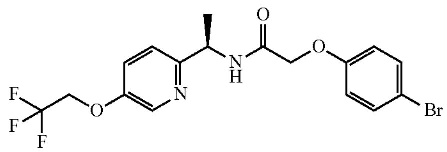 [SMILES: C[C@@H](NC(=O)COc1ccc(Br)cc1)c1ccc(OCC(F)(F)F)cn1] | | | 433.1 | 1.80 min | HPLC |
| Example 29 | (R)-2-(4-cyclopropylphenoxy)-N-(1-(5-(2,2,2-trifluoroethoxy)pyridin-2-yl)ethyl)acetamide | 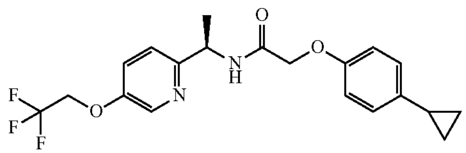 [SMILES: C[C@@H](NC(=O)COc1ccc(C2CC2)cc1)c1ccc(OCC(F)(F)F)cn1] | | Alternative route | 395.2 | 1.84 min | HPLC |
| Example 30 | (R)-3-(3-fluorophenyl)-N-(1-(5-(2,2,2-trifluoroethoxy)pyridin-2-yl)ethyl)propanamide | 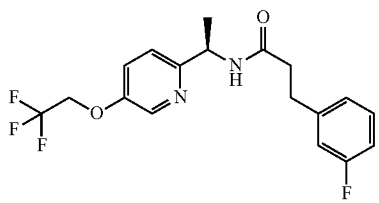 [SMILES: C[C@@H](NC(=O)CCc1cccc(F)c1)c1ccc(OCC(F)(F)F)cn1] | | | 371.2 | 1.65 min | HPLC |
| Example 31 | (R)-3-methyl-N-(1-(5-(2,2,2-trifluoroethoxy)pyridin-2-yl)ethyl)benzofuran-2-carboxamide | 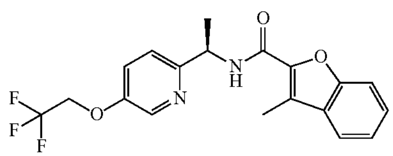 [SMILES: Cc1c(C(=O)N[C@H](C)c2ccc(OCC(F)(F)F)cn2)oc2ccccc12] | | | 379.2 | 1.88 min | HPLC |
| Example 32 | (R)-5-tert-butyl-2-methyl-N-(1-(5-(2,2,2-trifluoroethoxy)pyridin-2-yl)ethyl)furan-3-carboxamide | 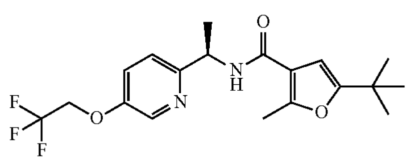 [SMILES: Cc1oc(C(C)(C)C)cc1C(=O)N[C@H](C)c1ccc(OCC(F)(F)F)cn1] | | | 385.2 | 1.93 min | HPLC |

TABLE 3-continued

| Example | Name | STRUCTURE | Structure of amine part | Structure of caboxylic acid part | Observed MS | Retention Time | Purification Method |
|---|---|---|---|---|---|---|---|
| Example 33 | (R)-3-(1H-indol-3-yl)-N-(1-(5-(2,2,2-trifluoroethoxy)pyridin-2-yl)ethyl)propanamide | 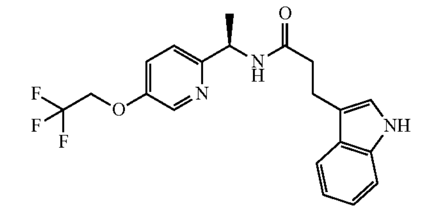 [SMILES: C[C@@H](NC(=O)CCc1c[nH]c2ccccc12)c1ccc(OCC(F)(F)F)cn1] | | | 392.2 | 1.59 min | HPLC |
| Example 34 | (R)-N-(1-(5-(2,2,2-trifluoroethoxy)pyridin-2-yl)ethyl)-3-(trifluoromethyl)benzamide | 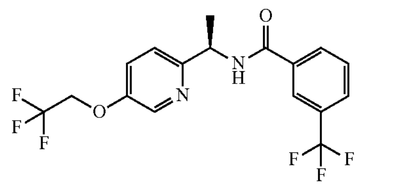 [SMILES: C[C@@H](NC(=O)c1cccc(C(F)(F)F)c1)c1ccc(OCC(F)(F)F)cn1] | | | 393.2 | 1.76 min | HPLC |
| Example 35 | (R)-N-(1-(5-(2,2,2-trifluoroethoxy)pyridin-2-yl)ethyl)-4-(trifluoromethyl)benzamide | 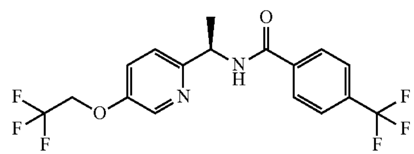 [SMILES: C[C@@H](NC(=O)c1ccc(C(F)(F)F)cc1)c1ccc(OCC(F)(F)F)cn1] | | | 393.2 | 1.76 min | HPLC |
| Example 36 | (R)-5-phenyl-N-(1-(5-(2,2,2-trifluoroethoxy)pyridin-2-yl)ethyl)-2-(trifluoromethyl)furan-3-carboxamide | 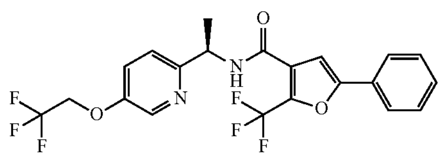 [SMILES: C[C@@H](NC(=O)c1cc(-c2ccccc2)oc1C(F)(F)F)c1ccc(OCC(F)(F)F)cn1] | | | 459.2 | 1.96 min | HPLC |
| Example 37 | (R)-3-methyl-5-phenyl-N-(1-(5-(2,2,2-trifluoroethoxy)pyridin-2-yl)ethyl)furan-3-carboxamide | 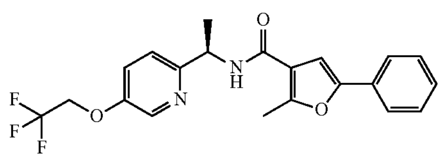 [SMILES: Cc1oc(-c2ccccc2)cc1C(=O)N[C@H](C)c1ccc(OCC(F)(F)F)cn1] | | | 405.2 | 1.89 min | HPLC |

TABLE 3-continued

| Example | Name | STRUCTURE | Structure of amine part | Structure of carboxylic acid part | Observed MS | Retention Time | Purification Method |
|---|---|---|---|---|---|---|---|
| Example 38 | (R)-3-fluoro-N-(1-(5-(2,2,2-trifluoroethoxy)pyridin-2-yl)ethyl)-5-(trifluoromethyl)benzamide | 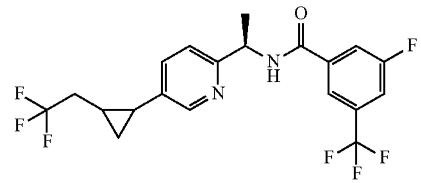 [SMILES: C[C@@H](NC(=O)c1cc(F)cc(C(F)(F)F)c1)c1ccc(C2CC2CC(F)(F)F)cn1] | | | 411.2 | 1.83 min | HPLC |
| Example 39 | (R)-3-fluoro-N-(1-(5-(2,2,2-trifluoroethoxy)pyridin-2-yl)ethyl)-4-(trifluoromethyl)benzamide | 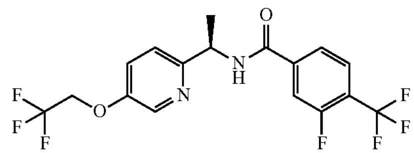 [SMILES: C[C@@H](NC(=O)c1ccc(C(F)(F)F)c(F)c1)c1ccc(OCC(F)(F)F)cn1] | | | 411.2 | 1.81 min | HPLC |
| Example 40 | (R)-4-fluoro-N-(1-(5-(2,2,2-trifluoroethoxy)pyridin-2-yl)ethyl)-3-(trifluoromethyl)benzamide | 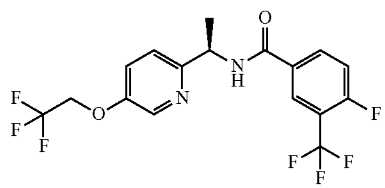 [SMILES: C[C@@H](NC(=O)c1ccc(F)c(C(F)(F)F)c1)c1ccc(OCC(F)(F)F)cn1] | | | 411.2 | 1.79 min | HPLC |
| Example 41 | (R)-2-methyl-N-(1-(5-(2,2,2-trifluoroethoxy)pyridin-2-yl)ethyl)-5-(trifluoromethyl)-2H-indazole-3-carboxamide | 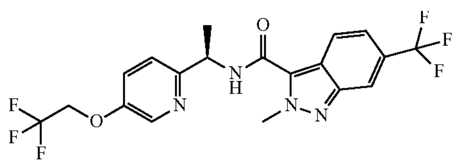 [SMILES: C[C@@H](NC(=O)c1c2ccc(C(F)(F)F)cc2nn1C)c1ccc(OCC(F)(F)F)cn1] | | | 446.9 | 1.87 min | HPLC |
| Example 42 | (R)-1-methyl-N-(1-(5-(2,2,2-trifluoroethoxy)pyridin-2-yl)ethyl)-6-(trifluoromethyl)-1H-indazole-3-carboxamide | 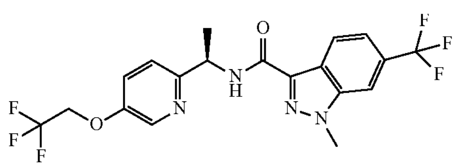 [SMILES: C[C@@H](NC(=O)c1nn(C)c2cc(C(F)(F)F)ccc12)c1ccc(OCC(F)(F)F)cn1] | | | 446.9 | 1.89 min | HPLC |

TABLE 3-continued

| Example | Name | STRUCTURE | Structure of amine part | Structure of carboxylic acid part | Observed MS | Retention Time | Purification Method |
|---|---|---|---|---|---|---|---|
| Example 43 | (R)-N-(1-(5-(2,2,2-trifluoroethoxy)pyridin-2-yl)ethyl)-5-(trifluoromethyl)picolinamide | 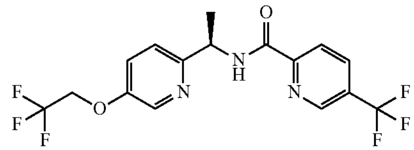 [SMILES: C[C@@H](NC(=O)c1ccc(C(F)(F)F)cn1)c1ccc(OCC(F)(F)F)cn1] | | | 393.9 | 1.83 min | HPLC |
| Example 44 | (R)-5-chloro-N-(1-(5-(2,2,2-trifluoroethoxy)pyridin-2-yl)ethyl)-1H-indole-2-carboxamide | 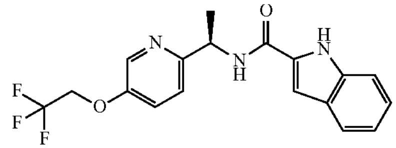 [SMILES: C[C@@H](NC(=O)c1cc2ccccc2[nH]1)c1ccc(OCC(F)(F)F)cn1] | | | 398.0 | 1.77 min | HPLC |
| Example 45 | (R)-5-methoxy-N-(1-(5-(2,2,2-trifluoroethoxy)pyridin-2-yl)ethyl)-1H-indole-2-carboxamide | 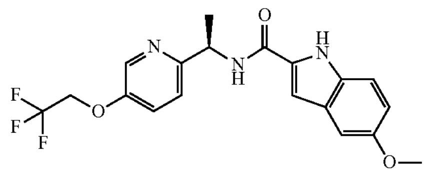 [SMILES: COc1ccc2[nH]c(C(=O)N[C@H](C)c3ccc(OCC(F)(F)F)cn3)cc2c1] | | | 394.0 | 1.64 min | HPLC |
| Example 46 | (R)-N-(1-(5-(2,2,2-trifluoroethoxy)pyridin-2-yl)ethyl)-1H-indole-3-carboxamide | 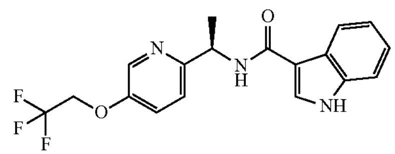 [SMILES: C[C@@H](NC(=O)c1c[nH]c2ccccc12)c1ccc(OCC(F)(F)F)cn1] | | | 364.0 | 1.55 min | HPLC |
| Example 47 | (R)-1-methyl-N-(1-(5-(2,2,2-trifluoroethoxy)pyridin-2-yl)ethyl)-1H-indole-3-carboxamide | 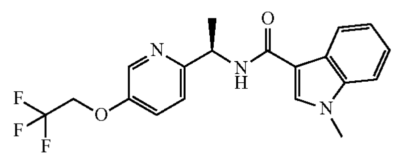 [SMILES: C[C@@H](NC(=O)c1cn(C)c2ccccc12)c1ccc(OCC(F)(F)F)cn1] | | | 378.0 | 1.66 min | HPLC |

TABLE 3-continued

| Example | Name | STRUCTURE | Structure of amine part | Structure of carboxylic acid part | Observed MS | Retention Time | Purification Method |
|---|---|---|---|---|---|---|---|
| Example 48 | (R)-8-fluoro-N-(1-(5-(2,2,2-trifluoroethoxy)pyridin-2-yl)ethyl)-1H-indole-1-carboxamide | 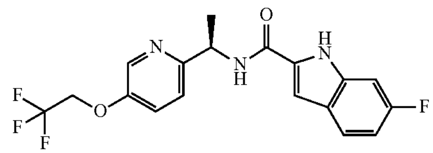 [SMILES: C[C@@H](NC(=O)c1cc2ccc(F)cc2[nH]1)c1ccc(OCC(F)(F)F)cn1] | | | 382.0 | 1.70 min | HPLC |
| Example 49 | (R)-7-fluoro-N-(1-(5-(2,2,2-trifluoroethoxy)pyridin-2-yl)ethyl)-1H-indole-2-carboxamide | 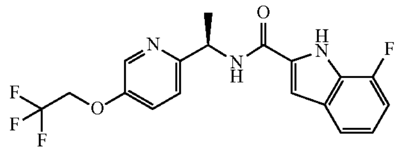 [SMILES: C[C@@H](NC(=O)c1cc2cccc(F)c2[nH]1)c1ccc(OCC(F)(F)F)cn1] | | | 382.0 | 1.70 min | HPLC |
| Example 50 | (R)-3-(1H-indol-1-yl)-N-(1-(5-(2,2,2-trifluoroethoxy)pyridin-2-yl)ethyl)propanamide | 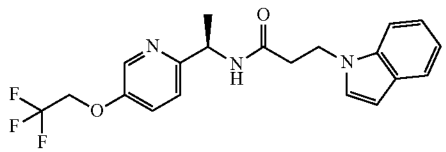 [SMILES: C[C@@H](NC(=O)CCn1ccc2ccccc21)c1ccc(OCC(F)(F)F)cn1] | | | 392.0 | 1.70 min | HPLC |
| Example 51 | (R)-5-methyl-N-(1-(5-(2,2,2-trifluoroethoxy)pyridin-2-yl)ethyl)-1H-indole-2-carboxamide | 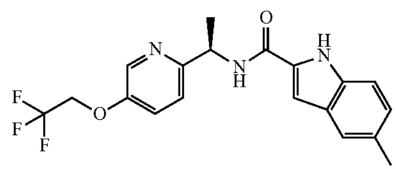 [SMILES: Cc1ccc2[nH]c(C(=O)N[C@H](C)c3ccc(OCC(F)(F)F)cn3)cc2c1] | | | 378.0 | 1.76 min | HPLC |
| Example 52 | (R)-1-methyl-N-(1-(5-(2,2,2-trifluoroethoxy)pyridin-2-yl)ethyl)-5-(trifluoromethyl)-1H-indole-2-carboxamide | 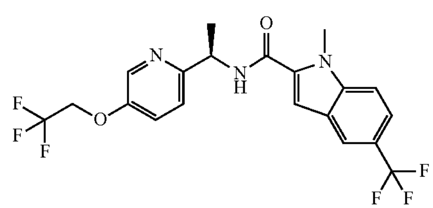 [SMILES: C[C@@H](NC(=O)c1cc2cc(C(F)(F)F)ccc2n1C)c1ccc(OCC(F)(F)F)cn1] | | | 446.0 | 1.93 min | HPLC |

TABLE 3-continued

| Example | Name | STRUCTURE | Structure of amine part | Structure of caboxylic acid part | Observed MS | Retention Time | Purification Method |
|---|---|---|---|---|---|---|---|
| Example 53 | (R)-N-(1-(5-(2,2,2-trifluoroethoxy)pyridin-2-yl)ethyl)-5-(trifluoromethyl)-1H-indole-2-carboxamide | 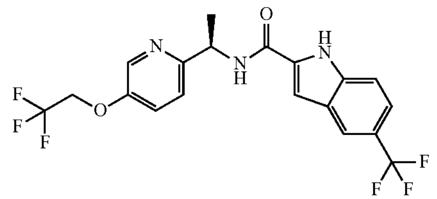 [SMILES: C[C@@H](NC(=O)c1cc2cc(C(F)(F)F)ccc2[nH]1)c1ccc(OCC(F)(F)F)cn1] | | | 432.0 | 1.82 min | HPLC |
| Example 54 | (R)-1-methyl-N-(1-(5-(2,2,2-trifluoroethoxy)pyridin-2-yl)ethyl)-6-(trifluoromethyl)-1H-indole-3-carboxamide | 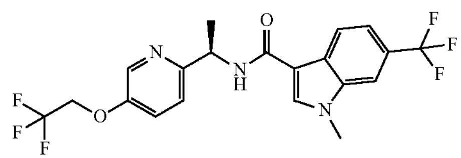 [SMILES: C[C@@H](NC(=O)c1cn(C)c2cc(C(F)(F)F)ccc12)c1ccc(OCC(F)(F)F)cn1] | | | 446.0 | 1.81 min | HPLC |
| Example 55 | (R)-N-(1-(5-(2,2,2-trifluoroethoxy)pyridin-2-yl)ethyl)-5-(trifluoromethyl)-1H-benzo[d]imadazole-2-carboxamide | 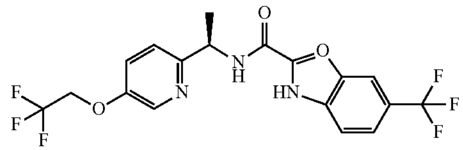 | | | 432.9 | 1.80 min | HPLC |
| Example 56 | (R)-N-(1-(5-(2,2,2-trifluoroethoxy)pyridin-2-yl)ethyl)-6-(trifluoromethyl)-1H-indazole-3-carboxamide | 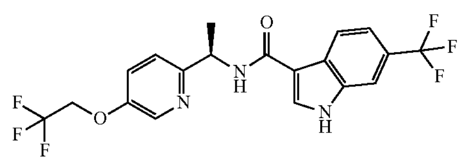 [SMILES: C[C@@H](NC(=O)c1c[nH]c2cc(C(F)(F)F)ccc12)c1ccc(OCC(F)(F)F)cn1] | | | 432.9 | 1.76 min | HPLC |
| Example 57 | (R)-4-(1H-indol-3-yl)-N-(1-(5-(2,2,2-trifluoroethoxy)pyridin-2-yl)ethyl)butanamide | 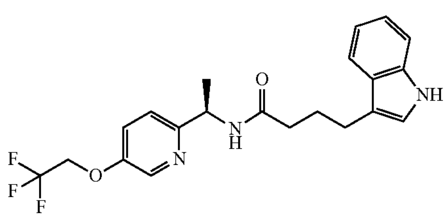 [SMILES: C[C@@H](NC(=O)CCCc1c[nH]c2ccccc12)c1ccc(OCC(F)(F)F)cn1] | | | 406.0 | 1.65 min | HPLC |

TABLE 3-continued

| Example | Name | STRUCTURE | Structure of amine part | Structure of caboxylic acid part | Observed MS | Retention Time | Purification Method |
|---|---|---|---|---|---|---|---|
| Example 58 | (R)-N-(1-(5-(2,2,2-trifluoroethoxy)pyridin-2-yl)ethyl)-6-(trifluoromethyl)-1H-indole-3-carboxamide | 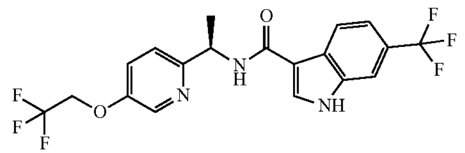 [SMILES: C[C@@H](NC(=O)c1c[nH]c2cc(C(F)(F)F)ccc12)c1ccc(OCC(F)(F)F)cn1] | | | 431.9 | 1.73 min | HPLC |
| Example 59 | (R)-N-(1-(5-(cyclopropyl-methoxy)pyridin-2-yl)ethyl)-2-(4-(trifluoromethyl)phenoxy)acetamide | 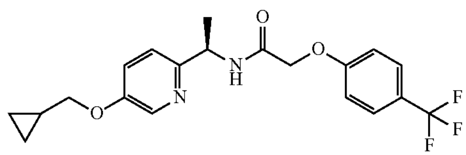 [SMILES: C[C@@H](NC(=O)COc1ccc(C(F)(F)F)cc1)c1ccc(OCC2CC2)cn1] | | | 395.0 | 1.87 min | HPLC |
| Example 60 | (R)-N-(1-(5-(cyclopropyl-methoxy)pyridin-2-yl)ethyl)-3-(1H-indol-3-yl)propanamide | 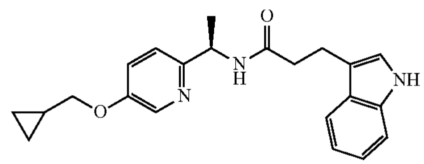 [SMILES: C[C@@H](NC(=O)CCc1c[nH]c2ccccc12)c1ccc(OCC2CC2)cn1] | | | 364.0 | 1.62 min | HPLC |
| Example 61 | (R)-N-(1-(5-(cyclopropyl-methoxy)pyridin-2-yl)ethyl)-5-fluoro-1H-indole-2-carboxamide | 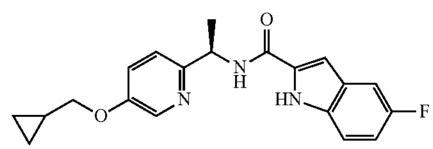 [SMILES: C[C@@H](NC(=O)c1cc2cc(F)ccc2[nH]1)c1ccc(OCC2CC2)cn1] | | | 354.0 | 1.74 min | HPLC |
| Example 62 | trans-2-(4-tert-butylphenyl)-N-((R)-1-(5-(cyclopropylmethoxy)pyridin-2-yl)ethyl)cyclopropane-carboxamide | 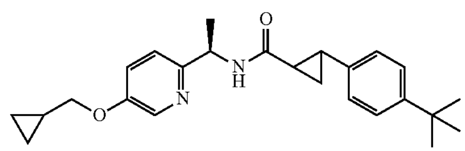 [SMILES: C[C@@H](NC(=O)C1CC1c1ccc(C(C)(C)C)cc1)c1ccc(OCC2CC2)cn1] | | | 393.0 | 2.06 min | HPLC |
| Example 63 | (R)-N-(1-(5-(benzyloxy)pyridin-3-yl)ethyl)-2-(4-(trifluoromethyl)phenoxy)acetamide | 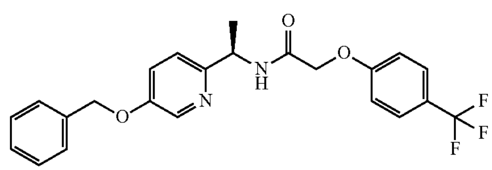 [SMILES: C[C@@H](NC(=O)COc1ccc(C(F)(F)F)cc1)c1ccc(OCc2ccccc2)cn1] | | | 430.9 | 1.94 min | HPLC |

TABLE 3-continued

| Example | Name | STRUCTURE | Structure of amine part | Structure of caboxylic acid part | Observed MS | Retention Time | Purification Method |
|---|---|---|---|---|---|---|---|
| Example 64 | (R)-N-(1-(5-(benzyloxy)pyridin-2-yl)ethyl)-3-(1H-indol-3-yl)propanamide | 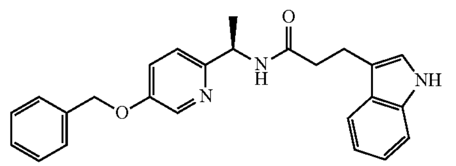 [SMILES: C[C@@H](NC(=O)CCc1c[nH]c2ccccc12)c1ccc(OCc2ccccc2)cn1] | | | 400.0 | 1.72 min | HPLC |
| Example 65 | (R)-N-(1-(5-(benzyloxy)pyridin-2-yl)ethyl)-5-fluoro-1H-indole-3-carboxamide | 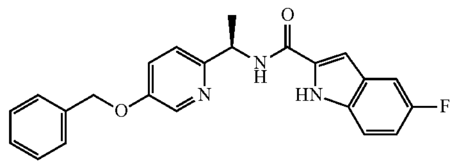 [SMILES: C[C@@H](NC(=O)c1cc2cc(F)ccc2[nH]1)c1ccc(OCc2ccccc2)cn1] | | | 390.0 | 1.82 min | HPLC |
| Example 66 | trans-N-((R)-1-(5-(benzyloxy)pyridin-2-yl)ethyl)-2-(4-tert-butylphenyl)cyclopropane-carboxamide | 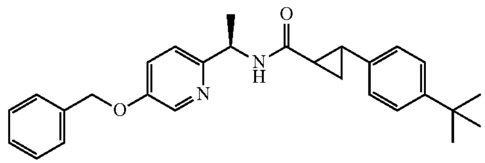 [SMILES: C[C@@H](NC(=O)C1CC1c1ccc(C(C)(C)C)cc1)c1ccc(OCc2ccccc2)cn1] | | | 429.0 | 2.11 min | HPLC |
| Example 67 | (R,E)-N-(1-(5-(2,2,2-trifluoroethoxy)pyridin-2-yl)ethyl)-3-(4-(trifluoromethyl)phenyl)acetamide | 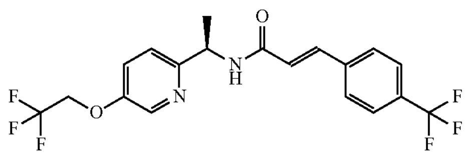 [SMILES: C[C@@H](NC(=O)/C=C/c1ccc(C(F)(F)F)cc1)c1ccc(OCC(F)(F)F)cn1] | | | 418.9 | 1.82 min | HPLC |
| Example 68 | (R,E)-N-(1-(5-(cyclopropyl-methoxy)pyridin-2-yl)ethyl)-3-(4-(trifluoromethyl)phenyl)acrylamide | 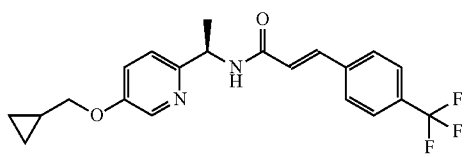 [SMILES: C[C@@H](NC(=O)/C=C/c1ccc(C(F)(F)F)cc1)c1ccc(OCC2CC2)cn1] | | | 391.0 | 1.85 min | HPLC |

TABLE 3-continued

| Example | Name | STRUCTURE | Structure of amine part | Structure of caboxylic acid part | Observed MS | Retention Time | Purification Method |
|---|---|---|---|---|---|---|---|
| Example 69 | (R,E)-N-(1-(5-(benzyloxy)pyridin-2-yl)ethyl)-3-(4-(trifluoromethyl)phenyl)acrylamide | 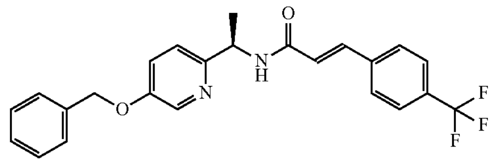 [SMILES: C[C@@H](NC(=O)/C=C/c1ccc(C(F)(F)F)cc1)c1ccc(OCc2ccccc2)cn1] | | | 427.0 | 1.92 min | HPLC |
| Example 70 | (R)-N-(1-(5-(2,2,2-trifluoroethoxy)pyridin-2-yl)ethyl)-2-(4-(trifluoromethyl)phenyl)thiazole-4-carboxamide | 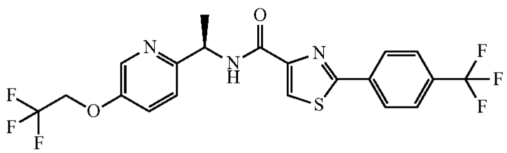 | | | 475.9 | 2.01 min | HPLC |
| Example 71 | (R)-3-(6-fluoro-1H-indol-3-yl)-N-(1-(5-(2,2,2-trifluoroethoxy)pyridin-2-yl)ethyl)propanamide | 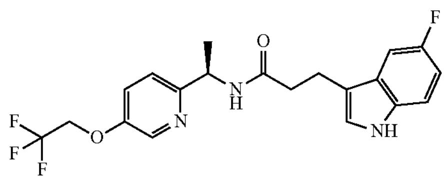 [SMILES: C[C@@H](NC(=O)CCc1c[nH]c2ccc(F)cc12)c1ccc(OCC(F)(F)F)cn1] | | | 410.0 | 1.62 min | HPLC |
| Example 72 | (R)-N-(1-(5-(cyclopropylmethoxy)pyridin-2-yl)ethyl)-3-5-fluoro-1H-indol-3-yl)propanamide | 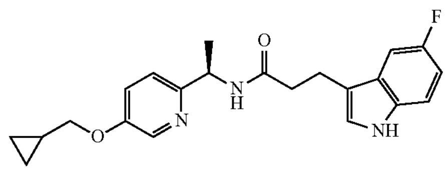 [SMILES: C[C@@H](NC(=O)CCc1c[nH]c2ccc(F)cc12)c1ccc(OCC2CC2)cn1] | | | 382.0 | 1.64 min | HPLC |
| Example 73 | (R)-3-(6-fluoro-1H-indol-1-yl)-N-(1-(5-(2,2,2-trifluoroethoxy)pyridin-2-yl)ethyl)propanamide | 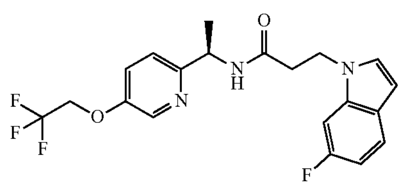 [SMILES: C[C@@H](NC(=O)CCn1ccc2ccc(F)cc21)c1ccc(OCC(F)(F)F)cn1] | | | 410.0 | 1.73 min | HPLC |

TABLE 3-continued

| Example | Name | STRUCTURE | Structure of amine part | Structure of caboxylic acid part | Observed MS | Retention Time | Purification Method |
|---|---|---|---|---|---|---|---|
| Example 74 | (R)-N-(1-(5-(cyclopropyl-methoxy)pyridin-2-yl)ethyl)-3-(8-fluoro-1H-indol-1-yl)propanamide | 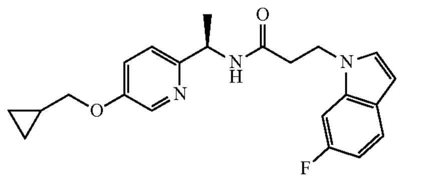 [SMILES: C[C@@H](NC(=O)CCn1ccc2ccc(F)cc21)c1ccc(OCC2CC2)cn1] | | | 382.0 | 1.76 min | HPLC |
| Example 75 | (R)-3-(5-fluoro-2-phenyl-1H-indol-3-yl)-N-(1-(5-(2,2,2-trifluoroethoxy)pyridin-2-yl)ethyl)propanamide | 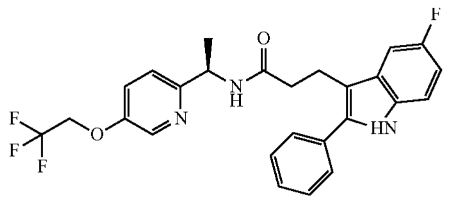 [SMILES: C[C@@H](NC(=O)CCc1c(-c2ccccc2)[nH]c2ccc(F)cc12)c1ccc(OCC(F)(F)F)cn1] | | | 486.0 | 1.81 min | HPLC |
| Example 76 | (R)-N-(1-(5-(cyclopropyl-methoxy)pyridin-2-yl)ethyl)-3-(5-fluoro-2-phenyl-1H-indol-3-yl)propanamide | 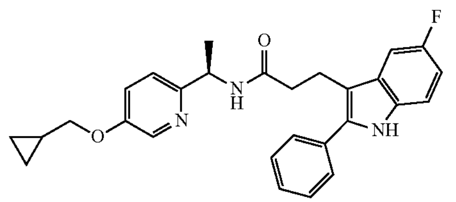 [SMILES: C[C@@H](NC(=O)CCc1c(-c2ccccc2)[nH]c2ccc(F)cc12)c1ccc(OCC2CC2)cn1] | | | 458.1 | 1.84 min | HPLC |
| Example 77 | (R)-N-(1-(5-(2-fluorobenzyloxy)pyridin-2-yl)ethyl)-2-(4-trifluoromethyl)phenoxy)acetamide | 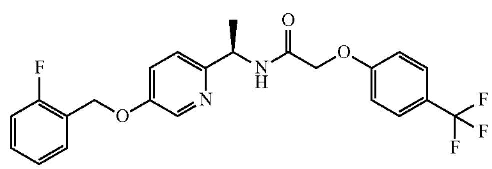 [SMILES: C[C@@H](NC(=O)COc1ccc(C(F)(F)F)cc1)c1ccc(OCc2ccccc2F)cn1] | | | 449.1 | 3.24 min | HPLC |
| Example 78 | (R)-N-(1-(5-(2,2,2-trifluoromethoxy)pyridin-2-yl)ethyl)-2-(4-trifluoromethyl)phenoxy)acetamide | 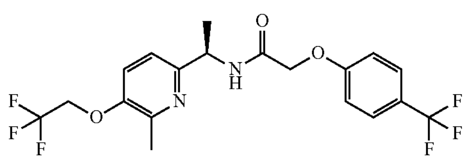 [SMILES: Cc1nc([C@@H](C)NC(=O)COc2ccc(C(F)(F)F)cc2)ccc1OCC(F)(F)F] | | | 436.9 | 1.92 min | HPLC |

TABLE 3-continued

| Example | Name | STRUCTURE | Structure of amine part | Structure of caboxylic acid part | Observed MS | Retention Time | Purification Method |
|---|---|---|---|---|---|---|---|
| Example 79 | (R)-5-fluoro-N-(1-(6-methyl-5-(2,2,2-trifluoroethoxy)pyridin-2-yl)ethyl)-1H-indole-2-carboxamide | 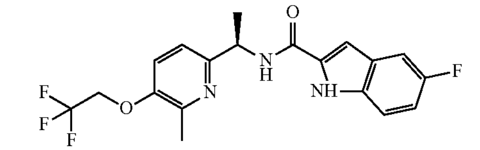 [SMILES: Cc1nc([C@@H](C)NC(=O)c2cc3cc(F)ccc3[nH]2)ccc1OCC(F)(F)F] | | | 395.8 | 1.80 min | HPLC |
| Example 80 | (R)-5-(2,2,2-trifluoroethoxy)-N-(1-(5-(2,2,2-trifluoroethoxy)pyridin-2-yl)ethyl)amide | 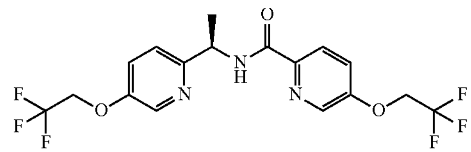 [SMILES: C[C@@H](NC(=O)c1ccc(OCC(F)(F)F)cn1)c1ccc(OCC(F)(F)F)cn1] | | | 423.9 | 1.79 min | HPLC |
| Example 81 | (R)-N-(1-(5-(pyridin-2-ylmethoxy)pyridin-2-yl)ethyl)-2-(4-trifluoromethyl)phenoxy)acetamide | 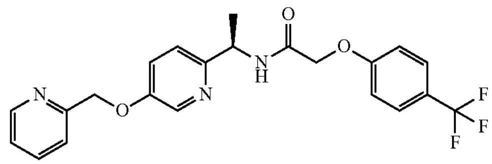 [SMILES: C[C@@H](NC(=O)COc1ccc(C(F)(F)F)cc1)c1ccc(OCc2ccccn2)cn1] | | Alternative route | 431.9 | 1.68 min | HPLC |
| Example 82 | (1S,2S)-N-((R)-1-(5-(2-fluorobenzyl)pyridin-2-yl)ethyl)-2-methyl-2-(4-trifluoromethyl)phenyl)cyclopropanecarboxamide | 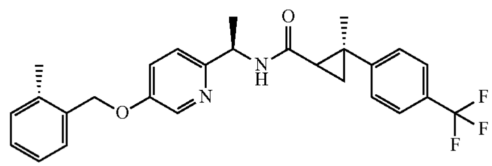 | | | 472.9 | 2.04 min | HPLC |
| Example 83 | (R)-N-(1-(5-(2,2,2-trifluoroethoxy)pyridin-2-yl)ethyl)-3-(4-trifluoromethyl)phenyl)propanamide | 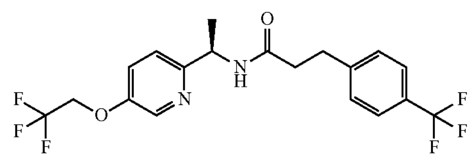 | | | 420.9 | 1.77 min | HPLC |

TABLE 3-continued

| Example | Name | STRUCTURE | Structure of amine part | Structure of caboxylic acid part | Observed MS | Retention Time | Purification Method |
|---|---|---|---|---|---|---|---|
| Example 84 | N-((R)-1-(5-(2,2,2-trifluoroethoxy)pyridin-2-yl)ethyl)-1,2,3,4-tetrahydronaphthalene-2-carboxamide | 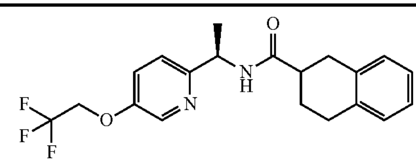 | | | 378.9 | 1.77 min | HPLC |
| Example 85 | (1S,2S)-N-((R)-1-(6-(2-fluorobenzyoxy)pyridin-3-yl)ethyl)-2-methyl-2-(4-trifluoromethyl)phenyl)cyclopropanecarboxamide | 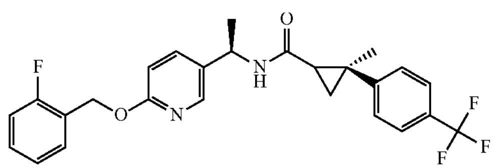 [SMILES: C[C@@H](NC(=O)C1C[C@]1(C)c1ccc(C(F)(F)F)cc1)c1ccc(OCc2ccccc2F)nc1] | | | 473.0 | 2.09 min | HPLC |
| Example 86 | (R)-N-(1-(8-(2-fluorobenzyoxy)pyridin-3-yl)ethyl)-3-(1H-indol-3-yl)propanamide | 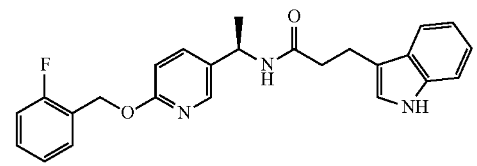 [SMILES: C[C@@H](NC(=O)CCc1c[nH]c2ccccc12)c1ccc(OCc2ccccc2F)nc1] | | | 418.0 | 1.79 min | HPLC |
| Example 87 | (R)-N-(1-(3-(2-fluorobenzyoxy)pyridin-3-yl)ethyl)-3-(1H-indol-3-yl)propanamide | 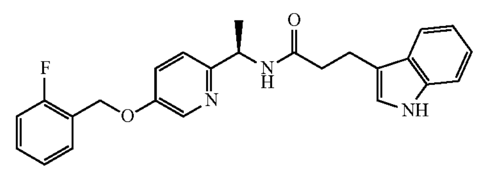 [SMILES: C[C@@H](NC(=O)CCc1c[nH]c2ccccc12)c1ccc(OCc2ccccc2F)cn1] | | | 418.0 | 1.72 min | HPLC |
| Example 88 | (R)-N-(1-(5-(2,2,2-trifluoroethoxy)pyridin-2-yl)ethyl)-2-(4-(trifluoromethyl)phenyl)oxozole-4-carboxamide | 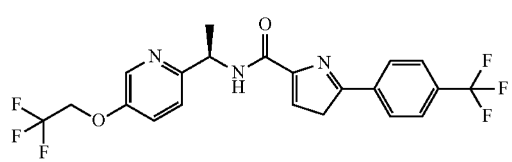 [SMILES: C[C@@H](NC(=O)C1=CCC(c2ccc(C(F)(F)F)cc2)=N1)c1ccc(OCC(F)(F)F)cn1] | | | 459.9 | 1.95 min | HPLC |

TABLE 3-continued

| Example | Name | STRUCTURE | Structure of amine part | Structure of caboxylic acid part | Observed MS | Retention Time | Purification Method |
|---|---|---|---|---|---|---|---|
| Example 89 | (R,E)-3-(1H-indol-3-yl)-N-(1-(5-(2,2,2-trifluoroethoxy)pyridin-2-yl)ethyl)acryamide | 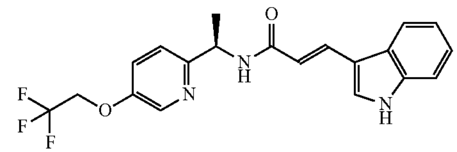 [SMILES: C[C@@H](NC(=O)/C=C/c1c[nH]c2ccccc12)c1ccc(OCC(F)(F)F)cn1] | | | 389.9 | 1.60 min | HPLC |
| Example 90 | (R,E)-3-(1H-indol-3-yl)-N-(1-(6-(2,2,2-trifluoroethoxy)pyridin-3-yl)ethyl)acryamide | 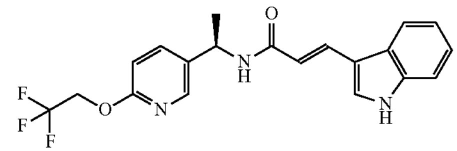 | | | 389.0 | 1.71 min | HPLC |
| Example 91 | (1R,2R)-N-((R)-1-(5-(2,2,2-trifluoroethoxy)pyridin-2-yl)ethyl)-2-(4-trifluoromethyl)phenyl)cyclopropanecarboxamide | 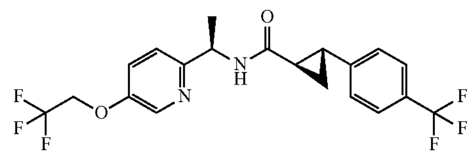 [SMILES: C[C@@H](NC(=O)[C@@H]1C[C@H]1c1ccc(C(F)(F)F)cc1)c1ccc(OCC(F)(F)F)cn1] | | | 433.1 | 3.15 min | HPLC |
| Example 92 | (1R,2R)-N-((R)-1-(6-(2,2,2-trifluoroethoxy)pyridin-3-yl)ethyl)-2-(4-trifluoromethyl)phenyl)cyclopropanecarboxamide | 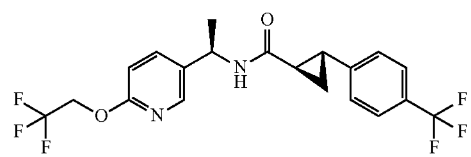 [SMILES: C[C@@H](NC(=O)[C@@H]1C[C@H]1c1ccc(C(F)(F)F)cc1)c1ccc(OCC(F)(F)F)nc1] | | | 433.1 | 3.32 min | HPLC |
| Example 93 | (R)-3-(1H-indol-3-yl)-N-(1-(6-(2,2,2-trifluoroethoxy)pyridin-3-yl)ethyl)propanamide | 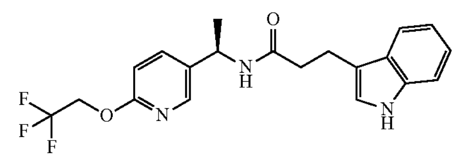 [SMILES: C[C@@H](NC(=O)CCc1c[nH]c2ccccc12)c1ccc(OCC(F)(F)F)nc1] | | | 392.2 | 2.92 min | HPLC |
| Example 94 | (1S,2S)-2-methyl-N-((R)-1-(6-(2,2,2-trifluoroethoxy)pyridin-3-yl)ethyl)-2-(4-trifluoromethyl)phenyl)cyclopropanecarboxamide | 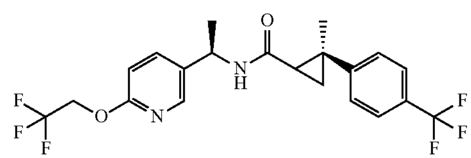 [SMILES: C[C@@H](NC(=O)C1C[C@]1(C)c1ccc(C(F)(F)F)cc1)c1ccc(OCC(F)(F)F)nc1] | | | 447.1 | 3.47 min | HPLC |

TABLE 3-continued

| Example | Name | STRUCTURE | Structure of amine part | Structure of caboxylic acid part | Observed MS | Retention Time | Purification Method |
|---|---|---|---|---|---|---|---|
| Example 95 | (R)-5-fluoro-N-(1-(5-(2-fluorobenzyloxy)pyridin-2-yl)ethyl)-1H-indole-2-carboxamide | 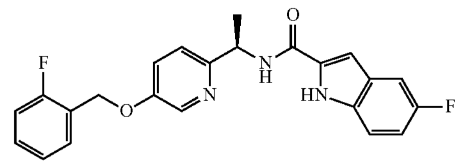 [SMILES: C[C@@H](NC(=O)c1cc2cc(F)ccc2[nH]1)c1ccc(OCc2ccccc2F)cn1] | | | 405.2 | 3.04 min | HPLC |
| Example 96 | (R)-N-(1-(5-((1-methylcyclopropyl)methoxy)pyridin-2-yl)ethyl)-2-(4-trifluoromethyl)phenoxy)acetamide | 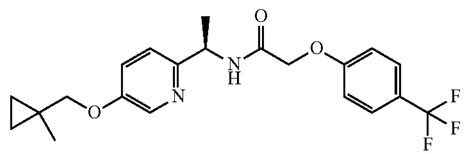 [SMILES: C[C@@H](NC(=O)COc1ccc(C(F)(F)F)cc1)c1ccc(OCC2(C)CC2)cn1] | | | 409.2 | 3.34 min | HPLC |
| Example 97 | (R)-3-(1H-indol-3-yl)-N-(1-(3-((1-methylcyclopropyl)methoxy)pyridin-2-yl)ethyl)propanamide | 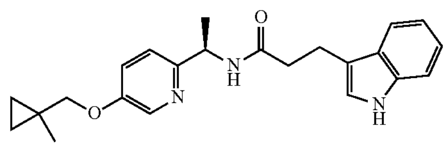 [SMILES: C[C@@H](NC(=O)CCc1c[nH]c2ccccc12)c1ccc(OCC2(C)CC2)cn1] | | | 378.2 | 2.80 min | HPLC |
| Example 98 | (R)-5-fluoro-N-(1-(5-((1-methylcyclopropyl)methoxy)pyridin-2-yl)ethyl)-1H-indole-2-carboxamide | 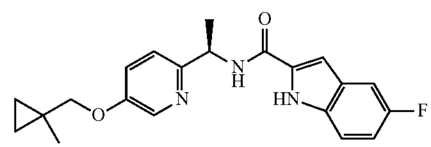 [SMILES: C[C@@H](NC(=O)c1cc2cc(F)ccc2[nH]1)c1ccc(OCC2(C)CC2)cn1] | | | 368.2 | 3.09 min | HPLC |
| Example 99 | (1S,2S)-2-methyl-N-((R)-1-(5-((1-methylcyclopropyl)methoxy)pyridin-2-yl)ethyl)-3-(4-(trifluoromethyl)phenyl)cyclopropanacarboxamide | 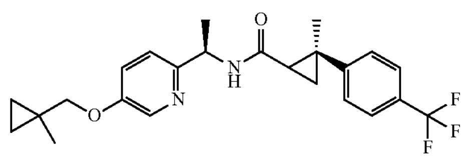 [SMILES: C[C@@H](NC(=O)C1C[C@]1(C)c1ccc(C(F)(F)F)cc1)c1ccc(OCC2(C)CC2)cn1] | | | 433.2 | 3.49 min | HPLC |

TABLE 3-continued

| Example | Name | STRUCTURE | Structure of amine part | Structure of caboxylic acid part | Observed MS | Retention Time | Purification Method |
|---|---|---|---|---|---|---|---|
| Example 100 | N-(3-(2,2,2-trifluoroethoxy)-5,6,7,8-tetrahydroquinolin-8-yl)-2-(4-(trifluoromethyl)phenoxy)carboxamide | 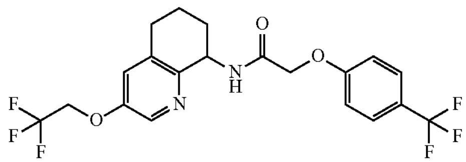 [SMILES: O=C(COc1ccc(C(F)(F)F)cc1)NC1CCCc2cc(OCC(F)(F)F)cnc21] | | | 449.2 | 3.19 min | HPLC |
| Example 101 | 3-(1H-indol-3-yl)-N-(2-(2,2,2-trifluoroethoxy)-5,6,7,8-tetrahydroquinolin-8-yl)propanamide | 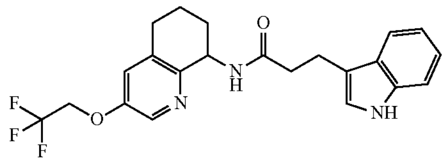 [SMILES: O=C(CCc1c[nH]c2ccccc12)NC1CCCc2cc(OCC(F)(F)F)cnc21] | | | 418.2 | 2.77 min | HPLC |
| Example 102 | trans-2-(4-tert-butyl)phenyl)-N-(3-(2,2,2-trifluoroethoxy)-5,6,7,8-tetrahydroquinolin-8-yl)cyclopropane-carboxamide | 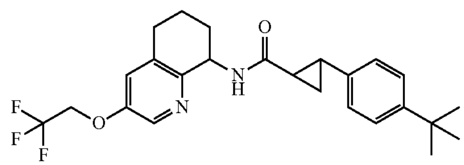 [SMILES: CC(C)(C)c1ccc(C2CC2C(=O)NC2CCCc3cc(OCC(F)(F)F)cnc32)cc1] | | | 447.2 | 3.47 min | HPLC |
| Example 103 | (R)-N-(1-(3-fluoro-6-(2,2,2-trifluoroethoxy)pyridin-2-yl)ethyl)-3-(1H-indol-3-yl)propanamide | 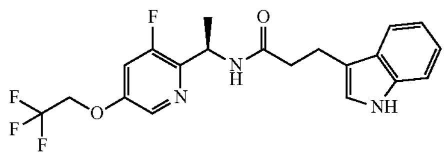 [SMILES: C[C@@H](NC(=O)CCc1c[nH]c2ccccc12)c1ncc(OCC(F)(F)F)cc1F] | | | 409.9 | 1.68 min | HPLC |
| Example 104 | (R)-3-(1H-indol-3-yl)-N-(1-(3-methyl-6-(2,2,2-trifluoroethoxy)pyridin-2-yl)ethyl)propanamide | 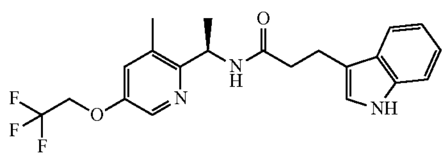 | | | 406.0 | 1.70 min | HPLC |

TABLE 3-continued

| Example | Name | STRUCTURE | Structure of amine part | Structure of caboxylic acid part | Observed MS | Retention Time | Purification Method |
|---|---|---|---|---|---|---|---|
| Example 105 | (R)-4-((1H-imidazol-1-yl)methyl)-N-(1-(6-(2,2,2-trifluoromethoxy)pyridin-2-yl)ethyl)-1H-indole-2-carboxamide | 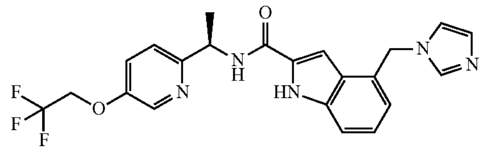 [SMILES: C[C@@H](NC(=O)c1cc2c(Cn3ccnc3)cccc2[nH]1)c1ccc(OCC(F)(F)F)cn1] | | | 444.1 | 1.47 min | HPLC |
| Example 106 | trans-2-(1-methyl-1H-indol-3-yl)-N-((R)-1-(5-(2,2,2-trifluoroethoxy)pyridin-2-yl)ethyl)cyclopropanecarboxamide | 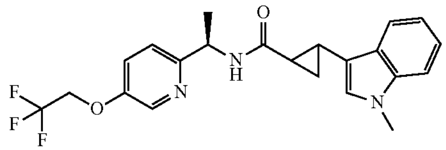 | | | 417.9 | 1.77 min | HPLC |
| Example 107 | (R)-2-(4-chlorophenexy)-N-(1-(5-(2,2,2-trifluoroethoxy)pyridin-2-yl)ethyl)nicotinamide | 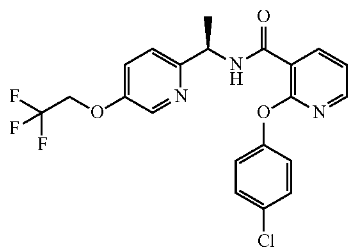 [SMILES: C[C@@H](NC(=O)c1cccnc1Oc1ccc(Cl)cc1)c1ccc(OCC(F)(F)F)cn1] | | | 451.9 | 1.92 min | HPLC |
| Example 108 | trans-2-(7-fluoro-1H-indol-3-yl)-N-((R)-1-(5-(2,2,2-trifluoroethoxy)pyridin-2-yl)ethyl)cyclopropanecarboxamide | 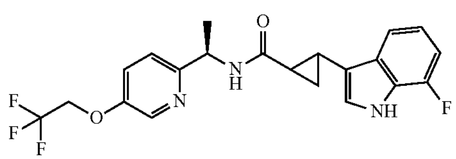 [SMILES: C[C@@H](NC(=O)C1CC1c1c[nH]c2c(F)cccc12)c1ccc(OCC(F)(F)F)cn1] | | | 421.9 | 1.68 min | HPLC |
| Example 109 | trans-2-(1H-indol-5-yl)-N-(R)-1-(5-(2,2,2-trifluoroethoxy)pyridin-2-yl)ethyl)cyclopropanecarboxamide | 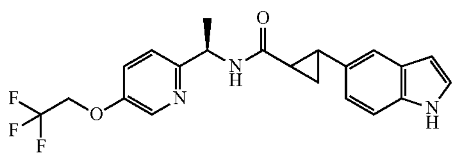 [SMILES: C[C@@H](NC(=O)C1CC1c1ccc2[nH]ccc2c1)c1ccc(OCC(F)(F)F)cn1] | | | 403.9 | 1.61 min | HPLC |

TABLE 3-continued

| Example | Name | STRUCTURE | Structure of amine part | Structure of caboxylic acid part | Observed MS | Retention Time | Purification Method |
|---|---|---|---|---|---|---|---|
| Example 110 | trans-2-(5-fluoro-1H-indol-3-yl)-N-((R)-1-(5-(2,2,2-trifluoroethoxy)pyridin-2-yl)ethyl)cyclopropanecarboxamide | 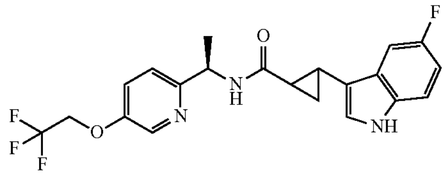 [SMILES: C[C@@H](NC(=O)C1CC1c1c[nH]c2ccc(F)cc12)c1ccc(OCC(F)(F)F)cn1] | | | 421.9 | 1.65 min | HPLC |
| Example 111 | trans-2-(5-cyano-1H-indol-3-yl)-N-((R)-1-(5-(2,2,2-trifluoroethoxy)pyridin-2-yl)ethyl)cyclopropanecarboxamide | 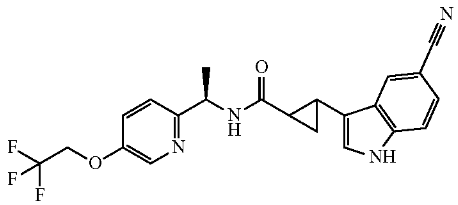 [SMILES: C[C@@H](NC(=O)C1CC1c1c[nH]c2ccc(C#N)cc12)c1ccc(OCC(F)(F)F)cn1] | | | 429.0 | 1.57 min | HPLC |
| Example 112 | (R)-3-chloro-4-methyl-N-(1-(5-(2,2,2-trifluoroethoxy)pyridin-2-yl)ethyl)benzamide | 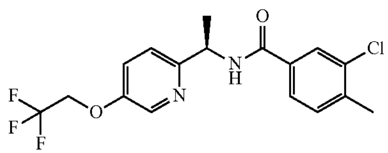 [SMILES: Cc1ccc(C(=O)N[C@H](C)c2ccc(OCC(F)(F)F)cn2)cc1Cl] | | | 372.6 | 1.80 min | HPLC |
| Example 113 | (R)-4-tert-butyl-N-(1-(6-(2,2,2-trifluoroethoxy)pyridin-3-yl)ethyl)benzamide | 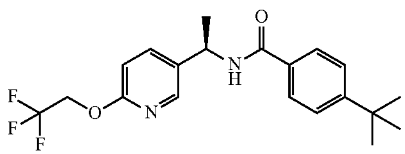 [SMILES: C[C@@H](NC(=O)c1ccc(C(C)(C)C)cc1)c1ccc(OCC(F)(F)F)nc1] | | | 381.0 | 1.98 min | HPLC |
| Example 114 | (R)-3-chloro-N-(1-(5-(2,2,2-trifluoroethoxy)pyridin-2-yl)ethyl)benzamide | 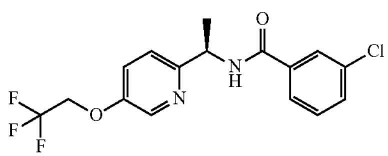 [SMILES: C[C@@H](NC(=O)c1cccc(Cl)c1)c1ccc(OCC(F)(F)F)cn1] | | | 358.9 | 1.72 min | HPLC |

TABLE 3-continued

| Example | Name | STRUCTURE | Structure of amine part | Structure of caboxylic acid part | Observed MS | Retention Time | Purification Method |
|---|---|---|---|---|---|---|---|
| Example 115 | (R)-N-(1-(5-(2,2,2-trifluoroethoxy)pyridin-2-yl)ethyl)isoquinoline-3-carboxamide | 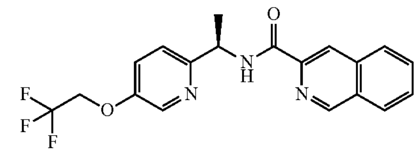 [SMILES: C[C@@H](NC(=O)c1cc2ccccc2cn1)c1ccc(OCC(F)(F)F)cn1] | | | 375.9 | 1.77 min | HPLC |
| Example 116 | (R)-N-(1-(5-(2,2,2-trifluoroethoxy)pyridin-2-yl)ethyl)quinoxaline-2-carboxamide | 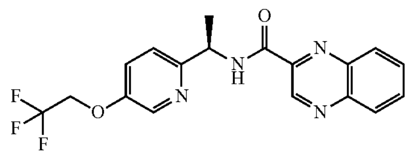 [SMILES: C[C@@H](NC(=O)c1cnc2ccccc2n1)c1ccc(OCC(F)(F)F)cn1] | | | 376.8 | 1.70 min | HPLC |
| Example 117 | (R)-1-methoxy-N-(1-(5-(2,2,2-trifluoroethoxy)pyridin-2-yl)ethyl)quinoline-2-carboxamide | 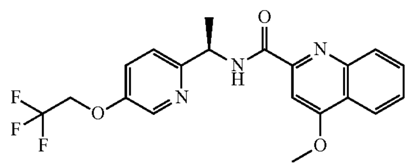 [SMILES: COc1cc(C(=O)N[C@H](C)c2ccc(OCC(F)(F)F)cn2)nc2ccccc12] | | | 405.9 | 1.90 min | HPLC |
| Example 118 | (R)-5-phenyl-N-(1-(5-(2,2,2-trifluoroethoxy)pyridin-2-yl)ethyl)pyrimidine-4-carboxamide | 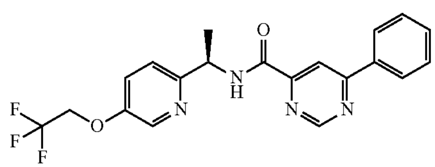 [SMILES: C[C@@H](NC(=O)c1cc(-c2ccccc2)ncn1)c1ccc(OCC(F)(F)F)cn1] | | | 402.9 | 1.87 min | HPLC |
| Example 119 | (R)-5-phenyl-N-(1-(5-(2,2,2-trifluoroethoxy)pyridin-2-yl)ethyl)nicotinamide | 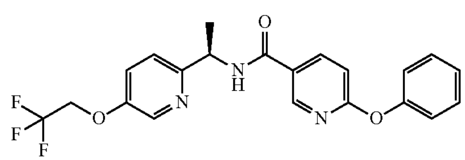 [SMILES: C[C@@H](NC(=O)c1ccc(Oc2ccccc2)nc1)c1ccc(OCC(F)(F)F)cn1] | | | 417.9 | 1.72 min | HPLC |
| Example 120 | (R)-5-isobutyl-N-(1-(5-(2,2,2-trifluoroethoxy)pyridin-2-yl)ethyl)isoxazole-3-carboxamide | 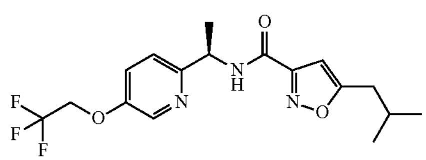 [SMILES: CC(C)Cc1cc(C(=O)N[C@H](C)c2ccc(OCC(F)(F)F)cn2)no1] | | | 371.9 | 1.86 min | HPLC |

TABLE 3-continued

| Example | Name | STRUCTURE | Structure of amine part | Structure of caboxylic acid part | Observed MS | Retention Time | Purification Method |
|---|---|---|---|---|---|---|---|
| Example 121 | (R)-2-benzyl-N-(1-(5-(2,2,2-trifluoroethoxy)pyridin-2-yl)ethyl)imidazole-4-carboxamide | 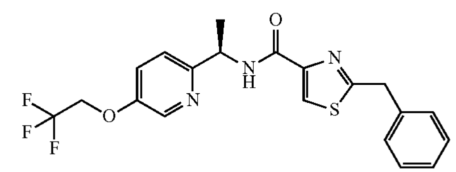 [SMILES: C[C@@H](NC(=O)c1csc(Cc2ccccc2)n1)c1ccc(OCC(F)(F)F)cn1] | | | 421.8 | 1.85 min | HPLC |
| Example 122 | (R)-5-methyl-2-phenyl-N-(1-(5-(2,2,2-trifluoroethoxy)pyridin-2-yl)ethyl)-2H-1,2,3-traizole-4-carboxamide | 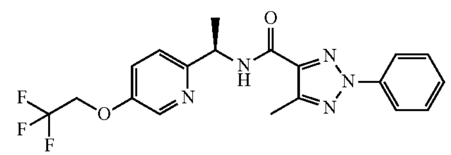 [SMILES: Cc1nn(-c2ccccc2)nc1C(=O)N[C@H](C)c1ccc(OCC(F)(F)F)cn1] | | | 405.9 | 1.92 min | HPLC |
| Example 123 | (R)-3-(2-methylthiazol-4-yl)-N-(1-(5-((2,2,2-trifluoroethoxy)pyridin-2-yl)ethyl)benzamide | 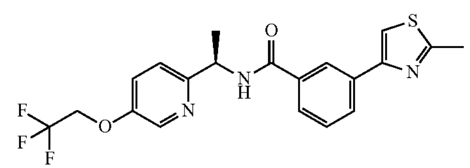 [SMILES: Cc1nc(-c2cccc(C(=O)N[C@H](C)c3ccc(OCC(F)(F)F)cn3)c2)cs1] | | | 421.9 | 1.70 min | HPLC |
| Example 124 | trans-2-(1H-indol-2-yl)-N-((R)-1-(5-(2,2,2-trifluoroethoxy)pyridin-2-yl)ethyl)cyclopropanecarboxamide | 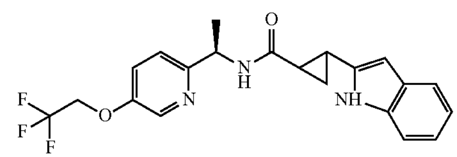 [SMILES: C[C@@H](NC(=O)C1CC1c1cc2ccccc2[nH]1)c1ccc(OCC(F)(F)F)cn1] | | | 404.0 | 1.72 min | HPLC |
| Example 125 | trans-2-(5-fluoro-1H-indol-2-yl)-N-((R)-1-(5-(2,2,2-trifluoroethoxy)pyridin-2-yl)ethyl)cyclopropanecarboxamide | 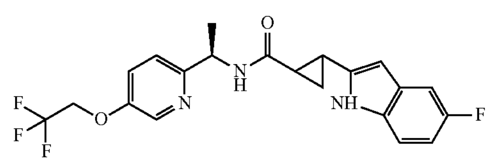 [SMILES: C[C@@H](NC(=O)C1CC1c1cc2cc(F)ccc2[nH]1)c1ccc(OCC(F)(F)F)cn1] | | | 422.0 | 1.72 min | HPLC |

TABLE 3-continued

| Example | Name | STRUCTURE | Structure of amine part | Structure of carboxylic acid part | Observed MS | Retention Time | Purification Method |
|---|---|---|---|---|---|---|---|
| Example 126 | trans-2-(4-fluoro-1H-indol-3-yl)-N-((R)-1-(5-(2,2,2-trifluoroethoxy)pyridin-2-yl)ethyl)cyclopropanecarboxamide | 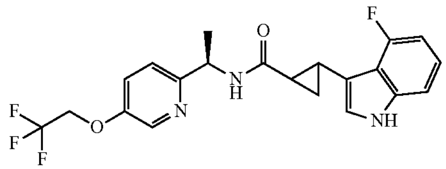 [SMILES: C[C@@H](NC(=O)C1CC1c1c[nH]c2cccc(F)c12)c1ccc(OCC(F)(F)F)cn1] | | | 422.0 | 1.64 min | HPLC |
| Example 127 | (R)-6-methoxy-N-(1-(5-(2,2,2-trifluoroethoxy)pyridin-2-yl)ethyl)-1H-indole-2-carboxamide | 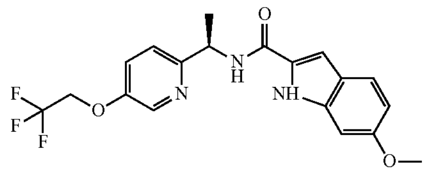 [SMILES: COc1ccc2cc(C(=O)N[C@H](C)c3ccc(OCC(F)(F)F)cn3)[nH]c2c1] | | | 394.0 | 1.66 min | HPLC |
| Example 128 | (R)-N-(1-(5-(2,2,2-trifluoroethoxy)pyridin-2-yl)ethyl)benzo[b]thiophene-2-carboxamide | 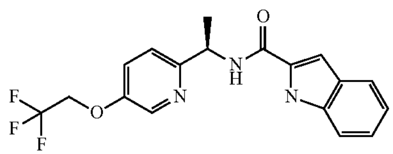 [SMILES: C[C@@H](NC(=O)c1cc2ccccc2[nH]1)c1ccc(OCC(F)(F)F)cn1] | | | 380.9 | 1.78 min | HPLC |
| Example 129 | (R)-3-(benzyloxy)-4-methoxy-N-(1-(5-(2,2,2-trifluoroethoxy)pyridin-2-yl)ethyl)benzamide | 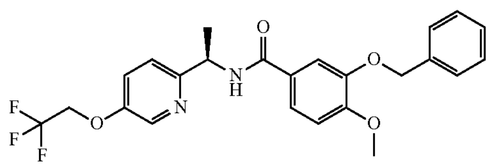 [SMILES: COc1ccc(C(=O)N[C@H](C)c2ccc(OCC(F)(F)F)cn2)cc1OCc1ccccc1] | | | 460.9 | 1.80 min | HPLC |
| Example 130 | (R)-4-phenoxy-N-(1-(5-(2,2,2-trifluoroethoxy)pyridin-2-yl)ethyl)benzamide | 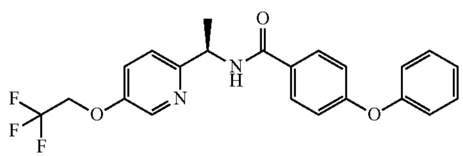 [SMILES: C[C@@H](NC(=O)c1ccc(Oc2ccccc2)cc1)c1ccc(OCC(F)(F)F)cn1] | | | 416.0 | 1.86 min | HPLC |

TABLE 3-continued

| Example | Name | STRUCTURE | Structure of amine part | Structure of caboxylic acid part | Observed MS | Retention Time | Purification Method |
|---|---|---|---|---|---|---|---|
| Example 131 | (R)-3-phenoxy-N-(1-(5-(2,2,2-trifluoroethoxy)pyridin-2-yl)ethyl)benzamide | 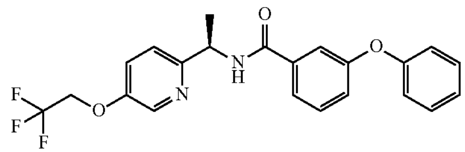 [SMILES: C[C@@H](NC(=O)c1cccc(Oc2ccccc2)c1)c1ccc(OCC(F)(F)F)cn1] | | | 416.9 | 1.88 min | HPLC |
| Example 132 | (R)-5-tert-butyl-2-methoxy-N-(1-(5-(2,2,2-trifluoroethoxy)pyridin-2-yl)ethyl)benzamide | 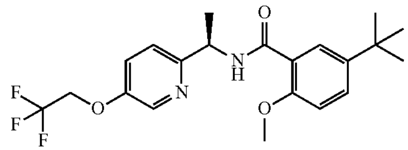 [SMILES: COc1ccc(C(C)(C)C)cc1C(=O)N[C@H](C)c1ccc(OCC(F)(F)F)cn1] | | | 411.0 | 1.99 min | HPLC |
| Example 133 | (1S*,2S*)-2-(1H-indol-3-yl)-N-((R)-1-(5-(2,2,2-trifluoroethoxy)pyridin-2-yl)ethyl)cyclopropanecarboxamide | 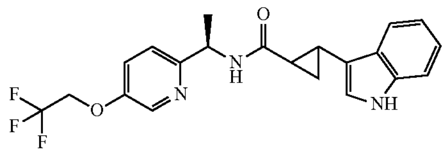 [SMILES: C[C@@H](NC(=O)C1CC1c1c[nH]c2ccccc12)c1ccc(OCC(F)(F)F)cn1] | | | Confirmed by NMR(see Table 2) | | Chiral-HPLC |
| Example 134 | (1R*,2R*)-2-(1H-indol-3-yl)-N-((R)-1-(5-(2,2,2-trifluoroethoxy)pyridin-2-yl)ethyl)cyclopropanecarboxamide | 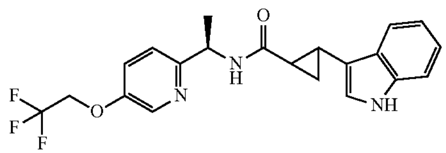 [SMILES: C[C@@H](NC(=O)C1CC1c1c[nH]c2ccccc12)c1ccc(OCC(F)(F)F)cn1] | | | Confirmed by NMR(see Table 2) | | Chiral-HPLC |
| Example 135 | (R)-5-chloro-1-methyl-N-(1-(5-(2,2,2-trifluoroethoxy)pyridin-2-yl)ethyl)-1H-indole-3-carboxamide | 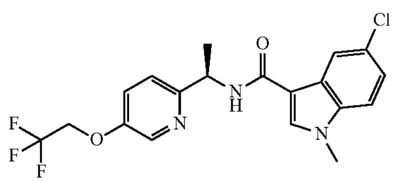 [SMILES: C[C@@H](NC(=O)c1cn(C)c2ccc(Cl)cc12)c1ccc(OCC(F)(F)F)cn1] | | | 410.1 | 1.75 min | HPLC |

TABLE 3-continued

| Example | Name | STRUCTURE | Structure of amine part | Structure of caboxylic acid part | Observed MS | Retention Time | Purification Method |
|---|---|---|---|---|---|---|---|
| Example 136 | (R)-5-methoxy-1-methyl-N-(1-(5-(2,2,2-trifluoroethoxy)pyridin-2-yl)ethyl)-1H-indole-3-carboxamide | 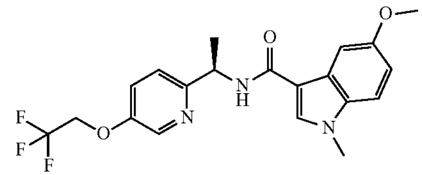 | | | 406.2 | 1.63 min | HPLC |
| Example 137 | (R)-1,6-dimethyl-N-(1-(5-(2,2,2-trifluoroethoxy)pyridin-2-yl)ethyl)-1H-indole-3-carboxamide | 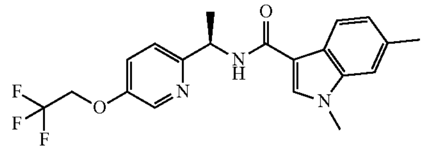 [SMILES: Cc1ccc2c(C(=O)N[C@H](C)c3ccc(OCC(F)(F)F)cn3)cn(C)c2c1] | | | 360.1 | 1.74 min | HPLC |
| Example 138 | (R)-6-fluoro-1-methyl-N-(1-(5-(2,2,2-trifluoroethoxy)pyridin-2-yl)ethyl)-1H-indole-3-carboxamide | 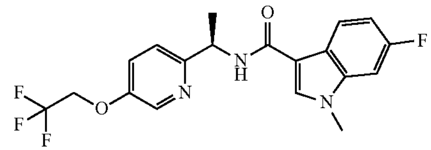 [SMILES: C[C@@H](NC(=O)c1cn(C)c2cc(F)ccc12)c1ccc(OCC(F)(F)F)cn1] | | | 394.1 | 1.68 min | HPLC |
| Example 139 | (R)-6-chloro-1-methyl-N-(1-(5-(2,2,2-trifluoroethoxy)pyridin-2-yl)ethyl)-1H-indole-3-carboxamide | 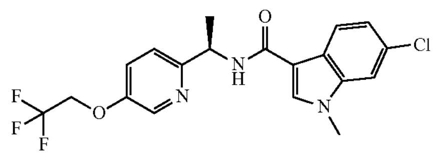 [SMILES: C[C@@H](NC(=O)c1cn(C)c2cc(Cl)ccc12)c1ccc(OCC(F)(F)F)cn1] | | | 410.1 | 1.77 min | HPLC |
| Example 140 | (R)-5-methyl-N-(1-(5-(2,2,2-trifluoroethoxy)pyridin-2-yl)ethyl)-1H-indole-3-carboxamide | 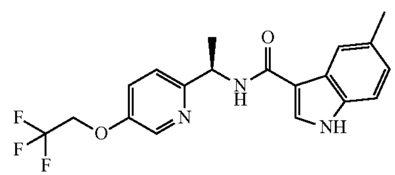 [SMILES: Cc1ccc2[nH]cc(C(=O)N[C@H](C)c3ccc(OCC(F)(F)F)cn3)c2c1] | | | 376.2 | 1.62 min | HPLC |

TABLE 3-continued

| Example | Name | STRUCTURE | Structure of amine part | Structure of caboxylic acid part | Observed MS | Retention Time | Purification Method |
|---|---|---|---|---|---|---|---|
| Example 141 | (R)-5-fluoro-N-(1-(5-(2,2,2-trifluoroethoxy)pyridin-2-yl)ethyl)-1H-indole-3-carboxamide | 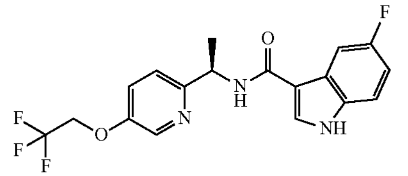 [SMILES: C[C@@H](NC(=O)c1c[nH]c2ccc(F)cc12)c1ccc(OCC(F)(F)F)cn1] | | | 380.2 | 1.57 min | HPLC |
| Example 142 | (R)-5-chloro-N-(1-(5-(2,2,2-trifluoroethoxy)pyridin-2-yl)ethyl)-1H-indole-3-carboxamide | 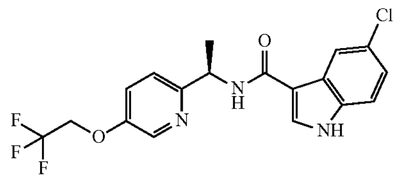 [SMILES: C[C@@H](NC(=O)c1c[nH]c2ccc(Cl)cc12)c1ccc(OCC(F)(F)F)cn1] | | | 396.1 | 1.65 min | HPLC |
| Example 143 | (R)-5-methoxy-N-(1-(5-(2,2,2-trifluoroethoxy)pyridin-2-yl)ethyl)-1H-indole-3-carboxamide | 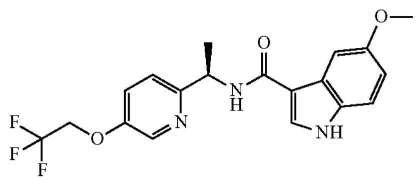 | | | 392.1 | 1.53 min | HPLC |
| Example 144 | (R)-5-chloro-N-(1-(5-(2,2,2-trifluoroethoxy)pyridin-2-yl)ethyl)-1H-indole-3-carboxamide | 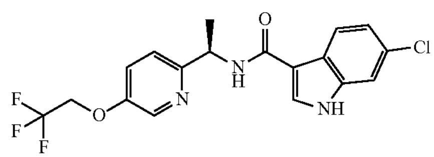 [SMILES: C[C@@H](NC(=O)c1c[nH]c2cc(Cl)ccc12)c1ccc(OCC(F)(F)F)cn1] | | | 396.1 | 1.65 min | HPLC |
| Example 145 | trans-2-(1H-indazol-3-yl)-N-((R)-1-(5-(2,2,2-trifluoroethoxy)pyridin-2-yl)ethyl)cyclopropanecarboxamide | 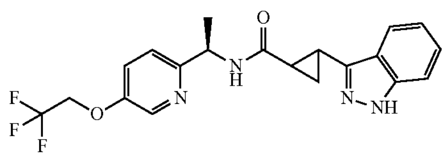 | | | 403.2 | 1.52 min | HPLC |

TABLE 3-continued

| Example | Name | STRUCTURE | Structure of amine part | Structure of caboxylic acid part | Observed MS | Retention Time | Purification Method |
|---|---|---|---|---|---|---|---|
| Example 146 | (R)-6-fluoro-N-(1-(6-(2,2,2-trifluoroethoxy)pyridin-3-yl)ethyl)-1H-indole-2-carboxamide | 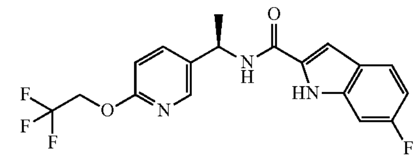 [SMILES: C[C@@H](NC(=O)c1cc2ccc(F)cc2[nH]1)c1ccc(OCC(F)(F)F)nc1] | | | 380.2 | 1.78 min | HPLC |
| Example 147 | trans-3-(1H-indol-5-yl)-N-((R)-1-(5-(2,2,2-trifluoroethoxy)pyridin-2-yl)ethyl)cyclopropanecarboxamide | 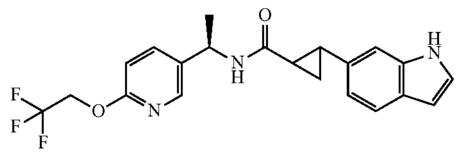 [SMILES: C[C@@H](NC(=O)C1CC1c1ccc2cc[nH]c2c1)c1ccc(OCC(F)(F)F)nc1] | | | 402.2 | 1.75 min | HPLC |
| Example 148 | (R)-1,5-isomethyl-N-(1-(5-(2,2,2-trifluoroethoxy)pyridin-2-yl)ethyl)-1H-indole-2-carboxamide | 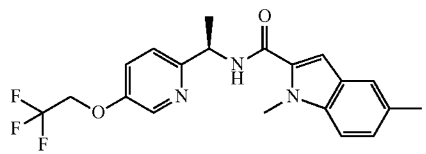 [SMILES: Cc1ccc2c(c1)cc(C(=O)N[C@H](C)c1ccc(OCC(F)(F)F)cn1)n2C] | | | 390.2 | 1.85 min | HPLC |
| Example 149 | (R)-5-fluoro-1-methyl-N-(1-(5-(2,2,2-trifluoroethoxy)pyridin-2-yl)ethyl)-1H-indole-2-carboxamide | 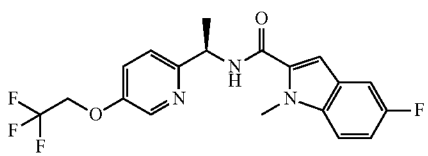 [SMILES: C[C@@H](NC(=O)c1cc2cc(F)ccc2n1C)c1ccc(OCC(F)(F)F)cn1] | | | 394.2 | 1.80 min | HPLC |
| Example 150 | (R)-5-chloro-1-methyl-N-(1-(5-(2,2,2-trifluoroethoxy)pyridin-3-yl)ethyl)-1H-indole-2-carboxamide | 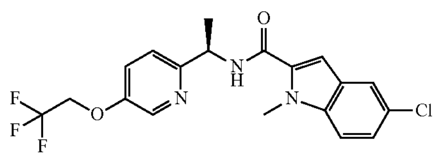 [SMILES: C[C@@H](NC(=O)c1cc2cc(Cl)ccc2n1C)c1ccc(OCC(F)(F)F)cn1] | | | 410.1 | 1.90 min | HPLC |

TABLE 3-continued

| Example | Name | STRUCTURE | Structure of amine part | Structure of carboxylic acid part | Observed MS | Retention Time | Purification Method |
|---|---|---|---|---|---|---|---|
| Example 151 | (R)-5-fluoro-1-methyl-N-(1-(5-(2,2,2-trifluoroethoxy)pyridin-2-yl)ethyl)-1H-indole-2-carboxamide | 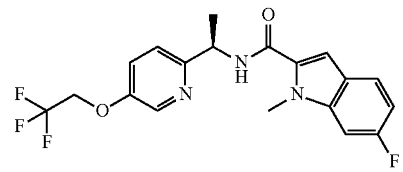 [SMILES: C[C@@H](NC(=O)c1cc2ccc(F)cc2n1C)c1ccc(OCC(F)(F)F)cn1] | | | 394.1 | 1.81 min | HPLC |
| Example 152 | (R)-1,2,3-trimethyl-N-(1-(5-(2,2,2-trifluoroethoxy)pyridin-2-yl)ethyl)-1H-indole-5-carboxamide | 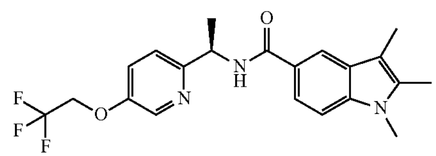 [SMILES: Cc1c(C)n(C)c2ccc(C(=O)N[C@H](C)c3ccc(OCC(F)(F)F)cn3)cc12] | | | 404.1 | 1.77 min | HPLC |
| Example 153 | (R)-5-methyl-N-(1-(5-(2,2,2-trifluoroethoxy)pyridin-2-yl)ethyl)-1H-indole-2-carboxamide | 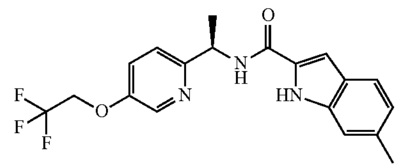 [SMILES: Cc1ccc2cc(C(=O)N[C@H](C)c3ccc(OCC(F)(F)F)cn3)[nH]c2c1] | | | 376.0 | 1.73 min | HPLC |
| Example 154 | (R)-5-chloro-N-(1-(5-(2,2,2-trifluoroethoxy)pyridin-2-yl)ethyl)-1H-indole-2-carboxamide | 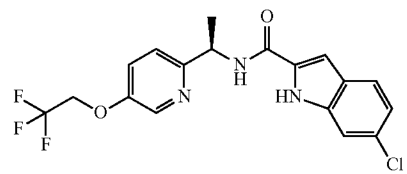 [SMILES: C[C@@H](NC(=O)c1cc2ccc(Cl)cc2[nH]1)c1ccc(OCC(F)(F)F)cn1] | | | 395.9 | 1.78 min | HPLC |
| Example 155 | (R)-4-fluoro-N-(1-(5-(2,2,2-trifluoroethoxy)pyridin-2-yl)ethyl)-1H-indole-3-carboxamide | 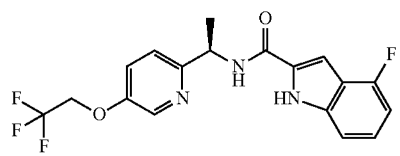 [SMILES: C[C@@H](NC(=O)c1cc2c(F)cccc2[nH]1)c1ccc(OCC(F)(F)F)cn1] | | | 380.0 | 1.71 min | HPLC |

TABLE 3-continued

| Example | Name | STRUCTURE | Structure of amine part | Structure of caboxylic acid part | Observed MS | Retention Time | Purification Method |
|---|---|---|---|---|---|---|---|
| Example 156 | (R)-N-(1-(5-(2,2,2-trifluoroethoxy)pyridin-2-yl)ethyl)-4-(trifluoromethoxy)benzamide | 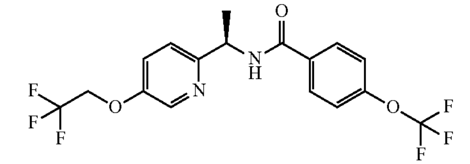 [SMILES: C[C@@H](NC(=O)c1ccc(OC(F)(F)F)cc1)c1ccc(OCC(F)(F)F)cn1] | | | 406.9 | 1.81 min | HPLC |
| Example 157 | (R)-5-phenyl-N-(1-(5-(2,2,2-trifluoroethoxy)pyridin-2-yl)ethyl)isoxazole-3-carboxamide | 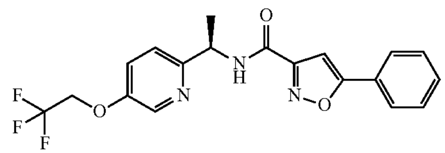 [SMILES: C[C@@H](NC(=O)c1cc(-c2ccccc2)on1)c1ccc(OCC(F)(F)F)cn1] | | | 390.0 | 1.84 min | HPLC |
| Example 158 | (R)-N-(1-(5-(2,2,2-trifluoroethoxy)pyridin-2-yl)ethyl)-3-(trifluoromethoxy)-1H-indole-2-carboxamide | 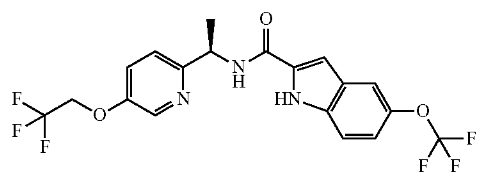 [SMILES: C[C@@H](NC(=O)c1cc2cc(OC(F)(F)F)ccc2[nH]1)c1ccc(OCC(F)(F)F)cn1] | | | 445.9 | 1.83 min | HPLC |
| Example 159 | (R)-5-bromo-N-(1-(5-(2,2,2-trifluoroethoxy)pyridin-2-yl)ethyl)-1H-indole-2-carboxamide | 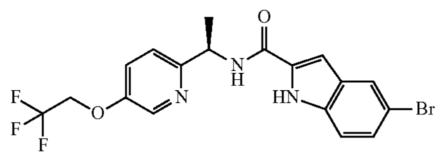 [SMILES: C[C@@H](NC(=O)c1cc2cc(Br)ccc2[nH]1)c1ccc(OCC(F)(F)F)cn1] | | | 439.8 | 1.80 min | HPLC |
| Example 160 | (R)-1,6-dimethyl-N-(1-(5-(2,2,2-trifluoroethoxy)pyridin-2-yl)ethyl)-1H-indole-2-carboxamide | 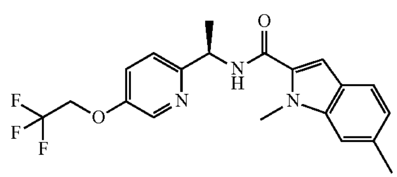 [SMILES: Cc1ccc2cc(C(=O)N[C@H](C)c3ccc(OCC(F)(F)F)cn3)n(C)c2c1] | | | 390.0 | 1.87 min | HPLC |

TABLE 3-continued

| Example | Name | STRUCTURE | Structure of amine part | Structure of caboxylic acid part | Observed MS | Retention Time | Purification Method |
|---|---|---|---|---|---|---|---|
| Example 161 | (R)-6-chloro-1-methyl-N-(1-(5-(2,2,2-trifluoroethoxy)pyridin-2-yl)ethyl)-1H-indole-2-carboxamide | 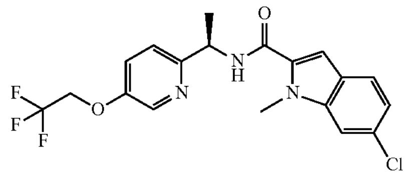 [SMILES: C[C@@H](NC(=O)c1cc2ccc(Cl)cc2n1C)c1ccc(OCC(F)(F)F)cn1] | | | 410.0 | 1.90 min | HPLC |
| Example 162 | (R)-1-methyl-N-(1-(5-(2,2,2-trifluoroethoxy)pyridin-2-yl)ethyl)-5-(trifluoromethoxy)-1H-indole-2-carboxamide | 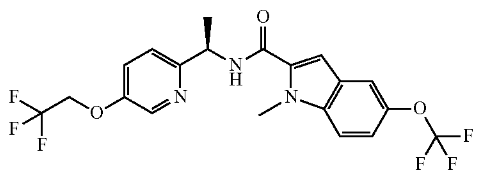 [SMILES: C[C@@H](NC(=O)c1cc2cc(OC(F)(F)F)ccc2n1C)c1ccc(OCC(F)(F)F)cn1] | | | 459.9 | 1.94 min | HPLC |
| Example 163 | (R)-N-(1-(5-(2,2,2-trifluoroethoxy)pyridin-2-yl)ethyl)-3-(trifluoromethoxy)benzamide | 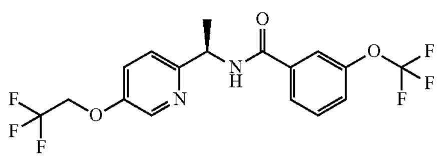 [SMILES: C[C@@H](NC(=O)c1cccc(OC(F)(F)F)c1)c1ccc(OCC(F)(F)F)cn1] | | | 406.8 | 1.79 min | HPLC |
| Example 164 | (R)-1,5-dimethyl-N-(1-(5-(2,2,2-trifluoroethoxy)pyridin-2-yl)ethyl)-1H-indazole-3-carboxamide | 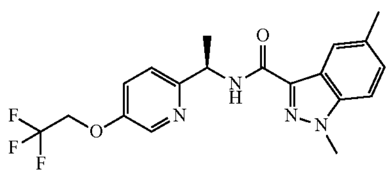 [SMILES: Cc1ccc2c(c1)c(C(=O)N[C@H](C)c1ccc(OCC(F)(F)F)cn1)nn2C] | | | 393.0 | 1.81 min | HPLC |
| Example 165 | (R)-5-chloro-1-methyl-N-(1-(6-(2,2,2-trifluoroethoxy)pyridin-2-yl)ethyl)-1H-indazole-3-carboxamide | 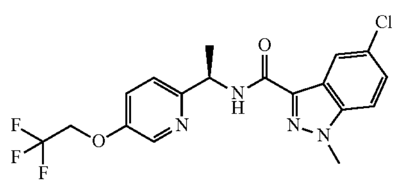 [SMILES: C[C@@H](NC(=O)c1nn(C)c2ccc(Cl)cc12)c1ccc(OCC(F)(F)F)cn1] | | | 411.1 | 1.84 min | HPLC |

| Example | Name | STRUCTURE | Structure of amine part | Structure of caboxylic acid part | Observed MS | Retention Time | Purification Method |
|---|---|---|---|---|---|---|---|
| Example 166 | trans-2-(quinolin-7-yl)-N-((R)-1-(5-(2,2,2-trifluoroethoxy)pyridin-2-yl)ethyl)cyclopropanecarboxamide | | | 414.1 | 1.55 min | HPLC |
| Example 167 | trans-2-(1-methyl-1H-indol-6-yl)-N-((R)-1-(5-(2,2,2-trifluoroethoxy)pyridin-2-yl)ethyl)cyclopropanecarboxamide | | | 418.0 | 1.74 min | HPLC |
| Example 168 | trans-2-(6-fluoro-1H-indol-3-yl)-N-((R)-1-(5-(2,2,2-trifluoroethoxy)pyridin-2-yl)ethyl)cyclopropanecarboxamide | | | 420.1 | 1.65 min | HPLC |
| Example 169 | trans-2-((4-chlorophenoxy)methyl)-N-((R)-1-(5-(2,2,2-trifluoroethoxy)pyridin-2-yl)ethyl)cyclopropanecarboxamide | | | 427.1 | 1.80 min | HPLC |
| Example 170 | trans-2-(quinolin-7-yl)-N-((R)-1-(5-(2,2,2-trifluoroethoxy)pyrazin-2-yl)ethyl)cyclopropanecarboxamide | | | 415.2 | 1.62 min | HPLC |
| Example 171 | trans-2-(5-fluoro-1H-indol-2-yl)-N-((R)-1-(5-(2,2,2-trifluoroethoxy)pyrazin-2-yl)ethyl)cyclopropanecarboxamide | | | 421.1 | 1.78 min | HPLC |

TABLE 3-continued

TABLE 3-continued

| Example | Name | STRUCTURE | Structure of amine part | Structure of caboxylic acid part | Observed MS | Retention Time | Purification Method |
|---|---|---|---|---|---|---|---|
| Example 172 | trans-2-(isoquinolin-3-yl)-N-((R)-1-(5-(2,2,2-trifluoroethoxy)pyridin-2-yl)ethyl)cyclopropanecarboxamide | 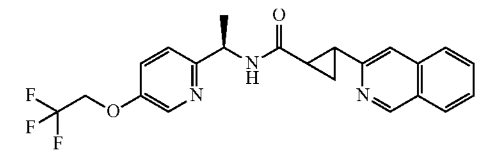 [SMILES: C[C@@H](NC(=O)C1CC1c1cc2ccccc2cn1)c1ccc(OCC(F)(F)F)cn1] | | | 414.2 | 1.66 min | HPLC |
| Example 173 | trans-2-(quinolin-3-yl)-N-((R)-1-(3-(2,2,2-trifluoroethoxy)pyridin-2-yl)ethyl)cyclopropanecarboxamide | 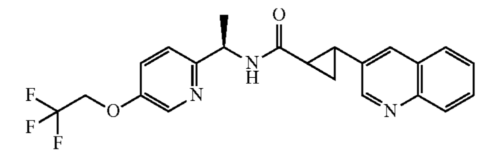 [SMILES: C[C@@H](NC(=O)C1CC1c1cnc2ccccc2c1)c1ccc(OCC(F)(F)F)cn1] | | | 414.2 | 1.58 min | HPLC |
| Example 174 | trans-2-(quinolin-3-yl)-N-((R)-1-(5-(2,2,2-trifluoroethoxy)pyridin-2-yl)ethyl)cyclopropanecarboxamide | 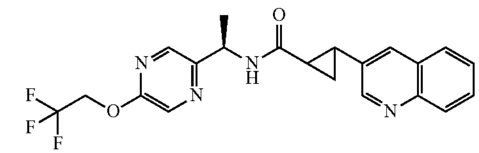 | | | 415.1 | 1.64 min | HPLC |
| Example 175 | trans-2-((4-chlorophenoxy)methyl)-N-((R)-1-(5-(2,2,2-trifluoroethoxy)pyridin-2-yl)ethyl)cyclopropanecarboxamide | 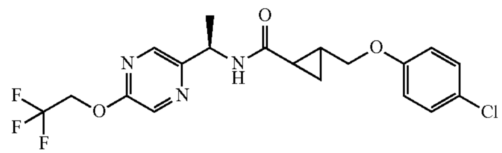 [SMILES: C[C@@H](NC(=O)C1CC1COc1ccc(Cl)cc1)c1cnc(OCC(F)(F)F)cn1] | | | 428.1 | 1.87 min | HPLC |
| Example 176 | trans-2-(3-(difluoromethoxy)phenyl)-N-((R)-1-(5-(2,2,2-trifluoroethoxy)pyridin-2-yl)ethyl)cyclopropanecarboxamide | 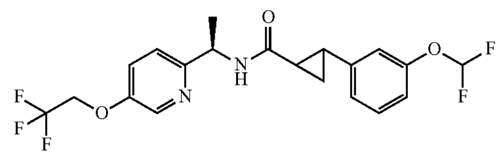 [SMILES: C[C@@H](NC(=O)C1CC1c1cccc(OC(F)F)c1)c1ccc(OCC(F)(F)F)cn1] | | | 429.1 | 1.72 min | HPLC |

| Example | Name | STRUCTURE | Structure of amine part | Structure of caboxylic acid part | Observed MS | Retention Time | Purification Method |
|---|---|---|---|---|---|---|---|
| Example 177 | trans-2-(2-fluoro-5-methoxyphenyl)-N-((R)-1-(5-(2,2,2-trifluoroethoxy)pyridin-2-yl)ethyl)cyclopropanecarboxamide | 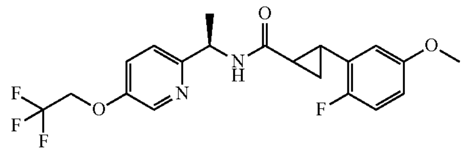 [SMILES: COc1ccc(F)c(C2CC2C(=O)N[C@H](C)c2ccc(OCC(F)(F)F)cn2)c1] | | | 411.1 | 1.71 min | HPLC |
| Example 178 | (R)-8-chloro-1-methyl-N-(1-(5-(2,2,2-trifluoroethoxy)pyridin-2-yl)ethyl)-1H-indazole-3-carboxamide | 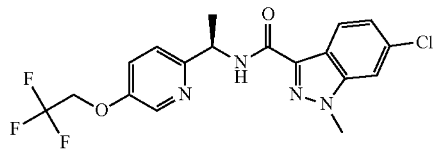 [SMILES: C[C@@H](NC(=O)c1nn(C)c2cc(Cl)ccc12)c1ccc(OCC(F)(F)F)cn1] | | | 411.1 | 1.88 min | HPLC |
| Example 179 | (R)-4-tert-butyl-N-(1-(5-(2,2,2-trifluoroethoxy)pyrazin-2-yl)ethyl)benzamide | 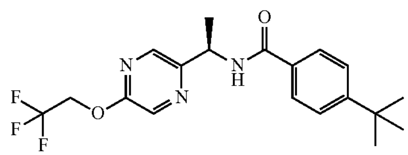 [SMILES: C[C@@H](NC(=O)c1ccc(C(C)(C)C)cc1)c1cnc(OCC(F)(F)F)cn1] | | | 380.2 | 1.96 min | HPLC |
| Example 180 | (R)-6-fluoro-N-(1-(5-(2,2,2-trifluoroethoxy)pyrazin-3-yl)ethyl)-1H-indole-2-carboxamide | 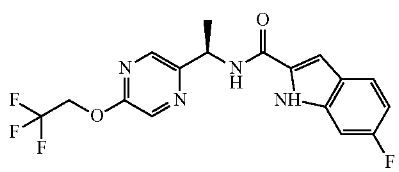 [SMILES: C[C@@H](NC(=O)c1cc2ccc(F)cc2[nH]1)c1cnc(OCC(F)(F)F)cn1] | | | 381.1 | 1.75 min | HPLC |
| Example 181 | trans-N-((R)-1-(5-(cyclopropylmethoxy)pyridin-2-yl)ethyl)-2-(5-fluoro-1H-indol-2-yl)cyclopropanecarboxamide | 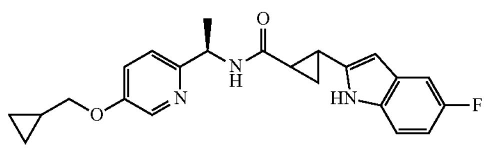 [SMILES: C[C@@H](NC(=O)C1CC1c1cc2cc(F)ccc2[nH]1)c1ccc(OCC2CC2)cn1] | | | 392.2 | 1.74 min | HPLC |
| Example 182 | trans-2-((1H-indol-1-yl)methyl)-N-((R)-1-(5-(2,2,2-trifluoroethoxy)pyridine-2-yl)ethyl)cyclopropanecarboxamide | 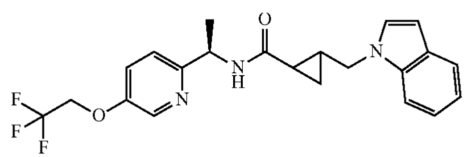 [SMILES: C[C@@H](NC(=O)C1CC1Cn1ccc2ccccc21)c1ccc(OCC(F)(F)F)cn1] | | | 416.1 | 1.75 min | HPLC |

TABLE 3-continued

| Example | Name | STRUCTURE | Structure of amine part | Structure of caboxylic acid part | Observed MS | Retention Time | Purification Method |
|---|---|---|---|---|---|---|---|
| Example 183 | (R)-5-fluoro-1-methyl-N-(1-(5-(2,2,2-trifluoroethoxy)pyrazin-2-yl)ethyl)-1H-indole-2-carboxamide | | | 1.88 | 1.88 min | HPLC |
| Example 184 | (R)-4-tert-butyl-N-(1-(5-(cyclopropylmethoxy)pyridin-2-yl)ethyl)benzamide | | | 353.0 | 1.94 min | HPLC |
| Example 185 | (R)-N-(1-(6-(cyclopropylmethoxy)pyridin-2-yl)ethyl)-6-fluoro-1H-indole-3-carboxamide | | | 352.2 | 1.72 min | HPLC |
| Example 186 | (R)-N-(1-(5-(cyclopropylmethoxy)pyridin-2-yl)ethyl)-6-fluoro-1-methyl-1H-indole-2-carboxamide | | | 366.1 | 1.85 min | HPLC |
| Example 187 | trans-2-(1H-indol-6-yl)-N-((R)-1-(5-(2,2,2-trifluoroethoxy)pyrazin-2-yl)ethyl)cyclopropane-carboxamide | | | 403.1 | 1.69 min | HPLC |

TABLE 3-continued

| Example | Name | STRUCTURE | Structure of amine part | Structure of caboxylic acid part | Observed MS | Retention Time | Purification Method |
|---|---|---|---|---|---|---|---|
| Example 188 | trans-N-((R)-1-(5-(cyclopropylmethoxy)pyridin-2-yl)ethyl)-2-(1H-indol-6-yl)cyclopropanecarboxamide | 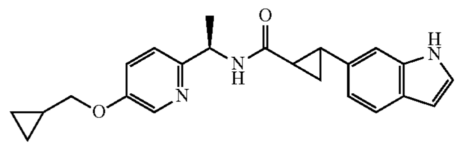 [SMILES: C[C@@H](NC(=O)C1CC1c1ccc2cc[nH]c2c1)c1ccc(OCC2CC2)cn1] | | | 374.1 | 1.65 min | HPLC |
| Example 189 | trans-2-(1-((3-methyloxetan-3-yl)methyl)-1H-indol-6-yl)-N-((R)-1-(5-(2,2,2-trifluoro-ethoxy)pyridin-2-yl)ethyl)cyclopropanecarboxamide | 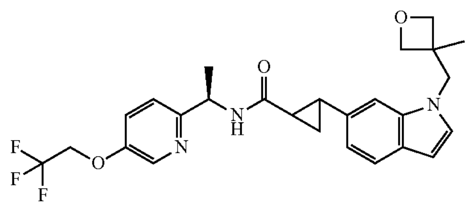 [SMILES: C[C@@H](NC(=O)C1CC1c1ccc2ccn(CC3(C)COC3)c2c1)c1ccc(OCC(F)(F)F)cn1] | | | 487.9 | 1.70 min | HPLC |
| Example 190 | trans-2-(1-((3-methyloxetan-3-yl)methyl)-1H-indol-8-yl)-N-((R)-1-(5-(2,2,2-trifluoroethoxy)pyrazin-2-yl)ethyl)cyclopropanecarboxamide | 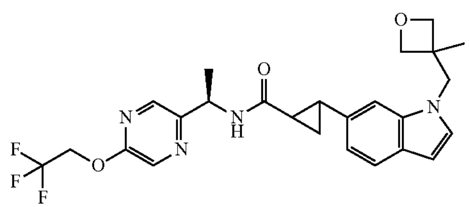 [SMILES: C[C@@H](NC(=O)C1CC1c1ccc2ccn(CC3(C)COC3)c2c1)c1cnc(OCC(F)(F)F)cn1] | | | 487.1 | 1.77 min | HPLC |
| Example 191 | trans-N-((R)-1-(5-(cyclopropylmethoxy)pyridin-2-yl)ethyl)-2-(1-((3-methyloxetan-3-yl)methyl)-1H-indol-6-yl)cyclopropanecarboxamide | 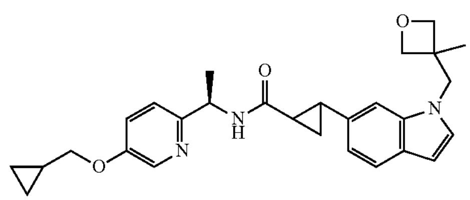 [SMILES: C[C@@H](NC(=O)C1CC1c1ccc2ccn(CC3(C)COC3)c2c1)c1ccc(OCC2CC2)cn1] | | | 460.0 | 1.73 min | HPLC |
| Example 192 | trans-N-((R)-1-(5-(cyclopropylmethoxy)pyridin-2-yl)ethyl)-2-(1-methyl-1H-indol-6-yl)cyclopropanecarboxamide | 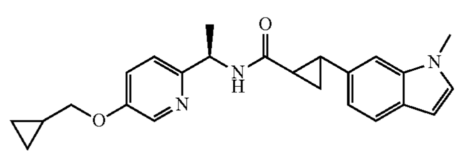 [SMILES: C[C@@H](NC(=O)C1CC1c1ccc2ccn(C)c2c1)c1ccc(OCC2CC2)cn1] | | | 390.0 | 1.77 min | HPLC |

TABLE 3-continued

| Example | Name | STRUCTURE | Structure of amine part | Structure of caboxylic acid part | Observed MS | Retention Time | Purification Method |
|---|---|---|---|---|---|---|---|
| Example 193 | trans-N-((R)-1-(5-(cyclopropylmethoxy)pyridin-2-yl)ethyl)-2-(3,5-difluorophenyl)cyclopropanecarboxamide | 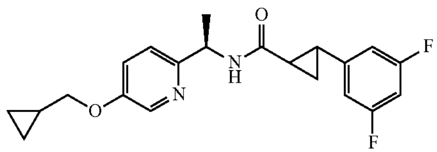 [SMILES: C[C@@H](NC(=O)C1CC1c1cc(F)cc(F)c1)c1ccc(OCC2CC2)cn1] | | | 371.1 | 1.78 min | HPLC |
| Example 194 | trans-2-(3,5-difluorophenyl)-N-((R)-1-(5-(2,2,2-trifluoroethoxy)pyrazin-2-yl)ethyl)cyclopropanecarboxamide | 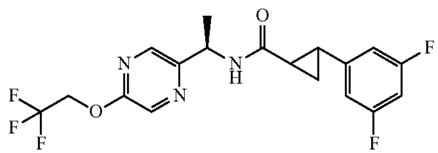 [SMILES: C[C@@H](NC(=O)C1CC1c1cc(F)cc(F)c1)c1cnc(OCC(F)(F)F)cn1] | | | 400.0 | 1.88 min | HPLC |
| Example 195 | trans-2-(2,5-difluorophenyl)-N-((R)-1-(5-(2,2,2-trifluoroethoxy)pyridin-2-yl)ethyl)cyclopropanecarboxamide | 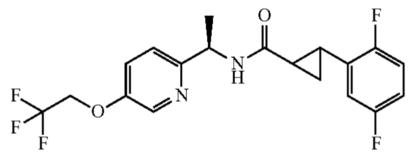 [SMILES: C[C@@H](NC(=O)C1CC1c1cc(F)ccc1F)c1ccc(OCC(F)(F)F)cn1] | | | 399.1 | 1.78 min | HPLC |
| Example 196 | trans-N-((R)-1-(5-(cyclopropylmethoxy)pyridin-2-yl)ethyl)-2-(2,5-difluorophenyl)cyclopropanecarboxamide | 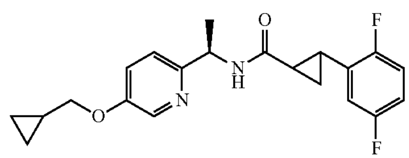 [SMILES: C[C@@H](NC(=O)C1CC1c1cc(F)ccc1F)c1ccc(OCC2CC2)cn1] | | | 371.1 | 1.77 min | HPLC |
| Example 197 | trans-2-(2,5-difluorophenyl)-N-((R)-1-(5-(2,2,2-trifluoroethoxy)pyrazin-2-yl)ethyl)cyclopropanecarboxamide | 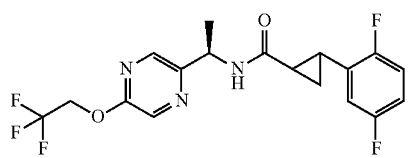 [SMILES: C[C@@H](NC(=O)C1CC1c1cc(F)ccc1F)c1cnc(OCC(F)(F)F)cn1] | | | 400.0 | 1.81 min | HPLC |

TABLE 3-continued

| Example | Name | STRUCTURE | Structure of amine part | Structure of carboxylic acid part | Observed MS | Retention Time | Purification Method |
|---|---|---|---|---|---|---|---|
| Example 198 | (R)-N-(1-(6-(2,2,2-trifluoroethoxy)pyridin-2-yl)ethyl)-6-(trifluoromethoxy)-1H-indazole-3-carboxamide | 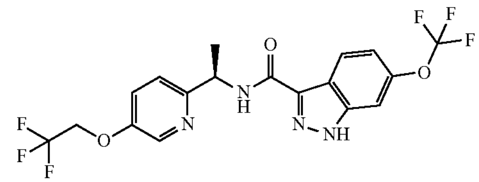 [SMILES: C[C@@H](NC(=O)c1n[nH]c2cc(OC(F)(F)F)ccc12)c1ccc(OCC(F)(F)F)cn1] | | | 447.0 | 1.79 min | HPLC |
| Example 199 | (R)-1-methyl-N-(1-(5-(2,2,2-trifluoroethoxy)pyrazin-2-yl)ethyl)-6-(trifluoromethoxy)-1H-indazole-3-carboxamide | 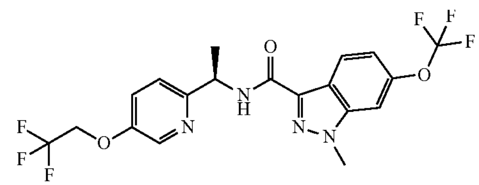 [SMILES: C[C@@H](NC(=O)c1nn(C)c2cc(OC(F)(F)F)ccc12)c1ccc(OCC(F)(F)F)cn1] | | | 461.0 | 1.93 min | HPLC |
| Example 200 | trans-2-(2-(isopropylamino)pyridin-4-yl)-N-((R)-1-(5-(2,2,2-trifluoroethoxy)pyrazin-2-yl)ethyl)cyclopropanecarboxamide | 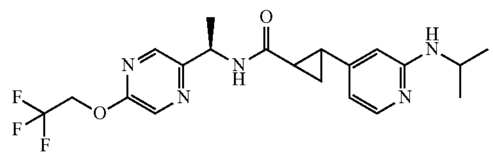 [SMILES: CC(C)Nc1cc(C2CC2C(=O)N[C@H](C)c2cnc(OCC(F)(F)F)cn2)ccn1] | | | 422.1 | 1.64 min | HPLC |
| Example 201 | trans-N-((R)-1-(5-(cyclopropylmethoxy)pyridin-2-yl)ethyl)-2-(1H-indol-4-yl)cyclopropanecarboxamide | 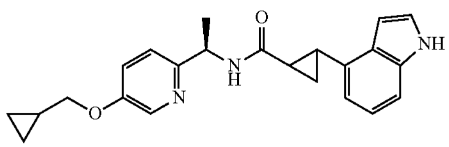 [SMILES: C[C@@H](NC(=O)C1CC1c1cccc2[nH]ccc12)c1ccc(OCC2CC2)cn1] | | | 374.1 | 1.62 min | HPLC |
| Example 202 | trans-2-(4-methoxy-3-methylphenyl)-N-((R)-1-(5-(2,2,2-trifluoroethoxy)pyridin-2-yl)ethyl)cyclopropanecarboxamide | 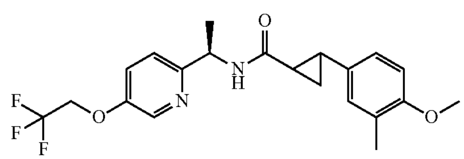 [SMILES: COc1ccc(C2CC2C(=O)N[C@H](C)c2ccc(OCC(F)(F)F)cn2)cc1C] | | | 408.6 | 1.79 min | HPLC |

TABLE 3-continued

| Example | Name | STRUCTURE | Structure of amine part | Structure of carboxylic acid part | Observed MS | Retention Time | Purification Method |
|---|---|---|---|---|---|---|---|
| Example 203 | (1S*,2S*)-2-(1H-indol-6-yl)-N-((R)-1-(5-(2,2,2-trifluoroethoxy)pyridin-2-yl)ethyl)cyclopropanecarboxamide | 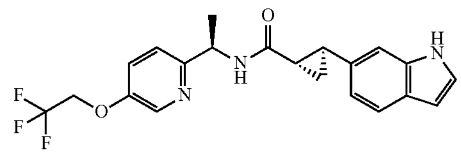 [SMILES: C[C@@H](NC(=O)[C@H]1C[C@@H]1c1ccc2cc[nH]c2c1)c1ccc(OCC(F)(F)F)cn1] | | | Confirmed by NMR(see Table 2) | | Chiral-HPLC |
| Example 204 | (1R*,2R*)-2-(1H-indol-5-yl)-N-((R)-1-(5-(2,2,2-trifluoroethoxy)pyridin-2-yl)ethyl)cyclopropanecarboxamide | 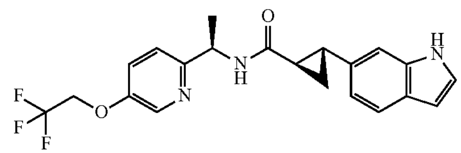 [SMILES: C[C@@H](NC(=O)[C@@H]1C[C@H]1c1ccc2cc[nH]c2c1)c1ccc(OCC(F)(F)F)cn1] | | | Confirmed by NMR(see Table 2) | | Chiral-HPLC |
| Example 205 | trans-2-(quinolin-2-yl)-N-((R)-1-(6-((2,2,2-trifluoroethoxy)pyridin-3-yl)ethyl)cyclopropanecarboxamide | 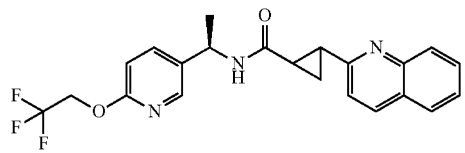 [SMILES: C[C@@H](NC(=O)C1CC1c1ccc2ccccc2n1)c1ccc(OCC(F)(F)F)nc1] | | | 414.1 | 1.82 min | HPLC |
| Example 206 | trans-2-(quinolin-7-yl)-N-((R)-1-(6-((2,2,2-trifluoroethoxy)pyridin-3-yl)ethyl)cyclopropanecarboxamide | 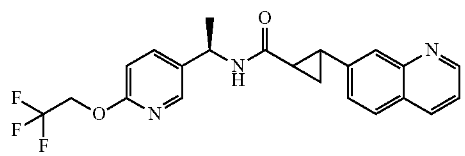 [SMILES: C[C@@H](NC(=O)C1CC1c1ccc2cccnc2c1)c1ccc(OCC(F)(F)F)nc1] | | | 414.1 | 1.68 min | HPLC |
| Example 207 | trans-2-(quinolin-6-yl)-N-((R)-1-(6-((2,2,2-trifluoroethoxy)pyridin-3-yl)ethyl)cyclopropanecarboxamide | 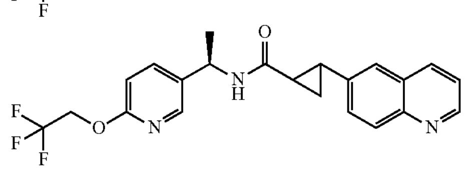 | | | 414.1 | 1.66 min | HPLC |
| Example 208 | trans-2-(1-methyl-1H-indol-6-yl)-N-((R)-1-(8-(2,2,2-trifluoroethoxy)pyridin-3-yl)ethyl)cyclopropanecarboxamide | 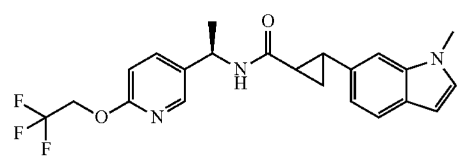 [SMILES: C[C@@H](NC(=O)C1CC1c1ccc2ccn(C)c2c1)c1ccc(OCC(F)(F)F)nc1] | | | 416.1 | 1.87 min | HPLC |

TABLE 3-continued

| Example | Name | STRUCTURE | Structure of amine part | Structure of caboxylic acid part | Observed MS | Retention Time | Purification Method |
|---|---|---|---|---|---|---|---|
| Example 209 | trans-2-((4-chlorophenoxy)methyl)-N-((R)-1-(6-(2,2,2-trifluoroethoxy)pyridin-3-yl)ethyl)cyclopropanecarboxamide | 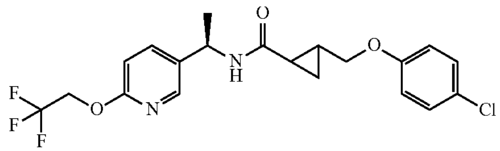 [SMILES: C[C@@H](NC(=O)C1CC1COc1ccc(Cl)cc1)c1ccc(OCC(F)(F)F)nc1] | | | 427.0 | 1.92 min | HPLC |
| Example 210 | trans-2-(5-fluoro-1H-indol-3-yl)-N-((R)-1-(6-(2,2,2-trifluoroethoxy)pyridin-3-yl)ethyl)cyclopropanecarboxamide | 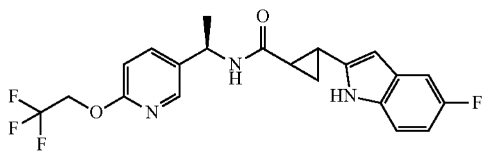 [SMILES: C[C@@H](NC(=O)C1CC1c1cc2cc(F)ccc2[nH]1)c1ccc(OCC(F)(F)F)nc1] | | | 420.1 | 1.83 min | HPLC |
| Example 211 | trans-2-(quinolin-3-yl)-N-((R)-1-(6-(2,2,2-trifluoroethoxy)pyridin-3-yl)ethyl)cyclopropanecarboxamide | 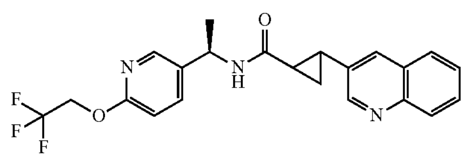 [SMILES: C[C@@H](NC(=O)C1CC1c1cnc2ccccc2c1)c1ccc(OCC(F)(F)F)nc1] | | | 414.1 | 1.71 min | HPLC |
| Example 212 | trans-2-(1H-indol-7-yl)-N-((R)-1-(6-(2,2,2-trifluoroethoxy)pyridin-3-yl)ethyl)cyclopropanecarboxamide | 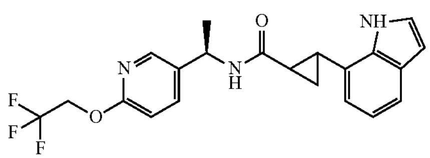 [SMILES: C[C@@H](NC(=O)C1CC1c1cccc2cc[nH]c12)c1ccc(OCC(F)(F)F)nc1] | | | 402.1 | 1.84 min | HPLC |
| Example 213 | trans-2-(1-((3-methoxetan-3-yl)methyl)-1H-indol-6-yl)-N-((R)-1-(6-(2,2,2-trifluoroethoxy)pyridin-3-yl)ethyl)cyclopropanecarboxamide | 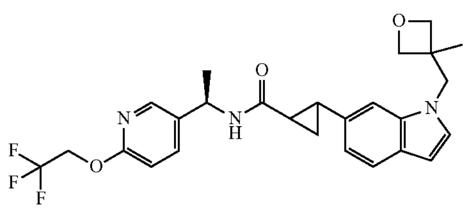 [SMILES: C[C@@H](NC(=O)C1CC1c1ccc2ccn(CC3(C)COC3)c2c1)c1ccc(OCC(F)(F)F)nc1] | | | 486.1 | 1.84 min | HPLC |

TABLE 3-continued

| Example | Name | STRUCTURE | Structure of amine part | Structure of caboxylic acid part | Observed MS | Retention Time | Purification Method |
|---|---|---|---|---|---|---|---|
| Example 214 | trans-2-(1H-indol-4-yl)-N-((R)-1-(6-(2,2,2-trifluoroethoxy)pyridin-3-yl)ethyl)cyclopropanecarboxamide | 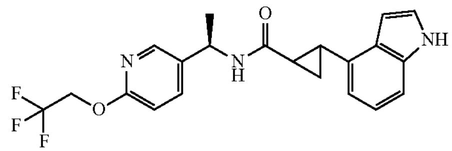 [SMILES: C[C@@H](NC(=O)C1CC1c1cccc2[nH]ccc12)c1ccc(OCC(F)(F)F)nc1] | | | 402.1 | 1.74 min | HPLC |
| Example 215 | (1S*,2S*)-2-(8-chloroquinolin-2-yl)-N-((R)-1-(5-(2,2,2-trifluoroethoxy)pyrazin-2-yl)ethyl)cyclopropanecarboxamide | 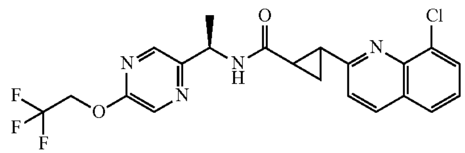 [SMILES: C[C@@H](NC(=O)C1CC1c1ccc2cccc(Cl)c2n1)c1cnc(OCC(F)(F)F)cn1] | | | Confirmed by NMR(see Table 2) | | MPLC |
| Example 216 | (R)-6-fluoro-1-methyl-N-(1-(6-(2,2,2-trifluoroethoxy)pyridin-3-yl)ethyl)-1H-indole-2-carboxamide | 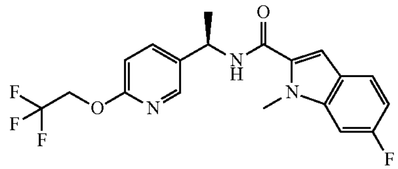 [SMILES: C[C@@H](NC(=O)c1cc2ccc(F)cc2n1C)c1ccc(OCC(F)(F)F)nc1] | | | 394.0 | 1.93 min | HPLC |
| Example 217 | (R)-6-methoxy-N-(1-(8-(2,2,2-trifluoroethoxy)pyridin-3-yl)ethyl)-1H-indole-2-carboxamide | 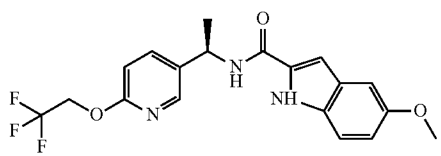 [SMILES: COc1ccc2[nH]c(C(=O)N[C@H](C)c3ccc(OCC(F)(F)F)nc3)cc2c1] | | | 392.1 | 1.74 min | HPLC |
| Example 218 | (R)-N-(1-(6-(2,2,2-trifluoroethoxy)pyridin-3-yl)ethyl)benzo[b]thiophene-2-carboxamide | 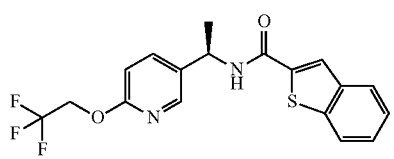 [SMILES: C[C@@H](NC(=O)c1cc2ccccc2s1)c1ccc(OCC(F)(F)F)nc1] | | | 379.0 | 1.88 min | HPLC |

| Example | Name | STRUCTURE | Structure of amine part | Structure of caboxylic acid part | Observed MS | Retention Time | Purification Method |
|---|---|---|---|---|---|---|---|
| Example 219 | (R)-N-(1-(6-(2,2,2-trifluoroethoxy)pyridin-3-yl)ethyl)-4-(trifluoromethoxy)benzamide | 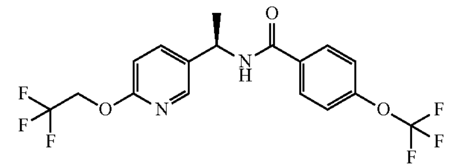 [SMILES: C[C@@H](NC(=O)c1ccc(OC(F)(F)F)cc1)c1ccc(OCC(F)(F)F)nc1] | | | 407.0 | 1.91 min | HPLC |
| Example 220 | (R)-2-phenoxy-N-(1-(6-(2,2,2-trifluoroethoxy)pyridin-3-yl)ethyl)benzamide | 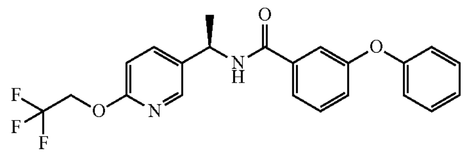 [SMILES: C[C@@H](NC(=O)c1cccc(Oc2ccccc2)c1)c1ccc(OCC(F)(F)F)nc1] | | | 415.0 | 1.97 min | HPLC |
| Example 221 | (R)-6-methoxy-N-(1-(6-(2,2,2-trifluoroethoxy)pyridin-3-yl)ethyl)quinoline-2-carboxamide | 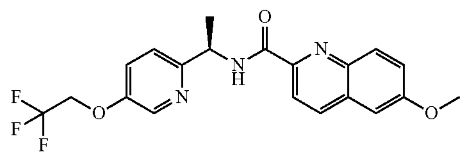 [SMILES: COc1ccc2nc(C(=O)N[C@H](C)c3ccc(OCC(F)(F)F)cn3)ccc2c1] | | | 405.6 | 1.85 min | HPLC |
| Example 222 | (1R*,2R*)-2-(quinolin-2-yl)-N-((R)-1-(5-(2,2,2-trifluoroethoxy)pyrazin-2-yl)ethyl)cyclopropanecarboxamide | 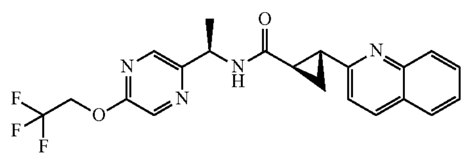 | | | Confirmed by NMR(see Table 2) | | Chiral-HPLC |
| Example 223 | (1S*,2S*)-2-(1H-indol-2-yl)-N-((R)-1-(6-(2,2,2-trifluoroethoxy)pyridin-3-yl)ethyl)cyclopropanecarboxamide | 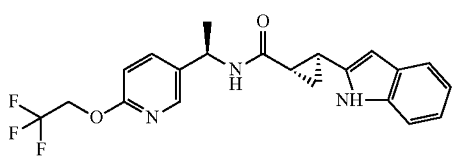 [SMILES: C[C@@H](NC(=O)[C@H]1C[C@@H]1c1cc2ccccc2[nH]1)c1ccc(OCC(F)(F)F)nc1] | | | Confirmed by NMR(see Table 2) | | Chiral-HPLC |
| Example 224 | (1R*,2R*)-2-(1H-indol-2-yl)-N-((R)-1-(6-(2,2,2-trifluoroethoxy)pyridin-3-yl)ethyl)cyclopropanecarboxamide | 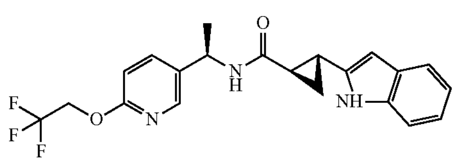 [SMILES: C[C@@H](NC(=O)[C@@H]1C[C@H]1c1cc2ccccc2[nH]1)c1ccc(OCC(F)(F)F)nc1] | | | Confirmed by NMR(see Table 2) | | Chiral-HPLC |

TABLE 3-continued

| Example | Name | STRUCTURE | Structure of amine part | Structure of caboxylic acid part | Observed MS | Retention Time | Purification Method |
|---|---|---|---|---|---|---|---|
| Example 225 | (1S*,2S*)-2-(1H-indol-2-yl)-N-((R)-1-(5-(2,2,2-trifluoroethoxy)pyrazin-2-yl)ethyl)cyclopropanecarboxamide | 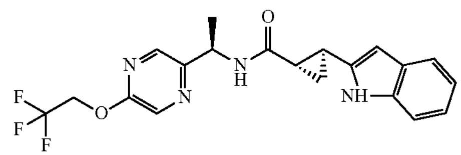 [SMILES: C[C@@H](NC(=O)[C@H]1C[C@@H]1c1cc2ccccc2[nH]1)c1cnc(OCC(F)(F)F)cn1] | | | Confirmed by NMR(see Table 2) | | MPLC |
| Example 226 | (1R*,2R*)-2-(1H-indol-2-yl)-N-((R)-1-(5-(2,2,2-trifluoroethoxy)pyrazin-2-yl)ethyl)cyclopropanecarboxamide | 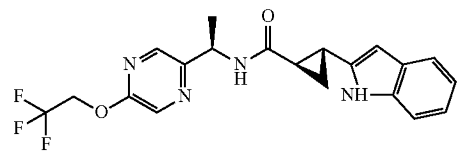 [SMILES: C[C@@H](NC(=O)[C@@H]1C[C@H]1c1cc2ccccc2[nH]1)c1cnc(OCC(F)(F)F)cn1] | | | Confirmed by NMR(see Table 2) | | MPLC |
| Example 227 | (1S*,2S*)-2-(1-methyl-1H-indazol-6-yl)-N-((R)-1-(5-(2,2,2-trifluoroethoxy)pyrazin-2-yl)ethyl)cyclopropanecarboxamide | 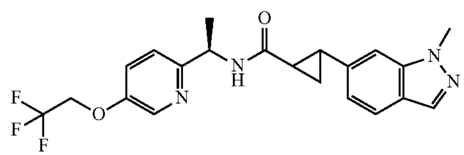 [SMILES: C[C@@H](NC(=O)C1CC1c1ccc2cnn(C)c2c1)c1ccc(OCC(F)(F)F)cn1] | | | Confirmed by NMR(see Table 2) | | Chiral-HPLC |
| Example 228 | trans-2-(1-methyl-1H-indazol-6-yl)-N-((R)-1-(6-(2,2,2-trifluoroethoxy)pyridin-3-yl)ethyl)cyclopropanecarboxamide | 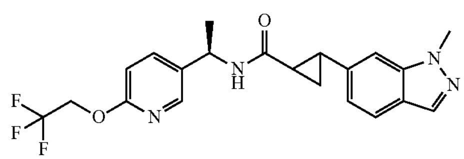 [SMILES: C[C@@H](NC(=O)C1CC1c1ccc2cnn(C)c2c1)c1ccc(OCC(F)(F)F)nc1] | | | 417.1 | 1.69 min | HPLC |
| Example 229 | trans-2-(1-methyl-1H-indazol-6-yl)-N-((R)-1-(5-(2,2,2-trifluoroethoxy)pyridin-2-yl)ethyl)cyclopropanecarboxamide | 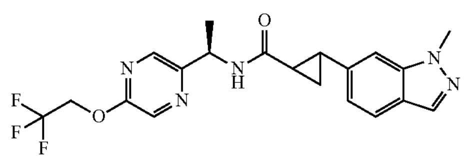 [SMILES: C[C@@H](NC(=O)C1CC1c1ccc2cnn(C)c2c1)c1cnc(OCC(F)(F)F)cn1] | | | 418.1 | 1.64 min | HPLC |

TABLE 3-continued

| Example | Name | STRUCTURE | Structure of amine part | Structure of carboxylic acid part | Observed MS | Retention Time | Purification Method |
|---|---|---|---|---|---|---|---|
| Example 230 | trans-N-((R)-1-(5-(cyclopropylmethoxy)pyridin-3-yl)ethyl)-2-(1-methyl-1H-imidazo-6-yl)cyclopropane-carboxamide | 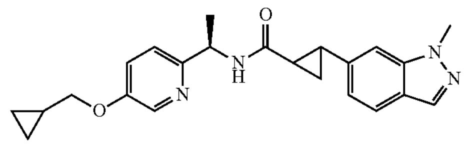 [SMILES: C[C@@H](NC(=O)C1CC1c1ccc2cnn(C)c2c1)c1ccc(OCC2CC2)cn1] | | | 389.2 | 1.59 min | HPLC |
| Example 231 | (R)-3-(pyridin-2-yloxy)-N-(1-(5-(2,2,2-trifluoroethoxy)pyridin-2-yl)ethyl)benzamide | 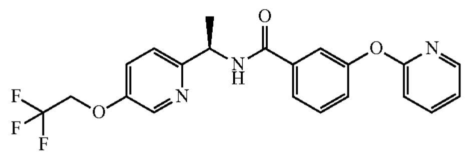 [SMILES: C[C@@H](NC(=O)c1cccc(Oc2ccccn2)c1)c1ccc(OCC(F)(F)F)cn1] | | | 416.1 | 1.66 min | HPLC |
| Example 232 | (R)-4-(tetrahydro-2H-pyran-4-yloxy)-N-(1-(5-(2,2,2-trifluoroethoxy)pyridin-2-yl)ethyl)benzamide | 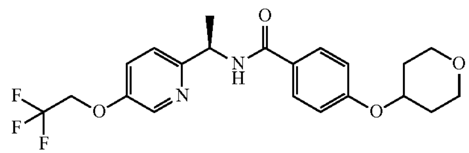 [SMILES: C[C@@H](NC(=O)c1ccc(OC2CCOCC2)cc1)c1ccc(OCC(F)(F)F)cn1] | | | 423.1 | 1.61 min | HPLC |
| Example 233 | (R)-N-(1-(3-(2,2,2-trifluoroethoxy)pyridin-2-yl)ethyl)pyrazolo[1,5-a]pyridine-2-carboxamide | 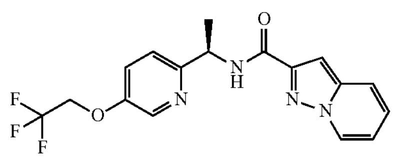 [SMILES: C[C@@H](NC(=O)c1cc2ccccn2n1)c1ccc(OCC(F)(F)F)cn1] | | | 363.1 | 1.60 min | HPLC |
| Example 234 | (R)-N-(1-(5-(2,2,2-trifluoroethoxy)pyridin-2-yl)ethyl)pyrazolo[1,5-a]pyridine-7-carboxamide | 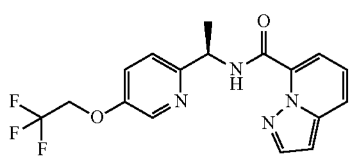 [SMILES: C[C@@H](NC(=O)c1cccc2ccnn12)c1ccc(OCC(F)(F)F)cn1] | | | 363.0 | 1.76 min | HPLC |

TABLE 3-continued

| Example | Name | STRUCTURE | Structure of amine part | Structure of caboxylic acid part | Observed MS | Retention Time | Purification Method |
|---|---|---|---|---|---|---|---|
| Example 235 | (R)-N-(1-(5-(2,2,2-trifluoroethoxy)pyridin-2-yl)ethyl)-1-(3-(trifluoromethyl)phenyl)-1H-imidazole-2-carboxamide | 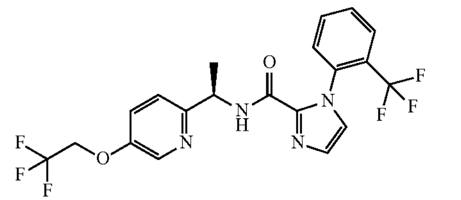 [SMILES: C[C@@H](NC(=O)c1nccn1-c1ccccc1C(F)(F)F)c1ccc(OCC(F)(F)F)cn1] | | | 457.1 | 1.78 min | HPLC |
| Example 236 | (R)-1-methyl-N-(1-(5-(2,2,2-trifluoroethoxy)pyridin-2-yl)ethyl)-4H-thieno[3,2-b]pyrrole-5-carboxamide | 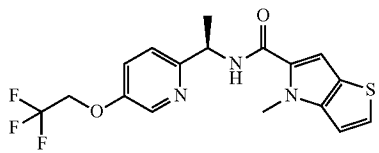 [SMILES: C[C@@H](NC(=O)c1cc2sccc2n1C)c1ccc(OCC(F)(F)F)cn1] | | | 382.1 | 1.75 min | HPLC |
| Example 237 | (1S*,2S*)-2-(4-(benzyloxy)phenyl)-N-((R)-1-(5-(2,2,2-trifluoroethoxy)pyridin-2-yl)ethyl)cyclopropanecarboxamide | 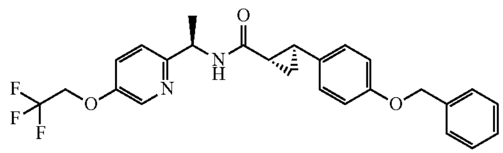 [SMILES: C[C@@H](NC(=O)[C@H]1C[C@@H]1c1ccc(OCc2ccccc2)cc1)c1ccc(OCC(F)(F)F)cn1] | | | Confirmed by NMR(see Table 2) | | MPLC |
| Example 238 | (1R*,2R*)-2-(4-(benzyloxy)phenyl)-N-((R)-1-(5-(2,2,2-trifluoroethoxy)pyridin-2-yl)ethyl)cyclopropanecarboxamide | 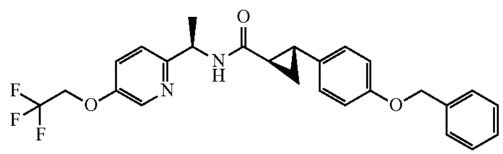 [SMILES: C[C@@H](NC(=O)[C@@H]1C[C@H]1c1ccc(OCc2ccccc2)cc1)c1ccc(OCC(F)(F)F)cn1] | | | Confirmed by NMR(see Table 2) | | MPLC |
| Example 239 | (R,E)-3-(quinolin-2-yl)-N-(1-(5-(2,2,2-trifluoroethoxy)pyridin-2-yl)ethyl)acrylamide | 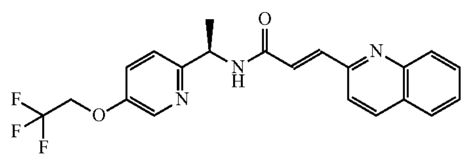 [SMILES: C[C@@H](NC(=O)/C=C/c1ccc2ccccc2n1)c1ccc(OCC(F)(F)F)cn1] | | | 400.1 | 1.52 min | MPLC |

TABLE 3-continued

| Example | Name | STRUCTURE | Structure of amine part | Structure of caboxylic acid part | Observed MS | Retention Time | Purification Method |
|---|---|---|---|---|---|---|---|
| Example 240 | (1S*,2S*)-2-(3-(benzyloxy)phenyl)-N-((R)-1-(5-(2,2,2-trifluoroethoxy)pyridin-2-yl)ethyl)cyclopropanecarboxamide | 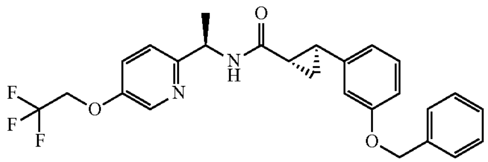 [SMILES: C[C@@H](NC(=O)[C@H]1C[C@@H]1c1cccc(OCc2ccccc2)c1)c1ccc(OCC(F)(F)F)cn1] | | | Confirmed by NMR(see Table 2) | | MPLC |
| Example 241 | (1R*,2R*)-2-(3-(benzyloxy)phenyl)-N-((R)-1-(6-(2,2,2-trifluoroethoxy)pyridin-2-yl)ethyl)cyclopropanecarboxamide | 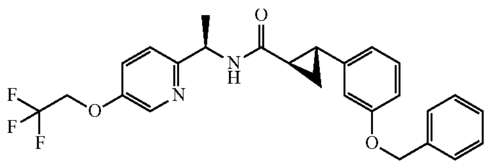 [SMILES: C[C@@H](NC(=O)[C@@H]1C[C@H]1c1cccc(OCc2ccccc2)c1)c1ccc(OCC(F)(F)F)cn1] | | | Confirmed by NMR(see Table 2) | | MPLC |
| Example 242 | (1S*,2S*)-2-(4-hydroxyphenyl)-N-((R)-1-(5-(2,2,2-trifluoroethoxy)pyridin-2-yl)ethyl)cyclopropanecarboxamide | 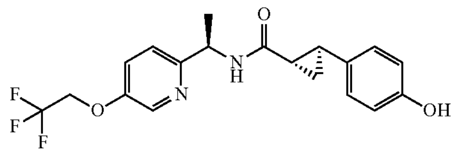 [SMILES: C[C@@H](NC(=O)[C@H]1C[C@@H]1c1ccc(O)cc1)c1ccc(OCC(F)(F)F)cn1] | | Alternative route | 378.9 | 1.48 min | HPLC |
| Example 243 | trans-2-(1-methyl-1H-benzo[d]imidazol-2-yl)-N-((R)-1-(5-(2,2,2-trifluoroethoxy)pyridin-2-yl)ethyl)cyclopropanecarboxamide | 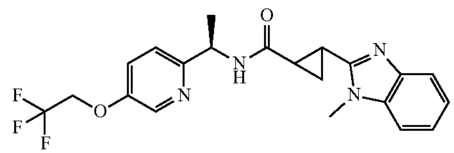 [SMILES: C[C@@H](NC(=O)C1CC1c1nc2ccccc2n1C)c1ccc(OCC(F)(F)F)cn1] | | | 416.9 | 1.52 min | HPLC |
| Example 244 | trans-2-(1-methyl-1H-benzo[d]imidazol-2-yl)-N-((R)-1-(5-(2,2,2-trifluoroethoxy)pyrazin-2-yl)ethyl)cyclopropanecarboxamide | 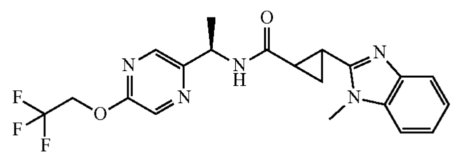 [SMILES: C[C@@H](NC(=O)C1CC1c1nc2ccccc2n1C)c1cnc(OCC(F)(F)F)cn1] | | | 418.0 | 1.58 min | HPLC |
| Example 245 | trans-2-(1-methyl-1H-benzo[d]imidazol-2-yl)-N-((R)-1-(5-(2,2,2-trifluoroethoxy)pyridin-3-yl)ethyl)cyclopropanecarboxamide | 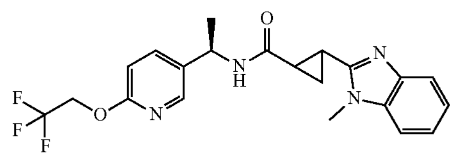 [SMILES: C[C@@H](NC(=O)C1CC1c1nc2ccccc2n1C)c1ccc(OCC(F)(F)F)nc1] | | | 416.9 | 1.64 min | HPLC |

| Example | Name | STRUCTURE | Structure of amine part | Structure of caboxylic acid part | Observed MS | Retention Time | Purification Method |
|---|---|---|---|---|---|---|---|
| Example 246 | (1S*,2S*)-2-(2-chloro-4-fluorophenyl)-N-((R)-1-(5-(2,2,2-trifluoroethoxy)pyridin-2-yl)ethyl)cyclopropanecarboxamide | 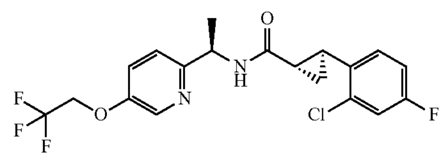 [SMILES: C[C@@H](NC(=O)[C@H]1C[C@@H]1c1ccc(F)cc1Cl)c1ccc(OCC(F)(F)F)cn1] | | | 414.9 | 1.81 min | MPLC |
| Example 247 | (1R*,2R*)-2-(2-chloro-4-fluorophenyl)-N-((R)-1-(5-(2,2,2-trifluoroethoxy)pyridin-2-yl)ethyl)cyclopropanecarboxamide | 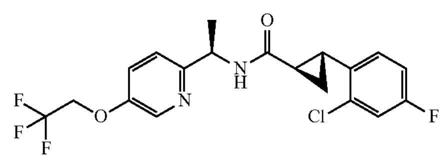 [SMILES: C[C@@H](NC(=O)[C@@H]1C[C@H]1c1ccc(F)cc1Cl)c1ccc(OCC(F)(F)F)cn1] | | | 414.9 | 1.79 min | MPLC |
| Example 248 | (SR*,2S*)-2-(2-fluoro-4-methoxyphenyl)-N-((R)-1-(5-(2,2,2-trifluoroethoxy)pyridin-3-yl)ethyl)cyclopropanecarboxamide | 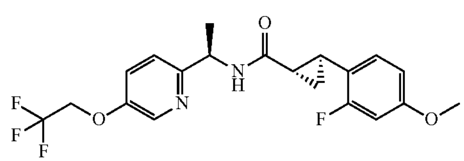 [SMILES: COc1ccc([C@H]2C[C@@H]2C(=O)N[C@H](C)c2ccc(OCC(F)(F)F)cn2)c(F)c1] | | | 411.0 | 1.73 min | MPLC |
| Example 249 | (1R*,2R*)-2-(2-fluoro-4-methoxyphenyl)-N-((R)-1-(5-(2,2,2-trifluoroethoxy)pyridin-2-yl)ethyl)cyclopropanecarboxamide | 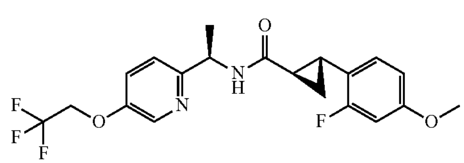 [SMILES: COc1ccc([C@@H]2C[C@H]2C(=O)N[C@H](C)c2ccc(OCC(F)(F)F)cn2)c(F)c1] | | | 411.0 | 1.72 min | MPLC |
| Example 250 | (1S*,2S*)-N-((R)-1-(5-(2,2,2-trifluoroethoxy)pyridin-2-yl)ethyl)-2-(2,4,6-trifluorophenyl)cyclopropanecarboxamide | 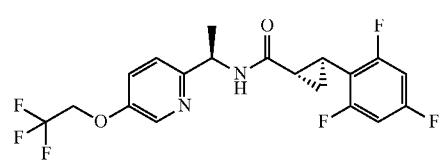 [SMILES: C[C@@H](NC(=O)[C@H]1C[C@@H]1c1c(F)cc(F)cc1F)c1ccc(OCC(F)(F)F)cn1] | | | 416.0 | 1.78 min | MPLC |

TABLE 3-continued

| Example | Name | STRUCTURE | Structure of amine part | Structure of caboxylic acid part | Observed MS | Retention Time | Purification Method |
|---|---|---|---|---|---|---|---|
| Example 251 | (1S*,2S*)-3-m-tolyl-N-((R)-1-(5-(2,2,2-trifluoroethoxy)pyridin-2-yl)ethyl)cyclopropanecarboxamide | 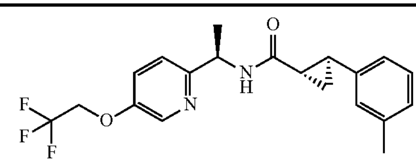 | | | 377.0 | 1.80 min | MPLC |
| Example 252 | (1R*,2R*)-3-m-tolyl-N-((R)-1-(5-(2,2,2-trifluoroethoxy)pyridin-2-yl)ethyl)cyclopropanecarboxamide | 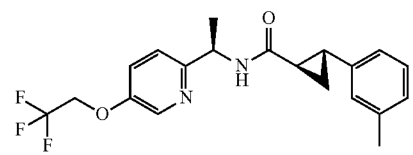 | | | 377.0 | 1.80 min | MPLC |
| Example 253 | (1S*,2S*)-2-(3,5-difluorophenyl)-N-((R)-1-(5-(2,2,2-trifluoroethoxy)pyridin-2-yl)ethyl)cyclopropanecarboxamide | 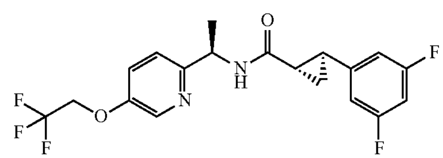 [SMILES: C[C@@H](NC(=O)[C@H]1C[C@@H]1c1cc(F)cc(F)c1)c1ccc(OCC(F)(F)F)cn1] | | | 399.0 | 1.77 min | MPLC |
| Example 254 | (1R*,2R*)-2-(3,5-difluorophenyl)-N-((R)-1-(5-(2,2,2-trifluoroethoxy)pyridin-2-yl)ethyl)cyclopropanecarboxamide | 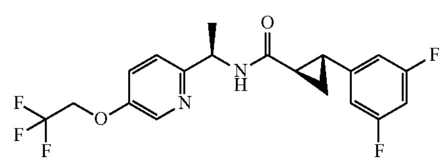 [SMILES: C[C@@H](NC(=O)[C@@H]1C[C@H]1c1cc(F)cc(F)c1)c1ccc(OCC(F)(F)F)cn1] | | | 399.0 | 1.77 min | MPLC |
| Example 255 | (1S*,2S*)-2-(3-hydroxyphenyl)-N-((R)-1-(5-(2,2,2-trifluoroethoxy)pyridin-2-yl)ethyl)cyclopropanecarboxamide | 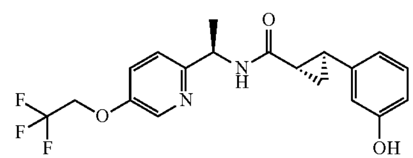 [SMILES: C[C@@H](NC(=O)[C@H]1C[C@@H]1c1cccc(O)c1)c1ccc(OCC(F)(F)F)cn1] | Alternative route | | 379.0 | 1.51 min | HPLC |

TABLE 3-continued

| Example | Name | STRUCTURE | Structure of amine part | Structure of caboxylic acid part | Observed MS | Retention Time | Purification Method |
|---|---|---|---|---|---|---|---|
| Example 256 | (1S*,2S*)-2-(4-(2-(4,4-difluoropiperidin-1-yl)-2-oxoethoxy)phenyl)-N-((R)-1-(5-(2,2,2-trifluoroethoxy)pyridin-2-yl)ethyl)cyclopropanecarboxamide | 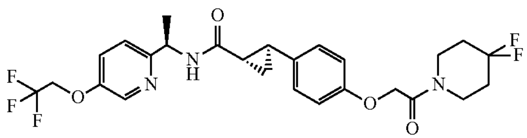 [SMILES: C[C@@H](NC(=O)[C@H]1C[C@@H]1c1ccc(OCC(=O)N2CCC(F)(F)CC2)cc1)c1ccc(OCC(F)(F)F)cn1] | Alternative route | | 539.9 | 1.66 min | HPLC |
| Example 257 | (1S*,2S*)-2-(3-(2-(4,4-difluoropiperidin-1-yl)-2-oxoethoxy)phenyl)-N-((R)-1-(5-(2,2,2-trifluoroethoxy)pyridin-2-yl)ethyl)cyclopropanecarboxamide | 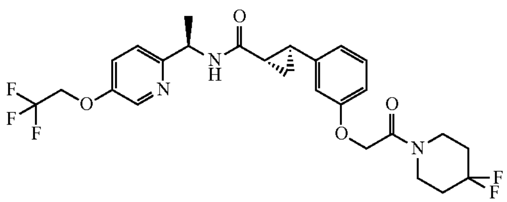 [SMILES: C[C@@H](NC(=O)[C@H]1C[C@@H]1c1cccc(OCC(=O)N2CCC(F)(F)CC2)c1)c1ccc(OCC(F)(F)F)cn1] | Alternative route | | 539.9 | 1.66 min | HPLC |
| Example 258 | (1S*,2S*)-2-(3-methoxyphenyl)-N-((R)-1-(5-(2,2,2-trifluoroethoxy)pyridin-2-yl)ethyl)cyclopropanecarboxamide | 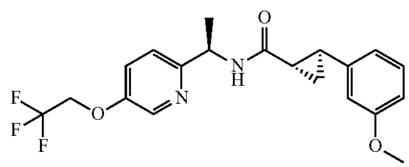 [SMILES: COc1cccc([C@H]2C[C@@H]2C(=O)N[C@H](C)c2ccc(OCC(F)(F)F)cn2)c1] | | | 393.0 | 1.69 min | MPLC |
| Example 259 | (1S*,2S*)-2-(4-methoxyphenyl)-N-((R)-1-(5-(2,2,2-trifluoroethoxy)pyridin-2-yl)ethyl)cyclopropanecarboxamide | 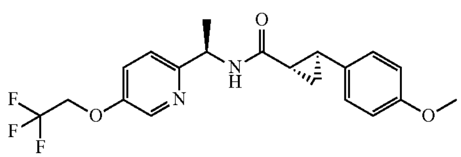 | | | 403.0 | 1.44 min | MPLC |
| Example 260 | (1R*,2R*)-2-(1H-benzo[d]imidazol-2-yl)-N-((R)-1-(5-(2,2,2-trifluoroethoxy)pyridin-2-yl)ethyl)cyclopropanecarboxamide | 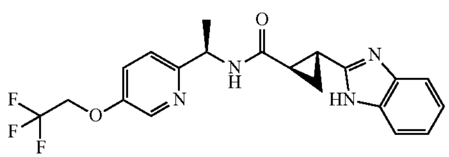 [SMILES: C[C@@H](NC(=O)[C@@H]1C[C@H]1c1nc2ccccc2[nH]1)c1ccc(OCC(F)(F)F)cn1] | | | 403.0 | 1.44 min | MPLC |

TABLE 3-continued

| Example | Name | STRUCTURE | Structure of amine part | Structure of caboxylic acid part | Observed MS | Retention Time | Purification Method |
|---|---|---|---|---|---|---|---|
| Example 261 | (1S*,2S*)-2-(2-chloro-4-fluorophenyl)-N-((R)-1-(5-(cyclopropylmethoxy)pyridin-2-yl)ethyl)cyclopropanecarboxamide | 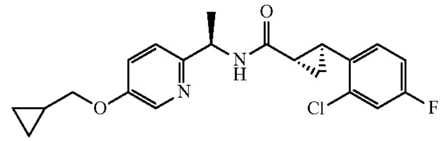 [SMILES: C[C@@H](NC(=O)[C@H]1C[C@@H]1c1ccc(F)cc1Cl)c1ccc(OCC2CC2)cn1] | | | 387.0 | 1.89 min | MPLC |
| Example 262 | (1R*,2R*)-2-(2-chloro-4-fluorophenyl)-N-((R)-1-(5-(cyclopropylmethoxy)pyridin-2-yl)ethyl)cyclopropanecarboxamide | 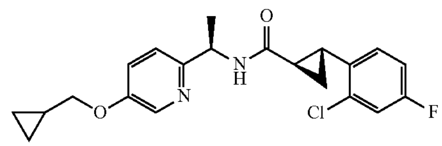 [SMILES: C[C@@H](NC(=O)[C@@H]1C[C@H]1c1ccc(F)cc1Cl)c1ccc(OCC2CC2)cn1] | | | 387.0 | 1.83 min | MPLC |
| Example 263 | (1S*,2S*)-N-((R)-1-(5-(cyclopropylmethoxy)pyridin-2-yl)ethyl)-2-(2-fluoro-4-methoxyphenyl)cyclopropanecarboxamide | 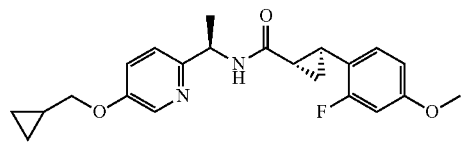 [SMILES: COc1ccc([C@H]2C[C@@H]2C(=O)N[C@H](C)c2ccc(OCC3CC3)cn2)c(F)c1] | | | 383.1 | 1.76 min | MPLC |
| Example 264 | (1R*,2R*)-N-((R)-1-(5-(cyclopropylmethoxy)pyridin-2-yl)ethyl)-2-(2-fluoro-4-methoxyphenyl)cyclopropanecarboxamide | 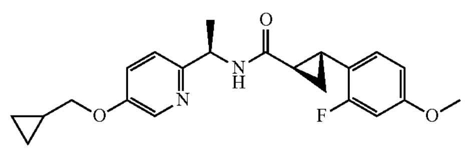 [SMILES: COc1ccc([C@@H]2C[C@H]2C(=O)N[C@H](C)c2ccc(OCC3CC3)cn2)c(F)c1] | | | 383.1 | 1.75 min | MPLC |
| Example 265 | (1S*,2S*)-N-((R)-1-(5-(cyclopropylmethoxy)pyridin-2-yl)ethyl)-2-(2,4,6-trifluorophenyl)cyclopropanecarboxamide | 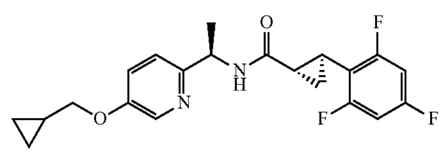 [SMILES: C[C@@H](NC(=O)[C@H]1C[C@@H]1c1c(F)cc(F)cc1F)c1ccc(OCC2CC2)cn1] | | | 389.0 | 1.81 min | MPLC |

TABLE 3-continued

| Example | Name | STRUCTURE | Structure of amine part | Structure of caboxylic acid part | Observed MS | Retention Time | Purification Method |
|---|---|---|---|---|---|---|---|
| Example 266 | (1R*,2R*)-N-((R)-1-(5-(cyclopropylmethoxy)pyridin-2-yl)ethyl)-2-(2,4,5-trifluorophenyl)cyclopropaneamide | 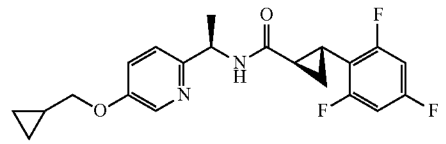 [SMILES: C[C@@H](NC(=O)[C@@H]1C[C@H]1c1c(F)cc(F)cc1F)c1ccc(OCC2CC2)cn1] | | | 389.0 | 1.82 min | MPLC |
| Example 267 | (1S*,2S*)-N-((R)-1-(5-(cyclopropylmethoxy)pyridin-2-yl)ethyl)-2-m-tolylcyclopropanecarboxamide | 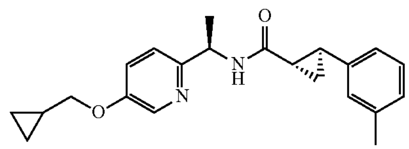 [SMILES: Cc1cccc([C@H]2C[C@@H]2C(=O)N[C@H](C)c2ccc(OCC3CC3)cn2)c1] | | | 349.1 | 1.83 min | MPLC |
| Example 268 | (1S*,2S*)-2-(2-chloro-4-fluorophenyl)-N-((R)-1-(5-(2,2,2-trifluoroethoxy)pyrazin-2-yl)ethyl)cyclopropanecarboxamide | 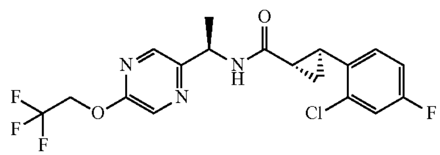 [SMILES: C[C@@H](NC(=O)[C@H]1C[C@@H]1c1ccc(F)cc1Cl)c1cnc(OCC(F)(F)F)cn1] | | | 415.9 | 1.87 min | MPLC |
| Example 269 | (1R*,2R*)-2-(2-chloro-4-fluorophenyl)-N-((R)-1-(5-(2,2,2-trifluoroethoxy)pyrazin-2-yl)ethyl)cyclopropanecarboxamide | 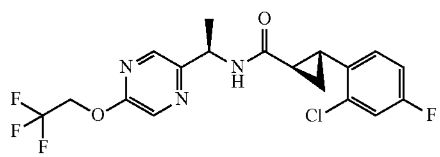 | | | 412.0 | 1.80 min | MPLC |
| Example 270 | (1S*,2S*)-2-(3-fluoro-4-methoxyphenyl)-N-((R)-1-(5-(2,2,2-trifluoroethoxy)pyrazin-2-yl)ethyl)cyclopropanecarboxamide | 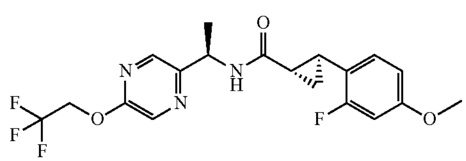 [SMILES: COc1ccc([C@H]2C[C@@H]2C(=O)N[C@H](C)c2cnc(OCC(F)(F)F)cn2)c(F)c1] | | | 412.0 | 1.80 min | MPLC |

TABLE 3-continued

| Example | Name | STRUCTURE | Structure of amine part | Structure of carboxylic acid part | Observed MS | Retention Time | Purification Method |
|---|---|---|---|---|---|---|---|
| Example 271 | (1S*,2S*)-N-((R)-1-(5-(2,2,2-trifluoroethoxy)pyrazin-2-yl)ethyl)-2-(2,4,6-trifluorophenyl)cyclopropanecarboxamide | 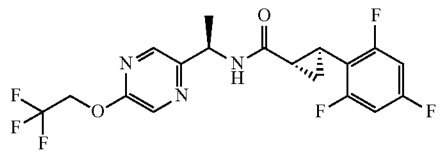 [SMILES: C[C@@H](NC(=O)[C@H]1C[C@@H]1c1c(F)cc(F)cc1F)c1cnc(OCC(F)(F)F)cn1] | | | 417.9 | 1.86 min | MPLC |
| Example 272 | (1R*,2R*)-N-((R)-1-(5-(2,2,2-trifluoroethoxy)pyrazin-2-yl)ethyl)-2-(2,4,5-trifluorophenyl)cyclopropanecarboxamide | 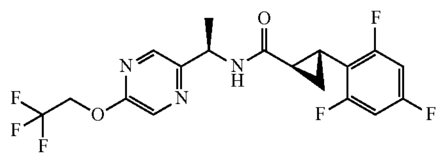 [SMILES: C[C@@H](NC(=O)[C@@H]1C[C@H]1c1c(F)cc(F)cc1F)c1cnc(OCC(F)(F)F)cn1] | | | 418.0 | 1.85 min | MPLC |
| Example 273 | (1S*,2S*)-2-m-tolyl-N-((R)-1-(5-(2,2,2-trifluoroethoxy)pyrazin-2-yl)ethyl)cyclopropanecarboxamide | 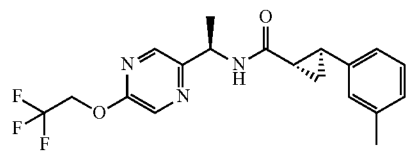 | | | 378.1 | 1.88 min | MPLC |
| Example 274 | (1R*,2R*)-2-m-tolyl-N-((R)-1-(5-(2,2,2-trifluoroethoxy)pyrazin-2-yl)ethyl)cyclopropanecarboxamide | 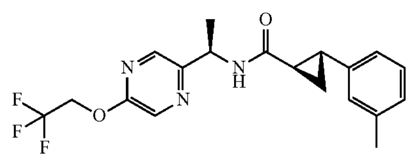 | | | 378.1 | 1.87 min | MPLC |
| Example 275 | (1S*,2S*)-2-(1H-indol-7-yl)-N-((R)-1-(5-(2,2,2-trifluoroethoxy)pyridin-2-yl)ethyl)cyclopropanecarboxamide | 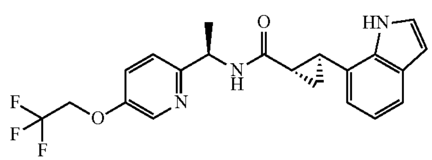 [SMILES: C[C@@H](NC(=O)[C@H]1C[C@@H]1c1cccc2cc[nH]c12)c1ccc(OCC(F)(F)F)cn1] | | | 402.0 | 1.75 min | Chiral-HPLC |
| Example 276 | (1R*,2R*)-2-(1H-indol-7-yl)-N-((R)-1-(5-(2,2,2-trifluoroethoxy)pyridin-2-yl)ethyl)cyclopropanecarboxamide | 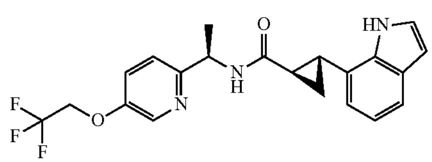 | | | 402.0 | 1.73 min | Chiral-HPLC |

TABLE 3-continued

| Example | Name | STRUCTURE | Structure of amine part | Structure of caboxylic acid part | Observed MS | Retention Time | Purification Method |
|---|---|---|---|---|---|---|---|
| Example 277 | (1R*,2R*)-2-(1H-indol-4-yl)-N-((R)-1-(5-(2,2,2-trifluoroethoxy)pyridin-2-yl)ethyl)cyclopropanecarboxamide | 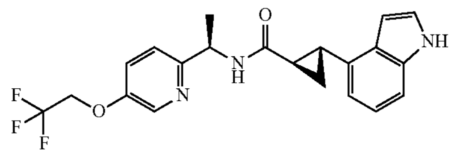 [SMILES: C[C@@H](NC(=O)[C@@H]1C[C@H]1c1cccc2[nH]ccc12)c1ccc(OCC(F)(F)F)cn1] | | | 402.0 | 1.62 min | Chiral-HPLC |
| Example 278 | (1S*,2S*)-2-(1H-indol-4-yl)-N-((R)-1-(5-(2,2,2-trifluoroethoxy)pyrazin-2-yl)ethyl)cyclopropanecarboxamide | 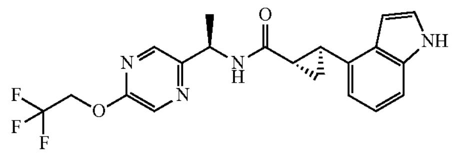 [SMILES: C[C@@H](NC(=O)[C@H]1C[C@@H]1c1cccc2[nH]ccc12)c1cnc(OCC(F)(F)F)cn1] | | | 403.0 | 1.67 min | Chiral-HPLC |
| Example 279 | (1R*,2R*)-2-(1H-indol-4-yl)-N-((R)-1-(5-(2,2,2-trifluoroethoxy)pyrazin-2-yl)ethyl)cyclopropanecarboxamide | 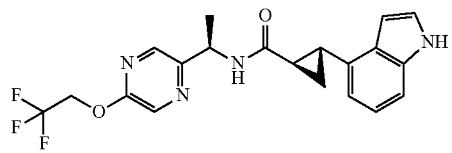 [SMILES: C[C@@H](NC(=O)[C@@H]1C[C@H]1c1cccc2[nH]ccc12)c1cnc(OCC(F)(F)F)cn1] | | | 403.0 | 1.69 min | Chiral-HPLC |
| Example 280 | (1S*,2S*)-2-phenyl-N-((R)-1-(5-(2,2,2-trifluoroethoxy)pyridin-2-yl)ethyl)cyclopropanecarboxamide | 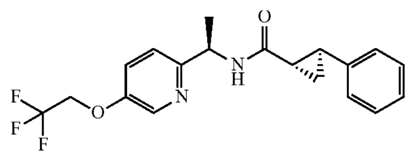 | | | 363.0 | 1.72 min | MPLC |
| Example 281 | (1R*,2R*)-2-phenyl-N-((R)-1-(5-(2,2,2-trifluoroethoxy)pyridin-2-yl)ethyl)cyclopropanecarboxamide | 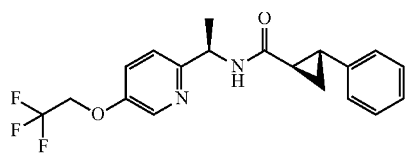 [SMILES: C[C@@H](NC(=O)[C@@H]1C[C@H]1c1ccccc1)c1ccc(OCC(F)(F)F)cn1] | | | 363.0 | 1.72 min | MPLC |
| Example 282 | (1S*,2S*)-2-phenyl-N-((R)-1-(5-(2,2,2-trifluoroethoxy)pyrazin-2-yl)ethyl)cyclopropanecarboxamide | 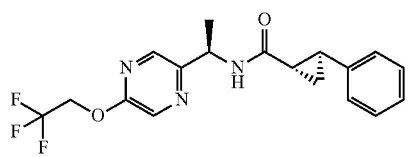 [SMILES: C[C@@H](NC(=O)[C@H]1C[C@@H]1c1ccccc1)c1ccc(OCC(F)(F)F)nc1] | | | 364.0 | 1.79 min | MPLC |

TABLE 3-continued

| Example | Name | STRUCTURE | Structure of amine part | Structure of caboxylic acid part | Observed MS | Retention Time | Purification Method |
|---|---|---|---|---|---|---|---|
| Example 283 | (1R*,2R*)-2-phenyl-N-((R)-1-(5-(2,2,2-trifluoroethoxy)pyrazin-2-yl)ethyl)cyclopropanecarboxamide | 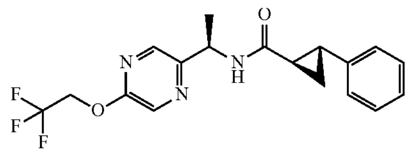 [SMILES: C[C@@H](NC(=O)[C@@H]1C[C@H]1c1ccccc1)c1ccc(OCC(F)(F)F)nc1] | | | 364.0 | 1.79 min | MPLC |
| Example 284 | (1S*,2S*)-2-phenyl-N-((R)-1-(6-(2,2,2-trifluoroethoxy)pyridin-3-yl)ethyl)cyclopropanecarboxamide | 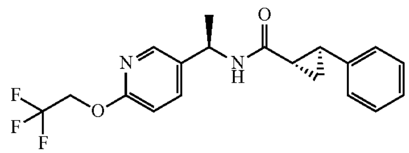 | | | 363.0 | 1.84 min | MPLC |
| Example 285 | (1R*,2R*)-2-phenyl-N-((R)-1-(6-(2,2,2-trifluoroethoxy)pyridin-3-yl)ethyl)cyclopropanecarboxamide | 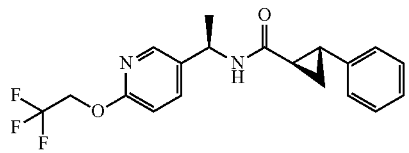 | | | 363.0 | 1.83 min | MPLC |
| Example 286 | (1S*,2S*)-2-(1H-benzo[d]imidazol-2-yl)-N-((R)-1-(5-(2,2,2-trifluoroethoxy)pyrazin-2-yl)ethyl)cyclopropanecarboxamide | 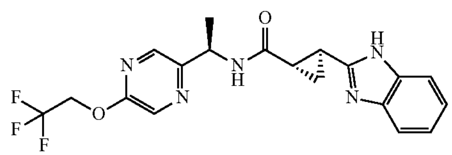 [SMILES: C[C@@H](NC(=O)[C@H]1C[C@@H]1c1nc2ccccc2[nH]1)c1cnc(OCC(F)(F)F)cn1] | | | 404.0 | 1.49 min | MPLC |
| Example 287 | (1S*,2S*)-2-(1H-benzo[d]imidazol-2-yl)-N-((R)-1-(6-(2,2,2-trifluoroethoxy)pyridin-3-yl)ethyl)cyclopropanecarboxamide | 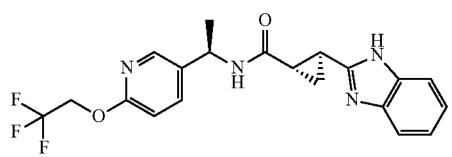 [SMILES: C[C@@H](NC(=O)[C@H]1C[C@@H]1c1nc2ccccc2[nH]1)c1ccc(OCC(F)(F)F)nc1] | | | 403.0 | 1.55 min | MPLC |
| Example 288 | (1R*,2R*)-2-(1H-benzo[d]imidazol-2-yl)-N-((R)-1-(6-(2,2,2-trifluoroethoxy)pyridin-3-yl)ethyl)cyclopropanecarboxamide | 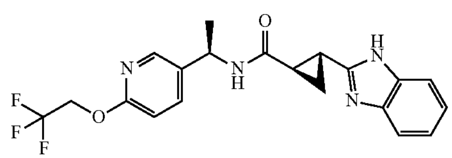 [SMILES: C[C@@H](NC(=O)[C@@H]1C[C@H]1c1nc2ccccc2[nH]1)c1ccc(OCC(F)(F)F)nc1] | | | 403.0 | 1.56 min | MPLC |

TABLE 3-continued

| Example | Name | STRUCTURE | Structure of amine part | Structure of caboxylic acid part | Observed MS | Retention Time | Purification Method |
|---|---|---|---|---|---|---|---|
| Example 289 | (1R*,2R*)-2-(5-fluoro-1H-benzo[d]imidazol-2-yl)-N-((R)-1-(6-(2,2,2-trifluoroethoxy)pyridin-3-yl)ethyl)cyclopropanecarboxamide | | | 421.0 | 1.69 min | MPLC |
| Example 290 | (1S*,2S*)-2-(5-fluoro-1H-benzo[d]imidazol-2-yl)-N-((R)-1-(6-(2,2,2-trifluoroethoxy)pyridin-3-yl)ethyl)cyclopropanecarboxamide | | | 421.0 | 1.59 min | MPLC |
| Example 291 | (1R*,2R*)-2-(5-cyano-1H-benzo[d]imidazol-2-yl)-N-((R)-1-(5-(2,2,2-trifluoroethoxy)pyridin-2-yl)ethyl)cyclopropanecarboxamide | | | 428.0 | 1.44 min | MPLC |
| Example 292 | (R)-4-tert-butyl-N-(1-(5-hydroxypyridin-2-yl)ethyl)benzamide | 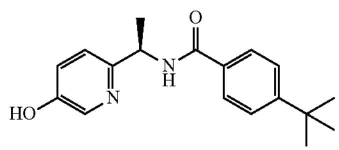 [SMILES: C[C@@H](NC(=O)c1ccc(C(C)(C)C)cc1)c1ccc(O)cn1] | Alternative route | Alternative route | Confirmed by NMR(see Table 2) | | HPLC |
| Example 293 | (1S*,2S*)-2-(phenoxymethyl)-N-((R)-1-(5-(2,2,2-trifluoroethoxy)pyridin-2-yl)ethyl)cyclopropanecarboxamide | 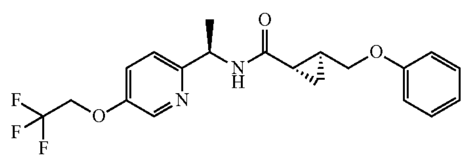 [SMILES: C[C@@H](NC(=O)[C@H]1C[C@@H]1COc1ccccc1)c1ccc(OCC(F)(F)F)cn1] | Alternative route | Alternative route | 393.0 | 1.72 min | HPLC |

TABLE 3-continued

| Example | Name | STRUCTURE | Structure of amine part | Structure of caboxylic acid part | Observed MS | Retention Time | Purification Method |
|---|---|---|---|---|---|---|---|
| Example 294 | (1S*,2S*)-2-((3-fluorophenoxy)methyl)-N-((R)-1-(5-(2,2,2-trifluoroethoxy)pyridin-2-yl)ethyl)cyclopropanecarboxamide | 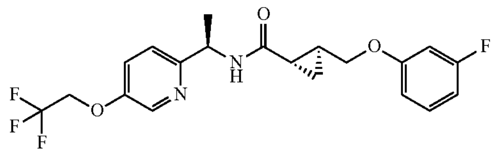 [SMILES: C[C@@H](NC(=O)[C@H]1C[C@@H]1COc1cccc(F)c1)c1ccc(OCC(F)(F)F)cn1] | | Alternative route | 411.0 | 1.75 min | HPLC |
| Example 295 | (1S*,2S*)-2-((3-cyanophenoxy)methyl)-N-((R)-1-(5-(2,2,2-trifluoroethoxy)pyridin-2-yl)ethyl)cyclopropanecarboxamide | 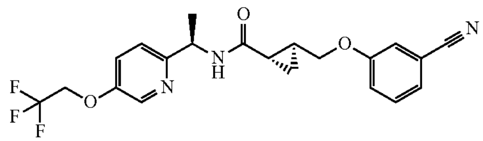 [SMILES: C[C@@H](NC(=O)[C@H]1C[C@@H]1COc1cccc(C#N)c1)c1ccc(OCC(F)(F)F)cn1] | | Alternative route | 418.0 | 1.66 min | HPLC |
| Example 296 | (1S*,2S*)-2-((4-fluorophenoxy)methyl)-N-((R)-1-(5-(2,2,2-trifluoroethoxy)pyridin-2-yl)ethyl)cyclopropanecarboxamide | 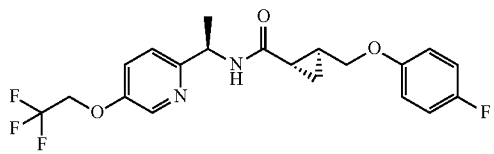 [SMILES: C[C@@H](NC(=O)[C@H]1C[C@@H]1COc1ccc(F)cc1)c1ccc(OCC(F)(F)F)cn1] | | Alternative route | 411.0 | 1.73 min | HPLC |
| Example 297 | (1S*,2S*)-2-((4-cyanophenoxy)methyl)-N-((R)-1-(5-(2,2,2-trifluoroethoxy)pyridin-2-yl)ethyl)cyclopropanecarboxamide | 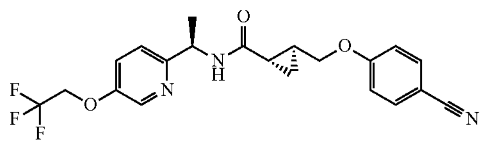 [SMILES: C[C@@H](NC(=O)[C@H]1C[C@@H]1COc1ccc(C#N)cc1)c1ccc(OCC(F)(F)F)cn1] | | Alternative route | 418.0 | 1.63 min | HPLC |
| Example 298 | (1R*,2R*)-2-(phenoxymethyl)-N-((R)-1-(5-(2,2,2-trifluoroethoxy)pyridin-2-yl)ethyl)cyclopropanecarboxamide | 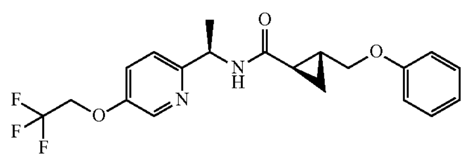 [SMILES: C[C@@H](NC(=O)[C@@H]1C[C@H]1COc1ccccc1)c1ccc(OCC(F)(F)F)cn1] | | Alternative route | 393.0 | 1.72 min | HPLC |

TABLE 3-continued

| Example | Name | STRUCTURE | Structure of amine part | Structure of caboxylic acid part | Observed MS | Retention Time | Purification Method |
|---|---|---|---|---|---|---|---|
| Example 299 | (1R*,2R*)-2-((3-fluorophenoxy)methyl)-N-((R)-1-(5-(2,2,2-trifluoroethoxy)pyridin-2-yl)ethyl)cyclopropanecarboxamide | 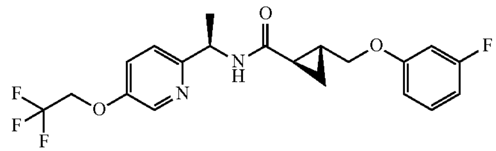 [SMILES: C[C@@H](NC(=O)[C@@H]1C[C@H]1COc1cccc(F)c1)c1ccc(OCC(F)(F)F)cn1] | | Alternative route | 411.0 | 1.75 min | HPLC |
| Example 300 | (1R*,2R*)-3-(3-cyanophenoxy)methyl)-N-((R)-1-(5-(2,2,2-trifluoroethoxy)pyridin-3-yl)ethyl)cyclopropanecarboxamide | 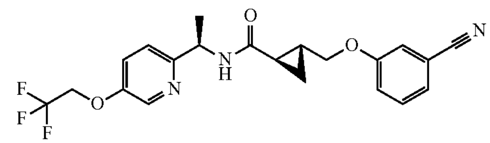 [SMILES: C[C@@H](NC(=O)[C@@H]1C[C@H]1COc1cccc(C#N)c1)c1ccc(OCC(F)(F)F)cn1] | | Alternative route | 418.0 | 1.66 min | HPLC |
| Example 301 | (1R*,2R*)-2-((4-fluorophenoxy)methyl)-N-((R)-1-(5-(2,2,2-trifluoroethoxy)pyridin-2-yl)ethyl)cyclopropanecarboxamide | 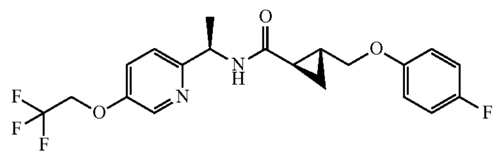 [SMILES: C[C@@H](NC(=O)[C@@H]1C[C@H]1COc1ccc(F)cc1)c1ccc(OCC(F)(F)F)cn1] | | Alternative route | 411.0 | 1.72 min | HPLC |
| Example 302 | (1R*,2R*)-2-((4-cyanophenoxy)methyl)-N-((R)-1-(5-(2,2,2-trifluoroethoxy)pyridin-2-yl)ethyl)cyclopropanecarboxamide | 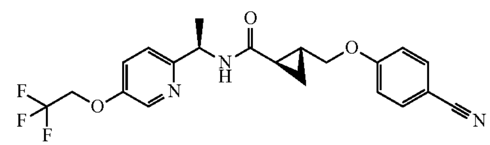 [SMILES: C[C@@H](NC(=O)[C@@H]1C[C@H]1COc1ccc(C#N)cc1)c1ccc(OCC(F)(F)F)cn1] | | Alternative route | 418.0 | 1.63 min | HPLC |
| Example 303 | (1S*,2S*)-2-(3-((3-methyloxetan-3-yl)methoxy)phenyl)-N-((R)-1-(5-(2,2,2-trifluoroethoxy)pyridin-2-yl)ethyl)cyclopropanecarboxamide | 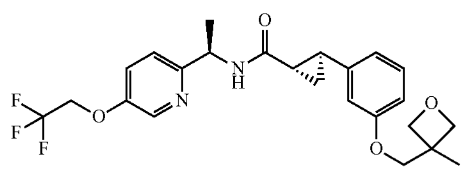 [SMILES: C[C@@H](NC(=O)[C@H]1C[C@@H]1c1cccc(OCC2(C)COC2)c1)c1ccc(OCC(F)(F)F)cn1] | | Alternative route | 463.0 | 1.72 min | HPLC |

TABLE 3-continued

| Example | Name | STRUCTURE | Structure of amine part | Structure of caboxylic acid part | Observed MS | Retention Time | Purification Method |
|---|---|---|---|---|---|---|---|
| Example 304 | (1S*,2S*)-2-(4-((3-methyloxetan-3-yl)methoxy)phenyl)-N-((R)-1-(5-(2,2,2-trifluoroethoxy)pyridin-2-yl)ethyl)cyclopropanecarboxamide | 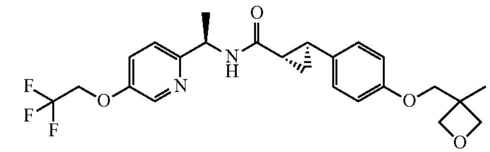 [SMILES: C[C@@H](NC(=O)[C@H]1C[C@@H]1c1ccc(OCC2(C)COC2)cc1)c1ccc(OCC(F)(F)F)cn1] | Alternative route | | 463.0 | 1.70 min | HPLC |
| Example 305 | (1S*,2S*)-2-(4-(pyridin-2-ylmethoxy)phenyl)-N-((R)-1-(5-(2,2,2-trifluoroethoxy)pyridin-2-yl)ethyl)cyclopropanecarboxamide | 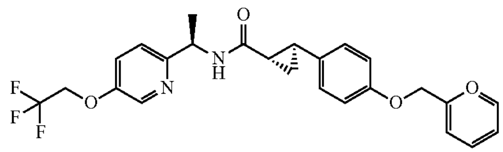 | Alternative route | | 470.0 | 1.68 min | HPLC |
| Example 306 | (1S*,2S*)-2-(3-(pyridin-2-ylmethoxy)phenyl)-N-((R)-1-(5-(2,2,2-trifluoroethoxy)pyridin-2-yl)ethyl)cyclopropanecarboxamide | 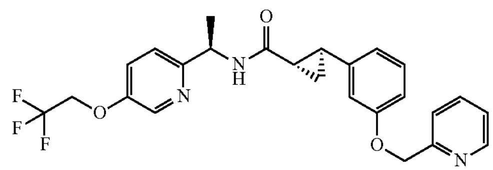 [SMILES: C[C@@H](NC(=O)[C@H]1C[C@@H]1c1cccc(OCc2ccccn2)c1)c1ccc(OCC(F)(F)F)cn1] | Alternative route | | 470.0 | 1.70 min | HPLC |
| Example 307 | (1S*,2S*)-N-((R)-1-(5-(cyclopropylmethoxy)pyridin-2-yl)ethyl)-2-(4-methoxy-3-methylphenyl)cyclopropanecarboxamide | 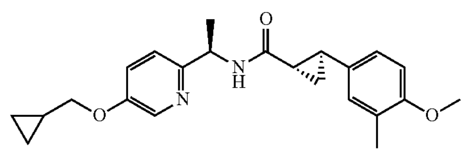 [SMILES: COc1ccc([C@H]2C[C@@H]2C(=O)N[C@H](C)c2ccc(OCC3CC3)cn2)cc1C] | | | 379.1 | 1.83 min | MPLC |
| Example 308 | (1R*,2R*)-N-((R)-1-(5-(cyclopropylmethoxy)pyridin-2-yl)ethyl)-2-(4-methoxy-3-methylphenyl)cyclopropanecarboxamide | 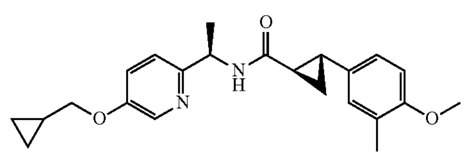 [SMILES: COc1ccc([C@@H]2C[C@H]2C(=O)N[C@H](C)c2ccc(OCC3CC3)cn2)cc1C] | | | 379.2 | 1.83 min | MPLC |

TABLE 3-continued

| Example | Name | STRUCTURE | Structure of amine part | Structure of caboxylic acid part | Observed MS | Retention Time | Purification Method |
|---|---|---|---|---|---|---|---|
| Example 309 | (1S*,2S*)-2-(4-methoxy-3-methylphenyl)-N-((R)-1-(5-(2,2,2-trifluoroethoxy)pyrazin-2-yl)ethyl)cyclopropanecarboxamide | 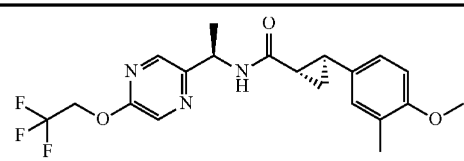 | | | 408.1 | 1.87 min | MPLC |
| Example 310 | (1R*,2R*)-2-(4-methoxy-3-methylphenyl)-N-((R)-1-(5-(2,2,2-trifluoroethoxy)pyrazin-2-yl)ethyl)cyclopropanecarboxamide | 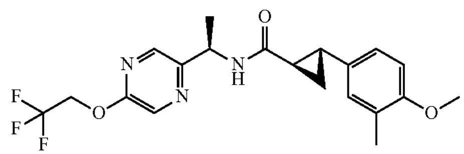 [SMILES: COc1ccc([C@@H]2C[C@H]2C(=O)N[C@H](C)c2cnc(OCC(F)(F)F)cn2)cc1C] | | | 408.0 | 1.86 min | MPLC |
| Example 311 | tert-butyl (R)-1-oxo-3-phenyl-1-((R)-1-(5-(2,2,2-trifluoroethoxy)pyridin-2-yl)ethyl)amino)propan-2-ylcarboxamide | 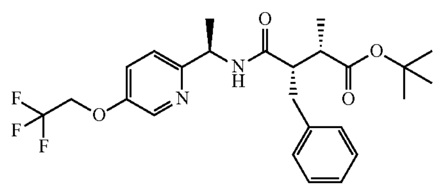 [SMILES: C[C@H](C(=O)OC(C)(C)C)[C@H](Cc1ccccc1)C(=O)N[C@H](C)c1ccc(OCC(F)(F)F)cn1] | | | 467.8 | 1.81 min | HPLC |
| Example 312 | tert-butyl (S)-1-oxo-2-phenyl-1-((R)-1-(5-(2,2,2-trifluoroethoxy)pyridin-2-yl)ethyl)amino)propan-2-ylcarboxamide | 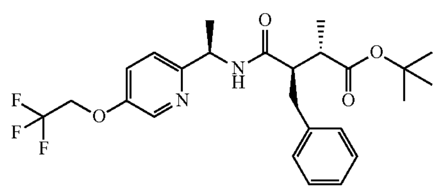 [SMILES: C[C@H](C(=O)OC(C)(C)C)[C@@H](Cc1ccccc1)C(=O)N[C@H](C)c1ccc(OCC(F)(F)F)cn1] | | | 467.5 | 1.82 min | HPLC |
| Example 313 | (R)-N-(1-(5-(benzyloxy)pyridin-2-yl)ethyl)-4-tert-butylbenzamide | 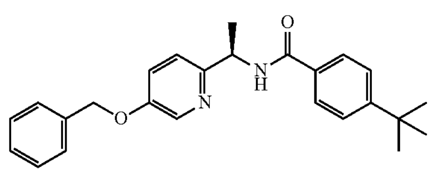 [SMILES: C[C@@H](NC(=O)c1ccc(C(C)(C)C)cc1)c1ccc(OCc2ccccc2)cn1] | | | 387.1 | 2.04 min | HPLC |

TABLE 3-continued

| Example | Name | STRUCTURE | Structure of amine part | Structure of caboxylic acid part | Observed MS | Retention Time | Purification Method |
|---|---|---|---|---|---|---|---|
| | | | | Alternative route | | | |
| Example 314 | (R)-4-tert-butyl-N-(1-(5-(pyridin-2-ylmethoxy)pyridin-2-yl)ethyl)benzamide | 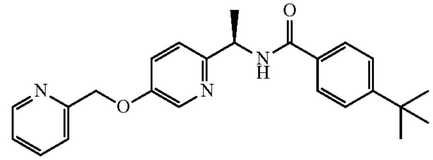 [SMILES: C[C@@H](NC(=O)c1ccc(C(C)(C)C)cc1)c1ccc(OCc2ccccn2)cn1] | | | 388.1 | 1.77 min | HPLC |
| Example 315 | (R)-4-tert-butyl-N-(1-(5-(methoxypyridin-2-yl)ethyl)benzamide | 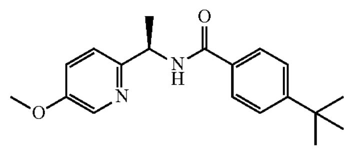 [SMILES: COc1ccc([C@@H](C)NC(=O)c2ccc(C(C)(C)C)cc2)nc1] | | | 311.2 | 1.78 min | HPLC |
| Example 316 | (1S*,2S*)-N-((R)-1-(5-cyclopropylmethoxy)pyridin-2-yl)ethyl)-2-(1H-indol-7-yl)cyclopropanecarboxamide | 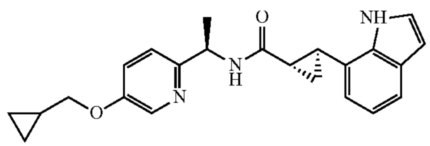 [SMILES: C[C@@H](NC(=O)[C@H]1C[C@@H]1c1cccc2cc[nH]c12)c1ccc(OCC2CC2)cn1] | | | 374.1 | 1.78 min | Chiral-HPLC |
| Example 317 | (1R*,2R*)-N-((R)-1-(5-cyclopropylmethoxy)pyridin-2-yl)ethyl)-2-(1H-indol-7-yl)cyclopropanecarboxamide | 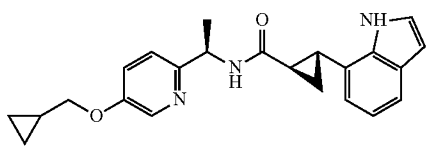 [SMILES: C[C@@H](NC(=O)[C@@H]1C[C@H]1c1cccc2cc[nH]c12)c1ccc(OCC2CC2)cn1] | | | 374.1 | 1.78 min | Chiral-HPLC |
| Example 318 | (1S*,2S*)-2-(phenoxymethyl)-N-((R)-1-(5-(2,2,2-trifluoroethoxy)pyrazin-2-yl)ethyl)cyclopropanecarboxamide | 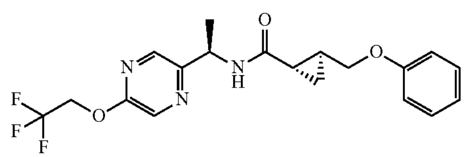 | | | 394.0 | 1.79 min | Chiral-HPLC |
| Example 319 | (1R*,2R*)-2-(phenoxymethyl)-N-((R)-1-(5-(2,2,2-trifluoroethoxy)pyrazin-2-yl)ethyl)cyclopropanecarboxamide | 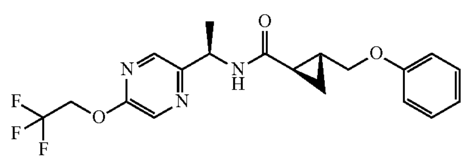 [SMILES: C[C@@H](NC(=O)[C@@H]1C[C@H]1COc1ccccc1)c1cnc(OCC(F)(F)F)cn1] | | | 394.0 | 1.78 min | Chiral-HPLC |

TABLE 3-continued

| Example | Name | STRUCTURE | Structure of amine part | Structure of caboxylic acid part | Observed MS | Retention Time | Purification Method |
|---|---|---|---|---|---|---|---|
| Example 320 | (1S*,2S*)-2-(phenoxymethyl)-N-((R)-1-(6-(2,2,2-trifluoroethoxy)pyridin-3-yl)ethyl)cyclopropanecarboxamide | 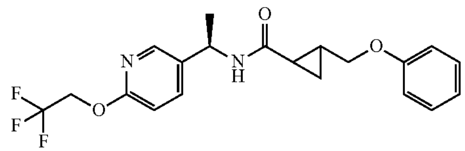 [SMILES: C[C@@H](NC(=O)C1CC1COc1ccccc1)c1ccc(OCC(F)(F)F)nc1] | | | 393.0 | 1.83 min | Chiral-HPLC |
| Example 321 | (1R*,2R*)-2-(phenoxymethyl)-N-((R)-1-(6-(2,2,2-trifluoroethoxy)pyridin-3-yl)ethyl)cyclopropanecarboxamide | 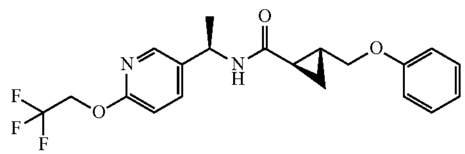 [SMILES: C[C@@H](NC(=O)[C@@H]1C[C@H]1COc1ccccc1)c1ccc(OCC(F)(F)F)nc1] | | | 393.0 | 1.83 min | Chiral-HPLC |
| Example 322 | (1S*,2S*)-3-(1H-indol-7-yl)-N-((R)-1-(5-(2,2,2-trifluoroethoxy)pyrazin-2-yl)ethyl)cyclopropanecarboxamide | 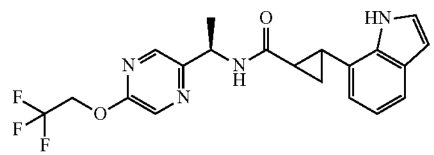 [SMILES: C[C@@H](NC(=O)C1CC1c1cccc2cc[nH]c12)c1cnc(OCC(F)(F)F)cn1] | | | 403.0 | 1.80 min | Chiral-HPLC |
| Example 323 | (1R*,2R*)-2-(1H-indol-7-yl)-N-((R)-1-(5-(2,2,2-trifluoroethoxy)pyrazin-2-yl)ethyl)cyclopropanecarboxamide | 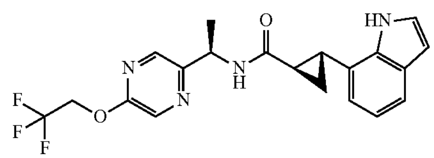 [SMILES: C[C@@H](NC(=O)[C@@H]1C[C@H]1c1cccc2cc[nH]c12)c1cnc(OCC(F)(F)F)cn1] | | | 403.0 | 1.80 min | Chiral-HPLC |
| Example 324 | (1S*,2S*)-2-(quinolin-2-yl)-N-((R)-1-(5-(2,2,2-trifluoroethoxy)pyridin-3-yl)ethyl)cyclopropanecarboxamide | 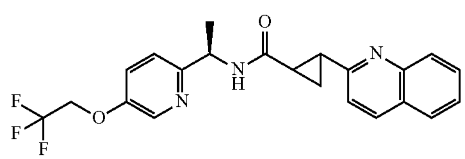 [SMILES: C[C@@H](NC(=O)C1CC1c1ccc2ccccc2n1)c1ccc(OCC(F)(F)F)cn1] | | | 414.0 | 1.70 min | Chiral-HPLC |
| Example 325 | (1R*,2R*)-2-(quinolin-2-yl)-N-((R)-1-(5-(2,2,2-trifluoroethoxy)pyridin-3-yl)ethyl)cyclopropanecarboxamide | 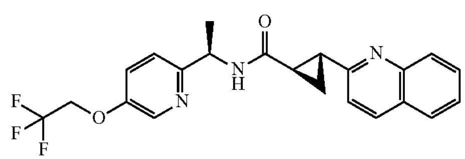 [SMILES: C[C@@H](NC(=O)[C@@H]1C[C@H]1c1ccc2ccccc2n1)c1ccc(OCC(F)(F)F)cn1] | | | 414.0 | 1.70 min | Chiral-HPLC |

TABLE 3-continued

| Example | Name | STRUCTURE | Structure of amine part | Structure of caboxylic acid part | Observed MS | Retention Time | Purification Method |
|---|---|---|---|---|---|---|---|
| Example 326 | (1R*,2R*)-N-((R)-1-(5-(cyclopropylmethoxy)pyridin-2-yl)ethyl)-2-m-tolylcyclopropanecarboxamide | 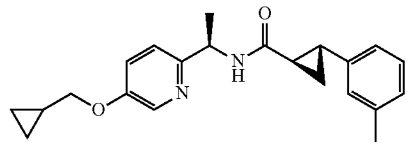 [SMILES: Cc1cccc([C@@H]2C[C@H]2C(=O)N[C@H](C)c2ccc(OCC3CC3)cn2)c1] | | | 349.3 | 1.83 min | MPLC |
| Example 327 | (1S*,2S*)-2-(2,5-difluorophenyl)-N-((R)-1-(5-(2,2,2-trifluoroethoxy)pyridin-2-yl)ethyl)cyclopropanecarboxamide | 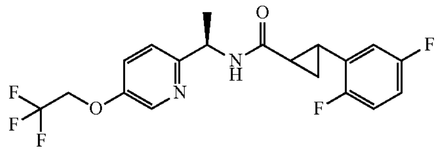 [SMILES: C[C@@H](NC(=O)C1CC1c1cc(F)ccc1F)c1ccc(OCC(F)(F)F)cn1] | | | 399.0 | 1.75 min | MPLC |
| Example 328 | (1R*,2R*)-2-(2,5-difluorophenyl)-N-((R)-1-(5-(2,2,2-trifluoroethoxy)pyridin-2-yl)ethyl)cyclopropanecarboxamide | 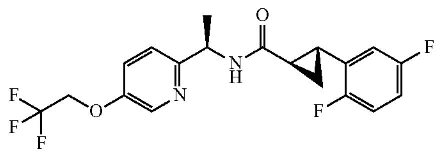 [SMILES: C[C@@H](NC(=O)[C@@H]1C[C@H]1c1cc(F)ccc1F)c1ccc(OCC(F)(F)F)cn1] | | | 399.0 | 1.74 min | MPLC |
| Example 329 | 4-(benzyloxy)-2-methoxy-N-((6-(trifluoromethyl)pyridin-3-yl)methyl)benzamide | 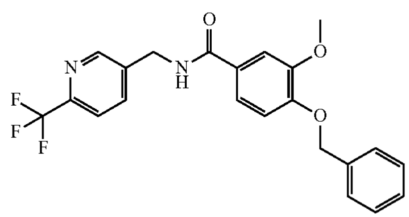 [SMILES: COc1cc(C(=O)NCc2ccc(C(F)(F)F)nc2)ccc1OCc1ccccc1] | | | 417.1 | 3.00 min | HPLC |
| Example 330 | 2-(4-(trifluoromethyl)phenoxy)-N-((6-(trifluoromethyl)pyridin-3-yl)methyl)acetamide | 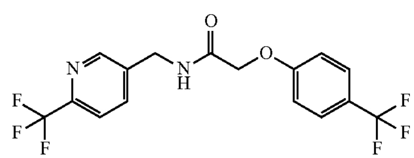 [SMILES: O=C(COc1ccc(C(F)(F)F)cc1)NCc1ccc(C(F)(F)F)nc1] | | | 379 | 2.95 min | HPLC |

TABLE 3-continued

| Example | Name | STRUCTURE | Structure of amine part | Structure of caboxylic acid part | Observed MS | Retention Time | Purification Method |
|---|---|---|---|---|---|---|---|
| Example 331 | N-(5,6,7,8-tetrahydroquinolin-8-yl)-2-(4-(trifluoromethyl)phenoxy)acetamide | 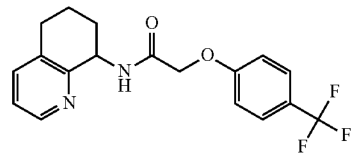 [SMILES: O=C(COc1ccc(C(F)(F)F)cc1)NC1CCCc2cccnc21] | | | 351.1 | 2.27 min | HPLC |
| Example 332 | 2-(4-(tert-butyl)phenyl)-N-(5,6,7,8-tetrahydroquinolin-8-yl)cyclopropanecarboxamide | 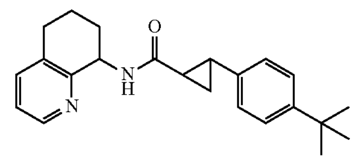 [SMILES: CC(C)(C)c1ccc(C2CC2C(=O)NC2CCCc3cccnc32)cc1] | | | 349.2 | 2.45 min | HPLC |
| Example 333 | (R)-N-(1-(6-methyl-3-(2,2,2-trifluoroethoxy)pyridin-2-yl)ethyl)-2-(4-(trifluoromethyl)phenoxy)acetamide | 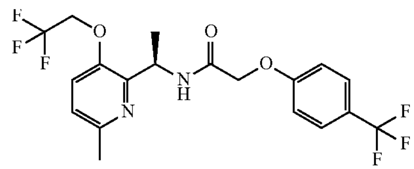 [SMILES: Cc1ccc(OCC(F)(F)F)c([C@@H](C)NC(=O)COc2ccc(C(F)(F)F)cc2)n1] | | | 436.8 | 1.95 min | HPLC |
| Example 334 | (R)-5-fluoro-N-(1-(6-methyl-5-(2,2,2-trifluoroethoxy)pyridin-2-yl)ethyl)-1H-indole-2-carboxamide | 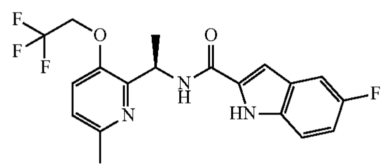 [SMILES: Cc1ccc(OCC(F)(F)F)c([C@@H](C)NC(=O)c2cc3cc(F)ccc3[nH]2)n1] | | | 395.8 | 1.84 min | HPLC |
| Example 335 | (R)-1-benzyl-2-oxo-N-(1-(5-(2,2,2-trifluoroethoxy)pyridin-2-yl)ethyl)-1,2-dihydropyridine-3-carboxamide | 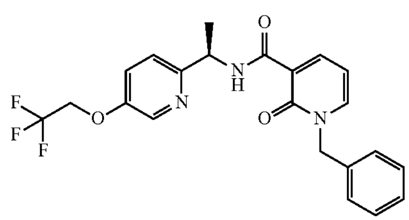 [SMILES: C[C@@H](NC(=O)c1cccn(Cc2ccccc2)c1=O)c1ccc(OCC(F)(F)F)cn1] | | | 430 | 1.72 min | HPLC |

TABLE 3-continued

| Example | Name | STRUCTURE | Structure of amine part | Structure of caboxylic acid part | Observed MS | Retention Time | Purification Method |
|---|---|---|---|---|---|---|---|
| Example 336 | (R)-1-benzyl-N-(1-(5-(2,2,2-trifluoroethoxy)pyridin-2-yl)ethyl)piperidine-4-carboxamide | 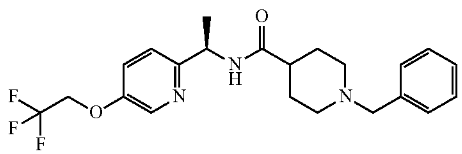 [SMILES: C[C@@H](NC(=O)C1CCN(Cc2ccccc2)CC1)c1ccc(OCC(F)(F)F)cn1] | | | 420.1 | 1.52 min | HPLC |
| Example 337 | (S)-3-phenoxy-N-(1-(5-(2,2,2-trifluoroethoxy)pyridin-2-yl)ethyl)benzamide | 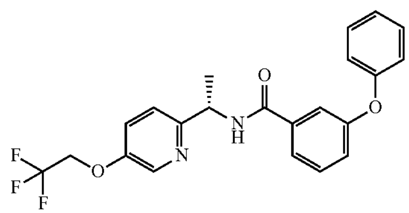 [SMILES: C[C@H](NC(=O)c1cccc(Oc2ccccc2)c1)c1ccc(OCC(F)(F)F)cn1] | | | 415 | 1.88 min | HPLC |
| Example 338 | (S)-4-isopropyl-N-(1-(5-(2,2,2-trifluoroethoxy)pyridin-2-yl)ethyl)benzamide | 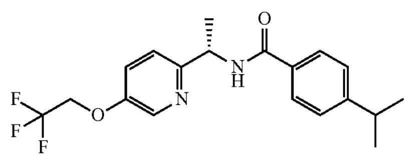 [SMILES: CC(C)c1ccc(C(=O)N[C@@H](C)c2ccc(OCC(F)(F)F)cn2)cc1] | | | 365.1 | 1.85 min | HPLC |
| Example 339 | (S)-N-(1-(5-(2,2,2-trifluoroethoxy)pyridin-2-yl)ethyl)-2-(2-(trifluoromethyl)phenoxy)acetamide | 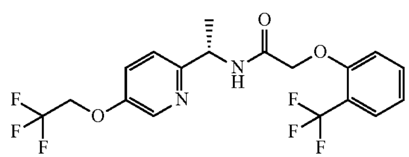 [SMILES: C[C@H](NC(=O)COc1ccccc1C(F)(F)F)c1ccc(OCC(F)(F)F)cn1] | | | 421 | 1.87 min | HPLC |
| Example 340 | (S)-2-(4-chlorophenoxy)-N-(1-(5-(2,2,2-trifluoroethoxy)pyridin-2-yl)ethyl)acetamide | 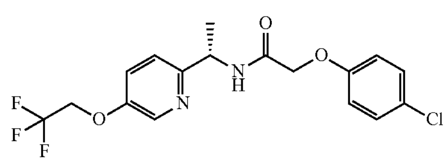 [SMILES: C[C@H](NC(=O)COc1ccc(Cl)cc1)c1ccc(OCC(F)(F)F)cn1] | | | 387 | 1.79 min | HPLC |

TABLE 3-continued

| Example | Name | STRUCTURE | Structure of amine part | Structure of caboxylic acid part | Observed MS | Retention Time | Purification Method |
|---|---|---|---|---|---|---|---|
| Example 341 | (S)-2-(4-chloro-3-trifluoromethyl)phenoxy)-N-(1-(5-(2,2,2-trifluoroethoxy)pyridin-2-yl)ethyl) acetamide | 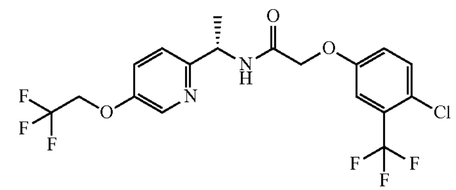 [SMILES: C[C@H](NC(=O)COc1ccc(Cl)c(C(F)(F)F)c1)c1ccc(OCC(F)(F)F)cn1] | | | 454.9 | 1.90 min | HPLC |
| Example 342 | (S)-8-methoxy-N-(1-(5-(2,2,2-trifluoroethoxy)pyridin-2-yl)ethyl) quinolin-2-carboxamide | 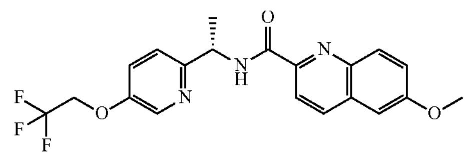 [SMILES: COc1ccc2nc(C(=O)N[C@@H](C)c3ccc(OCC(F)(F)F)cn3)ccc2c1] | | | 405.8 | 1.84 min | HPLC |
| Example 343 | (S)-4-(2,2,2-trifluoroethoxy)-N-(1-(5-(2,2,2-trifluoroethoxy)pyridin-2-yl)ethyl)benzamide | 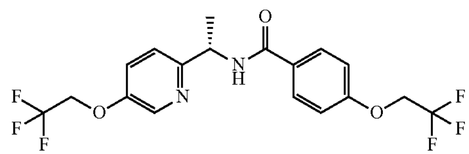 [SMILES: C[C@H](NC(=O)c1ccc(OCC(F)(F)F)cc1)c1ccc(OCC(F)(F)F)cn1] | | | 421 | 1.74 min | HPLC |
| Example 344 | (S)-5-(2,2,2-trifluoroethoxy)-N-(1-(5-(2,2,2-trifluoroethoxy)pyridin-2-yl)ethyl)picolinamide | 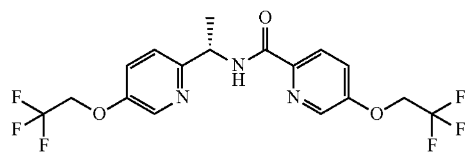 [SMILES: C[C@H](NC(=O)c1ccc(OCC(F)(F)F)cn1)c1ccc(OCC(F)(F)F)cn1] | | | 422 | 1.79 min | HPLC |
| Example 345 | (1S*,2S*)-2-(5-(benzyloxy)phenyl)-N-((S)-1-(5-(2,2,2-trifluoroethoxy)pyridin-2-yl)ethyl) cyclopropanecarboxamide | 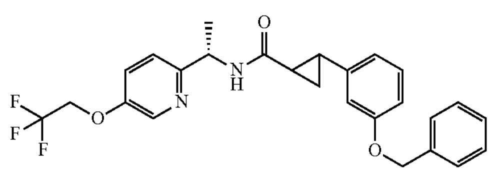 [SMILES: C[C@H](NC(=O)C1CC1c1cccc(OCc2ccccc2)c1)c1ccc(OCC(F)(F)F)cn1] | | | 469.1 | 1.94 min | MPLC |

TABLE 3-continued

| Example | Name | STRUCTURE | Structure of amine part | Structure of caboxylic acid part | Observed MS | Retention Time | Purification Method |
|---|---|---|---|---|---|---|---|
| Example 346 | (1R*,2R*)-2-(3-(benzyloxy)phenyl)-N-((S)-1-(5-(2,2,2-trifluoroethoxy)pyridin-2-yl)ethyl)cyclopropanecarboxamide | 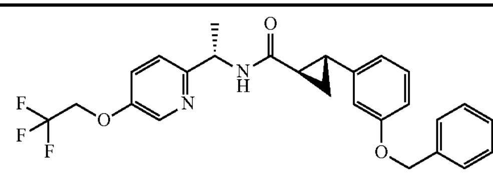 | | | 469.1 | 1.94 min | MPLC |
| Example 347 | (1S*,2S*)-2-(4-(benzyloxy)phenyl)-N-((S)-1-(5-(2,2,2-trifluoroethoxy)pyridin-2-yl)ethyl)cyclopropanecarboxamide | 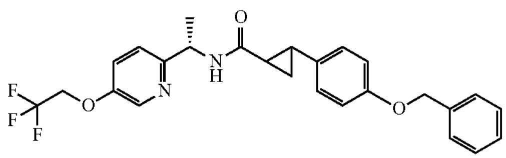 [SMILES: C[C@H](NC(=O)C1CC1c1ccc(OCc2ccccc2)cc1)c1ccc(OCC(F)(F)F)cn1] | | | 469.1 | 1.93 min | MPLC |
| Example 348 | (1R*,2R*)-2-(4-(benzyloxy)phenyl)-N-((S)-1-(5-(2,2,2-trifluoroethoxy)pyridin-2-yl)ethyl)cyclopropanecarboxamide | 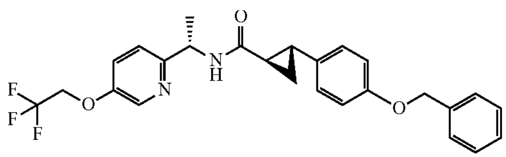 [SMILES: C[C@H](NC(=O)[C@@H]1C[C@H]1c1ccc(OCc2ccccc2)cc1)c1ccc(OCC(F)(F)F)cn1] | | | 469.1 | 1.93 min | MPLC |
| Example 349 | (1S*,2S*)-2-(2-fluoro-4-methoxyphenyl)-N-((S)-1-(6-(2,2,2-trifluoroethoxy)pyridin-2-yl)ethyl)cyclopropanecarboxamide | 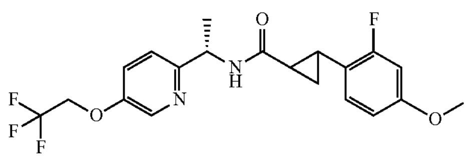 [SMILES: COc1ccc(C2CC2C(=O)N[C@@H](C)c2ccc(OCC(F)(F)F)cn2)c(F)c1] | | | 411.1 | 1.73 min | MPLC |
| Example 350 | (1R*,2R*)-2-(2-fluoro-4-methoxyphenyl)-N-((R)-1-(5-(2,2,2-trifluoroethoxy)pyridin-2-yl)ethyl)cyclopropanecarboxamide | 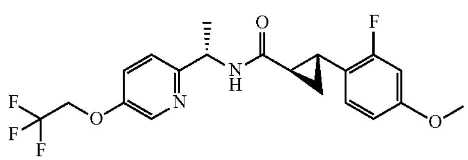 [SMILES: COc1ccc([C@@H]2C[C@H]2C(=O)N[C@@H](C)c2ccc(OCC(F)(F)F)cn2)c(F)c1] | | | 411.1 | 1.72 min | MPLC |

TABLE 3-continued

| Example | STRUCTURE | Name | Structure of amine part | Structure of caboxylic acid part | Observed MS | Retention Time | Purification Method |
|---|---|---|---|---|---|---|---|
| Example 351 | 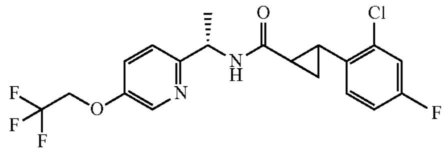 [SMILES: C[C@H](NC(=O)C1CC1c1ccc(F)cc1Cl)c1ccc(OCC(F)(F)F)cn1] | (1S*,2S*)-2-(2-chloro-4-fluorophenyl)-N-((S)-1-(5-(2,2,2-trifluoroethoxy)pyridin-2-yl)ethyl)cyclopropanecarboxamide | | | 415 | 1.81 min | MPLC |
| Example 352 | 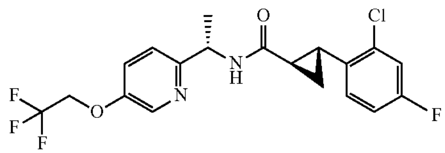 [SMILES: C[C@H](NC(=O)[C@@H]1C[C@H]1c1ccc(F)cc1Cl)c1ccc(OCC(F)(F)F)cn1] | (1R*,2R*)-3-(2-chloro-4-fluorophenyl)-N-((S)-1-(5-(2,2,2-trifluoroethoxy)pyridin-2-yl)ethyl)cyclopropanecarboxamide | | | 415 | 1.79 min | MPLC |
| Example 353 | 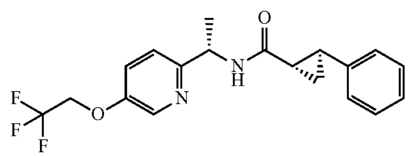 [SMILES: C[C@H](NC(=O)[C@H]1C[C@@H]1c1ccccc1)c1ccc(OCC(F)(F)F)cn1] | (1S*,2S*)-2-phenyl-N-((S)-1-(5-(2,2,2-trifluoroethoxy)pyridin-2-yl)ethyl)cyclopropanecarboxamide | | | 363.1 | 1.71 min | MPLC |
| Example 354 | 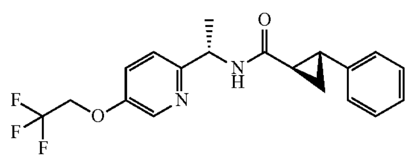 [SMILES: C[C@H](NC(=O)[C@@H]1C[C@H]1c1ccccc1)c1ccc(OCC(F)(F)F)cn1] | (1R*,2R*)-2-phenyl-N-((S)-1-(5-(2,2,2-trifluoroethoxy)pyridin-2-yl)ethyl)cyclopropanecarboxamide | | | 385.1 | 1.71 min | MPLC |
| Example 355 | 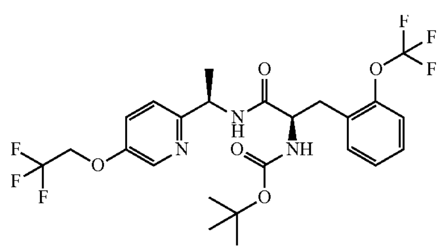 [SMILES: C[C@@H](NC(=O)[C@@H](Cc1ccccc1OC(F)(F)F)NC(=O)OC(C)(C)C)c1ccc(OCC(F)(F)F)cn1] | tert-butyl ((R)-1-oxo-1-(((R)-1-(5-(2,2,2-trifluoroethoxy)pyridin-2-yl)ethyl)amino)-3-(2-(trifluoromethoxy)phenyl)propan-2-yl)carbamate | | | 552.1 | 3.42 min | HPLC |

TABLE 3-continued

| Example | Name | STRUCTURE | Structure of amine part | Structure of caboxylic acid part | Observed MS | Retention Time | Purification Method |
|---|---|---|---|---|---|---|---|
| Example 356 | tert-butyl ((R)-1-oxo-1-(((R)-1-(5-(2,2,2-trifluoroethoxy)pyridin-2-yl)ethyl)amino)-3-(2-(trifluoromethyl)phenyl)propan-2-yl)carbamate | 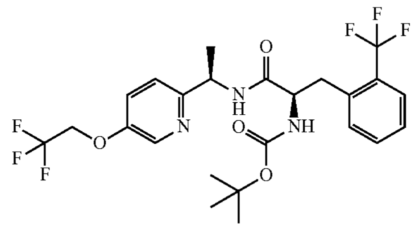 [SMILES: C[C@@H](NC(=O)[C@@H](Cc1ccccc1C(F)(F)F)NC(=O)OC(C)(C)C)c1ccc(OCC(F)(F)F)cn1] | | | 536.1 | 3.37 min | HPLC |
| Example 357 | (1R*,2R*)-2-(3-methoxyphenyl)-N-((R)-1-(5-(2,2,2-trifluoroethoxy)pyridin-2-yl)ethyl)cyclopropanecarboxamide | 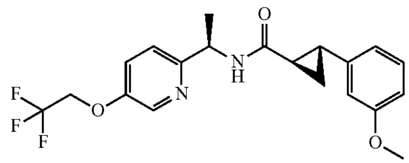 [SMILES: COc1cccc([C@@H]2C[C@H]2C(=O)N[C@H](C)c2ccc(OCC(F)(F)F)cn2)c1] | | | Confirmed by NMR(see Table 2) | | MPLC |
| Example 358 | (R)-2-amino-N-((R)-1-(5-(2,2,2-trifluoroethoxy)pyridin-2-yl)ethyl)-3-(2-(trifluoromethoxy)phenyl)propanamide | 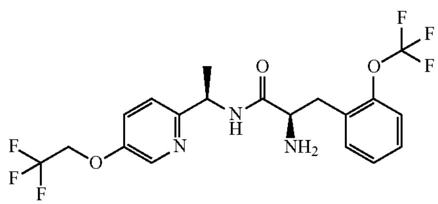 [SMILES: C[C@@H](NC(=O)[C@H](N)Cc1ccccc1OC(F)(F)F)c1ccc(OCC(F)(F)F)cn1] | | | 450 | 1.66 min | HPLC |
| Example 359 | (R)-N-(1-(5-(benzyloxy)pyridin-2-yl)ethyl)-3-phenoxybenzamide | 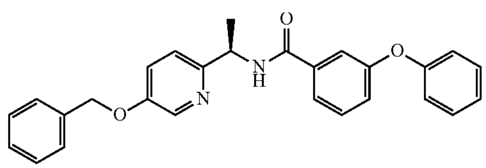 [SMILES: C[C@@H](NC(=O)c1cccc(Oc2ccccc2)c1)c1ccc(OCc2ccccc2)cn1] | | | 423.1 | 2.00 min | HPLC |
| Example 360 | (R)-N-(1-(5-methoxypyridin-2-yl)ethyl)-3-phenoxybenzamide | 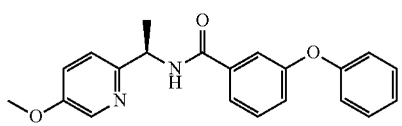 [SMILES: COc1ccc([C@@H](C)NC(=O)c2cccc(Oc3ccccc3)c2)nc1] | | | 347.1 | 1.76 min | HPLC |

TABLE 3-continued

| Example | Name | STRUCTURE | Structure of amine part | Structure of caboxylic acid part | Observed MS | Retention Time | Purification Method |
|---|---|---|---|---|---|---|---|
| Example 361 | (S)-2-(dimethylamino)-3-phenyl-N-((R)-1-(5-(2,2,2-trifluoroethoxy)pyridin-2-yl)ethyl)propanamide | 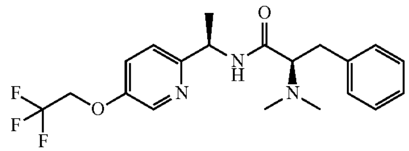 [SMILES: C[C@@H](NC(=O)[C@@H](Cc1ccccc1)N(C)C)c1ccc(OCC(F)(F)F)cn1] | | | 394.2 | 1.64 min | HPLC |
| Example 362 | (R)-2-hydroxy-4-phenyl-N-((R)-1-(5-(2,2,2-trifluoroethoxy)pyridin-2-yl)ethyl)butanamide | 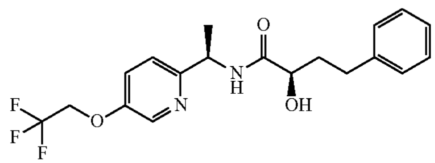 [SMILES: C[C@@H](NC(=O)[C@H](O)CCc1ccccc1)c1ccc(OCC(F)(F)F)cn1] | | | 381.1 | 1.64 min | HPLC |
| Example 363 | (S)-5-fluoro-1-methyl-N-(1-(5-(2,2,2-trifluoroethoxy)pyridin-2-yl)ethyl)-1H-indole-2-carboxamide | 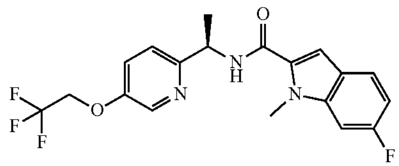 [SMILES: C[C@@H](NC(=O)c1cc2ccc(F)cc2n1C)c1ccc(OCC(F)(F)F)cn1] | | | 394.1 | 1.83 min | HPLC |
| Example 364 | (S)-4-(tert-butyl)-2-methoxy-N-(1-(5-(2,2,2-trifluoroethoxy)pyridin-2-yl)ethyl)benzamide | 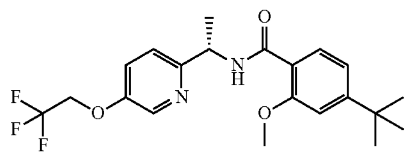 [SMILES: COc1cc(C(C)(C)C)ccc1C(=O)N[C@@H](C)c1ccc(OCC(F)(F)F)cn1] | | | 409.1 | 2.00 min | HPLC |
| Example 365 | tert-butyl ((S)-3-oxo-3-(((R)-1-(5-(2,2,2-trifluoroethoxy)pyridin-2-yl)ethyl)amino)-1-(4-(trifluoromethyl)phenyl)propyl)carbamate | 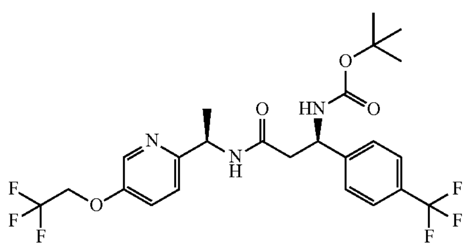 [SMILES: C[C@@H](NC(=O)C[C@@H](NC(=O)OC(C)(C)C)c1ccc(C(F)(F)F)cc1)c1ccc(OCC(F)(F)F)cn1] | | | 534 | 1.88 min | HPLC |

| Example | Name | STRUCTURE | Structure of amine part | Structure of caboxylic acid part | Observed MS | Retention Time | Purification Method |
|---|---|---|---|---|---|---|---|
| Example 366 | tert-butyl ((S)-1-(4-chlorophenyl)-3-oxo-3-(((R)-1-(5-(2,2,2-trifluoroethoxy)pyridin-2-yl)ethyl)amino)propyl)carbamate | 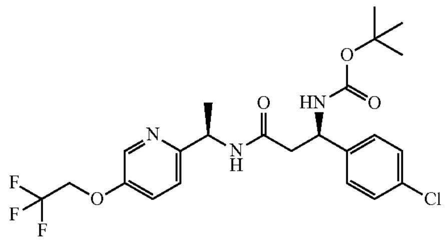 [SMILES: C[C@@H](NC(=O)C[C@@H](NC(=O)OC(C)(C)C)c1ccc(Cl)cc1)c1ccc(OCC(F)(F)F)cn1] | | | 500.1 | 1.84 min | HPLC |
| Example 367 | tert-butyl ((R)-1-(4-chlorophenyl)-3-oxo-3-(((R)-1-(5-(2,2,2-trifluoroethoxy)pyridin-2-yl)ethyl)amino)propyl)carbamate | 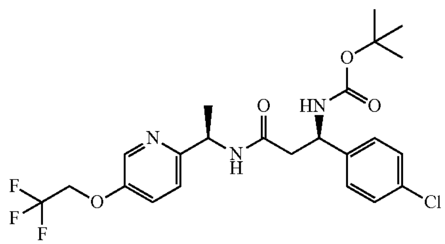 [SMILES: C[C@@H](NC(=O)C[C@@H](NC(=O)OC(C)(C)C)c1ccc(Cl)cc1)c1ccc(OCC(F)(F)F)cn1] | | | 500 | 1.82 min | HPLC |
| Example 368 | tert-butyl ((R)-3-oxo-3-((((R)-1-(5-(2,2,2-trifluoroethoxy)pyridin-2-yl)ethyl)amino)-1-(4-(trifluoromethyl)phenyl)propyl)carbamate | 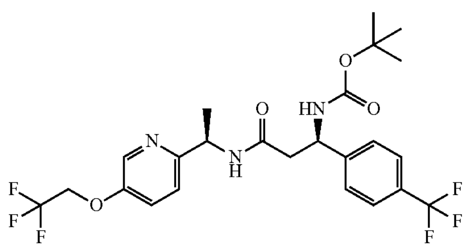 [SMILES: C[C@@H](NC(=O)C[C@@H](NC(=O)OC(C)(C)C)c1ccc(C(F)(F)F)cc1)c1ccc(OCC(F)(F)F)cn1] | | | 534.1 | 1.87 min | HPLC |
| Example 369 | tert-butyl ((S)-3-(4-fluorophenyl)-1-oxo-1-(((R)-1-(5-(2,2,2-trifluoroethoxy)pyridin-2-yl)ethyl)amino)propan-2-yl)carbamate | 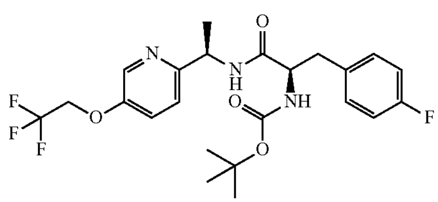 [SMILES: C[C@@H](NC(=O)[C@@H](Cc1ccc(F)cc1)NC(=O)OC(C)(C)C)c1ccc(OCC(F)(F)F)cn1] | | | 485.8 | 1.82 min | HPLC |

TABLE 3-continued

| Example | Name | STRUCTURE | Structure of amine part | Structure of caboxylic acid part | Observed MS | Retention Time | Purification Method |
|---|---|---|---|---|---|---|---|
| Example 370 | tert-butyl ((S)-3-(4-chlorophenyl)-1-oxo-1-(((R)-1-(5-(2,2,2-trifluoroethoxy)pyridin-2-yl)ethyl)amino)propan-2-yl)carbamate | 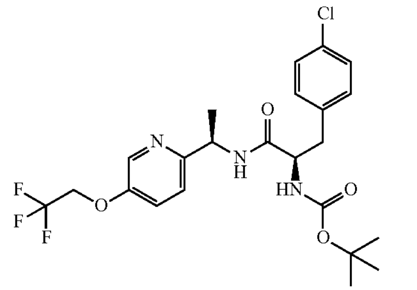 [SMILES: C[C@@H](NC(=O)[C@@H](Cc1ccc(Cl)cc1)NC(=O)OC(C)(C)C)c1ccc(OCC(F)(F)F)cn1] | | | 501.8 | 1.90 min | HPLC |
| Example 371 | tert-butyl ((R)-3-(4-chlorophenyl)-1-oxo-1-(((R)-1-(5-(2,2,2-trifluoroethoxy)pyridin-2-yl)ethyl)amino)propan-2-yl)carbamate | 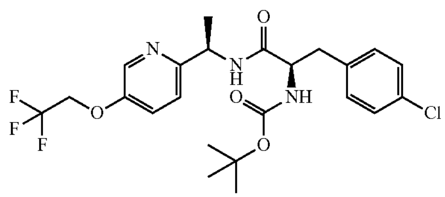 [SMILES: C[C@@H](NC(=O)[C@@H](Cc1ccc(Cl)cc1)NC(=O)OC(C)(C)C)c1ccc(OCC(F)(F)F)cn1] | | | 501.8 | 1.89 min | HPLC |
| Example 372 | tert-butyl ((S)-1-oxo-1-(((R)-1-(5-(2,2,2-trifluoroethoxy)pyridin-2-yl)ethyl)amino)-3-(4-(trifluoromethyl)phenyl)propan-2-yl)carbamate | 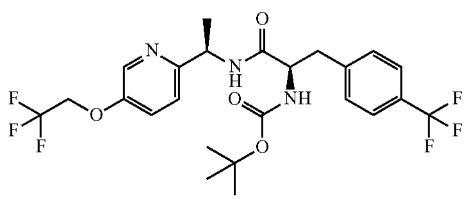 [SMILES: C[C@@H](NC(=O)[C@@H](Cc1ccc(C(F)(F)F)cc1)NC(=O)OC(C)(C)C)c1ccc(OCC(F)(F)F)cn1] | | | 534.1 | 1.93 min | HPLC |
| Example 373 | tert-butyl ((S)-3-(2-chlorophenyl)-1-oxo-1-(((R)-1-(5-(2,2,2-trifluoroethoxy)pyridin-2-yl)ethyl)amino)propan-2-yl)carbamate | 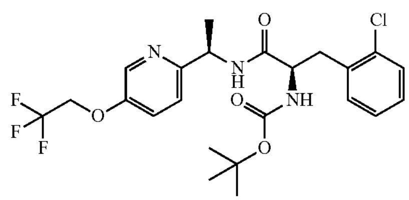 [SMILES: C[C@@H](NC(=O)[C@@H](Cc1ccccc1Cl)NC(=O)OC(C)(C)C)c1ccc(OCC(F)(F)F)cn1] | | | 501.8 | 1.89 min | HPLC |

TABLE 3-continued

| Example | Name | STRUCTURE | Structure of amine part | Structure of caboxylic acid part | Observed MS | Retention Time | Purification Method |
|---|---|---|---|---|---|---|---|
| Example 374 | tert-butyl ((S)-3-(2-fluorophenyl)-1-oxo-1-(((R)-1-(5-(2,2,2-trifluoroethoxy)pyridin-2-yl)ethyl)amino)propan-2-yl)carbamate | 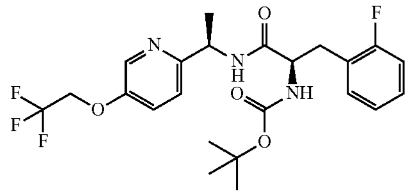 | | | 485.8 | 1.83 min | HPLC |
| Example 375 | tert-butyl ((S)-3-(2-chlorophenyl)-1-oxo-1-(((R)-1-(5-(2,2,2-trifluoroethoxy)pyridin-2-yl)ethyl)amino)propan-2-yl)carbamate | 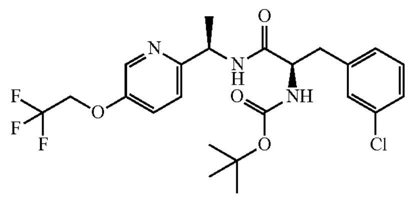 [SMILES: C[C@@H](NC(=O)[C@@H](Cc1cccc(Cl)c1)NC(=O)OC(C)(C)C)c1ccc(OCC(F)(F)F)cn1] | | | 500.1 | 1.90 min | HPLC |
| Example 376 | tert-butyl ((S)-1-oxo-1-(((R)-1-(5-(2,2,2-trifluoroethoxy)pyridin-2-yl)ethyl)amino)-3-(2-trifluoromethyl)phenyl)propan-2-yl)carbamate | 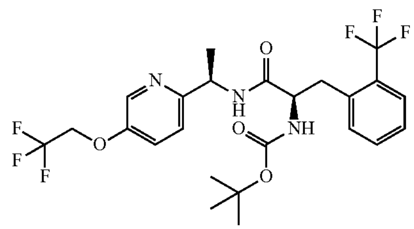 [SMILES: C[C@@H](NC(=O)[C@@H](Cc1ccccc1C(F)(F)F)NC(=O)OC(C)(C)C)c1ccc(OCC(F)(F)F)cn1] | | | 535.8 | 1.93 min | HPLC |
| Example 377 | tert-butyl ((S)-1-oxo-1-(((R)-1-(5-(2,2,2-trifluoroethoxy)pyridin-2-yl)ethyl)amino)-3-(3-(trifluoromethyl)phenyl)propan-2-yl)carbamate | 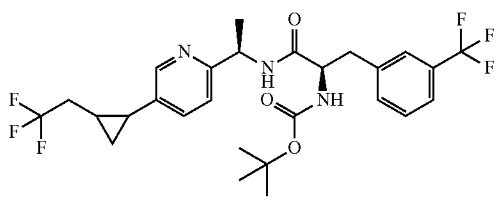 [SMILES: C[C@@H](NC(=O)[C@@H](Cc1cccc(C(F)(F)F)c1)NC(=O)OC(C)(C)C)c1ccc(C2CC2CC(F)(F)F)cn1] | | | 534 | 1.93 min | HPLC |

TABLE 3-continued

| Example | Name | STRUCTURE | Structure of amine part | Structure of caboxylic acid part | Observed MS | Retention Time | Purification Method |
|---|---|---|---|---|---|---|---|
| Example 378 | (R)-2-(2-chlorophenoxy)-N-(1-(5-(2,2,2-trifluoroethoxy)pyridin-2-yl)ethyl)acetamide | 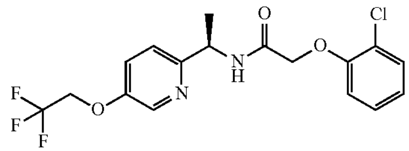 [SMILES: C[C@@H](NC(=O)COc1ccccc1Cl)c1ccc(OCC(F)(F)F)cn1] | | | 387.1 | 1.81 min | HPLC |
| Example 379 | (R)-2-(3-chlorophenoxy)-N-(1-(5-(2,2,2-trifluoroethoxy)pyridin-2-yl)ethyl)acetamide | 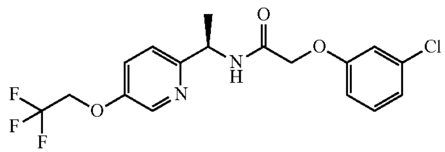 [SMILES: C[C@@H](NC(=O)COc1cccc(Cl)c1)c1ccc(OCC(F)(F)F)cn1] | | | 387.1 | 1.79 min | HPLC |
| Example 380 | (R)-2-(2-chlorophenoxy)-2-methyl-N-(1-(5-(2,2,2-trifluoroethoxy)pyridin-2-yl)ethyl)propanamide | 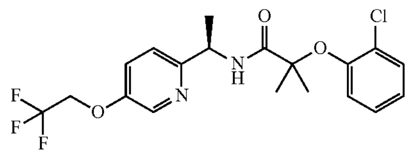 [SMILES: C[C@@H](NC(=O)C(C)(C)Oc1ccccc1Cl)c1ccc(OCC(F)(F)F)cn1] | | | 415.1 | 1.95 min | HPLC |
| Example 381 | (R)-2-(2,3-dichlorophenoxy)-N-(1-(5-(2,2,2-trifluoroethoxy)pyridin-2-yl)ethyl)acetamide | 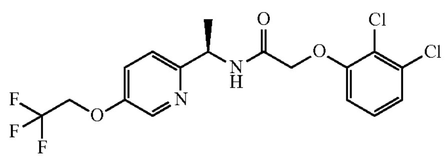 [SMILES: C[C@@H](NC(=O)COc1cccc(Cl)c1Cl)c1ccc(OCC(F)(F)F)cn1] | | | 421 | 1.91 min | HPLC |
| Example 382 | (R)-2-(o-tolyloxy)-N-(1-(5-(2,2,2-trifluoroethoxy)pyridin-2-yl)ethyl)acetamide | 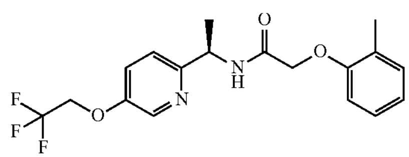 [SMILES: Cc1ccccc1OCC(=O)N[C@H](C)c1ccc(OCC(F)(F)F)cn1] | | | 367.1 | 1.83 min | HPLC |
| Example 383 | (R)-2-(m-tolyloxy)-N-(1-(5-(2,2,2-trifluoroethoxy)pyridin-2-yl)ethyl)acetamide | 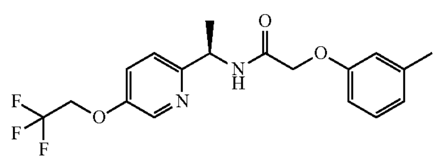 [SMILES: Cc1cccc(OCC(=O)N[C@H](C)c2ccc(OCC(F)(F)F)cn2)c1] | | | 367.1 | 1.97 min | HPLC |

TABLE 3-continued

| Example | Name | STRUCTURE | Structure of amine part | Structure of caboxylic acid part | Observed MS | Retention Time | Purification Method |
|---|---|---|---|---|---|---|---|
| Example 384 | (R)-2-(2,4-dimethylphenoxy)-N-(1-(5-(2,2,2-trifluoroethoxy)pyridin-2-yl)ethyl)acetamide | 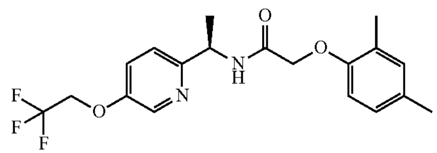 [SMILES: Cc1ccc(OCC(=O)N[C@H](C)c2ccc(OCC(F)(F)F)cn2)c(C)c1] | | | 381.2 | 1.92 min | HPLC |
| Example 385 | (R)-2-(3,5-dimethylphenoxy)-N-(1-(5-(2,2,2-trifluoroethoxy)pyridin-2-yl)ethyl)acetamide | 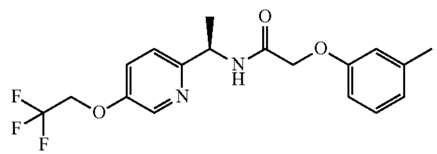 [SMILES: Cc1cccc(OCC(=O)N[C@H](C)c2ccc(OCC(F)(F)F)cn2)c1] | | | 381.2 | 1.87 min | HPLC |
| Example 386 | (R)-2-(2-chloro-6-methylphenoxy)-N-(1-(5-(2,2,2-trifluoroethoxy)pyridin-2-yl)ethyl)acetamide | 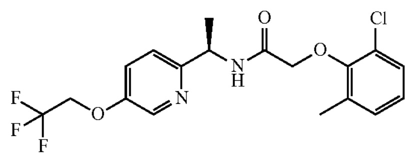 [SMILES: Cc1cccc(Cl)c1OCC(=O)N[C@H](C)c1ccc(OCC(F)(F)F)cn1] | | | 401.1 | 1.88 min | HPLC |
| Example 387 | (R)-2-(4-(tert-butyl)phenoxy)-N-(1-(5-methoxypyridin-2-yl)ethyl)acetamide | 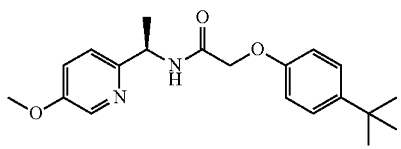 [SMILES: COc1ccc([C@@H](C)NC(=O)COc2ccc(C(C)(C)C)cc2)nc1] | | | 341.1 | 1.88 min | HPLC |
| Example 388 | (R)-2-amino-N-(R)-1-(5-(2,2,2-trifluoroethoxy)pyridin-2-yl)ethyl)-3-(2-(trifluoromethyl)phenyl)propanamide | 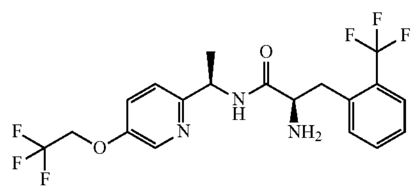 [SMILES: C[C@@H](NC(=O)[C@H](N)Cc1ccccc1C(F)(F)F)c1ccc(OCC(F)(F)F)cn1] | | | 434.1 | 1.62 min | HPLC |

TABLE 3-continued

| Example | Name | STRUCTURE | Structure of amine part | Structure of caboxylic acid part | Observed MS | Retention Time | Purification Method |
|---|---|---|---|---|---|---|---|
| Example 389 | isobutyl ((R)-1-oxo-1-(((R)-1-(5-(2,2,2-trifluoroethoxy)pyridin-2-yl)ethyl)amino)-3-(2-(trifluoromethyl)phenyl)propan-2-yl)carbamate | 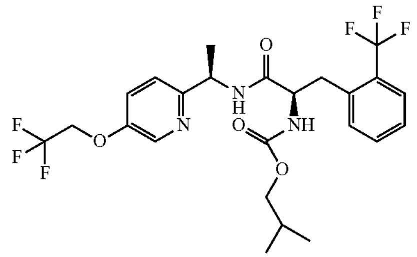 [SMILES: CC(C)COC(=O)N[C@H](Cc1ccccc1C(F)(F)F)C(=O)N[C@H](C)c1ccc(OCC(F)(F)F)cn1] | | | 535.6 | 1.92 min | HPLC |
| Example 390 | ethyl ((R)-1-oxo-1-(((R)-1-(5-(2,2,2-trifluoroethoxy)pyridin-2-yl)ethyl)amino)-3-(2-(trifluoromethyl)phenyl)propan-2-yl)carbamate | 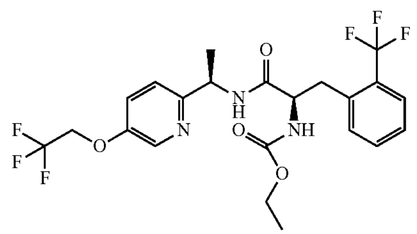 [SMILES: CCOC(=O)N[C@H](Cc1ccccc1C(F)(F)F)C(=O)N[C@H](C)c1ccc(OCC(F)(F)F)cn1] | | | 506 | 8.11 min | HPLC |
| Example 391 | N-((5-(2,2,2-trifluoroethoxy)pyridin-2-yl)methyl)-4-(trifluoromethoxy)benzamide | 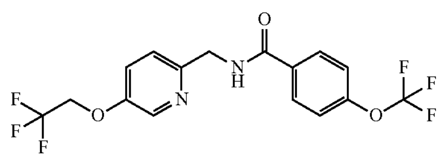 [SMILES: O=C(NCc1ccc(OCC(F)(F)F)cn1)c1ccc(OC(F)(F)F)cc1] | | | 393.3 | 1.72 min | HPLC |
| Example 392 | N-((5-(2,2,2-trifluoroethoxy)pyridin-2-yl)methyl)-3-(trifluoromethoxy)benzamide | 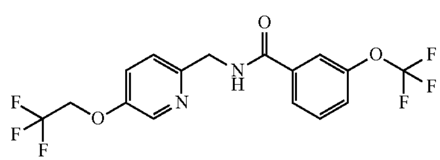 [SMILES: O=C(NCc1ccc(OCC(F)(F)F)cn1)c1cccc(OC(F)(F)F)c1] | | | 393.3 | 1.73 min | HPLC |

TABLE 3-continued

| Example | Name | STRUCTURE | Structure of amine part | Structure of caboxylic acid part | Observed MS | Retention Time | Purification Method |
|---|---|---|---|---|---|---|---|
| Example 393 | 4-(2,2,2-trifluoroethoxy)-N-((5-(2,2,2-trifluoroethoxy)pyridin-2-yl)methyl)benzamide | 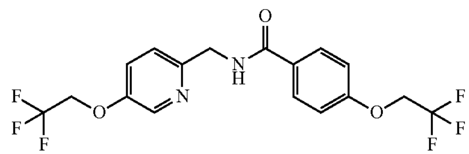 [SMILES: O=C(NCc1ccc(OCC(F)(F)F)cn1)c1ccc(OCC(F)(F)F)cc1] | | | 407 | 1.56 min | HPLC |
| Example 394 | 6-fluoro-1-methyl-N-((5-(2,2,2-trifluoroethoxy)pyridin-2-yl)methyl)-1H-indole-2-carboxamide | 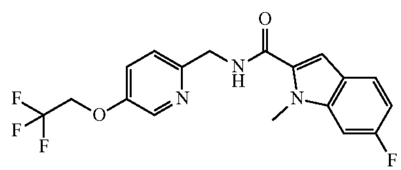 [SMILES: Cn1c(C(=O)NCc2ccc(OCC(F)(F)F)cn2)cc2ccc(F)cc21] | | | 380.1 | 1.73 min | HPLC |
| Example 395 | N-((5-(2,2,2-trifluoroethoxy)pyridin-2-yl)methyl)-2-(4-(trifluoromethyl)phenoxy)acetamide | 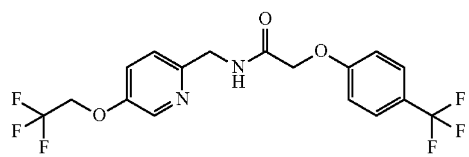 [SMILES: O=C(COc1ccc(C(F)(F)F)cc1)NCc1ccc(OCC(F)(F)F)cn1] | | | 407.1 | 1.73 min | HPLC |
| Example 396 | 4-(tert-butyl)-2-methoxy-N-((5-(2,2,2-trifluoroethoxy)pyridin-2-yl)methyl)benzamide | 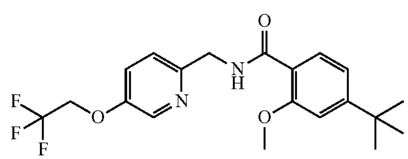 [SMILES: COc1cc(C(C)(C)C)ccc1C(=O)NCc1ccc(OCC(F)(F)F)cn1] | | | 395.2 | 1.89 min | HPLC |
| Example 397 | 4-(tert-butyl)-N-((5-(2,2,2-trifluoroethoxy)pyridin-2-yl)methyl)benzamide | 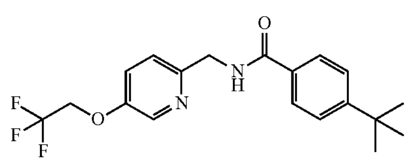 [SMILES: CC(C)(C)c1ccc(C(=O)NCc2ccc(OCC(F)(F)F)cn2)cc1] | | | 365.2 | 1.82 min | HPLC |
| Example 398 | 3-(2,2,2-trifluoroethoxy)-N-((5-(2,2,2-trifluoroethoxy)pyridin-2-yl)methyl)benzamide | 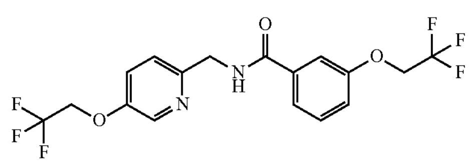 [SMILES: O=C(NCc1ccc(OCC(F)(F)F)cn1)c1cccc(OCC(F)(F)F)c1] | | | 407.1 | 1.69 min | HPLC |

TABLE 3-continued

| Example | Name | STRUCTURE | Structure of amine part | Structure of caboxylic acid part | Observed MS | Retention Time | Purification Method |
|---|---|---|---|---|---|---|---|
| Example 399 | (R)-N-(1-(5-(2,2,2-trifluoroethoxy)pyridin-2-yl)ethyl)-2-(3-(trifluoromethoxy)phenoxy)acetamide | 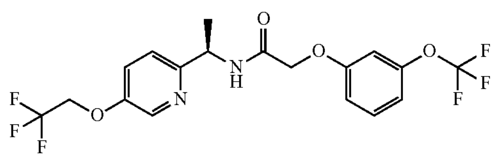 [SMILES: C[C@@H](NC(=O)COc1cccc(OC(F)(F)F)c1)c1ccc(OCC(F)(F)F)cn1] | | | 437.1 | 1.85 min | HPLC |
| Example 400 | (R)-N-(1-(5-(2,2,2-trifluoroethoxy)pyridin-2-yl)ethyl)-2-(3-(trifluoromethyl)phenoxy)acetamide | 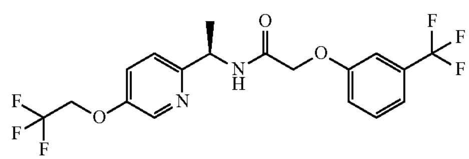 [SMILES: C[C@@H](NC(=O)COc1cccc(C(F)(F)F)c1)c1ccc(OCC(F)(F)F)cn1] | | | 421.1 | 1.81 min | HPLC |
| Example 401 | (R)-N-(1-(5-(2,2,2-trifluoroethoxy)pyridin-2-yl)ethyl)-2-(2-(trifluoromethoxy)phenoxy)acetamide | 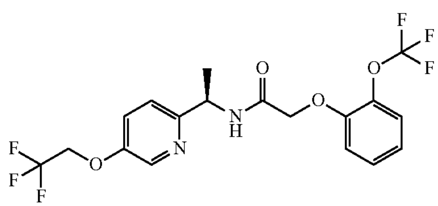 [SMILES: C[C@@H](NC(=O)COc1ccccc1OC(F)(F)F)c1ccc(OCC(F)(F)F)cn1] | | | 437.1 | 1.87 min | HPLC |
| Example 402 | (R)-N-(1-(5-methoxypyridin-2-yl)ethyl)-2-(3-(trifluoromethyl)phenoxy)acetamide | 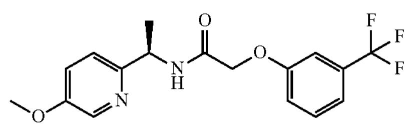 [SMILES: COc1ccc([C@@H](C)NC(=O)COc2cccc(C(F)(F)F)c2)nc1] | | | 353.2 | 1.68 min | HPLC |
| Example 403 | (R)-N-(1-(5-methoxypyridin-2-yl)ethyl)-2-(2-(trifluoromethoxy)phenoxy)acetamide | 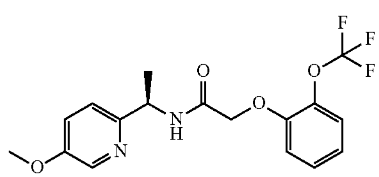 [SMILES: COc1ccc([C@@H](C)NC(=O)COc2ccccc2OC(F)(F)F)nc1] | | | 369.1 | 1.75 min | HPLC |

TABLE 3-continued

| Example | Name | STRUCTURE | Structure of amine part | Structure of caboxylic acid part | Observed MS | Retention Time | Purification Method |
|---|---|---|---|---|---|---|---|
| Example 404 | (R)-3-(4-chlorophenoxy)-N-(1-(5-(2,2,2-trifluoroethoxy)pyridin-2-yl)ethyl)propanamide | 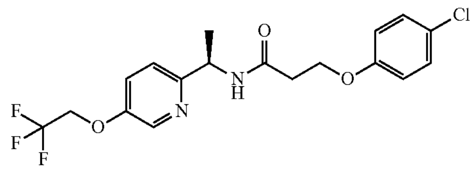 [SMILES: C[C@@H](NC(=O)CCOc1ccc(Cl)cc1)c1ccc(OCC(F)(F)F)cn1] | | | 404.1 | 1.74 min | HPLC |
| Example 405 | (R)-3-(2,2,2-trifluoroethoxy)-N-(1-(6-(2,2,2-trifluoroethoxy)pyridin-2-yl)ethyl)benzamide | 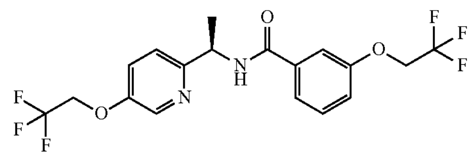 [SMILES: C[C@@H](NC(=O)c1cccc(OCC(F)(F)F)c1)c1ccc(OCC(F)(F)F)cn1] | | | 421.1 | 1.76 min | HPLC |
| Example 406 | (R)-2-(2-(tert-butyl)phenoxy)-N-(1-(5-methoxypyridin-2-yl)ethyl)acetamide | 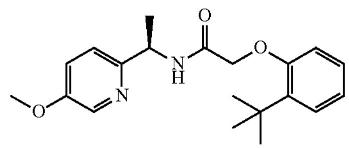 [SMILES: COc1ccc([C@@H](C)NC(=O)COc2ccccc2C(C)(C)C)nc1] | | | 341.3 | 1.95 min | HPLC |
| Example 407 | (R)-N-(1-(5-methoxypyridin-2-yl)ethyl)-2-(2-(trifluoromethyl)phenoxy)acetamide | 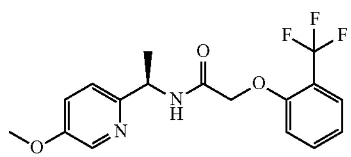 [SMILES: COc1ccc([C@@H](C)NC(=O)COc2ccccc2C(F)(F)F)nc1] | | | 353.2 | 1.72 min | HPLC |
| Example 408 | (R)-N-(1-(5-methoxypyridin-2-yl)ethyl)-2-(3-(trifluoromethoxy)phenoxy)acetamide | 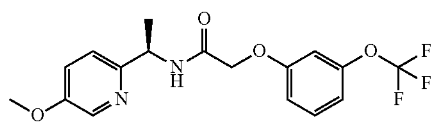 [SMILES: COc1ccc([C@@H](C)NC(=O)COc2cccc(OC(F)(F)F)c2)nc1] | | | 369.3 | 1.73 min | HPLC |
| Example 409 | (R)-N-(1-(5-methoxypyridin-2-yl)ethyl)-2-(2-(trifluoromethyl)phenyl)thiazole-4-carboxamide | 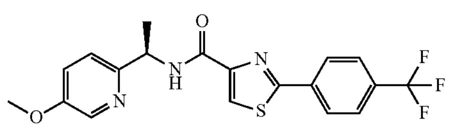 [SMILES: COc1ccc([C@@H](C)NC(=O)c2csc(-c3ccc(C(F)(F)F)cc3)n2)nc1] | | | 406.1 | 1.90 min | HPLC |

TABLE 3-continued

| Example | Name | STRUCTURE | Structure of amine part | Structure of caboxylic acid part | Observed MS | Retention Time | Purification Method |
|---|---|---|---|---|---|---|---|
| Example 410 | (R)-N-(1-(5-methoxypyridin-2-yl)ethyl)-5-phenylisoxazole-3-carboxamide | 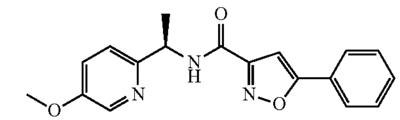 [SMILES: COc1ccc([C@@H](C)NC(=O)c2cc(-c3ccccc3)on2)nc1] | | | 324.1 | 1.71 min | HPLC |
| Example 411 | (R)-N-(1-(5-methoxypyridin-2-yl)ethyl)-5-methyl-2-phenyl-2H-1,2,3-triazole-4-carboxamide | 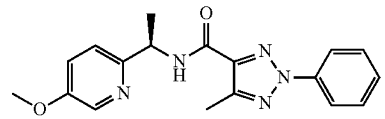 [SMILES: COc1ccc([C@@H](C)NC(=O)c2nn(-c3ccccc3)nc2C)nc1] | | | 338.1 | 1.80 min | HPLC |
| Example 412 | (R)-N-(1-(5-methoxypyridin-2-yl)ethyl)-5-(trifluoromethoxy)-1H-indole-2-carboxamide | 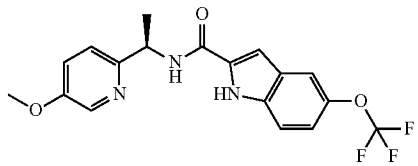 [SMILES: COc1ccc([C@@H](C)NC(=O)c2cc3cc(OC(F)(F)F)ccc3[nH]2)nc1] | | | 378.1 | 1.73 min | HPLC |
| Example 413 | (R)-N-(1-(5-methoxypyridin-2-yl)ethyl)-1-methyl-5-(trifluoromethoxy)-1H-indole-2-carboxamide | 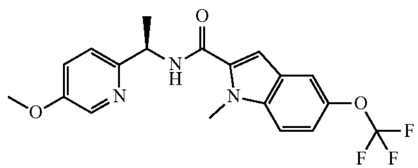 [SMILES: COc1ccc([C@@H](C)NC(=O)c2cc3cc(OC(F)(F)F)ccc3n2C)nc1] | | | 392.1 | 1.85 min | HPLC |
| Example 414 | (R)-N-(tert-butyl)-N-(1-(5-(2,2,2-trifluoroethoxy)pyrazin-2-yl)ethyl)nicotinamide | 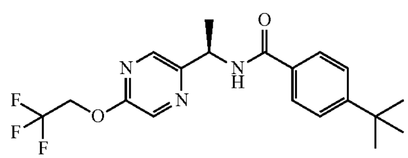 [SMILES: C[C@@H](NC(=O)c1ccc(C(C)(C)C)cc1)c1cnc(OCC(F)(F)F)cn1] | | | 381.1 | 1.79 min | HPLC |
| Example 415 | (R)-2-(4-ethoxyphenoxy)-N-(1-(5-(2,2,2-trifluoroethoxy)pyrazin-2-yl)ethyl)acetamide | 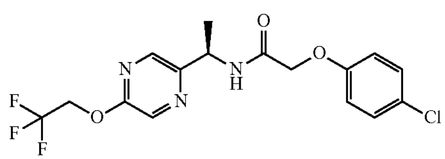 [SMILES: C[C@@H](NC(=O)COc1ccc(Cl)cc1)c1cnc(OCC(F)(F)F)cn1] | | | 388.1 | 1.83 min | HPLC |

TABLE 3-continued

| Example | Name | STRUCTURE | Structure of amine part | Structure of caboxylic acid part | Observed MS | Retention Time | Purification Method |
|---|---|---|---|---|---|---|---|
| Example 416 | (R)-5-(2,2,2-trifluoroethoxy)-N-(1-(5-(2,2,2-trifluoroethoxy)pyrazin-2-yl)ethyl)picolinamide | 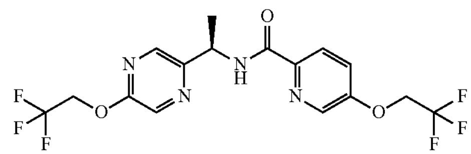 | | | 423.1 | 1.84 min | HPLC |
| Example 417 | (R)-N-(1-(5-(2,2,2-trifluoroethoxy)pyrazin-2-yl)ethyl)-2-(4-(trifluoromethyl)phenoxy)acetamide | 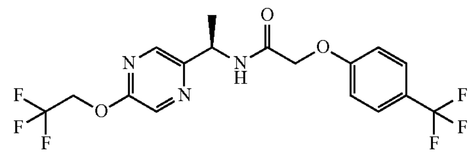 [SMILES: C[C@@H](NC(=O)COc1ccc(C(F)(F)F)cc1)c1cnc(OCC(F)(F)F)cn1] | | | 422.1 | 1.86 min | HPLC |
| Example 418 | (R)-N-(1-(5-(2,2,2-trifluoroethoxy)pyrazin-2-yl)ethyl)-3-(trifluoromethoxy)benzamide | 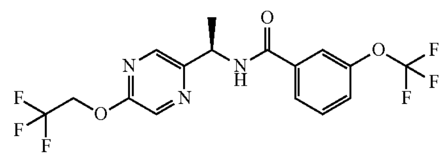 | | | 408 | 1.87 min | HPLC |
| Example 419 | (R)-4-fluoro-3-phenoxy-N-(1-(5-(2,2,2-trifluoroethoxy)pyridin-2-yl)ethyl)benzamide | 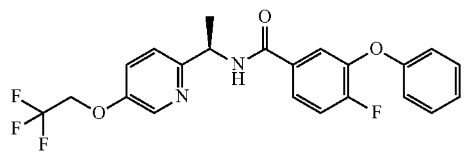 [SMILES: C[C@@H](NC(=O)c1ccc(F)c(Oc2ccccc2)c1)c1ccc(OCC(F)(F)F)cn1] | | | 433.1 | 1.87 min | HPLC |
| Example 420 | (R)-3-(4-fluorophenoxy)-N-(1-(5-(2,2,2-trifluoroethoxy)pyridin-2-yl)ethyl)benzamide | 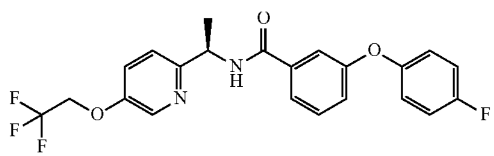 [SMILES: C[C@@H](NC(=O)c1cccc(Oc2ccc(F)cc2)c1)c1ccc(OCC(F)(F)F)cn1] | | | 433.1 | 1.87 min | HPLC |

TABLE 3-continued

| Example | Name | STRUCTURE | Structure of amine part | Structure of caboxylic acid part | Observed MS | Retention Time | Purification Method |
|---|---|---|---|---|---|---|---|
| Example 421 | 4-(tert-butyl)-N-((5-methoxypyridin-3-yl)methyl)benzamide | 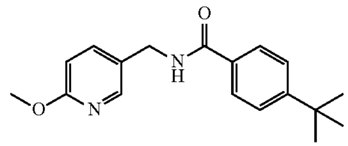 [SMILES: COc1ccc(CNC(=O)c2ccc(C(C)(C)C)cc2)cn1] | | | 297.3 | 1.74 min | HPLC |
| Example 422 | N-((6-methoxypyridin-3-yl)methyl)-2-(4-(trifluoromethyl)phenoxy)acetamide | 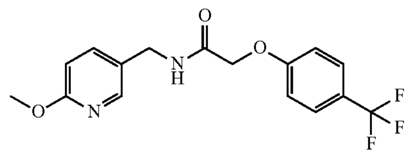 [SMILES: COc1ccc(CNC(=O)COc2ccc(C(F)(F)F)cc2)cn1] | | | 339.1 | 1.64 min | HPLC |
| Example 423 | 4-(tert-butyl)-N-((5-methoxypyridin-2-yl)methyl)benzamide | 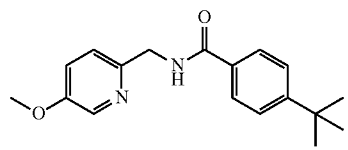 [SMILES: COc1ccc(CNC(=O)c2ccc(C(C)(C)C)cc2)nc1] | | | 297.3 | 1.68 min | HPLC |
| Example 424 | (R)-8-fluoro-N,1-dimethyl-N-(1-(5-2,2,2-trifluoroethoxy)pyridin-2-yl)ethyl)-1H-indole-2-carboxamide | 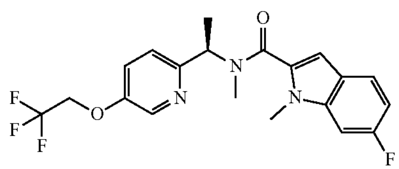 [SMILES: C[C@H](c1ccc(OCC(F)(F)F)cn1)N(C)C(=O)c1cc2ccc(F)cc2n1C] | Alternative route | | 409.9 | 1.89 min | HPLC |
| Example 425 | (1S*,2S*)-N-methyl-2-(quinolin-2-yl)-N-((R)-1-(5-2,2,2-trifluoroethoxy)pyrazin-2-yl)ethyl)cyclopropanecarboxamide | 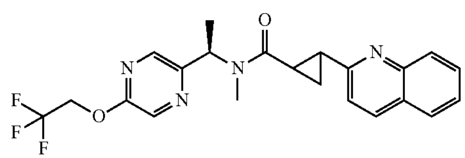 [SMILES: C[C@H](c1cnc(OCC(F)(F)F)cn1)N(C)C(=O)C1CC1c1ccc2ccccc2n1] | Alternative route | | 430.9 | 1.92 min | HPLC |
| Example 426 | (1R*,2R*)-N-methyl-2-(quinolin-2-yl)-N-((R)-1-(5-2,2,2-trifluoroethoxy)pyrazin-2-yl)ethyl)cyclopropanecarboxamide | 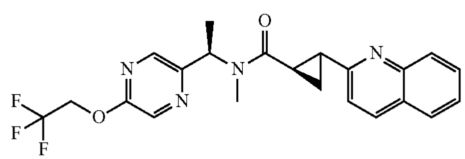 | Alternative route | | 430.9 | 1.91 min | HPLC |

TABLE 3-continued

| Example | Name | STRUCTURE | Structure of amine part | Structure of caboxylic acid part | Observed MS | Retention Time | Purification Method |
|---|---|---|---|---|---|---|---|
| Example 427 | (S)-4-(tert-butyl)-N-(1-(5-(2,2,2-trifluoroethoxy)pyridin-2-yl)ethyl)benzamide | 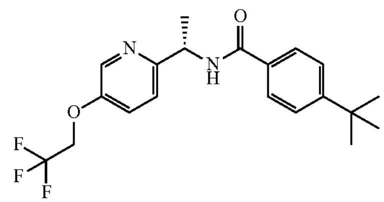 [SMILES: C[C@H](NC(=O)c1ccc(C(C)(C)C)cc1)c1ccc(OCC(F)(F)F)cn1] | | | 379.3 | 1.90 min | HPLC |
| Example 428 | (S)-N-(1-(5-(2,2,2-trifluoroethoxy)pyridin-2-yl)ethyl)-3-(trifluoromethoxy)benzamide | 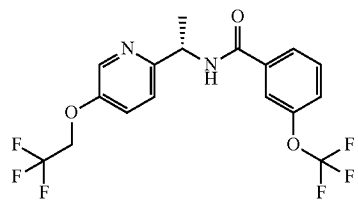 [SMILES: C[C@H](NC(=O)c1cccc(OC(F)(F)F)c1)c1ccc(OCC(F)(F)F)cn1] | | | 407.2 | 1.81 min | HPLC |
| Example 429 | (S)-N-(1-(5-(2,2,2-trifluoroethoxy)pyridin-2-yl)ethyl)-4-(trifluoromethoxy)benzamide | 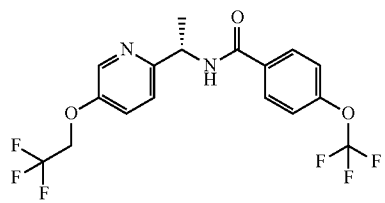 [SMILES: C[C@H](NC(=O)c1ccc(OC(F)(F)F)cc1)c1ccc(OCC(F)(F)F)cn1] | | | 407.2 | 1.80 min | HPLC |
| Example 430 | (S)-3-(2,2,2-trifluoroethoxy)-N-(1-(5-(2,2,2-trifluoroethoxy)pyridin-2-yl)ethyl)benzamide | 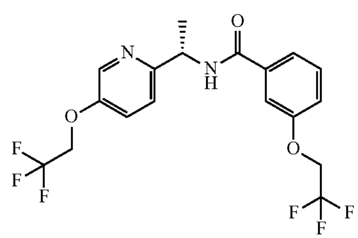 [SMILES: C[C@H](NC(=O)c1cccc(OCC(F)(F)F)c1)c1ccc(OCC(F)(F)F)cn1] | | | 421.2 | 1.76 min | HPLC |

TABLE 3-continued

| Example | Name | STRUCTURE | Structure of amine part | Structure of caboxylic acid part | Observed MS | Retention Time | Purification Method |
|---|---|---|---|---|---|---|---|
| Example 431 | (R)-N-(1-(5-(2,2,2-trifluoroethoxy)pyrazin-2-yl)ethyl)-4-(trifluoromethoxy)benzamide | 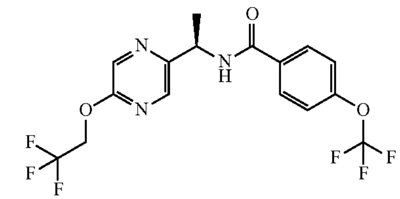 [SMILES: C[C@@H](NC(=O)c1ccc(OC(F)(F)F)cc1)c1cnc(OCC(F)(F)F)cn1] | | | 408.1 | 1.86 min | HPLC |
| Example 432 | (R)-4-(2,2,2-trifluoroethoxy)-N-(1-(5-(2,2,2-trifluoroethoxy)pyrazin-2-yl)ethyl)benzamide | 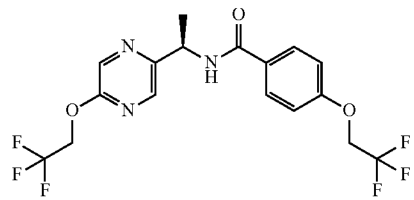 [SMILES: C[C@@H](NC(=O)c1ccc(OCC(F)(F)F)cc1)c1cnc(OCC(F)(F)F)cn1] | | | 422.3 | 1.79 min | HPLC |
| Example 433 | (R)-3-(2,2,2-trifluoroethoxy)-N-(1-(5-(2,2,2-trifluoroethoxy)pyrazin-2-yl)ethyl)benzamide | 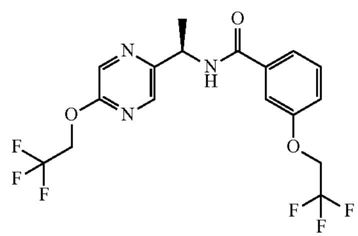 [SMILES: C[C@@H](NC(=O)c1cccc(OCC(F)(F)F)c1)c1cnc(OCC(F)(F)F)cn1] | | | 422.1 | 1.82 min | HPLC |
| Example 434 | 4-(tert-butyl)-N-((6-(trifluoromethyl)pyridin-2-yl)methyl)benzamide | 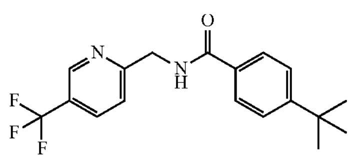 [SMILES: CC(C)(C)c1ccc(C(=O)NCc2ccc(C(F)(F)F)cn2)cc1] | | | 335.3 | 1.86 min | HPLC |

TABLE 3-continued

| Example | Name | STRUCTURE | Structure of amine part | Structure of caboxylic acid part | Observed MS | Retention Time | Purification Method |
|---|---|---|---|---|---|---|---|
| Example 435 | 3-(trifluoroethoxy)-N-((5-(trifluoromethyl)pyridin-2-yl)methyl)benzamide | 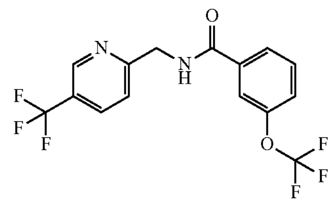 [SMILES: O=C(NCc1ccc(C(F)(F)F)cn1)c1cccc(OC(F)(F)F)c1] | | | 363.1 | 1.76 min | HPLC |
| Example 436 | 4-(trifluoromethoxy)-N-((5-(trifluoromethyl)pyridin-2-yl)methyl)benzamide | 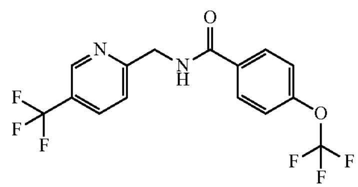 [SMILES: O=C(NCc1ccc(C(F)(F)F)cn1)c1ccc(OC(F)(F)F)cc1] | | | 363.2 | 1.75 min | HPLC |
| Example 437 | 4-(2,2,2-trifluoroethoxy)-N-((5-(trifluoromethyl)pyridin-2-yl)methyl)acetamide | 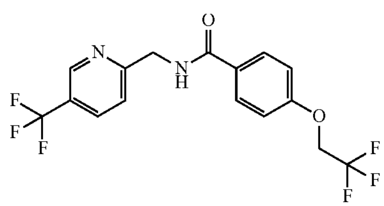 [SMILES: O=C(NCc1ccc(C(F)(F)F)cn1)c1ccc(OCC(F)(F)F)cc1] | | | 377.1 | 1.68 min | HPLC |
| Example 438 | 3-(2,2,2-trifluoroethoxy)-N-((5-(trifluoromethyl)pyridin-2-yl)methyl)benzamide | 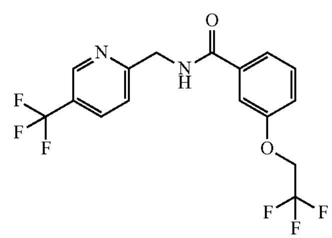 [SMILES: O=C(NCc1ccc(C(F)(F)F)cn1)c1cccc(OCC(F)(F)F)c1] | | | 377.2 | 1.71 min | HPLC |

TABLE 3-continued

| Example | Name | STRUCTURE | Structure of amine part | Structure of caboxylic acid part | Observed MS | Retention Time | Purification Method |
|---|---|---|---|---|---|---|---|
| Example 439 | 4-(tert-butyl)-N-((6-(piperidin-1-yl)pyridin-3-yl)methyl)benzamide | 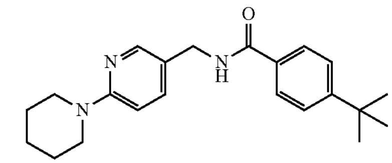 [SMILES: CC(C)(C)c1ccc(C(=O)NCc2ccc(N3CCCCC3)nc2)cc1] | | | 350.4 | 1.95 min | HPLC |
| Example 440 | N-((6-(piperidin-1-yl)pyridin-3-yl)methyl)-3-(trifluoromethoxy)benzamide | 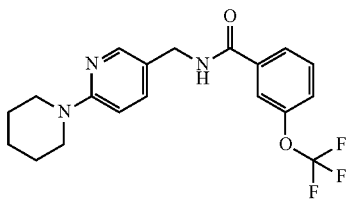 [SMILES: O=C(NCc1ccc(N2CCCCC2)nc1)c1cccc(OC(F)(F)F)c1] | | | 378.3 | 1.87 min | HPLC |
| Example 441 | N-((5-(piperidin-1-yl)pyridin-3-yl)methyl)-4-(2,2,2-trifluoroethoxy)benzamide | 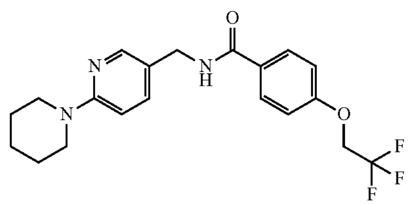 [SMILES: O=C(NCc1ccc(N2CCCCC2)nc1)c1ccc(OCC(F)(F)F)cc1] | | | 392.3 | 1.77 min | HPLC |
| Example 442 | 4-(tert-butyl)-N-((5-(pyrrolidin-1-yl)pyridin-3-yl)methyl)benzamide | 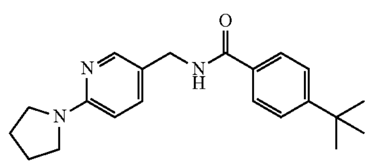 [SMILES: CC(C)(C)c1ccc(C(=O)NCc2ccc(N3CCCC3)nc2)cc1] | | | 336.4 | 1.81 min | HPLC |
| Example 443 | N-((6-(pyrrolidin-1-yl)pyridin-3-yl)methyl)-3-(trifluoromethoxy)benzamide | 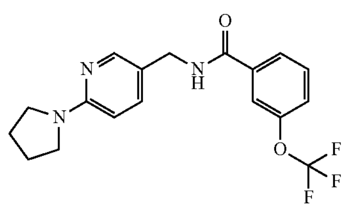 [SMILES: O=C(NCc1ccc(N2CCCC2)nc1)c1cccc(OC(F)(F)F)c1] | | | 364.3 | 1.73 min | HPLC |

TABLE 3-continued

| Example | Name | STRUCTURE | Structure of amine part | Structure of caboxylic acid part | Observed MS | Retention Time | Purification Method |
|---|---|---|---|---|---|---|---|
| Example 444 | N-((6-(pyrrolidin-1-yl)pyridin-3-yl)methyl)-4-(2,2,2-trifluoroethoxy)benzamide | 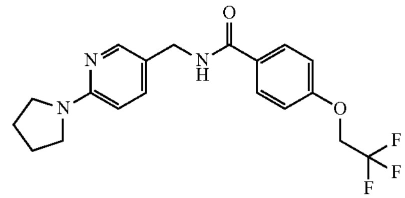 [SMILES: O=C(NCc1ccc(N2CCCC2)nc1)c1ccc(OCC(F)(F)F)cc1] | | | 378.3 | 1.64 min | HPLC |
| Example 445 | 4-(tert-butyl)-N-((6-(trifluoromethyl)pyridin-3-yl)methyl)benzamide | 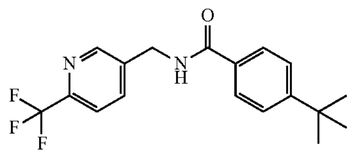 [SMILES: CC(C)(C)c1ccc(C(=O)NCc2ccc(C(F)(F)F)nc2)cc1] | | | 335.3 | 1.84 min | HPLC |
| Example 446 | 3-(trifluoromethoxy)-N-((6-(trifluoromethyl)pyridin-3-yl)methyl)benzamide | 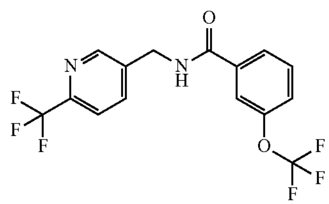 | | | 363.2 | 1.75 min | HPLC |
| Example 447 | 4-(tert-butyl)-N-((6-(pyrrolidin-1-yl)pyridin-2-yl)methyl)benzamide | 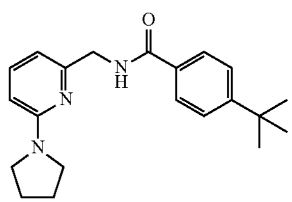 [SMILES: CC(C)(C)c1ccc(C(=O)NCc2cccc(N3CCCC3)n2)cc1] | | | 335.3 | 2.05 min | HPLC |
| Example 448 | N-((6-(pyrrolidin-1-yl)pyridin-2-yl)methyl)-3-(trifluoromethoxy)benzamide | 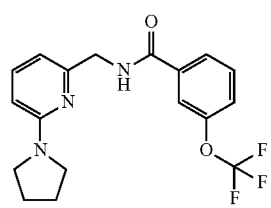 [SMILES: O=C(NCc1cccc(N2CCCC2)n1)c1cccc(OC(F)(F)F)c1] | | | 363.2 | 1.95 min | HPLC |

TABLE 3-continued

| Example | Name | STRUCTURE | Structure of amine part | Structure of caboxylic acid part | Observed MS | Retention Time | Purification Method |
|---|---|---|---|---|---|---|---|
| Example 449 | N-((8-(pyrrolidin-1-yl)pyridin-2-yl)methyl)-4-(2,2,2-trifluoroethoxy)benzamide | 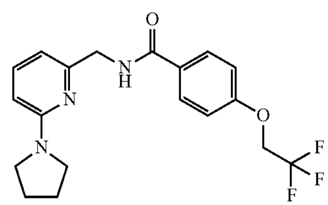 [SMILES: O=C(NCc1cccc(N2CCCC2)n1)c1ccc(OCC(F)(F)F)cc1] | | | 378.8 | 1.84 min | HPLC |
| Example 450 | (R)-4-chloro-2-methoxy-N-(1-(5-(2,2,2-trifluoroethoxy)pyridin-2-yl)ethyl)benzamide | 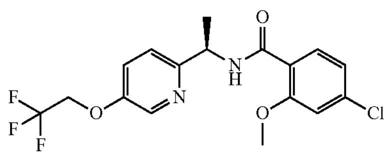 [SMILES: COc1cc(Cl)ccc1C(=O)N[C@H](C)c1ccc(OCC(F)(F)F)cn1] | | | 387.2 | 1.82 min | HPLC |
| Example 451 | (R)-4-(2-cyanopropan-2-yl)-N-(1-(5-(2,2,2-trifluoroethoxy)pyridin-2-yl)ethyl)benzamide | 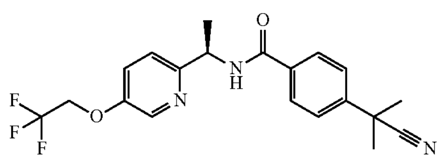 [SMILES: C[C@@H](NC(=O)c1ccc(C(C)(C)C#N)cc1)c1ccc(OCC(F)(F)F)cn1] | | | 390.3 | 1.67 min | HPLC |
| Example 452 | (R)-3-chloro-4-methoxy-N-(1-(5-(2,2,2-trifluoroethoxy)pyridin-2-yl)ethyl)benzamide | 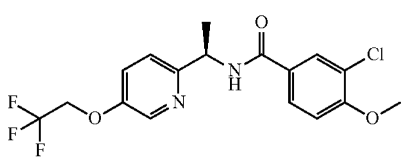 [SMILES: COc1ccc(C(=O)N[C@H](C)c2ccc(OCC(F)(F)F)cn2)cc1Cl] | | | 387.2 | 1.70 min | HPLC |
| Example 453 | (R)-6-methoxy-1-methyl-N-(1-(5-(2,2,2-trifluoroethoxy)pyridin-2-yl)ethyl)-1H-indole-2-carboxamide | 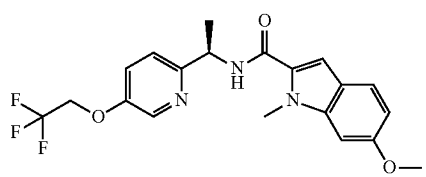 [SMILES: COc1ccc2cc(C(=O)N[C@H](C)c3ccc(OCC(F)(F)F)cn3)n(C)c2c1] | | | 406.3 | 1.77 min | HPLC |

TABLE 3-continued

| Example | Name | STRUCTURE | Structure of amine part | Structure of carboxylic acid part | Observed MS | Retention Time | Purification Method |
|---|---|---|---|---|---|---|---|
| Example 454 | (R)-N-(1-(6-methyl-3-(2,2,2-trifluoroethoxy)pyridin-2-yl)ethyl)-3-(trifluoromethoxy)benzamide | 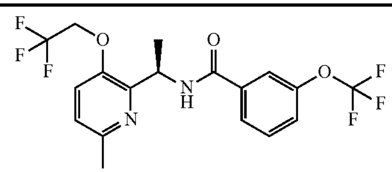 | | | 421.2 | 1.95 min | HPLC |
| Example 455 | (R)-N-(1-(6-methyl-3-(2,2,2-trifluoroethoxy)pyridin-2-yl)ethyl)-4-(2,2,2-trifluoroethoxy)benzamide | 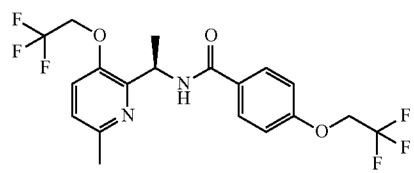 [SMILES: Cc1ccc(OCC(F)(F)F)c([C@@H](C)NC(=O)c2ccc(OCC(F)(F)F)cc2)n1] | | | 435.2 | 1.86 min | HPLC |
| Example 456 | (S)-2-(3-chlorophenoxy)-N-(1-(5-(2,2,2-trifluoroethoxy)pyridin-2-yl)ethyl)acetamide | 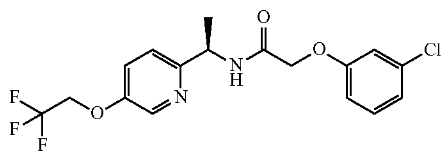 [SMILES: C[C@@H](NC(=O)COc1cccc(Cl)c1)c1ccc(OCC(F)(F)F)cn1] | | | 387.2 | 1.79 min | HPLC |
| Example 457 | 2-(2-chlorophenoxy)-N-((5-(2,2,2-trifluoroethoxy)pyridin-2-yl)methyl)acetamide | 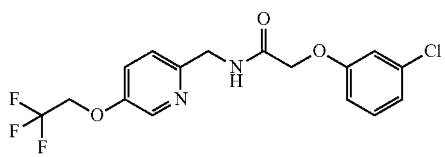 [SMILES: O=C(COc1cccc(Cl)c1)NCc1ccc(OCC(F)(F)F)cn1] | | | 373.2 | 1.69 min | HPLC |
| Example 458 | (R)-2-(3-chlorophenoxy)-N-(1-(5-(2,2,2-trifluoroethoxy)pyrazin-2-yl)ethyl)acetamide | 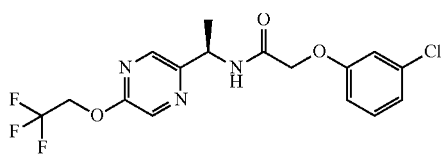 [SMILES: C[C@@H](NC(=O)COc1cccc(Cl)c1)c1cnc(OCC(F)(F)F)cn1] | | | 388.2 | 1.84 min | HPLC |

TABLE 3-continued

| Example | Name | STRUCTURE | Structure of amine part | Structure of caboxylic acid part | Observed MS | Retention Time | Purification Method |
|---|---|---|---|---|---|---|---|
| Example 459 | (R)-4-ethyl-N-(1-(5-(2,2,2-trifluoroethoxy)pyridin-2-yl)ethyl)benzamide | 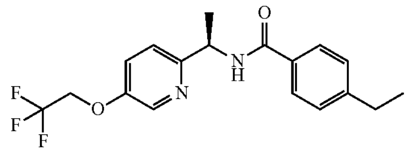 [SMILES: CCc1ccc(C(=O)N[C@H](C)c2ccc(OCC(F)(F)F)cn2)cc1] | | | 351 | 1.75 min | HPLC |
| Example 460 | (R)-3-fluoro-4-methyl-N-(1-(5-(2,2,2-trifluoroethoxy)pyridin-2-yl)ethyl)benzamide | 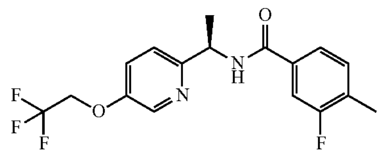 [SMILES: Cc1ccc(C(=O)N[C@H](C)c2ccc(OCC(F)(F)F)cn2)cc1F] | | | 357.2 | 1.71 min | HPLC |
| Example 461 | (R)-5-chloro-2-methoxy-N-(1-(5-(2,2,2-trifluoroethoxy)pyridin-2-yl)ethyl)benzamide | 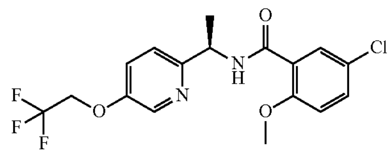 [SMILES: COc1ccc(Cl)cc1C(=O)N[C@H](C)c1ccc(OCC(F)(F)F)cn1] | | | 387.2 | 1.81 min | HPLC |
| Example 462 | (R)-6-(2,2,2-trifluoroethoxy)-N-(1-(5-(2,2,2-trifluoroethoxy)pyridin-2-yl)ethyl)nicotinamide | 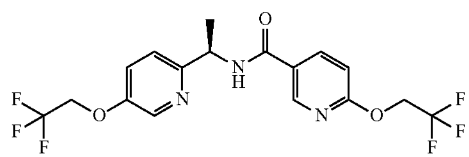 [SMILES: C[C@@H](NC(=O)c1ccc(OCC(F)(F)F)nc1)c1ccc(OCC(F)(F)F)cn1] | | | 423.9 | 1.74 min | HPLC |

TABLE 3-continued

| Example | Name | STRUCTURE | Structure of amine part | Structure of caboxylic acid part | Observed MS | Retention Time | Purification Method |
|---|---|---|---|---|---|---|---|
| Example 463 | (R)-N-(1-(5-(2,2,2-trifluoroethoxy)pyrazin-2-yl)ethyl)quinoxaline-2-carboxamide | 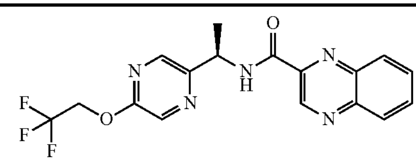 | | | 376.1 | 1.78 min | HPLC |
| Example 464 | (R)-N-(1-(5-(2,2,2-trifluoroethoxy)pyrazin-2-yl)ethyl)-5-(trifluoromethyl)picolinamide | 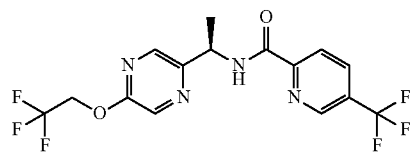 [SMILES: C[C@@H](NC(=O)c1ccc(C(F)(F)F)cn1)c1cnc(OCC(F)(F)F)cn1] | | | 393.1 | 1.86 min | HPLC |

TABLE 4

| Example | spectra data |
|---|---|
| Example 133 | $^1$H-NMR (300 MHz, DMSO-d$_6$) δ 10.85 (1H, s), 8.57 (1H, d, J = 8.0 Hz), 8.36 (1H, d, J = 2.9 Hz), 7.55 (1H, dd, J = 8.8, 2.9 Hz), 7.47 (1H, d, J = 7.3 Hz), 7.37 (1H, d, J = 8.8 Hz), 7.34 (7.3 Hz), 7.15-6.95 (3H, m), 5.04 (1H, m), 4.88 (2H, q, J = 8.8 Hz), 2.23 (1H, m), 1.97 (1H, m), 1.39 (3H, d, J = 8.6 Hz), 1.31 (1H, m), 1.16 (1H, m) |
| Example 134 | $^1$H-NMR (300 MHz, DMSO-d$_6$) δ 10.86 (1H, s), 8.57 (1H, d, J = 8.1 Hz), 8.36 (1H, s), 7.53 (2H, d, J = 7.4 Hz), 7.35 (2H, d, J = 8.1 Hz), 7.15-6.95 (3H, m), 5.04 (1H, m), 4.88 (2H, q, J = 8.8 Hz), 2.31 (1H, m), 1.99 (1H, m), 1.39 (3H, d, J = 6.6 Hz), 1.25 (1H, m), 1.18 (1H, m) |
| Example 203 | $^1$H-NMR (300 MHz, DMSO-d$_6$) δ 8.28 (1H, brs), 8.26 (1H, s), 7.53 (1H, d, J = 8.1 Hz), 7.23-7.13 (4H, m), 6.99 (1H, d, J = 7.3 Hz), 6.82 (1H, dd, J = 8.0, 1.5 Hz) 6.50 (1H, t, J = 2.9 Hz), 5.20 (1H, m), 4.36 (2H, q, J = 8.0 Hz), 2.60 (1H, m), 1.77-1.60 (2H, m), 1.49 (3H, d, J = 6.6 Hz), 1.31 (1H, m) |
| Example 204 | $^1$H-NMR (300 MHz, CDCl$_3$) δ 8.30 (1H, t, J = 1.4 Hz), 8.20 (1H, brs), 7.56 (1H, d, J = 8.0 Hz), 7.25 (2H, d, J = 2.2 Hz), 7.19 (2H, t, J = 2.2 Hz), 6.94 (1H, d, J = 8.1 Hz), 6.87 (1H, dd, J = 8.0, 1.5 Hz), 6.53 (1H, t, J = 2.2 Hz), 5.20 (1H, m), 4.38 (2H, q, J = 7.3 Hz), 2.64 (1H, m), 1.74 (1H, m), 1.63 (1H, m), 1.47 (3H, d, J = 7.3 Hz), 1.27 (1H, m). |
| Example 215 | $^1$H-NMR (300 MHz, CDCl$_3$) δ 8.27 (1H, s), 8.05 (1H, s), 8.03 (1H, d, J = 8.6 Hz), 7.78 (1H, d, J = 6.6 Hz), 7.69 (1H, d, J = 7.9 Hz), 7.44-7.34 (2H, m) 6.82 (1H, brd, J = 7.3 Hz), 5.29 (1H, m), 4.75 (2H, q, J = 7.9 Hz), 2.75 (1H, m), 2.39 (1H, m), 1.84-1.70 (2H, m), 1.52 (3H, d, J = 6.6 Hz), |
| Example 222 | $^1$H-NMR (300 MHz, CDCl$_3$) δ 8.30 (1H, s), 8.10 (1H, s), 8.04 (1H, d, J = 8.0 Hz), 7.92 (1H, d, J = 8.0 Hz), 7.76 (1H, d, J = 8.0 Hz), 7.66 (1H, t, J = 8.0 Hz), 7.46 (1H, t, J = 8.0 Hz), 7.38 (1H, d, J = 6.0 Hz), 6.59 (1H, d, J = 7.3 Hz), 5.27 (1H, quintet, J = 7.3 Hz), 4.81-4.72 (2H, m), 2.82-2.74 (1H, m), 2.37-2.30 (1H, m), 1.68-1.60 (2H, m), 1.47 (3H, d, J = 7.3 Hz). |
| Example 223 | $^1$H-NMR (300 MHz, DMSO-d$_6$) δ 11.0 (1H, s), 8.68 (1H, d, J = 7.7 Hz), 8.11 (1H, d, J = 2.2 Hz), 7.73 (1H, dd, J = 8.4, 2.2 Hz), 7.36 (1H, d, J = 7.3 Hz), 7.23 (1H, d, J = 7.7 Hz), 7.00-6.88 (3H, m), 6.12 (1H, s), 5.00-4.91 (3H, m), 2.34 (1H, m), 1.93 (1H, m), 1.37-1.27 (2H, m), 1.35 (3H, d, J = 7.0 Hz). |
| Example 224 | $^1$H-NMR (300 MHz, DMSO-d$_6$) δ 11.0 (1H, s), 8.65 (1H, d, J = 8.1 Hz), 8.11 (1H, d, J = 2.2 Hz), 7.74 (1H, dd, J = 8.4, 2.2 Hz), 7.35 (1H, d, J = 7.7 Hz), 7.21 (1H, d, J = 7.7 Hz), 6.99-6.86 (2H, m), 6.09 (1H, s), 4.99-4.90 (3H, m), 2.28 (1H, m), 1.93 (1H, m), 1.74 (1H, m), 1.36 (3H, d, J = 7.3 Hz), 1.31 (1H, m). |
| Example 225 | $^1$H-NMR (300 MHz, DMSO-d$_6$) δ 11.0 (1H, s), 8.73 (1H, d, J = 7.3 Hz), 8.43 (1H, d, J = 1.1 Hz), 8.18 (1H, d, J = 1.1 Hz), 7.36 (1H, d, J = 7.7 Hz), 7.23 (1H, d, J = 7.7 Hz), 7.00-6.88 (2H, m), 6.12 (1H, s), 5.06-4.97 (3H, m), 2.34 (1H, m), 2.01 (1H, m), 1.39 (3H, d, J = 7.0 Hz), 1.30-1.26 (2H, m). |
| Example 226 | $^1$H-NMR (300 MHz, DMSO-d$_6$) δ 11.0 (1H, s), 8.72 (1H, d, J = 7.7 Hz), 8.42 (1H, d, J = 1.1 Hz), 8.20 (1H, d, J = 1.1 Hz), 7.35 (1H, d, J = 7.7 Hz), 7.21 (1H, d, J = 8.1 Hz), 6.99-6.87 (2H, m), 6.09 (1H, s), 5.06-4.97 (3H, m), 2.29 (1H, m), 2.01 (1H, m), 1.39 (3H, d, J = 7.0 Hz), 1.37-1.29 (2H, m). |
| Example 227 | $^1$H-NMR (300 MHz, DMSO-d$_6$) δ 8.60 (1H, d, J = 7.7 Hz), 8.31 (1H, d, J = 2.9 Hz), 7.94 (1H, s), 7.62 (1H, d, J = 8.4 Hz), 7.49 (1H, dd, J = 8.4, 2.9 Hz), 7.40 (1H, s), 7.30 (1H, d, J = 8.8 Hz), 6.87 (1H, d, J = 8.4 Hz), 4.97 (1H, quintet, J = 7.3 Hz), 4.83 (2H, q, J = 8.8 Hz), 3.98 (3H, s), 2.39 (1H, m), 2.07 (1H, m), 1.33 (3H, d, J = 7.3 Hz), 1.35-1.28 (2H, m) |
| Example 237 | $^1$H-NMR (300 MHz, DMSO-d$_6$) δ 8.55 (1H, d, J = 7.7 Hz), 8.30 (1H, d, J = 2.9 Hz), 7.48 (1H, dd, J = 8.8, 2.9 Hz), 7.42-7.27 (6H, m), 7.02 (2H, d, J = 8.8 Hz), 6.89 (2H, d, J = 8.4 Hz), 5.05 (2H, s), 4.95 (1H, quintet, J = 7.3 Hz), 4.83 (2H, q, J = 8.8 Hz), 2.17 (1H, m), 1.88 (1H, m), 1.32 (3H, d, J = 7.3 Hz), 1.21 (1H, m), 1.08 (1H, m). |
| Example 238 | $^1$H-NMR (300 MHz, DMSO-d$_6$) δ 8.54 (1H, d, J = 8.1 Hz), 8.28 (1H, d, J = 2.9 Hz), 7.47 (1H, dd, J = 8.8, 2.9 Hz), 7.41-7.26 (6H, m), 6.99 (2H, d, J = 8.8 Hz), 6.88 (2H, d, J = 8.4 Hz), 5.04 (2H, s), 4.95 (1H, quintet, J = 7.3 Hz), 4.81 (2H, q, J = 8.8 Hz), 2.11 (1H, m), 1.90 (1H, m), 1.33 (3H, d, J = 7.3 Hz), 1.27 (1H, m), 1.09 (1H, m) |
| Example 240 | $^1$H-NMR (300 MHz, DMSO-d$_6$) δ 8.57 (1H, d, J = 7.7 Hz), 8.30 (1H, d, J = 2.9 Hz), 7.50-7.27 (7H, m), 7.16 (1H, t, J = 7.7 Hz), 8.81-6.76 (2H, m), 6.68 (1H, d, J = 7.3 Hz), 5.06 (2H, s), 4.95 (1H, quintet, J = 7.0 Hz), 4.83 (2H, q, J = 8.8 Hz), 2.19 (1H, m), 1.88 (1H, m), 1.32 (3H, d, J = 7.0 Hz), 1.25 (1H, m), 1.15 (1H, m). |
| Example 241 | $^1$H-NMR (300 MHz, DMSO-d$_6$) δ 8.56 (1H, d, J = 8.1 Hz), 8.28 (1H, d, J = 2.9 Hz), 7.49-7.27 (7H, m), 7.15 (1H, t, J = 7.7 Hz), 6.81-6.64 (3H, m), 5.04 (2H, s), 4.96 (1H, quintet, J = 7.0 Hz), 4.81 (2H, q, J = 8.8 Hz), 2.14 (1H, m), 2.01 (1H, m), 1.33 (3H, d, J = 7.0 Hz), 1.32 (1H, m), 1.16 (1H, m). |
| Example 246 | $^1$H-NMR (300 MHz, CDCl$_3$) δ 8.29 (1H, s), 7.31-7.21 (2H, m), 7.13 (1H, dd, J = 8.8, 2.9 Hz), 7.08-6.85 (3H, m), 5.19 (1H, m), 4.40 (2H, q, J = 8.1 Hz), 2.65 (1H, m), 1.63-1.61 (2H, m), 1.48 (3H, d, J = 6.6 Hz), 1.21 (1H, m) |
| Example 247 | $^1$H-NMR (300 Mhz, CDCl$_3$) δ 8.30 (1H, s), 7.26 (2H, m), 7.08 (1H, dd, J = 7.1, 2.2 Hz), 7.00 (1H, m), 6.96-6.83 (2H, m), 5.19 (1H, m), 4.40 (2H, q, J = 7.3 Hz), 2.58 (1H, m), 1.65 (1H, m), 1.54 (1H, m), 1.47 (3H, d, J = 6.6 Hz), 1.23 (1H, m) |
| Example 248 | $^1$H-NMR (300 Mhz, CDCl$_3$) δ 8.29 (1H, s), 7.24 (2H, d, J = 2.2 Hz), 6.90 (2H, t, J = 8.1 Hz), 6.63-6.57 (2H, m), 5.17 (1H, m), 4.39 (2H, q, J = 8.0 Hz), 3.78 (3H, s), 2.55 (1H, m), 1.67 (1H, m), 1.53 (1H, m), 1.47 (3H, d, J = 6.6 Hz), 1.19 (1H, m) |
| Example 249 | $^1$H-NMR (300 MHz, CDCl$_3$) δ 8.28 (1H, s), 7.24 (2H, d, J = 1.5 Hz), 6.95-6.80 (2H, m) 6.84-6.51 (2H, m), 5.17 (1H, m), 4.39 (2H, q, J = 8.0 Hz), 3.76 (3H, s), 2.50 (1H, m), 1.67 (1H, m), 1.58 (1H, m), 1.46 (3H, d, J = 6.6 Hz), 1.23 (1, m) |
| Example 250 | $^1$H-NMR (300 MHz, CDCl$_3$) δ 8.30 (1H, s), 7.25 (2H, d, J = 6.6 Hz), 6.94 (1H, brd, J = 7.3 Hz), 6.65-6.55 (2H, m), 5.18 (1H, m), 4.40 (2H, q, J = 8.0 Hz), 2.39 (1H, m), 1.93 (1H, m), 1.55 (1H, m), 1.48 (3H, d, J = 6.6 Hz), 1.32 (1H, m) |
| Example 251 | $^1$H-NMR (300 MHz, CDCl$_3$) δ 8.29 (1H, s), 7.25 (2H, m), 7.18 (1H, t, J = 7.3 Hz), 7.02 (1H, d, J = 7.3 Hz), 6.96-6.85 (3H, m), 5.16 (1H, m), 4.39 (2H, q, J = 8.0 Hz), 2.45 (1H, m), 2.33 (3H, s), 1.68 (1H, m), 1.58 (1H, m), 1.45 (3H, d, J = 6.6 Hz), 1.21 (1H, m) |
| Example 252 | $^1$H-NMR (300 MHz, CDCl$_3$) δ 8.26 (1H, s), 7.26-7.29 (2H, m), 7.15 (1H, t, J = 7.3 Hz), 6.99 (1H, d, J = 7.4 Hz), 6.94-6.84 (3H, m), 5.16 (1H, m), 4.38 (2H, q, J = 8.1 Hz), 2.41 (1H, m), 2.30 (3H, s), 1.71-1.59 (2H, m), 1.46 (3H, d, J = 6.6 Hz), 1.26 (1H, m) |
| Example 253 | $^1$H-NMR (300 MHz, CDCl$_3$) δ 8.28 (1H, d, J = 1.5 Hz), 7.28-7.20 (2H, m), 6.99 (1H, brd, J = 8.4 Hz), 6.70-6.55 (3H, m), 5.15 (1H, m), 4.40 (2H, q, J = 8.1 Hz), 2.49 (1H, m), 1.70 (1H, m), 1.62 (1H, m), 1.46 (3H, d, J = 6.6 Hz), 1.18 (1H, m) |
| Example 254 | $^1$H-NMR (300 MHz, CDCl$_3$) δ 8.27 (1H, d, J = 1.5 Hz), 7.26-7.20 (2H, m), 9.96 (1H, brd, J = 7.3 Hz), 6.67-6.53 (3H, m), 5.15 (1H, m), 4.39 (2H, q, J = 8.1 Hz), 2.44 (1H, m), 1.74-1.62 (1H, m), 1.46 (3H, d, J = 6.6 Hz), 1.22 (1H, m) |

TABLE 4-continued spectra data

| Example | spectra data |
|---|---|
| Example 260 | ¹H-NMR (300 MHz, CDCl₃) δ 8.29 (1H, s), 7.57-7.50 (2H, m), 7.30-7.20 (4H, m), 5.16 (1H, quintet, J = 6.6 Hz), 4.39 (2H, q, J = 8.1 Hz), 2.75-2.68 (1H, m), 2.45-2.37 (1H, m), 1.75-1.65 (2H, m), 1.44 (3H, d, J = 6.6 Hz), (signals due to two NH were not observed) |
| Example 261 | ¹H-NMR (300 MHz, CDCl₃) δ 8.33 (1H, s), 7.41 (2H, s), 7.31-7.25 (2H, m), 7.19-7.13 (2H, m), 7.05 (1H, m), 5.29 (1H, m), 3.97 (2H, d, J = 6.6 Hz), 2.79 (1H, m), 1.72 (1H, m), 1.61 (3H, d, J = 6.6 Hz), 1.42 (1H, m), 1.33 (1H, m), 0.81 (2H, m), 0.51 (2H, m) |
| Example 262 | ¹H-NMR (300 MHz, CDCl₃) δ 8.37 (1H, s), 7.32 (2H, d, J = 2.2 Hz), 7.22 (1H, dd, J = 8.8, 2.9 Hz), 7.17-7.10 (2H, m), 7.03 (1H, m), 5.30 (1H, m), 3.98 (2H, d, J = 6.6 Hz), 2.73 (1H, m), 1.77 (1H, m), 1.60 (3H, d, J = 6.6 Hz), 1.50-1.30 (2H, m), 0.82 (2H, m), 0.52 (2H, m) |
| Example 263 | ¹H-NMR (300 MHz, CDCl₃) δ 8.37 (1H, s), 7.30 (2H, s), 7.10-7.00 (2H, m), 6.80-8.70 (2H, m), 5.27 (1H, m), 3.97 (2H, d, J = 6.6 Hz), 3.92 (3H, s), 2.69 (1H, m), 1.81 (1H, m), 1.65 (1H, m), 1.60 (3H, d, J = 6.6 Hz), 1.42 (1H, m), 1.32 (1H, m), 0.81 (2H, m), 0.51 (1H, m) |
| Example 264 | ¹H-NMR (300 MHz, CDCl₃) δ 8.37 (1H, s), 7.30 (2H, s), 7.10-6.98 (2H, m), 6.75-6.65 (2H, m), 5.28 (1H, m), 3.97 (2H, d, J = 7.3 Hz), 3.90 (3H, s), 2.65 (1H, m), 1.82 (1H, m), 1.75 (1H, m), 1.59 (3H, d, J = 6.6 Hz), 1.45-1.30 (2H, m), 0.82 (2H, m), 0.51 (2H, m) |
| Example 265 | ¹H-NMR (300 MHz, CDCl₃) δ 8.38 (1H, s), 7.31 (2H, d, J = 1.5 Hz), 7.16 (1H, brd, J = 7.3 Hz), 6.80-6.65 (2H, m), 5.28 (1H, m), 3.98 (2H, d, J = 7.4 Hz), 2.50 (1H, m), 2.10 (1H, m), 1.77-1.60 (2H, m), 1.60 (3H, d, J = 7.3 Hz), 1.53 (1H, m), 1.42 (1H, m), 0.81 (2H, m), 0.52 (2H, m) |
| Example 266 | ¹H-NMR (300 MHz, CDCl₃) δ 8.38 (1H, s), 7.31 (1H, d, J = 1.5 Hz), 7.15 (1H, brd, J = 7.3 Hz), 6.80-6.70 (2H, m), 5.28 (1H, m), 3.98 (2H, d, J = 7.3 Hz), 2.53 (1H, m), 2.07 (1H, m), 1.68 (1H, m), 1.61 (3H, d, J = 6.6 Hz), 1.50-1.40 (2H, m), 0.80 (2H, m), 0.51 (2H, m) |
| Example 267 | ¹H-NMR (300 MHz, CDCl₃) δ 8.37 (1H, s), 7.35-7.28 (3H, m), 7.15 (1H, d, J = 8.0 Hz), 7.10-7.00 (2H, m), 5.26 (1H, m), 3.97 (2H, d, J = 7.3 Hz), 2.61 (1H, m), 2.47 (3H, s), 1.83 (1H, m), 1.73 (1H, m), 1.58 (3H, d, J = 6.6 Hz), 1.42 (1H, m), 1.33 (1H, m), 0.82 (2H, m), 0.51 (2H, m) |
| Example 268 | ¹H-NMR (300 MHz, CDCl₃) δ 8.33 (1H, s), 8.12 (1H, d, J = 1.5 Hz), 7.18 (1H, dd, J = 8.1, 2.2 Hz), 7.05 (1H, dd, J = 8.8, 5.9 Hz), 6.94 (1H, m), 8.57 (1H, brd, J = 8.1 Hz), 5.31 (1H, m), 4.79 (2H, q, J = 8.1 Hz), 2.65 (1H, m), 1.65-1.49 (2H, m), 1.53 (3H, d, J = 6.6 Hz), 1.23 (1H, m) |
| Example 269 | ¹H-NMR (300 MHz, CDCl₃) δ 8.33 (1H, s), 8.14 (1H, s), 7.11 (1H, dd, J = 8.1, 2.2 Hz), 7.03 (1H, dd, J = 8.1, 6.6 Hz), 6.90 (1H, m), 6.57 (1H, brd, J = 8.0 Hz), 5.30 (1H, m), 4.85-4.70 (2H, m), 2.57 (1H, m), 1.68 (1H, m), 1.52 (3H, d, J = 7.3 Hz), 1.52 (1H, m), 1.27 (1H, m) |
| Example 270 | ¹H-NMR (300 MHz, CDCl₃) δ 8.33 (1H, s), 8.12 (1H, s), 6.93 (1H, t, J = 8.0 Hz), 6.66-6.60 (2H, m), 6.51 (1H, brd, J = 8.1 Hz), 5.29 (1H, m), 4.79 (2H, q, J = 8.8 Hz), 3.81 (3H, s), 2.57 (1H, m), 1.67 (1H, m), 1.54 (1H, m), 1.52 (3H, d, J = 6.6 Hz), 1.23 (1H, m) |
| Example 271 | ¹H-NMR (300 MHz, CDl₃) δ 8.34 (1H, s), 8.12 (1H, s), 6.70-6.55 (3H, m), 5.29 (1H, m), 4.83-4.73 (2H, m), 2.42 (1H, m), 1.89 (1H, m), 1.58 (1H, m), 1.54 (3H, d, J = 6.6 Hz), 1.35 (1H, m) |
| Example 272 | ¹H-NMR (300 MHz, CDCl₃) δ 8.34 (1H, s), 8.12 (1H, s), 6.67-6.55 (3H, m), 5.29 (1H, m), 4.83-4.73 (2H, m), 2.35 (1H, m), 1.90 (1H, m), 1.61 (1H, m), 1.53 (3H, d, J = 7.3 Hz), 1.40 (1H, m) |
| Example 273 | ¹H-NMR (300 MHz, CDCl₃) δ 8.33 (1H, s), 8.11 (1H, d, J = 1.5 Hz), 7.21 (1H, t, J = 7.4 Hz), 7.04 (1H, d, J = 7.3 Hz), 6.94 (1H, s), 6.92 (1H, d, J = 8.8 Hz), 6.50 (1H, brd, J = 8.1 Hz), 5.28 (1H, m), 4.79 (2H, q, J = 7.3 Hz), 2.50 (1H, m), 2.36 (3H, s), 1.70-1.55 (2H, m), 1.50 (3H, d, J = 7.3 Hz) 1.23 (1H, m) |
| Example 274 | ¹H-NMR (300 MHz, CDCl₃) δ 8.30 (1H, s), 8.10 (1H, s), 7.17 (1H, t, J = 7.3 Hz), 7.02 (1H, d, J = 8.0 Hz), 6.89 (1H, s), 6.88 (1H, d, J = 7.3 Hz), 6.52 (1H, brd, J = 8.1 Hz), 5.28 (1H, m), 4.83-4.70 (2H, m), 2.43 (1H, m), 2.33 (3H, s), 1.69-1.55 (2H, m), 1.51 (3H, d, J = 6.6 Hz), 1.29 (1H, m) |
| Example 275 | ¹H-NMR (300 MHz, CDCl₃) δ 9.58 (1H, brs), 8.29 (1H, s), 7.54 (1H, d, J = 8.0 Hz), 7.29-7.26 (3H, m), 7.04 (1H, t, J = 8.0 Hz), 6.89 (1H, d, J = 6.6 Hz), 6.71 (1H, d, J = 8.0 Hz), 6.59 (1H, s), 5.19 (1H, m), 4.38 (2H, q, J = 8.0 Hz), 2.53 (1H, m), 1.75-1.65 (2H, m), 1.49 (3H, d, J = 6.6 Hz), 1.42 (1H, m). |
| Example 276 | ¹H-NMR (300 MHz, CDCl₃) δ 8.75 (1H, brs), 8.29 (1H, s), 7.53 (1H, d, J = 8.1 Hz), 7.30-7.20 (3H, m), 7.07-7.90 (2H, m), 6.85 (1H, d, J = 7.3 Hz), 6.58 (1H, s), 5.18 (1H, m), 4.39 (2H, q, J = 8.1 Hz), 2.72 (1H, m), 1.78 (1H, m), 1.58 (1H, m), 1.49 (3H, d, J = 6.6 Hz), 1.35 (1H, m) |
| Example 277 | ¹H-NMR (300 MHz, CDCl₃) δ 8.28 (1H, s), 1.25 (1H, brs), 7.29-7.23 (4H, m), 7.13 (1H, t, J = 8.0 Hz), 6.89 (1H, d, J = 7.3 Hz), 6.77-6.72 (2H, m), 5.21 (1H, m), 4.39 (2H, q, J = 7.3 Hz), 2.85 (1H, m), 1.83 (1H, m), 1.66 (1H, m), 1.48 (3H, d, J = 6.6 Hz), 1.38 (1H, m) |
| Example 278 | ¹H-NMR (300 MHz, CDCl₃) δ 8.28 (1H, d, J = 1.4 Hz), 8.22 (1H, brs), 8.10 (1H, d, J = 1.5 Hz), 7.25 (1H, m), 7.20 (1H, m), 7.10 (1H, t, J = 7.4 Hz), 6.71 (1H, d, J = 2.9 Hz), 6.51 (1H, brd, J = 8.1 Hz), 5.29 (1H, m), 4.81-4.70 (2H, m), 2.78 (1H, m), 1.79 (1H, m), 1.73 (1H, m), 1.50 (3H, d, J = 7.3 Hz), 1.44 (1H, m) |
| Example 279 | ¹H-NMR (300 MHz, CDCl₃) δ 6.30 (1H, d, J = 1.5 Hz), 8.25 (1H, brs), 8.11 (1H, s), 7.29-7.25 (2H, m), 7.13 (1H, t, J = 7.3 Hz), 6.75-6.70 (2H, m), 6.50 (1H, brd, J = 7.3 Hz), 5.30 (1H, m), 4.80-4.70 (2H, m), 2.86 (1H, m), 1.77 (1H, m), 1.64 (1H, m), 1.50 (3H, d, J = 6.6 Hz), 1.39 (1H, m) |
| Example 280 | ¹H-NMR (300 MHz, CDCl₃) δ 8.29 (1H, s), 7.32-7.10 (7H, m), 6.88 (1H, brs), 5.15 (1H, m), 4.40 (2H, q, J = 8.0 Hz), 2.53 (1H, m), 1.70 (1H, m), 1.660 (1H, m), 1.46 (3H, d, J = 6.6 Hz), 1.21 (1H, m) |
| Example 281 | ¹H-NMR (300 MHz, CDCl₃) δ 8.26 (1H, d, J = 1.5 Hz), 7.29-7.14 (5H, m), 7.06 (2H, d, J = 6.6 Hz), 6.89 (1H, brd, J = 8.0 Hz), 5.16 (1H, m), 4.38 (2H, q, J = 6.0 Hz), 2.45 (1H, m), 1.73-1.60 (2H, m), 1.46 (3H, d, J = 6.6 Hz), 1.25 (1H, m) |
| Example 282 | ¹H-NMR (300 MHz, CDCl₃) δ 8.30 (1H, d, J = 1.5 Hz), 8.09 (1H, s), 7.35-7.17 (3H, m), 7.10 (2H, d, J = 6.6 Hz), 6.48 (1H, brd, J = 7.3 Hz), 5.27 (1H, m), 4.75 (2H, q, J = 7.3 Hz), 2.50 (1H, m), 1.67-1.54 (2H, m), 1.47 (3H, d, J = 6.6 Hz), 1.21 (1H, m) |
| Example 283 | ¹H-NMR (300 MHz, CDCl₃) δ 8.27 (1H, d, J = 1.5 Hz), 8.07 (1H, d, J = 1.5 Hz), 7.26-2.14 (3H, m), 7.05 (2H, d, J = 7.5 Hz), 6.50 (1H, brd, J = 7.3 Hz), 5.25 (1H, m), 4.81-4.68 (2H, m), 2.45 (1H, m), 1.67-1.62 (2H, m), 1.48 (3H, d, J = 6.6 Hz), 1.26 (1H, m) |
| Example 284 | ¹H-NMR (300 MHz, CDCl₃) δ 8.12 (1H, d, J = 2.2 Hz), 7.61 (1H, dd, J = 8.8, 2.9 Hz), 7.31-7.18 (3H, m), 7.08 (2H, d, J = 6.6 Hz), 6.85 (1H, d, J = 8.1 Hz), 5.81 (1H, brd, J = 7.3 Hz), 5.13 (1H, m), 4.75 (2H, q, J = 8.8 Hz), 2.49 (1H, m), 1.65-1.55 (2H, m), 1.50 (3H, d, J = 6.6 Hz), 1.23 (1H, m) |
| Example 285 | ¹H-NMR (300 MHz, CDCl₃) δ 8.11 (1H, d, J = 2.2 Hz), 7.61 (1H, m), 7.29-7.06 (3H, m), 7.05 (2H, d, J = 6.6 Hz), 6.83 (1H, d, J = 8.8 Hz), 5.80 (1H, brd, J = 7.3 Hz), 5.13 (1H, m), 4.73 (2H, q, J = 8.8 Hz), 2.46 (1H, m), 1.67-1.55 (2H, m), 1.51 (3H, d, J = 6.6 Hz), 1.25 (1H, m) |

TABLE 4-continued spectra data

| Example | spectra data |
|---|---|
| Example 286 | ¹H-NMR (300 MHz, CDCl₃) δ 11.67 (1H, brs), 8.29 (1H, s), 8.11 (1H, s), 7.68-7.30 (3H, m), 7.23-7.12 (2H, m), 5.20 (1H, m), 4.77 (2H, q, J = 8.8 Hz), 2.60 (1H, m), 2.37 (1H, m), 1.66-1.56 (2H, m), 1.48 (3H, d, J = 6.6 Hz) |
| Example 287 | ¹H-NMR (300 MHz, CDCl₃) δ 11.78 (1H, s), 8.13 (1H, s), 7.91 (1H, m), 7.68 (1H, d, J = 8.8 Hz), 7.55 (1H, m), 7.40 (1H, m), 7.23-7.08 (2H, m), 6.83 (1H, m), 5.08 (1H, m), 4.84-4.67 (2H, m), 2.60 (1H, m), 2.37 (1H, m), 1.61 (2H, m), 1.46 (3H, d, J = 6.6 Hz) |
| Example 288 | ¹H-NMR (300 MHz, CDCl₃) δ 11.66 (1H, brs), 8.10 (1H, d, J = 2.2 Hz), 7.71 (1H, d, J = 7.3 Hz), 7.64 (1H, dd, J = 8.0, 2.2 Hz), 7.47 (1H, m), 7.37 (1H, m), 7.21-7.11 (2H, m), 6.79 (1H, d, J = 8.1 Hz), 5.07 (1H, m), 4.74 (2H, q, J = 8.8 Hz), 2.56 (1H, m), 2.32 (1H, m), 1.70-1.60 (2H, m), 1.48 (3H, d, J = 6.6 Hz) |
| Example 289 | ¹H-NMR (300 MHz, CDCl₃) δ 8.13 (1H, d, J = 2.9 Hz), 7.61 (1H, dd, J = 2.2 & 8.8 Hz), 7.45-7.35 (1H, m), 7.20-7.13 (1H, m), 6.97 (1H, dt, J = 2.2 & 8.8 Hz), 6.87 (1H, d, J = 8.8 Hz), 6.23 (1H, d, J = 7.3 Hz), 5.10 (1H, quintet, J = 7.3 Hz), 4.76 (2H, q, J = 8.8 Hz), 2.70-2.80 (1H, m), 2.36-2.29 (1H, m), 1.70-1.58 (2H, m), 1.50 (3H, d, J = 7.3 Hz) (a signal due to NH was not observed) |
| Example 290 | ¹H-NMR (300 MHz, CDCl₃) δ 7.97 (1H, d, J = 2.2 Hz), 7.46 (1H, dd, J = 2.2 & 8.8 Hz), 7.40-7.34 (1H, m), 7.17-7.10 (1H, m), 6.94 (1H, dt, J = 2.2 & 8.8 Hz), 6.70 (1H, d, J = 7.4 Hz), 6.62 (1H, d, J = 8.8 Hz), 5.05 (1H, quintet, J = 7.3 Hz), 4.62 (2H, q, J = 7.3 Hz), 2.62-2.53 (1H, m), 2.30-2.23 (1H, m), 1.77-1.69 (2H, m), 1.51 (3H, d, J = 7.3 Hz) (a signal due to NH was not observed) |
| Example 291 | ¹H-NMR (300 MHz, CDCl₃) δ 8.31 (1H, d, J = 2.9 Hz), 7.90-7.80 (1H, m), 7.63-7.50 (1H, m), 7.50-7.44 (2H, m), 7.32-7.24 (1H, m), 5.16 (1H, quintet, J = 7.3 Hz), 4.42 (2H, q, J = 8.1 Hz), 2.82-2.76 (1H, m), 2.52-2.45 (1H, m), 1.75-1.68 (2H, m), 1.45 (3H, d, J = 7.3 Hz) (a signal due to NH was not observed) |
| Example 292 | ¹H-NMR (300 MHz, DMSO-d₆) δ 9.74 (1H, s), 8.60 (1H, d, J = 8.1 Hz), 8.04 (1H, d, J = 2.9 Hz), 7.81 (2H, d, J = 8.4 Hz), 7.45 (2H, d, J = 8.1 Hz), 7.19 (1H, d, J = 8.4 Hz), 7.10 (1H, dd, J = 8.4, 2.9 Hz), 5.11 (1H, quintet, J = 7.0 Hz), 1.43 (3H, d, J = 7.0 Hz), 1.28 (9H, s), LCMS (Method A) m/z: M + 1 obs 299.2, tR = 3.21 min. |
| Example 307 | ¹H-NMR (300 MHz, CDCl₃) δ 8.23 (1H, s), 7.16 (2H, d, J = 1.4 Hz), 6.96-7.84 (3H, m), 6.74 (1H, d, J = 7.7 Hz), 5.12 (1H, m), 3.83 (2H, d, J = 7.3 Hz), 3.81 (3H, s), 2.44 (1H, m), 2.20 (3H, s), 1.82 (1H, m), 1.53 (1H, m), 1.44 (3H, d, J = 6.6 Hz), 1.28 (1H, m), 1.14 (1H, m), 0.67 (2H, m), 0.37 (2H, m) |
| Example 308 | ¹H-NMR (300 MHz, CDCl₃) δ 8.21 (1H, s), 7.15 (2H, s), 6.98-6.79 (3H, m), 6.71 (1H, d, J = 8.1 Hz), 5.12 (1H, m), 3.82 (2H, d, J = 7.3 Hz), 3.79 (3H, s), 2.38 (1H, m), 2.17 (3H, s), 1.66-1.53 (2H, m), 1.44 (3H, d, J = 6.6 Hz), 1.27 (1H, m), 1.19 (1H, m), 0.67 (2H, m), 0.36 (2H, m) |
| Example 309 | ¹H-NMR (300 MHz, CDCl₃) δ 8.30 (1H, s), 8.09 (1H, s), 6.92 (1H, d, J = 7.9 Hz), 6.87 (1H, s), 6.74 (1H, d, J = 7.9 Hz), 6.44 (1H, brd, J = 7.3 Hz), 5.25 (1H, m), 4.76 (2H, q, J = 8.8 Hz), 3.81 (3H, s), 2.44 (1H, m), 2.20 (3H, s), 1.58-1.50 (2H, m), 1.47 (3H, d, J = 6.6 Hz), 1.16 (1H, m) |
| Example 310 | ¹H-NMR (300 MHz, CDCl₃) δ 8.28 (1H, s), 8.08 (1H, s), 6.87 (1H, d, J = 8.1 Hz), 6.82 (1H, s), 6.71 (1H, d, J = 8.1 Hz), 6.47 (1H, brd, J = 7.3 Hz), 5.26 (1H, m), 4.81-4.69 (2H, m), 3.79 (3H, s), 2.38 (1H, m), 2.17 (3H, s), 1.62-1.53 (2H, m), 1.48 (3H, d, J = 6.6 Hz), 1.21 (1H, m) |
| Example 316 | ¹H-NMR (300 MHz, CDCl₃) δ 8.79 (1H, brs), 8.24 (1H, s), 7.54 (1H, d, J = 8.0 Hz), 7.178 (2H, d, J = 1.4 Hz), 7.08-7.02 (2H, m), 6.85 (1H, d, J = 6.6 Hz), 6.58 (1H, m), 5.14 (1H, m), 3.84 (2H, d, J = 7.4 Hz), 2.72 (1H, m), 1.79 (1H, m), 1.59 (1H, m), 1.49 (3H, d, J = 6.6 Hz), 1.36 (1H, m), 1.28 (1H, m), 0.68 (2H, m), 0.37 (2H, m) |
| Example 317 | ¹H-NMR (300 MHz, CDCl₃) δ 9.77 (1H, brs), 8.24 (1H, s), 7.54 (1H, d, J = 8.0 Hz), 7.26 (1H, m), 7.21 (2H, d, J = 1.4 Hz), 7.04 (1H, t, J = 7.3 Hz), 6.89 (1H, d, J = 6.6 Hz), 6.71 (1H, brd, J = 8.1 Hz), 6.59 (1H, m), 5.17 (1H, m), 3.82 (2H, d, J = 6.6 Hz), 2.52 (1H, m), 1.73-1.62 (2H, m), 1.48 (3H, d, J = 6.6 Hz), 1.45 (1H, m), 1.27 (1H, m), 0.66 (2H, m), 0.35 (2H, m) |
| Example 318 | ¹H-NMR (300 MHz, CDCl₃) δ 8.31 (1H, s), 8.08 (1H, s), 7.31-7.26 (2H,, m), 6.96 (1H, t, J = 7.4 Hz), 6.89 (2H, t, J = 8.3 Hz), 6.47 (1H, d, J = 7.3 Hz), 5.23 (1H, m), 4.75 (2H, q, J = 8.8 Hz), 4.04 (1H, dd, J = 10.3, 2.9 Hz), 3.84 (1H, dd, J = 10.3, 6.6 Hz), 1.89 (1H, m), 1.52 (1H, m), 1.49 (3H, d, J = 6.6 Hz), 1.24 (1H, m), 0.89 (1H, m) |
| Example 319 | ¹H-NMR (300 MHz, CDCl₃) δ 8.31 (1H, s), 8.08 (1H, s), 7.28-7.23 (2H, m), 6.94 (1H, t, J = 6.6 Hz), 6.84 (2H, d, J = 8.8 Hz), 6.50 (1H, d, J = 7.4 Hz), 5.23 (1H, m), 4.77 (2H, q, J = 8.0 Hz), 3.99 (1H, dd, J = 10.3, 5.9 Hz), 3.82 (1H, dd, J = 10.3, 6.6 Hz), 1.84 (1H, m), 1.52 (1H, m), 1.48 (3H, d, J = 6.6 Hz), 1.31 (1H, m), 0.93 (1H, m) |
| Example 320 | ¹H-NMR (300 MHz, CDCl₃) δ 8.11 (1H, d, J = 2.9 Hz), 7.61 (1H, dd, J = 8.8, 2.9 Hz), 7.31-7.26 (2H, m), 6.96 (1H, t, J = 7.3 Hz), 6.90-6.82 (3H, m), 5.82 (1H, brd, J = 7.3 Hz), 5.11 (1H, m), 4.75 (2H, q, J = 8.8 Hz), 4.08 (1H, dd, J = 10.3, 5.1 Hz,), 3.79 (1H, dd, J = 10.3, 4.5 Hz), 1.88 (1H, m), 1.51 (3H, d, J = 6.6 Hz), 1.45 (1H, m), 1.26 (1H, m), 0.89 (1H, m) |
| Example 321 | ¹H-NMR (300 MHz, CDCl₃) δ 8.11 (1H, d, J = 2.2 Hz), 7.59 (1H, dd, J = 8.0, 1.9 Hz), 7.29-7.24 (2H, m), 6.95 (1H, t, J = 7.3 Hz), 6.87-6.82 (3H, m), 5.80 (1H, brd, J = 8.1 Hz), 5.11 (1H, m), 4.75 (2H, q, J = 8.8 Hz), 4.05 (1H, dd, J = 10.2, 5.9 Hz), 3.61 (1H, dd, J = 10.2, 7.4 Hz), 1.84 (1H, m), 1.51 (3H, d, J = 6.6 Hz), 1.45 (1H, m), 1.30 (1H, m), 0.93 (1H, m) |
| Example 322 | ¹H-NMR (300 MHz, CDDCl₃) δ 8.99 (1H, brs), 8.32 (1H, s), 8.14 (1H, s), 7.53 (1H, d, J = 8.1 Hz), 7.24 (1H, m), 7.04 (1H, t, J = 7.3 Hz), 6.85 (1H, d, J = 7.3 Hz), 6.58 (1H, t, J = 2.2 Hz), 6.51 (1H, brd, J = 7.4 Hz), 5.29 (1H, m), 4.84-4.70 (2H, m), 2.55 (1H, m), 1.71-1.61 (2H, m), 1.52 (3H, d, J = 6.6 Hz), 1.44 (1H, m) |
| Example 323 | ¹H-NMR (300 MHz, CDCl₃) δ 8.71 (1H, brs), 8.31 (1H, s), 8.11 (1H, s), 7.54 (1H, d, J = 7.3 Hz), 7.06 (1H, t, J = 10.3 Hz), 6.83 (1H, d, J = 7.3 Hz), 6.64-6.55 (3H, m), 5.28 (1H, m), 4.77 (2H, q, J = 8.1 Hz), 2.73 (1H, m), 1.75 (1H, m), 1.58 (1H, m), 1.52 (3H, d, J = 6.6 Hz), 1.37 (1H, m) |
| Example 324 | ¹H-NMR (300 MHz, CDCl₃) δ 8.24 (1H, s), 8.00 (1H, d, J = 8.0 Hz), 7.92 (1H, d, J = 8.8 Hz), 7.75 (1H, d, J = 8.1 Hz), 7.66 (1H, t, J = 7.3 Hz), 7.45 (1H, t, J = 7.3 Hz), 7.33 (1H, d, J = 8.0 Hz), 7.22 (2H, d, J = 1.4 Hz), 6.96 (1H, brd, J = 7.3 Hz), 5.18 (1H, m), 4.36 (2H, q, J = 8.0 Hz), 2.73 (1H, m), 2.33 (1H, m), 1.70 (2H, t, J = 7.3 Hz), 1.48 (3H, d, J = 6.5 Hz) |
| Example 325 | ¹H-NMR (300 MHz, CDCl₃) δ 8.29 (1H, t, J = 2.2 Hz), 8.04 (1H, d, J = 8.0 Hz), 7.93 (1H, d, J = 8.8 Hz), 7.77 (1H, d, J = 8.1 Hz), 7.66 (1H, m), 7.39 (1H, d, J = 8.1 Hz), 7.30-7.22 (2H, m), 6.99 (1H, brd, J = 7.3 Hz), 5.18 (1H, m), 4.40 (2H, q, J = 8.0 Hz), 2.78 (1H, m), 2.36 (1H, m), 1.65 (2H, t, J = 7.3 Hz), 1.46 (3H, d, 6.6 Hz) |
| Example 326 | ¹H-NMR (300 MHz, CDCl₃) δ 8.20 (1H, s), 7.19-7.11 (3H, m), 6.99-6.85 (4H, m), 5.12 (1H, m), 3.82 (2H, d, J = 7.3 Hz), 2.43 (1H, m), 2.30 (3H, s), 1.65 (1H, m), 1.49 (1H, m), 1.45 (3H, d, J = 6.6 Hz), 1.40-1.20 (2H, m), 0.66 (2H, m), 0.35 (2H, m) |
| Example 327 | ¹H-NMR (300 MHz, CDCl₃) δ 8.29 (1H, s), 7.26-7.21 (2H, m), 7.03-76.92 (2H, m), 6.85 (1H, m), 6.66 (1H, m), 5.17 (1H, m), 4.40 (2H, q, J = 8.1 Hz), 2.64 (1H, m), 1.75 (1H, m), 1.60 (1H, m), 1.47 (3H, d, J = 6.6 Hz), 1.22 (1H, m) |
| Example 328 | ¹H-NMR (300 MHz, CDCl₃) δ 8.38 (1H, s), 7.26-7.21 (2H, m), 6.99-6.89 (2H, m), 6.82 (1H, m), 6.64 (1H, m), 5.17 (1H, m), 4.39 (2H, q, J = 8.0 Hz), 2.58 (1H, m), 1.75 (1H, m), 1.65 (1H, m), 1.47 (3H, 6.6 Hz), 1.26 (1H, m) |

TABLE 4-continued spectra data

| Example | spectra data |
|---|---|
| Example 345 | $^1$H-NMR (300 MHz, CDCl$_3$) δ 8.30 (1H, m), 7.48-7.17 (7H, m), 6.90 (1H, d, J = 7.3 Hz), 6.82 (1H, m), 6.74 (1H, s), 6.73 (1H, d, J = 7.3 Hz), 5.17 (1H, m), 5.07 (2H, s), 4.41 (2H, q, J = 8.0 Hz), 2.50 (1H, m), 1.70 (1H, m), 1.60 (1H, m), 1.46 (3H, d, J = 6.6 Hz), 1.21 (1H, m) |
| Example 346 | $^1$H-NMR (300 MHz, CDCl$_3$) δ 8.28 (1H, d, J = 1.5 Hz), 7.45-7.15 (7H, m), 6.90 (1H, d, J = 7.3 Hz), 6.80 (1H, m), 6.71 (1H, s), 6.69 (1H, d, J = 7.3 Hz), 5.17 (1H, m), 5.04 (2H, s), 4.40 (2H, q, J = 8.1 Hz), 2.44 (1H, m), 1.72-1.60 (2H, m), 1.47 (3H, d, J = 6.6 Hz), 1.26 (1H, m) |
| Example 347 | $^1$H-NMR (300 MHz, CDCl$_3$) δ 8.29 (1H, s), 7.45-7.22 (6H, m), 7.04 (2H, d, J = 8.8 Hz), 6.91 (2H, d, J = 8.8 Hz), 6.87 (1H, m), 5.17 (1H, m), 5.07 (2H, s), 4.40 (2H, q, J = 8.1 Hz), 2.48 (1H, m), 1.66-1.52 (2H, m), 1.46 (3H, d, J = 6.6 Hz), 1.17 (1H, m) |
| Example 348 | $^1$H-NMR (300 MHz, CDCl$_3$) δ 8.28 (1H, m), 7.47-7.21 (6H, m), 7.01 (2H, d, J = 8.0 Hz), 6.89 (1H, m), 6.88 (2H, d, J = 8.0 Hz), 5.17 (1H, m), 5.05 (2H, s), 4.40 (2H, q, J = 8.1 Hz), 2.44 (1H, m), 1.69-1.60 (2H, m), 1.47 (3H, d, J = 6.6 Hz), 1.22 (1H, m) |
| Example 349 | $^1$H-NMR (300 MHz, CDCl$_3$) δ 8.31 (1H, s), 7.28-7.25 (2H, m), 6.95-6.87 (2H, m), 6.65-6.58 (2H, m), 5.18 (1H, m), 4.41 (2H, q, J = 8.1 Hz), 3.80 (3H, s), 2.56 (1H, m), 1.69 (1H, m), 1.54 (1H, m), 1.48 (3H, d, J = 6.6 Hz), 1.20 (1H, m) |
| Example 350 | $^1$H-NMR (300 MHz, CDCl$_3$) δ 8.29 (1H, m), 7.31-7.25 (2H, m), 6.93-8.86 (2H, m), 6.63-6.54 (2H, m), 5.19 (1H, m), 4.41 (2H, q, J = 8.0 Hz), 3.77 (3H, s), 2.51 (1H, m), 1.69 (1H, m), 1.59 (1H, m), 1.48 (3H, d, J = 6.6 Hz), 1.24 (1H, m) |
| Example 351 | $^1$H-NMR (300 MHz, CDCl$_3$) δ 8.30 (1H, m), 7.29-7.26 (2H, m), 7.15 (1H, m), 7.03 (1H, m), 7.00-6.88 (2H, m), 5.21 (1H, m), 4.41 (2H, q, J = 8.1 Hz), 2.66 (1H, m), 1.65-1.53 (2H, m), 1.49 (3H, d, J = 6.6 Hz), 1.20 (1H, m) |
| Example 352 | $^1$H-NMR (300 MHz, CDCl$_3$) δ 8.30 (1H, m), 7.38-6.87 (6H, m), 5.20 (1H, m), 4.41 (2H, q, J = 8.1 Hz), 2.59 (1H, m), 1.73-1.47 (2H, m), 1.46 (3H, d, J = 6.6 Hz), 1.26 (1H, m) |
| Example 353 | $^1$H-NMR (300 MHz, CDCl$_3$) δ 8.29 (1H, m), 7.33-7.11 (7H, m), 6.90 (1H, d, J = 7.3 Hz), 5.18 (1H, m), 4.41 (2H, q, J = 8.0 Hz), 2.53 (1H, m), 1.72 (1H, m), 1.60 (1H, m), 1.46 (3H, d, J = 6.6 Hz), 1.22 (1H, m) |
| Example 354 | $^1$H-NMR (300 MHz, CDCl$_3$) δ 8.27 (1H, m), 7.29-7.06 (7H, m), 6.90 (1H, d, J = 7.3 Hz), 5.18 (1H, m), 4.39 (2H, q, J = 8.0 Hz), 2.47 (1H, m), 1.73-1.61 (2H, m), 1.47 (3H, d, J = 6.6 Hz), 1.27 (1H, m) |
| Example 357 | $^1$H-NMR (300 MHz, CDCl$_3$) δ 8.27 (1H, d, J = 2.2 Hz), 7.27-7.14 (3H, m), 6.89 (1H, brd, J = 7.3 Hz), 6.74-6.62 (3H, m), 5.16 (1H, m), 4.39 (2H, q, J = 8.1 Hz), 3.78 (3H, s), 2.44 (1H, m), 1.72-1.59 (2H, m), 1.46 (3H, d, J = 7.3 Hz), 1.26 (1H, m) |

Pharmacological Assays

In Vitro Human T-Type Ca$^{2+}$ Channel Activity

T-type calcium channel activity of compounds was determined by methodology well known in the art, including the "Ca$^{2+}$ influx Assay" and the "T-type Ca$^{2+}$ Blocker Voltage-Clamp Assay".

Ca$^{2+}$ Influx Assay

Inhibition of T-type calcium channel activity was determined by cell-based fluorescent Ca$^{2+}$ influx assay, in which potassium ionophore was added to decrease resting membrane potential and extra-cellular high-K$^+$ stimulation was used to modulate the membrane potential of the cell. The changes in fluorescent signal were monitored by the cell imaging technology by Hamamatsu Photonics's Functional Drug Screening System (FDSS).

Cell Maintenance:

HEK 293 cells expressing the human T-type channel alpha-1H (CaV 3.2) were maintained in DMEM supplemented with 10% heat-inactivated FBS, 100 units/ml Penicillin, 100 microg/ml Streptomycin, 150 microg/ml Zeocin, 300 microg/ml Geneticin. The cells were grown in a 5% CO$_2$ humidified incubator at 37° C.

Assay Protocol:

Day One:
1. Cells were harvested and seeded in a poly-D-lysine coated black-sided clear bottom 384-well plate at density of 10,000 cells/well at 24 hours prior to assay.
2. Incubate at 37° C. in 5% CO$_2$.

Day Two:
1. Wash each well with assay buffer (see below) and leave 20 µl using plate washer, ELx-405 Select CVV (BIO-TEK).
2. Add 20 µL of assay buffer containing 6 µM Fluo4-AM (Molecular Probes) and 0.005% Plutonic F-127 to each well.
3. Incubate the plate at 37° C. for 1 hour.
4. Wash each well assay buffer (see below) and leave 20 µl using plate washer, ELx-405 Select CW (BSO-TEK).
5. Add 10 µl of compound solution into each well by FDSS6000 and leave the plate for 4.5 min, and then add 10 µl of potassium ionophore solution.
6. Add 20 µl of high-K$^+$ depolarizing solution (see below) and monitor the change of fluorescent signal.

The IC$_{50}$ values for compounds of the present invention were determined from 7-point dose-response studies. Curves were generated using the average of duplicate wells for each data point. Finally, the IC$_{50}$ values are calculated with the best-fit dose curve determined by XLfit.

TABLE 5

Assay buffer (pH 7.4, Adjusted by HCl)

| Regent | Final conc. (mM) | Volume (mL) |
|---|---|---|
| NMDG (1.4M) | 140 | 100 |
| KCl (1.17M) | 5 | 4.25 |
| MgCl$_2$ (80 mM) | 1 | 12.5 |
| Glucose (0.5M) | 5 | 10 |
| CaCl$_2$ (1M) | 1 | 1 |
| HEPES buffer (1M) | 16 | 16 |
| MQ water | — | 856.25 |

TABLE 6

High-K$^+$ depolarizing solution

| Regent | Final conc. (mM) | Volume (mL) |
|---|---|---|
| KCl (1.17M) | 90 | 83.3 |
| MgSO$_4$ (1M) | 0.5 | 0.5 |
| KH$_2$PO$_4$ (1M) | 1.2 | 1.2 |
| Glucose (0.5M) | 11.7 | 23.4 |
| CaCl$_2$ (1M) | 2 | 2 |

TABLE 6-continued

High-K+ depolarizing solution

| Regent | Final conc. (mM) | Volume (mL) |
|---|---|---|
| HEPES buffer (1M) | 18.4 | 18.4 |
| MQ water | — | 871.2 |

Electrophysiology Assay for T-Type $Ca^{2+}$

In a typical experiment ion channel function from HEK 293 cells expressing the human T-type channel alpha-1H (CaV 3.2) is recorded to determine the activity of compounds in blocking the calcium current mediated by the T-type channel. Cells expressing the T-type channels were grown in growth media which comprised: DMEM, 10% heat-inactivated FBS, 100 units/ml Penicillin, 100 mg/ml Streptomycin, 150 mg/ml Zeocin, 300 mg/ml Geneticin. T-type Ca channel expressing HEK293 cells were dissociated by 0.05% Trypsine-EDTA, and then seeded on cover glass for 24 hr.

Glass pipettes are pulled to a tip diameter of 1-2 micrometer on a pipette puller. The pipettes are filled with the intracellular solution and a chloridized silver wire is inserted along its length, which is then connected to the headstage of the voltage-clamp amplifier. The extracellular recording solution consists of (mM): 150 mM NMDG, 2 mM $CaCl_2$, 10 mM HEPES, 10 mM Glucose, pH 7.4. The internal solution consists of (mM): 110 CsF, 10 EGTA, 10 HEPES, 3 ATP-Mg, 0.6 GTP pH 7.2; Upon insertion of the pipette tip into the bath, the series resistance is noted (acceptable range is between 1-4 megaohm). The junction potential between the pipette and bath solutions is zeroed on the amplifier. The cell is then patched, the patch broken, and, after compensation for series resistance (>=80%), the voltage protocol is applied while recording the whole cell $Ca^{2+}$ current response. Voltage protocols: (1) –80 mV holding potential every 30 seconds pulse to –20 mV for 100 msec duration; the effectiveness of the drug in inhibiting the current mediated by the channel is measured directly from measuring the reduction in peak current amplitude initiated by the voltage shift from –80 mV to –20 mV; (2), –140 mV holding potential every 30 seconds pulse to –20 mV for 100 msec duration; the effectiveness of the drug in inhibiting the current mediated by the channel is measured directly from measuring the reduction in peak current amplitude initiated by the shift in potential from –140 mV to –20 mV. The difference in block at the two holding potentials was used to determine the effect of drug at differing levels of inactivation induced by the level of resting state potential of the cells. After obtaining control baseline calcium currents, extracellular solutions containing increasing concentrations of a test compound are washed on. Once steady state inhibition at a given compound concentration is reached, a higher concentration of compound is applied. % inhibition of the peak inward control $Ca^{2+}$ current during the depolarizing step to –20 mV is plotted as a function of compound concentration.

(3) The normalized steady-steady inactivation curve is constructed using 5 sec (for vehicle) or 60 sec (for drugs) conditioning pulse to different potentials followed immediately by the test pulse to –20 mV. Peak currents are plotted as fraction of the maximum current at the conditioning potentials ranging from –140 mV to –20 mV, V1/2 or k values are estimated front Boltzmann fits. The affinity of drugs to resting state of T-type Ca channels ($K_{resting}$ or Kr) is assessed by 30 msec test pulse from a negative holding potential of –140 mV, where virtually all channels are in the resting state. $K_r$ value is calculated by a conventional 1:1 binding model:

$K_{resting}(Kr)=\{[drug]Imax,drug/(Imax,control-Imax, drug)\}$ where $K_{resting}$ ($=K_r$) is a dissociation constant for the resting state and [drug] is compound concentration, $I_{max}$, control and $I_{max}$, drug are peak currents in the absence and presence of compound, respectively.

The affinity of drug to inactivated state of T-type Ca channels ($K_{inact}$ or Ki) is estimated from the shift of the availability curve by compound. Interaction of the compound with the inactivated state channel is evaluated as suggested by Bean et. al (1983 Journal of general pharmacology 81, 613-) by fitting experimental points of the compound-induced steady-state inactivation mid-point potential shifts to the equation:

$K_{inact}(Ki)=\{[drug]/((1+[drug]/Kr)*exp(-\Delta V/k)-1)\}$ [Math.1]

where $K_{inact}$ ($=K_i$) is a dissociation constant for the inactivated state. $\Delta V$ is the compound-induced voltage shift of half maximal voltage of Boltzmann curve and k is the slope factor of compound.

All examples of the invention have an $IC_{50}$=<1 microM in the $Ca^{2+}$ Influx Assay or $IC_{50}$=<3 microM in $Na_{v1.3}$ FRET Assays or $Na_{v1.7}$ FRET Assays.

Especially, Example 3, Example 33, Example 57, Example 104, Example 106, Example 108, Example 110, Example 111, Example 124, Example 125, Example 133, Example 134, Example 147, Example 167, Example 168, Example 169, Example 171, Example 172, Example 181, Example 182, Example 190, Example 193, Example 194, Example 202, Example 203, Example 204, Example 205, Example 206, Example 207, Example 208, Example 210, Example 211, Example 212, Example 213, Example 222, Example 223, Example 224, Example 225, Example 226, Example 227, Example 228, Example 229, Example 237, Example 240, Example 243, Example 244, Example 245, Example 246, Example 248, Example 250, Example 251, Example 253, Example 258, Example 259, Example 260, Example 261, Example 263, Example 266, Example 267, Example 268, Example 270, Example 271, Example 273, Example 275, Example 276, Example 277, Example 279, Example 280, Example 282, Example 284, Example 286, Example 287, Example 289, Example 294, Example 296, Example 305, Example 306, Example 307, Example 309, Example 310, Example 316, Example 317, Example 318, Example 320, Example 322, Example 323, Example 325, Example 327, and Example 346 of the invention have an $IC_{50}$=<0.3 microM in the $Ca^{2+}$ Influx assay.

In Vitro Human Voltage Gated Sodium Channels Activity

Voltage gated sodium channels activity of compounds was determined by methodology well known in the art.

The ability of the aryl substituted carboxamid derivatives of the formula (I) to inhibit the $Na_{v1.3}$, $Na_{v1.7}$ and $Na_{v1.5}$ channels was measured by FRET assay and electrophysiology assay described below.

FRET Assay for Navs

This screen, is used to determine the effects of compounds on human $Na_{v1.3}$, human $Na_{v1.7}$, and human $Na_{v1.5}$ channels, utilising the cell imaging technology by Hamamatsu Photonics's Functional Drug Screening System (FDSS). This experiment is based on FRET (Fluorescence Resonance Energy Transfer) and uses two fluorescent molecules. The first molecule, Oxonol (DiSBAC2(3)), is a highly fluorescent, negatively charged, hydrophobic ion that "senses" the trans-membrane electrical potential. In response to changes in membrane potential, it ears rapidly redistribute between two binding sites on opposite sides of the plasma membrane. The voltage dependent redistribution is transduced into a ratiometric fluorescent readout via a second fluorescent molecule (Coumarin (CC2-DMPE)) that binds specifically to one face of the plasma membrane and functions as a FRET partner to the mobile voltage-sensing ion. To enable the assay to work, the channels have to be pharmacologically held in the open state. This is achieved by treating the cells with veratridine.

Cell Maintenance:

Each HEK293 cells expressing human $Na_{v1.3}$ channels and HEK293 cells expressing human $Na_{v1.5}$ channels were grown in T225 flasks, in a 5% $CO_2$ humidified incubator to about 80% confluence. Media composition consisted of Dulbecco's Modified Eagle Medium (high glucose), 10% fetal calf serum (FCS), 100 units/ml Penicillin, 100 microg/ml Streptomycin and 500 microg/ml Geneticine.

CHO cells expressing human $Na_{v1.7}$ channels were grown in T225 flasks, in a 5% $CO_2$ humidified incubator to about 80% confluence. Media composition consisted of HAM/F12 with Glutamax I 10% fetal calf serum (FCS), 100 units/ml Penicillin and 100 microg/ml Hygromycin.

Protocol:

Seed each cell lines ($1.5 \times 10^4$ cells/well) into poly-D-lysine coated 384-well plates prior to experimentation.

Incubate at 37° C. in 5% $CO_2$ for 24 hours.

Wash each well with buffer #1 (140 mM NaCl, 4.5 mM KCl, 10 mM D-Glucose, 2 mM $CaCl_2$, 1 mM $MgCl_2$, 10 mM HEPES, pH 7.4 adjusted with NaOH) twice using plate washer.

Add 1st loading solution containing 5 µM CC2-DMPE and 0.02% Pluronic F-127 in buffer #1.

Incubate the plate at room temperature in dark for 0.5 hours.

Wash each well with buffer #2 (160 mM Choline, 10 mM D-Glucose, 0.1 mM $CaCl_2$, 1 mM $MgCl_2$, 10 mM HEPES, pH 7.4 adjusted with KOH) twice using plate washer.

Add 2nd loading solution containing 15 µM DiSBAC2(3), 0.5 mM VABSC-1, 10 µM veratridine and 0.004% Pluronic F-127 in buffer #2.

Add compound solutions into the assay plate and leave the plate for 30 minutes under the dark at room temperature.

Measure by FDSS.

The data was analyzed and reported as normalized ratios of intensities measured in the 465 nm and 575 nm channels. The process of calculating these ratios was performed as follows:

"F14658"=the mean of fluorescence intensity as baseline (before Na+ ligand addition) at 465 nm.

"F1575B"=the mean of fluorescence intensity as baseline (before Na+ ligand addition) at 575 nm "FI1465Max"=maximum fluorescence intensity at 465 nm after Na+ stimulation "FI1575Min"=minimum fluorescence intensity at 575 nm after Na+ stimulation "FR"=fluorescence ratio=(FI465Max/FI575Min)-(FI465B/FI575B)

$$\text{Inhibition (\%)} = 100 - \frac{(FR \text{ of each well}) - (\text{median } FR \text{ in positive controls})}{(\text{median } FR \text{ in negative controls}) - (\text{median } FR \text{ in negative controls})} \times 100 \quad [\text{Math. 2}]$$

This analysis is performed using a computerized specific program designed for FDSS generated data. Fluorescence ratio values are plotted using XLfit to determine an IC50 value for each compound.

Electrophysiology Assay for Navs

Whole cell patch clamp recording was used to assess the efficacy or selectivity of Na channel blocker on human $Na_{v1.3}$ (hSCN3A) expressing HEK293 cells or human $Na_{v1.7}$ (hSCN9A) expressing CHO cells. Human $Na_{v1.3}$ expressing HEK293 cells were grown in growth media which comprised: DMEM, 10% heat-inactivated FBS (Hyclone Laboratories Inc), 100 microgram/ml Penicillin/100 U/ml Streptomycin, 150 microgram/ml Zeocin, 3 microgram/ml Geneticin, Human $Na_{v1.7}$ expressing CHO cells were grown in growth media which comprised: HAM/F-12, 9% heat-inactivated FBS (Hyclone Laboratories Inc), 1.00 microgram/ml Penicillin/100 U/ml Streptomycin, 100 microgram/ml Hygromycin.

Na channel expressing cells were dissociated by 0.05% Trypsine-EDTA, and then seeded on cover glass for 24-48 hr.

Glass pipettes were pulled to a tip diameter of 1-2 micrometer on a pipette puller. The pipettes were filled with the intracellular solution and a chloridized silver wire was inserted along its length, which was then connected to the headstage of the voltage-clamp amplifier (Axon Instruments or HEKA electronik). The extracellular recording solution consists of (mM): 140 NaCl, 5 KCl, 2 $CaCl_2$, 1 $MgCl_2$, 10 HEPES, 10 Glucose, pH 7.4 adjusted with NaOH. The internal solution consists of (mM): 120 CsF, 15 NaCl, 10 EGTA, 10 HEPES, pH 7.2 adjusted with CsOH; Upon insertion of the pipette tip into the bath, the pipette resistance was noted (acceptable range is between 1-3 megaohm). The junction potential between the pipette and bath solutions was zeroed on the amplifier. After establishing the whole-cell configuration, approximately 10 minutes were allowed for the pipette solution to equilibrate within the cell before beginning recording. Currents were lowpass filtered between 2-5 kHz and digitally sampled at 10 kHz. Series resistance was compensated (>80%) and was monitored continuously.

The normalized steady-steady inactivation curve was constructed using 5 sec (for vehicle) or 60 sec (for drugs) conditioning pulse to different potentials followed immediately by the test pulse to 0 mV. Peak currents were plotted as fraction of the maximum current at the conditioning potentials ranging from −120 mV to −40 mV. V1/2 or k values were estimated from Boltzmann fits. The affinity of drugs to resting state of Na channels ($K_{resting}$ or Kr) was assessed by 30 msec test pulse from a negative holding potential of −120 mV, where virtually all channels are in the resting state. $K_r$ value was calculated by a conventional 1:1 binding model:

$$K_{resting}(Kr) = \{[\text{drug}]I\text{max,drug}/(I\text{max,control}-I\text{max, drug})\}$$

where $K_{resting}$ (=$K_r$) is a dissociation constant for the testing state and [drug] is compound concentration. $I_{max}$, control and $I_{max}$, drug are peak currents in the absence and presence of compound, respectively.

The affinity of drug to inactivated state of Na channels ($K_{inact}$ or Ki) was estimated from the shift of the availability curve by compound. Interaction of the compound with the channel on inactivated state was evaluated by the following equation:

$$K_{inact}(Ki)=\{[drug]/((1+[drug]/Kr)*\exp(-\Delta V/k)-1)\} \quad \text{[Math.3]}$$

where $K_{inact}$ (=$K_i$) is a dissociation constant for the inactivated state. $\Delta V$ is the compound-induced voltage shift of half maximal voltage of Boltzmann curve and k is the slope factor on presence of compound.

The compounds of the examples were tested in the above-described assay. The results are as follows:

All examples of the invention have an $IC_{50}$=<1 microM in the $Ca^{2+}$ Influx Assay or $IC_{50}$=<3 microM in $Na_{v1.3}$ FRET or $Na_{v1.7}$ FRET Assays.

Especially, Example 1, Example 4, Example 5, Example 6, Example 9, Example 10, Example 11, Example 12, Example 13, Example 14, Example 15, Example 16, Example 18, Example 20, Example 21, Example 22, Example 23, Example 28, Example 29, Example 32, Example 36, Example 37, Example 41, Example 42, Example 44, Example 45, Example 48, Example 51, Example 52, Example 53, Example 54, Example 56, Example 59, Example 62, Example 63, Example 64, Example 65, Example 66, Example 67, Example 68, Example 69, Example 70, Example 74, Example 75, Example 76, Example 77, Example 78, Example 80, Example 82, Example 85, Example 86, Example 87, Example 88, Example 89, Example 90, Example 91, Example 92, Example 93, Example 94, Example 95, Example 99, Example 102, Example 103, Example 113, Example 130, Example 131, Example 138, Example 143, Example 146, Example 150, Example 151, Example 152, Example 154, Example 156, Example 157, Example 158, Example 161, Example 162, Example 175, Example 184, Example 192, Example 195, Example 196, Example 197, Example 201, Example 209, Example 214, Example 220, Example 238, Example 241, Example 269, Example 274, Example 285, Example 308, Example 313, Example 314, Example 315, Example 321, Example 324, Example 326, Example 328, Example 332, Example 333, Example 337, Example 338, Example 339, Example 341, Example 345, Example 359, Example 377, Example 424, Example 3, Example 57, Example 104, Example 124, Example 125, Example 147, Example 169, Example 182, Example 194, Example 202, Example 204, Example 205, Example 206, Example 208, Example 210, Example 211, Example 212, Example 213, Example 226, Example 240, Example 246, Example 248, Example 251, Example 253, Example 261, Example 267, Example 268, Example 273, Example 279, Example 294, Example 306, Example 307, Example 310, Example 316, Example 317, Example 318, Example 320, Example 322, Example 323, Example 325, Example 327, Example 346, Example 329, Example 347, Example 355, Example 386, Example 396, Example 397, Example 399, Example 400, Example 413, Example 415, Example 417, Example 419, Example 420, Example 427, Example 431, Example 432, Example 434, Example 439, Example 440, Example 441, Example 442, Example 443, Example 444, Example 447, Example 448, Example 449, Example 454, Example 455, Example 456, and Example 458 of the invention have an $IC_{50}$=<1.0 microM in $Na_{v1.3}$ FRET or $Na_{v1.7}$ FRET Assays.

In Vivo Assay

Chronic Constriction Injury (CCI)-Induced Static Allodynia

Male Sprague-Dawley rats weighing 210-240 g were purchased from Charles River Japan (Kanagawa, Japan). Animals were housed in groups of two under a 12-h light/dark cycle (lights on at 07:00) with access to food and water ad libitum. The CCI was made according to the method of Bennett G J and Xie Y K (Pain 1988, 33:87-107). Animals were anesthetized with intraperitoneal injection of sodium pentobarbital. The left common sciatic nerve was exposed at the level of the middle of the thigh and four ligatures were loosely tided around it by using 4-0 silk thread (Ethicon Inc, Brussels, Belgium) with approximately 1 mm apart. The incision was sutured, and the rats were allowed to recover. Sham operation was performed in the same manner except of sciatic nerve ligation. After 2 to 3 weeks, static allodynia was assessed using von Frey hairs (VFHs; North Coast Medical Inc., San Jose, Calif.) as described by Field M J et al. (Pain 1999, 83: 303-311). The animals were placed in grid bottom cages and allowed to acclimate for at least 30 min prior to the start of experiment. VFHs in ascending order of force (0.16, 0.4, 0.6, 1, 1.4, 2.4, 6, 8, 10, 15 and 26 g) were applied to the plantar surface of the hind paw. Each VFH was applied to the ipsilateral paw for 6 seconds or until a withdrawal response occurred. Once a withdrawal response was happened, the paw was re-tested, starting with the next descending VFH until no response was occurred. The lowest amount of force required to elicit a response was defined as paw withdrawal threshold (PWT) in g. Animals with <2 g of PWTs were selected for evaluation and randomized to be nearly equal across all groups. The compounds of the invention or their vehicles were administered systemically. All tested compounds of the invention showed potent activities in this model.

Complete Freund's Adjuvant (CFA)-Induced Thermal Hyperalgesia

Male Sprague-Dawley rats weighing 200-250 g were purchased from Charles River Japan (Kanagawa, Japan), Animals were housed under a 12-h light/dark cycle (lights on at 07:00) with access to food and water ad libitum, CFA-Induced thermal hyperalgesia was assessed using the plantar test apparatus (Ugo Basile, Verse, Italy) as describe by Hargreaves K et al. (Pain 1988, 32: 77-88). Animals were placed in an apparatus consisting of individual testing box on an elevated glass table and allowed to acclimate for at least 10 min. Following habituation, a mobile radiant heat source was located under the table and heat stimulation was applied to the plantar surface of the right hind paw. The latency to remove its hind paw was defined as paw withdrawal latency (PWL) in sec. CFA was prepared at a concentration of 200 microg/100 microl of Mycobacterium tuberculosis H-37 RA (Difco Laboratories Inc.) in liquid paraffin and injected into the plantar surface of the right hind paw. PWL was measured before and 2 days after CFA injection. Animals showing decrease of the PWL on day 2 were selected for evaluation and randomized to be nearly equal across all groups. The compounds of the invention or their vehicles were administered systemically. PWLs were measured at the appropriated time after compound administration.

Metabolic Stability Assay:

Half-Life in Human Liver Microsomes (HLM)

Test compounds (1 microM) were incubated with 3.3 mM $MgCl_2$ and 0.78 mg/mL HLM (HL101) in 100 mM potassium phosphate buffer (pH 7.4) at 37° C. on the 96-deep well plate. The reaction mixture was split into two groups, a non-P450 and a P450 group. NADPH was only added to the reaction mixture of the P450 group. (NADPH generation system was also used instead of NADPH.) An aliquot of samples of P450 group was collected at 0, 10, 30, and 60 min time point, where 0 min time point indicated the time when NADPH was added into the reaction mixture of P450 group. An aliquot of samples of non-P450 group was collected at −10 and 65 min time point. Collected aliquots were extracted with acetonitrile solution containing an internal standard. The precipitated protein was spun down in centrifuge (2000 rpm, 15 min). The compound concentration in supernatant was measured by LC/MS/MS system.

The half-life value was obtained by plotting the natural logarithm of the peak area ratio of compounds/internal standard versus time. The slope of the line of best fit through the points yields the rate of metabolism (k). This was converted to a half-life value using following equations:
Half-life=ln 2/k Drug-Drug Interaction Assay This method essentially involves determining the percent inhibition of metabolites formation from probes (Tacrine (Sigma A3773-IG) 2 microM, Dextromethorphan (Sigma D-9684) 5 microM, Diclofenac (Sigma D-6899-10G) 5 microM, and Midazolam (ULTRAFINE UC-429) 2 microM) at 3 microM of the each compound.

More specifically, the assay is carried out as follows. The compounds (60 microM, 10 microL) were pre-incubated in 170 microL of mixture including human liver microsomes, 100 mM potassium phosphate buffer and probes as substrate for 5 min. Reaction was started by adding a NADPH (10 mM, 20 microL) (NADPH generating system, which consist of 0.5 mM NADP, 10 mM $MgCl_2$, 6.2 mM DL-Isocitric acid and 0.5 U/ml Isocitric Dehydrogenase, was also used). The assay plate was incubated at 37° C. Acetonitril was added to the incubate solution at appropriate time (e.g. 8 min).

The metabolites concentration in the supernatant was measured by LC/MS/MS system.

The degree of drug interaction was interpreted based on generation % of metabolites in the presence or absence of test compound.

Human Dofetilide Binding Assay

Human HERG transfected HEK293S cells were prepared and grown in-house. The collected cells were suspended in 50 mM Tris-HCl, 10 mM KCl, 1 mM $MgCl_2$, Complete (Roche) (pH 7.4 at 4° C.) and homogenized using a hand held Polytron PT 1300 D disrupter set at 15,000 rpm for 20 sec on ice. The homogenates were centrifuged at 48,000×g at 4° C. for 20 min. The pellets were then resuspended, homogenized, and centrifuged once more in the same manner. The final pellets were resuspended in an appropriate volume of 50 mM Tris-HCl, 10 mM KCl, 1 mM $MgCl_2$, Complete (pH 7.4 at 4° C.), homogenized, aliquoted and stored at −80° C. until use. An aliquot of membrane fractions was used for protein concentration determination using BCA protein assay kit (PIERCE) and ARVOsx plate reader (Wallac). Binding assays were conducted in a total volume of 30 microL in 384-well plates. The activity was measured by PHERAstar (BMG LABTECH) using fluorescence polarization technology. Ten microL of test compounds were incubated with 10 microL of fluorescence ligand (6 nM Cy3B tagged dofetilide derivative) and 10 microL of membrane homogenate (6 microg protein) for 120 minutes at room temperature. Nonspecific binding was determined by 10 microM E4031 at the final concentration. The IC50 values were calculated using Dose Response One Site Models, 4 Parameter Logistic Model (XLfit).

All publications, including but not limited to, issued patents, patent applications, and journal articles, cited in this application are each herein incorporated by reference in their entirety. Although the invention has been described above with reference to the disclosed embodiments, those skilled in the art will readily appreciate that the specific experiments detailed are only illustrative of the invention. It should be understood that various modifications can be made without departing from the spirit of the invention. Accordingly, the invention is limited only by the following claims.

The invention claimed is:

1. A compound of the formula (I):

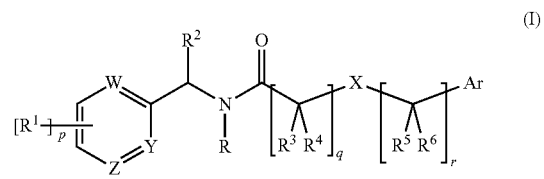

wherein:

R is hydrogen or $C_{1-6}$ alkyl which may be substituted with one or more substituents independently selected from $R^7$;

$R^1$ is independently selected from the group consisting of;
(1) hydrogen, (2) —$O_n$—$C_{1-6}$ alkyl, where the alkyl is unsubstituted or substituted with one or more substituents independently selected from $R^7$, (3) —$O_n$—$C_{3-6}$ cycloalkyl, where the cycloalkyl is unsubstituted or substituted with one or more substituents independently selected from $R^7$, and (4) —$O_n$-heterocyclic group, where the heterocyclic group is unsubstituted or substituted with one or more substituents independently selected from $R^7$;

wherein n is 0 or 1, when n is 0, a chemical bond is present in the place of $O_n$;

p is 1, 2, 3, or 4; when p is two or more than two, $R^1$ may be same or different;

$R^2$ is selected from the group consisting of:
(1) hydrogen, (2) $C_{1-6}$ alkyl, which is unsubstituted or substituted with one or more substituents independently selected from $R^7$, (3) $C_{3-6}$ cycloalkyl, which is unsubstituted or substituted with one or more substituents independently selected from $R^7$, (4) $C_{2-6}$ alkenyl, which is unsubstituted or substituted with one or more substituents independently selected from $R^7$, (5) $C_{2-6}$ alkynyl, which is unsubstituted or substituted with one or more substituents independently selected from $R^7$, (6) phenyl, which is unsubstituted or substituted with one or more substituents independently selected from $R^7$, (7) —(C═O)—$NR^9R^{10}$, and (8) —(C═O)—O—$C_{1-6}$ alkyl, which is unsubstituted or substituted with one or more substituents independently selected from $R^7$;

or $R^2$ form a 5 to 7 membered ring with $R^1$ which may contain nitrogen atom, oxygen atom, sulfur atom or double bond, wherein the 5 to 7 membered ring is optionally substituted with 1 to 6 substituents independently selected from the group consisting of: (1) hydrogen, (2) hydroxyl, (3) halogen, (4) $C_{1-6}$ alkyl, which is unsubstituted or substituted with one or more substituents independently selected from $R^7$, (5) $C_{3-6}$ cycloalkyl, which is unsubstituted or substituted with one or more substituents independently selected from $R^7$, (6) —O—$C_{1-6}$ alkyl, which is unsubstituted or substituted with one or more substituents independently selected from $R^7$, and (7) —O—$C_{3-6}$ cycloalkyl, which is unsubstituted or substituted with one or more substituents independently selected from $R^7$;

X is -cycloalkylene-, wherein the said substituent X may have a substituent independently selected from the definitions of $R^9$ and $R^{10}$;

W, Y and Z are independently selected from nitrogen atom and carbon atom, which are independently optionally substituted with $R^1$;

at least one of W, Y and Z is nitrogen and W, Y and Z are not carbon at the same time;

$R^3$, $R^4$, $R^5$ and $R^6$ are independently selected from the group consisting of:

(1) hydrogen, (2) hydroxyl, (3) halogen, (4) $C_{1-6}$ alkyl, which is unsubstituted or substituted with one or more substituents independently selected from $R^7$, (5) $C_{3-6}$ cycloalkyl, which is unsubstituted or substituted with one or more substituents independently selected from $R^7$, (6) —O—$C_{1-6}$ alkyl, which is unsubstituted or substituted with one or more substituents independently selected from $R^7$, (7) —O—$C_{3-6}$ cycloalkyl, which is unsubstituted or substituted with one or more substituents independently selected from $R^7$, and (8) —$NR^7R^8$;

or $R^3$ and $R^4$ and the carbon atom to which they are attached form an oxo group;

or $R^3$ and $R^4$ and the carbon atom to which they are attached form a $C_{3-6}$ cycloalkyl ring, which is unsubstituted or substituted with $R^7$;

or $R^5$ and $R^6$ and the carbon atom to which they are attached form an oxo group;

or $R^5$ and $R^6$ and the carbon atom to which they are attached form a $C_{3-6}$ cycloalkyl ring, which is unsubstituted or substituted with $R^7$;

q is 0;
r is 0;

$R^7$ is selected from the group consisting of:

(1) hydrogen, (2) halogen, (3) hydroxyl, (4) —(C=O)$_m$—O$_l$—$C_{1-6}$ alkyl, where the alkyl is unsubstituted or substituted with one or more substituents independently selected from $R^8$, (5) —O$_l$—($C_{1-3}$)perfluoroalkyl, (6) —(C=O)$_m$—O$_l$—$C_{3-6}$ cycloalkyl, where the cycloalkyl is unsubstituted or substituted with one or more substituents independently selected from $R^8$, (7) —(C=O)$_m$—O$_l$-phenyl, where the phenyl is unsubstituted or substituted with one or more substituents independently selected from $R^8$, and (8) —(C=O)$_m$—O$_l$-heterocyclic group, where the heterocyclic group is unsubstituted or substituted with one or more substituents independently selected from $R^8$;

wherein l is 0 or 1 and m is 0 or 1; when l is 0 or m is 0, a chemical bond is present in the place of (C=O)$_m$ or O$_l$, and when l is 0 and m is 0, a chemical bond is present in the place of (C=O)$_m$—O$_l$;

$R^8$ is independently selected from the group consisting of:
(1) hydrogen and (2) halogen;

$R^9$ and $R^{10}$ are independently hydrogen or $C_{1-6}$ alkyl, which is unsubstituted or substituted with one or more substituents independently selected from halogen, hydroxyl, and —O—$C_{1-6}$ alkyl;

Ar is aryl which is optionally substituted with 1 to 5 substituents independently selected from the group consisting of:

(1) halogen, (2) hydroxyl, (3) —O$_n$—$C_{1-6}$ alkyl, where the alkyl is unsubstituted or substituted with one or more substituents independently selected from $R^7$, (4) —$NR^9R^{10}$, and (5) —CN;

wherein n is 0 or 1; when n is 0, a chemical bond is present in the place of O$_n$;

or a pharmaceutically acceptable salt thereof.

2. A compound of the formula (I):

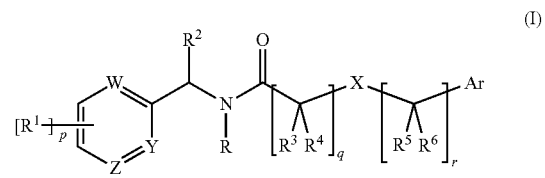

wherein:

R is hydrogen or $C_{1-6}$ alkyl which may be substituted with one or more substituents independently selected from $R^7$;

$R^1$ is independently selected from the group consisting of;

(1) hydrogen, (2) —O$_n$—$C_{1-6}$ alkyl, where the alkyl is unsubstituted or substituted with one or more substituents independently selected from $R^7$, and (4) —O$_n$-heterocyclic group, where the heterocyclic group is unsubstituted or substituted with one or more substituents independently selected from $R^7$;

wherein n is 0 or 1, when n is 0, a chemical bond is present in the place of O$_n$;

p is 1;

$R^2$ is (1) hydrogen or (2) $C_{1-6}$ alkyl, which is unsubstituted or substituted with one or more substituents independently selected from $R^7$;

X is -cycloalkylene-, wherein the said substituent X may have a substituent independently selected from the definitions of $R^9$ and $R^{10}$;

W, Y and Z are independently selected from nitrogen atom and carbon atom, which are independently optionally substituted with $R^1$;

at least one of W, Y and Z is nitrogen and W, Y and Z are not carbon at the same time;

q is 0;
r is 0;

$R^7$ is selected from the group consisting of:

(1) hydrogen, (2) halogen, (3) hydroxyl, (4) —(C=O)$_m$—O$_l$—$C_{1-6}$ alkyl, where the alkyl is unsubstituted or substituted with one or more substituents independently selected from $R^8$, (5) —O$_l$—($C_{1-3}$)perfluoroalkyl, (6) —(C=O)$_m$—O$_l$—$C_{3-6}$ cycloalkyl, where the cycloalkyl is unsubstituted or substituted with one or more substituents independently selected from $R^8$, (7) —(C=O)$_m$—O$_l$-phenyl, where the phenyl is unsubstituted or substituted with one or more substituents independently selected from $R^8$, and (8) —(C=O)$_m$—O$_l$-heterocyclic group, where the heterocyclic group is unsubstituted or substituted with one or more substituents independently selected from $R^8$;

wherein l is 0 or 1 and m is 0 or 1; when l is 0 or m is 0, a chemical bond is present in the place of (C=O)$_m$ or O$_l$, and when l is 0 and m is 0, a chemical bond is present in the place of (C=O)$_m$—O$_l$;

R⁸ is independently selected from the group consisting of:
(1) hydrogen and (2) halogen;
R⁹ and R¹⁰ are independently hydrogen or $C_{1-6}$ alkyl;
Ar is aryl which is optionally substituted with 1 to 5 substituents independently selected from the group consisting of:
(1) halogen, (2) hydroxyl, (3) —$O_n$—$C_{1-6}$ alkyl, where the alkyl is unsubstituted or substituted with one or more substituents independently selected from R⁷, (4) —NR⁹R¹⁰, and (5) —CN;
wherein n is 0 or 1; when n is 0, a chemical bond is present in the place of $O_n$;
or a pharmaceutically acceptable salt thereof.

3. The compound of claim 1 which is selected from the group consisting of:
(1R,2R)-2-methyl-N—((R)-1-(5-(2,2,2-trifluoroethoxy)pyridin-2-yl)ethyl)-2-(4-(trifluoromethyl)phenyl)cyclopropanecarboxamide;
(R)—N-(1-(5-(cyclopropylmethoxy)pyridin-2-yl)ethyl)-3-(6-fluoro-1H-indol-1-yl)propanamide;
(1R,2R)—N—((R)-1-(6-(2,2,2-trifluoroethoxy)pyridin-3-yl)ethyl)-2-(4-(trifluoromethyl)phenyl)cyclopropanecarboxamide; trans-2-(7-fluoro-1H-indol-3-yl)-N—((R)-1-(5-(2,2,2-trifluoroethoxy)pyridin-2-yl)ethyl)cyclopropanecarboxamide;
(1 S*,2 S*)-2-(1H-indol-3-yl)-N—((R)-1-(5-(2,2,2-trifluoroethoxy)pyridin-2-yl)ethyl)cyclopropanecarboxamide;
(1R*,2R*)-2-(1H-indol-3-yl)-N—((R)-1-(5-(2,2,2-trifluoroethoxy)pyridin-2-yl)ethyl)cyclopropanecarboxamide;
trans-2-(1H-indol-6-yl)-N—((R)-1-(6-(2,2,2-trifluoroethoxy)pyridin-3-yl)ethyl)cyclopropanecarboxamide;
trans-2-(quinolin-7-yl)-N—((R)-1-(5-(2,2,2-trifluoroethoxy)pyridin-2-yl)ethyl)cyclopropanecarboxamide;
trans-2-(quinolin-7-yl)-N—((R)-1-(5-(2,2,2-trifluoroethoxy)pyrazin-2-yl)ethyl)cyclopropanecarboxamide;
trans-2-(isoquinolin-3-yl)-N—((R)-1-(5-(2,2,2-trifluoroethoxy)pyridin-2-yl)ethyl)cyclopropanecarboxamide;
trans-2-(quinolin-3-yl)-N—((R)-1-(5-(2,2,2-trifluoroethoxy)pyrazin-2-yl)ethyl)cyclopropanecarboxamide;
trans-2-((4-chlorophenoxy)methyl)-N—((R)-1-(5-(2,2,2-trifluoroethoxy)pyrazin-2-yl)ethyl)cyclopropanecarboxamide;
trans-2-(2-fluoro-5-methoxyphenyl)-N—((R)-1-(5-(2,2,2-trifluoroethoxy)pyridin-2-yl)ethyl)cyclopropanecarboxamide;
trans-2-((1H-indol-1-yl)methyl)-N—((R)-1-(5-(2,2,2-trifluoroethoxy)pyridin-2-yl)ethyl)cyclopropanecarboxamide;
trans-2-(2,5-difluorophenyl)-N—((R)-1-(5-(2,2,2-trifluoroethoxy)pyridin-2-yl)ethyl)cyclopropanecarboxamide;
trans-N—((R)-1-(5-(cyclopropylmethoxy)pyridin-2-yl)ethyl)-2-(2,5-difluorophenyl)cyclopropanecarboxamide;
trans-2-(2,5-difluorophenyl)-N—((R)-1-(5-(2,2,2-trifluoroethoxy)pyrazin-2-yl)ethyl)cyclopropanecarboxamide;
trans-N—((R)-1-(5-(cyclopropylmethoxy)pyridin-2-yl)ethyl)-2-(1H-indol-4-yl)cyclopropanecarboxamide;
trans-2-(4-methoxy-3-methylphenyl)-N—((R)-1-(5-(2,2,2-trifluoroethoxy)pyridin-2-yl)ethyl)cyclopropanecarboxamide;
(1R*,2R*)-2-(1H-indol-6-yl)-N—((R)-1-(5-(2,2,2-trifluoroethoxy)pyridin-2-yl)ethyl)cyclopropanecarboxamide;
trans-2-(quinolin-6-yl)-N—((R)-1-(6-(2,2,2-trifluoroethoxy)pyridin-3-yl)ethyl)cyclopropanecarboxamide;
trans-2-(5-fluoro-1H-indol-2-yl)-N—((R)-1-(6-(2,2,2-trifluoroethoxy)pyridin-3-yl)ethyl)cyclopropanecarboxamide;
trans-2-(quinolin-3-yl)-N—((R)-1-(6-(2,2,2-trifluoroethoxy)pyridin-3-yl)ethyl)cyclopropanecarboxamide;
trans-2-(1H-indol-4-yl)-N—((R)-1-(6-(2,2,2-trifluoroethoxy)pyridin-3-yl)ethyl)cyclopropanecarboxamide;
(1S*,2S*)-2-(8-chloroquinolin-2-yl)-N—((R)-1-(5-(2,2,2-trifluoroethoxy)pyrazin-2-yl)ethyl)cyclopropanecarboxamide;
(1S*,2S*)-2-(1H-indol-2-yl)-N—((R)-1-(6-(2,2,2-trifluoroethoxy)pyridin-3-yl)ethyl)cyclopropanecarboxamide;
(1R*,2R*)-2-(1H-indol-2-yl)-N—((R)-1-(6-(2,2,2-trifluoroethoxy)pyridin-3-yl)ethyl)cyclopropanecarboxamide;
(1S*,2S*)-2-(1H-indol-2-yl)-N—((R)-1-(5-(2,2,2-trifluoroethoxy)pyrazin-2-yl)ethyl)cyclopropanecarboxamide;
trans-2-(1-methyl-1H-indazol-6-yl)-N—((R)-1-(6-(2,2,2-trifluoroethoxy)pyridin-3-yl)ethyl)cyclopropanecarboxamide;
(1R*,2R*)-2-(4-(benzyloxy)phenyl)-N—((R)-1-(5-(2,2,2-trifluoroethoxy)pyridin-2-yl)ethyl)cyclopropanecarboxamide;
(R,E)-3-(quinolin-2-yl)-N-(1-(5-(2,2,2-trifluoroethoxy)pyridin-2-yl)ethyl)acrylamide;
(1S*,2S*)—N—((R)-1-(5-(2,2,2-trifluoroethoxy)pyridin-2-yl)ethyl)-2-(2,4,6-trifluorophenyl)cyclopropanecarboxamide;
(1S*,2S*)-2-(3,5-difluorophenyl)-N—((R)-1-(5-(2,2,2-trifluoroethoxy)pyridin-2-yl)ethyl)cyclopropanecarboxamide;
(1S*,2S*)-2-(3-methoxyphenyl)-N—((R)-1-(5-(2,2,2-trifluoroethoxy)pyridin-2-yl)ethyl)cyclopropanecarboxamide;
(1S*,2S*)-2-(4-methoxyphenyl)-N—((R)-1-(5-(2,2,2-trifluoroethoxy)pyridin-2-yl)ethyl)cyclopropanecarboxamide;
(1R*,2R*)-2-(2-chloro-4-fluorophenyl)-N—((R)-1-(5-(cyclopropylmethoxy)pyridin-2-yl)ethyl)cyclopropanecarboxamide;
(1R*,2R*)—N—((R)-1-(5-(cyclopropylmethoxy)pyridin-2-yl)ethyl)-2-(2-fluoro-4-methoxyphenyl)cyclopropanecarboxamide;
(1S*,2S*)—N—((R)-1-(5-(cyclopropylmethoxy)pyridin-2-yl)ethyl)-2-(2,4,6-trifluorophenyl)cyclopropanecarboxamide;
(1S*,2S*)—N—((R)-1-(5-(2,2,2-trifluoroethoxy)pyrazin-2-yl)ethyl)-2-(2,4,6-trifluorophenyl)cyclopropanecarboxamide;
(1R*,2R*)—N—((R)-1-(5-(2,2,2-trifluoroethoxy)pyrazin-2-yl)ethyl)-2-(2,4,6-trifluorophenyl)cyclopropanecarboxamide;
(1S*,2S*)-2-(1H-indol-4-yl)-N—((R)-1-(5-(2,2,2-trifluoroethoxy)pyrazin-2-yl)ethyl)cyclopropanecarboxamide;
(1R*,2R*)-2-phenyl-N—((R)-1-(5-(2,2,2-trifluoroethoxy)pyridin-2-yl)ethyl)cyclopropanecarboxamide;
(1S*,2S*)-2-phenyl-N—((R)-1-(5-(2,2,2-trifluoroethoxy)pyrazin-2-yl)ethyl)cyclopropanecarboxamide;

(1R*,2R*)-2-phenyl-N—((R)-1-(5-(2,2,2-trifluoroethoxy)pyrazin-2-yl)ethyl)cyclopropanecarboxamide;
(1S*,2S*)-2-phenyl-N—((R)-1-(6-(2,2,2-trifluoroethoxy)pyridin-3-yl)ethyl)cyclopropanecarboxamide;
(1R*,2R*)-2-phenyl-N—((R)-1-(6-(2,2,2-trifluoroethoxy)pyridin-3-yl)ethyl)cyclopropanecarboxamide;
(1S*,2S*)-2-(1H-benzo[d]imidazol-2-yl)-N—((R)-1-(5-(2,2,2-trifluoroethoxy)pyrazin-2-yl)ethyl)cyclopropanecarboxamide;
(1S*,2S*)-2-(1H-benzo[d]imidazol-2-yl)-N—((R)-1-(6-(2,2,2-trifluoroethoxy)pyridin-3-yl)ethyl)cyclopropanecarboxamide;
(1R*,2R*)-2-(1H-benzo[d]imidazol-2-yl)-N—((R)-1-(6-(2,2,2-trifluoroethoxy)pyridin-3-yl)ethyl)cyclopropanecarboxamide;
(1S*,2S*)-2-(phenoxymethyl)-N—((R)-1-(5-(2,2,2-trifluoroethoxy)pyridin-2-yl)ethyl)cyclopropanecarboxamide;
(1S*,2S*)-2-((3-fluorophenoxy)methyl)-N—((R)-1-(5-(2,2,2-trifluoroethoxy)pyridin-2-yl)ethyl)cyclopropanecarboxamide;
(1S*,2S*)-2-((3-cyanophenoxy)methyl)-N—((R)-1-(5-(2,2,2-trifluoroethoxy)pyridin-2-yl)ethyl)cyclopropanecarboxamide;
(1S*,2S*)-2-((4-fluorophenoxy)methyl)-N—((R)-1-(5-(2,2,2-trifluoroethoxy)pyridin-2-yl)ethyl)cyclopropanecarboxamide;
(1S*,2S*)-2-((4-cyanophenoxy)methyl)-N—((R)-1-(5-(2,2,2-trifluoroethoxy)pyridin-2-yl)ethyl)cyclopropanecarboxamide;
(1R*,2R*)-2-(phenoxymethyl)-N—((R)-1-(5-(2,2,2-trifluoroethoxy)pyridin-2-yl)ethyl)cyclopropanecarboxamide;
(1R*,2R*)-2-((3-fluorophenoxy)methyl)-N—((R)-1-(5-(2,2,2-trifluoroethoxy)pyridin-2-yl)ethyl)cyclopropanecarboxamide;
(1R*,2R*)-2-((3-cyanophenoxy)methyl)-N—((R)-1-(5-(2,2,2-trifluoroethoxy)pyridin-2-yl)ethyl)cyclopropanecarboxamide;
(1R*,2R*)-2-((4-fluorophenoxy)methyl)-N—((R)-1-(5-(2,2,2-trifluoroethoxy)pyridin-2-yl)ethyl)cyclopropanecarboxamide;
(1R*,2R*)-2-((4-cyanophenoxy)methyl)-N—((R)-1-(5-(2,2,2-trifluoroethoxy)pyridin-2-yl)ethyl)cyclopropanecarboxamide;
(1S*,2S*)-2-(4-((3-methyloxetan-3-yl)methoxy)phenyl)-N—((R)-1-(5-(2,2,2-trifluoroethoxy)pyridin-2-yl)ethyl)cyclopropanecarboxamide;
(1S*,2S*)—N—((R)-1-(5-(cyclopropylmethoxy)pyridin-2-yl)ethyl)-2-(1H-indol-7-yl)cyclopropanecarboxamide;
(1S*,2 S*)-2-(phenoxymethyl)-N—((R)-1-(6-(2,2,2-trifluoroethoxy)pyridin-3-yl)ethyl)cyclopropanecarboxamide;
(1R*,2R*)-2-(quinolin-2-yl)-N—((R)-1-(5-(2,2,2-trifluoroethoxy)pyridin-2-yl)ethyl)cyclopropanecarboxamide;
(1S*,2S*)-2-(4-(benzyloxy)phenyl)-N—((S)-1-(5-(2,2,2-trifluoroethoxy)pyridin-2-yl)ethyl)cyclopropanecarboxamide;
(1R*,2R*)-2-(4-(benzyloxy)phenyl)-N—((S)-1-(5-(2,2,2-trifluoroethoxy)pyridin-2-yl)ethyl)cyclopropanecarboxamide;
(1S*,2 S*)-2-(2-fluoro-4-methoxyphenyl)-N—((S)-1-(5-(2,2,2-trifluoroethoxy)pyridin-2-yl)ethyl)cyclopropanecarboxamide;
(1R*,2R*)-2-(2-fluoro-4-methoxyphenyl)-N—((S)-1-(5-(2,2,2-trifluoroethoxy)pyridin-2-yl)ethyl)cyclopropanecarboxamide;
(1S*,2 S*)-2-(2-chloro-4-fluorophenyl)-N—((S)-1-(5-(2,2,2-trifluoroethoxy)pyridin-2-yl)ethyl)cyclopropanecarboxamide;
(1R*,2R*)-2-(2-chloro-4-fluorophenyl)-N—((S)-1-(5-(2,2,2-trifluoroethoxy)pyridin-2-yl)ethyl)cyclopropanecarboxamide;
(1S*,2 S*)-2-phenyl-N—((S)-1-(5-(2,2,2-trifluoroethoxy)pyridin-2-yl)ethyl)cyclopropanecarboxamide; and
(1R*,2R*)-2-phenyl-N—((S)-1-(5-(2,2,2-trifluoroethoxy)pyridin-2-yl)ethyl)cyclopropanecarboxamide;
and salts thereof.

4. A method for the treatment of a condition or disorder in which T-type calcium channels or voltage gated sodium channels are involved in a mammalian subject, which comprises administering to a mammal in need of such treatment a therapeutically effective amount of a compound of the formula (I)

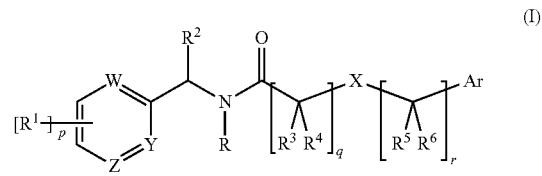

wherein:
R is hydrogen or $C_{1-6}$ alkyl which may be substituted with one or more substituents independently selected from $R^7$;
$R^1$ is independently selected from the group consisting of:
(1) hydrogen, (2) —$O_n$—$C_{1-6}$ alkyl, where the alkyl is unsubstituted or substituted with one or more substituents independently selected from $R^7$, (3) —$O_n$—$C_{3-6}$ cycloalkyl, where the cycloalkyl is unsubstituted or substituted with one or more substituents independently selected from $R^7$, and (4) —$O_n$-heterocyclic group, where the heterocyclic group is unsubstituted or substituted with one or more substituents independently selected from $R^7$;
wherein n is 0 or 1, when n is 0, a chemical bond is present in the place of $O_n$;
p is 1, 2, 3, or 4; when p is two or more than two, $R^1$ may be same or different;
$R^2$ is selected from the group consisting of:
(1) hydrogen, (2) $C_{1-6}$ alkyl, which is unsubstituted or substituted with one or more substituents independently selected from $R^7$, (3) $C_{3-6}$ cycloalkyl, which is unsubstituted or substituted with one or more substituents independently selected from $R^7$, (4) $C_{2-6}$ alkenyl, which is unsubstituted or substituted with one or more substituents independently selected from $R^7$, (5) $C_{2-6}$ alkynyl, which is unsubstituted or substituted with one or more substituents independently selected from $R^7$, (6) phenyl, which is unsubstituted or substituted with one or more substituents independently selected from $R^7$, (7) —(C=O)—$NR^9R^{10}$, and (8) —(C=O)—O—$C_{1-6}$ alkyl, which is unsubstituted or substituted with one or more substituents independently selected from $R^7$;
or $R^2$ form a 5 to 7 membered ring with $R^1$ which may contain nitrogen atom, oxygen atom, sulfur atom or double bond, wherein the 5 to 7 membered ring is optionally substituted with 1 to 6 substituents independently selected from the group consisting of: (1) hydrogen, (2) hydroxyl, (3) halogen, (4) $C_{1-6}$ alkyl, which is unsubstituted or substituted with one or more substituents independently selected from $R^7$, (5) $C_{3-6}$ cycloalkyl, which is unsubstituted or substituted with one or more substituents independently selected from $R^7$, (6) —O—$C_{1-6}$ alkyl, which is unsubstituted or substituted with one or more substituents independently selected from $R^7$, and (7) —O—$C_{3-6}$ cycloalkyl, which is unsubstituted or substituted with one or more substituents independently selected from $R^7$;

X is -cycloalkylene-, wherein the said substituent X may have a substituent independently selected from the definitions of $R^9$ and $R^{10}$;

W, Y and Z are independently selected from nitrogen atom and carbon atom, which are independently optionally substituted with $R^1$;

at least one of W, Y and Z is nitrogen and W, Y and Z are not carbon at the same time;

$R^3$, $R^4$, $R^5$ and $R^6$ are independently selected from the group consisting of:

(1) hydrogen, (2) hydroxyl, (3) halogen, (4) $C_{1-6}$ alkyl, which is unsubstituted or substituted with one or more substituents independently selected from $R^7$, (5) $C_{3-6}$ cycloalkyl, which is unsubstituted or substituted with one or more substituents independently selected from $R^7$, (6) —O—$C_{1-6}$ alkyl, which is unsubstituted or substituted with one or more substituents independently selected from $R^7$, (7) —O—$C_{3-6}$ cycloalkyl, which is unsubstituted or substituted with one or more substituents independently selected from $R^7$, and (8) —$NR^7R^8$;

or $R^3$ and $R^4$ and the carbon atom to which they are attached form an oxo group;

or $R^3$ and $R^4$ and the carbon atom to which they are attached form a $C_{3-6}$ cycloalkyl ring, which is unsubstituted or substituted with $R^7$;

or $R^5$ and $R^6$ and the carbon atom to which they are attached form an oxo group;

or $R^5$ and $R^6$ and the carbon atom to which they are attached form a $C_{3-6}$ cycloalkyl ring, which is unsubstituted or substituted with $R^7$;

q is 0;

r is 0;

$R^7$ is selected from the group consisting of:

(1) hydrogen, (2) halogen, (3) hydroxyl, (4) —(C=O)$_m$—O$_l$—$C_{1-6}$ alkyl, where the alkyl is unsubstituted or substituted with one or more substituents independently selected from $R^8$, (5) —O$_l$—($C_{1-3}$)perfluoroalkyl, (6) —(C=O)$_m$—O$_l$—$C_{3-6}$ cycloalkyl, where the cycloalkyl is unsubstituted or substituted with one or more substituents independently selected from $R^8$, (7) —(C=O)$_m$—O$_l$-phenyl, where the phenyl is unsubstituted or substituted with one or more substituents independently selected from $R^8$, and (8) —(C=O)$_m$—O$_l$-heterocyclic group, where the heterocyclic group is unsubstituted or substituted with one or more substituents independently selected from $R^8$;

wherein l is 0 or 1 and m is 0 or 1; when l is 0 or m is 0, a chemical bond is present in the place of (C=O)$_m$ or O$_l$, and when l is 0 and m is 0, a chemical bond is present in the place of (C=O)$_m$—O$_l$;

$R^8$ is independently selected from the group consisting of:

(1) hydrogen and (2) halogen;

$R^9$ and $R^{10}$ are independently hydrogen or $C_{1-6}$ alkyl, which is unsubstituted or substituted with one or more substituents independently selected from halogen, hydroxyl, and —O—$C_{1-6}$ alkyl;

Ar is aryl which is optionally substituted with 1 to 5 substituents independently selected from the group consisting of:

(1) halogen, (2) hydroxyl, (3) —O$_n$—$C_{1-6}$ alkyl, where the alkyl is unsubstituted or substituted with one or more substituents independently selected from $R^7$, (4) —$NR^9R^{10}$, and (5) —CN;

wherein n is 0 or 1; when n is 0, a chemical bond is present in the place of O$_n$;

or a pharmaceutically acceptable salt thereof.

* * * * *